US012502393B2

(12) United States Patent
Koch et al.

(10) Patent No.: US 12,502,393 B2
(45) Date of Patent: Dec. 23, 2025

(54) DUAL MODE OF ACTION SOLUBLE GUANYLATE CYCLASE ACTIVATORS AND PHOSPHODIESTERASE INHIBITORS AND USES THEREOF

(71) Applicant: TOPADUR PHARMA AG, Schlieren (CH)

(72) Inventors: Guido Koch, Schlieren (CH); Esra Lone, Schlieren (CH); Selena Di Maio, Schlieren (CH); Reto Naef, Schlieren (CH); Jeanette Peterke, Schlieren (CH); Michael Spoerri, Schlieren (CH); Hermann Tenor, Schlieren (CH); Elia Martini, Schlieren (CH)

(73) Assignee: TOPADUR PHARMA AG, Schlieren (CH)

( * ) Notice: Subject to any disclaimer, the term of this patent is extended or adjusted under 35 U.S.C. 154(b) by 955 days.

(21) Appl. No.: 17/297,369

(22) PCT Filed: Nov. 27, 2019

(86) PCT No.: PCT/EP2019/082668
§ 371 (c)(1),
(2) Date: May 26, 2021

(87) PCT Pub. No.: WO2020/109354
PCT Pub. Date: Jun. 4, 2020

(65) Prior Publication Data

US 2022/0031704 A1 Feb. 3, 2022

(30) Foreign Application Priority Data

Nov. 28, 2018 (EP) .................................... 18208939

(51) Int. Cl.
*A61K 31/519* (2006.01)
*A61K 31/506* (2006.01)
(Continued)

(52) U.S. Cl.
CPC .......... *A61K 31/519* (2013.01); *A61K 31/506* (2013.01); *A61K 31/53* (2013.01); *C07D 487/04* (2013.01)

(58) Field of Classification Search
CPC .... A61K 31/519; A61K 31/506; A61K 31/53; A61K 45/06; C07D 487/04; A61P 3/10; A61P 7/02; A61P 9/08
See application file for complete search history.

(56) References Cited

U.S. PATENT DOCUMENTS 6,225,315 B1 5/2001 Ellis
6,362,178 B1 3/2002 Niewöhner et al.
2002/0182162 A1 12/2002 Shahinpoor et al.

FOREIGN PATENT DOCUMENTS

DE 19834044 A1 2/2000
DE 19834047 A1 2/2000
(Continued)

OTHER PUBLICATIONS

Database Registry [Online] Chemical Abstracts Service, Columbus OH retrieved from STN Database Accession No. 586349-65-7, abstract (2003).
(Continued)

*Primary Examiner* — Joseph K McKane
*Assistant Examiner* — Meghan C Heasley
(74) *Attorney, Agent, or Firm* — MEDLER FERRO WOODHOUSE & MILLS PLLC

(57) ABSTRACT

The present invention relates to compounds of formula (I) or formula (II) or pharmaceutically acceptable salt, solvate or hydrate thereof, wherein said compound of formula (I) and said compound of formula II each comprises at least one $ONO_2$ or ONO moiety; $R_1$ is $C_1$-$C_3$alkyl; $R_2$ is H, $C_1$-$C_6$alkyl, $C_3$-$C_6$cycloalkyl, $C_1$-$C_2$alkoxy, $C_2$-$C_4$alkenyl; $R_3$ is $C_1$-$C_4$alkyl optionally substituted with $C_1$-$C_2$alkoxy, $C_3$-$C_4$cycloalkyl, $C_2$-$C_4$alkenyl; $R_4$ and $R_5$ are each independently H or $C_1$-$C_6$alkyl optionally substituted with F, OH, ONO, $ONO_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homo-piperazine, 2,5-diazabicyclo[2,2,1]heptane and 3,7-diazabicyclo[3,3,0]octane, wherein said heterocyclic ring is optionally substituted with independently one or more $R_6$; $R_6$ is $C_1$-$C_6$alkyl optionally substituted with independently one or more halogen, OH, ONO, $ONO_2$, $C_1$-$C_3$alkoxy, $C_1$-$C_3$haloalkoxy, $COOR_7$, $NR_8R_9$, $C{=}NR_{10}$; $R_7$ is H, or $C_1$-$C_4$alkyl optionally substituted with F, OH, ONO, ONO2, $NR_8R_9$; $R_8$ and $R_9$ are independently H, or $C_1$-$C_4$alkyl optionally substituted with ONO, $ONO_2$; $R_{10}$ is $C_1$-$C_4$alkyl optionally substituted with F, ONO, $ONO_2$; $C_3$-$C_6$cycloalkyl; pharmaceutical compositions thereof, and their use in methods of treating or preventing a disease alleviated by inhibition of PDE5 in a human or in a non-human mammal.

(I)

(Continued)

-continued

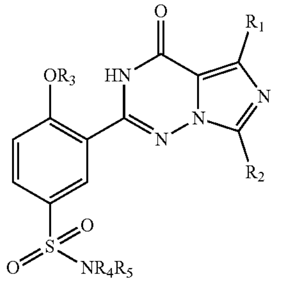

(II)

18 Claims, 3 Drawing Sheets

(51) Int. Cl.
*A61K 31/53* (2006.01)
*C07D 487/04* (2006.01)

(56) References Cited

FOREIGN PATENT DOCUMENTS

| | | | | |
|---|---|---|---|---|
| DE | 19942809 | A1 | 3/2001 | |
| EP | 0463756 | A1 | 1/1992 | |
| EP | 0667345 | A1 | 8/1995 | |
| EP | 0995751 | A2 | 4/2000 | |
| EP | 1 174 431 | A2 | 1/2002 | |
| EP | 1336602 | A1 * | 8/2003 | ........... C07C 291/02 |
| JP | 2000-159672 | A | 6/2000 | |
| JP | 2001-522851 | A | 11/2001 | |
| RU | 2485119 | C2 | 6/2013 | |
| WO | 1999/024433 | A1 | 5/1995 | |
| WO | 2000/027394 | A1 | 5/2000 | |
| WO | 2001/060825 | A1 | 8/2001 | |
| WO | 2002/089808 | A1 | 11/2002 | |
| WO | 2003/086407 | A1 | 10/2003 | |
| WO | 2003/095451 | A1 | 11/2003 | |
| WO | 2005/026145 | A2 | 3/2005 | |
| WO | 2009/010491 | A1 | 1/2009 | |
| WO | 2009/032249 | A1 | 3/2009 | |
| WO | 2009/094242 | A1 | 7/2009 | |
| WO | 2010/065275 | A1 | 6/2010 | |
| WO | 2010/081647 | A2 | 7/2010 | |
| WO | 2010/099054 | A2 | 9/2010 | |
| WO | 2011/075655 | A1 | 6/2011 | |
| WO | 2011/119518 | A1 | 9/2011 | |
| WO | 2011/149921 | A1 | 12/2011 | |
| WO | 2012/058132 | A1 | 5/2012 | |
| WO | 2013/075680 | A1 | 5/2013 | |
| WO | 2017/085056 | A1 | 5/2017 | |
| WO | 2018/215433 | A1 | 11/2018 | |

OTHER PUBLICATIONS

International Search Report in PCT/EP2019/082668, mailed Jan. 21, 2020.
Toque et al., "Synthesis and Pharmacological Evaluations of Sildenafil Analogues for Treatment of Erectile Dysfunction," J Med Chem. 51(9):2807-2815 (2008).
Barone et al., "Phosphodiesterase type 5 and cancers: progress and challenges," Oncotarget 8(58):99179-99202 (2017).
Beedimani and Kalmath, "Current and emerging uses of phosphodiesterase 5 inhibitors," Int. J. Pharm. Bio. Sci. 5(2):530-539 (2014), Abstract.
Buys et al., "Discovery and development of next generation sGC stimulators with diverse multidimensional pharmacology and broad therapeutic potential," Nitric Oxide 78:72-80 (2018).
Costell et al., "Comparison of soluble guanylate cyclase stimulators and activators in models of cardiovascular disease associated with oxidative stress," Front. Pharmacol. 3(128):1-14 (2012).
Dobhal et al., "Current Status and Future Prospects of PDE5 Inhibitors for Various Therapeutic Implications," Critical Review in Pharmaceutical Sciences 1(3):13-27 (2012).
Dunn, "Synthesis of Commercial Phosphodiesterase(V) Inhibitors," Organic Process Research & Development 9(1):88-97 (2005).
Flores-Costa et al., "The soluble guanylate cyclase stimulator IW-1973 prevents inflammation and fibrosis in experimental non-alcoholic steatohepatitis," Br. J. Pharmacol. 175(6):953-967 (2018).
Follmann et al., "Discovery of the soluble guanylate cyclase stimulator vericiguat (BAY 1021189) for the treatment of chronic heart failure," J. Med. Chem. 60(12):5146-5161 (2017).
Ge et al., "The soluble guanylate cyclase stimulator IWP-953 increases conventional outflow facility in mouse eyes," Invest. Ophthalmol. Vis. Sci. 57(3):1317-1326 (2016).
Horst and Marletta, "Physiological activation and deactivation of soluble guanylate cyclase," Nitric Oxide 77:65-74 (2018).
Huang et al., "Use of phosphodiesterase 5 inhibitors is associated with lower risk of colorectal cancer in men with benign colorectal neoplasms," Gastroenterology 157:672-681 (2019).
Jovani et al., "Are phosphodiesterase-5 inhibitors a new frontier for prevention of colorectal cancer?" Gastroenterology 157(3):602-604 (2019).
Ko et al., "YC-1, a novel activator of platelet guanylate cyclase," Blood 84(12):4226-4233 (1994).
Lee and Piazza, "The interaction between the Wnt/β-catenin signaling cascade and PKG activation in cancer," J. Biomed. Res. 31(3):189-196 (2017).
Liu et al., "The soluble guanylate cyclase stimulator IWP-550 inhibits neuroinflammation in vitro and in vivio," The FASEB Journal 32:823 (2018).
Miller et al., "A-350619: a novel activator of soluble guanylyl cyclase," Life Sci. 72(9):1015-1025 (2003).
Mittendorf et al., "Discovery of riociguat (BAY 63-2521): a potent, oral stimulator of soluble guanylate cyclase for the treatment of pulmonary hypertension," ChemMedChem, 4(5):853-865 (2009).
Monica et al., "Modulating cGMP levels as therapeutic drug targets in cardiovascular and non-cardiovascular diseases," OA Biochemistry 2(1):3 (2014).
Mülsch et al., "Effect of YC-1, an NO-independent, superoxide-sensitive stimulator of soluble guanylyl cyclase, on smooth muscle responsiveness to nitrovasodilators," British Journal of Pharmacology 120:681-689 (1997).
Nakai et al., "Discovery of IWP-051, a novel orally bioavailable sGC stimulator with once-daily dosing potential in humans," ACS Med. Chem. Lett. 7(5):465-469 (2016).
Papapetropoulos et al., "Extending the translational potential of targeting NO/cGMP-regulated pathways in the CVS," British Journal of Pharmacology 172:1397-1414 (2015).
Sandner et al., "Discovery and development of sGC stimulators for the treatment of pulmonary hypertension and rare diseases," Nitric Oxide 77:88-95 (2018).
Sandner et al., "The potential of sGC modulators for the treatment of age-related fibrosis: a mini-review," Gerontology 63:216-227 (2017).
Selwood et al., "Synthesis and biological evaluation of novel pyrazoles and indazoles as activators of the nitric oxide receptor, soluble guanylate cyclase," J. Med. Chem. 44(1):78-93 (2001).
Stasch et al., "Pharmacological actions of a novel NO-independent guanylyl cyclase stimulator, BAY 41-8543: in vitro studies," Br. J. Pharmacol. 135(2):333-343 (2002).
Stasch et al., "Cardiovascular actions of a novel NO-independent guanylyl cyclase stimulator, BAY 41-8543: in vivo studies," Br. J. Pharmacol. 135(2):344-355 (2002).
Stasch and Evgenov, "Soluble guanylate cyclase stimulators in pulmonary hypertension," Pharmacotherapy of Pulmonary Hypertension 218:279-313 (2013).
Straub et al., "NO-independent stimulators of soluble guanylate cyclase," Bioorg. Med. Chem. Lett 11(6):781-784 (2001).
Vighi et al., "New cGMP analogues restrain proliferation and migration of melanoma cells," Oncotarget 9(4):5301-5320 (2018).

(56) References Cited

OTHER PUBLICATIONS

Wales et al., "Discovery of stimulator binding to a conserved pocket in the heme domain of soluble guanylyl cyclase," J. Biol. Chem. 293(5):1850-1864 (2018).
Wilck et al., "Nitric oxide-sensitive guanylyl cyclase stimulation improves experimental heart failure with preserved ejection fraction," JCI Insight 3(4):1-17 (2018).
Wronski, "the new horizons of pharmacotherapy. Unexpected pharmacological actions and a new therapeutic strategy of phosphodiesterase-5 inhibitors," Cent. European J. Urol. 67:314-318 (2014).
Ye et al., "Increased CYP4B1 mRNA is associated with the inhibition of dextran sulfate sodium-induced colitis by caffeic acid in mice," Exp. Biol. Med. 234:605-616 (2009).
Zhang et al., "A concise synthesis of ortho-substituted arylacrylamides—potent activators of soluble guanylyl cyclase," Tetrahedron Letters 44(48):8661-8663 (2003).

* cited by examiner

DUAL MODE OF ACTION SOLUBLE GUANYLATE CYCLASE ACTIVATORS AND PHOSPHODIESTERASE INHIBITORS AND USES THEREOF

The present invention relates to pharmaceutically useful compounds, in particular to compounds which are activators of the enzyme soluble guanylate cyclase (sGC) and at the same time inhibit cyclic guanosine 3',5'-monophosphate phosphodiesterases (cGMP PDEs), in particular type 5 cyclic guanosine 3',5'-monophosphate phosphodiesterase (cGMP PDE5). The compounds of the present invention have utility in a variety of therapeutic areas, including male erectile dysfunction (MED), priapism, female sexual dysfunction, Alzheimer's disease and neuro degenerative diseases, pulmonary artery hypertension (PAH), chronic thromboembolic pulmonary hypertension (CTEPH), livedoid vasculopathy, thromboangitis obliterans, chronic anal fissure, skin fibrosis, skin aging, glaucoma, diabetic retinopathy, age dependent macular degeneration, Retinopathia pigmentosa, endothelial dysfunction (ED), benign prostatic hyperplasia (BPH) and lower urinary tract symptoms (LUTS), hair loss, cystic fibrosis, peripheral vascular disease, vascular disorders such as Raynaud's disease, systemic sclerosis (SSc), scleroderma, diabetes, wound healing, in particular chronic wound healing, diabetic foot, diabetic foot ulcer, leg ulcer, diabetic neuropathy and pressure ulcer, and particularly for pulmonary artery hypertension (PAH), chronic thromboembolic pulmonary hypertension, male erectile dysfunction, priapism, female sexual dysfunction, scleroderma, skin aging, glaucoma, diabetic retinopathy, age dependent macular degeneration, Retinopathia pigmentosa, wound healing, in particular chronic wound healing, diabetic foot, diabetic foot ulcer, leg ulcer, diabetic neuropathy, pressure ulcer and cancer such as cancer such as breast, gastrointestinal, lung, skin, prostate, pancreatic, colon and rectal cancers, in particular colorectal cancer.

RELATED ART

Phosphodiesterases (PDEs) are enzymes that catalyzes the hydrolysis and thus the degradation of cyclic adenosine monophosphate (cAMP) and cyclic guanosine monophosphate (cGMP) and thereby regulates intracellular levels of second messengers Inhibition of PDEs leads to increasing intracellular concentrations of endogenous cAMP/cGMP. Therefore, inhibition of PDE can mediate a variety of physiological mechanisms at different cell and organ levels.

Phosphodiesterase type 5 (PDE5) hydrolyses cyclic guanylate monophosphate (cGMP) specifically to 5' GMP. The selective inhibition of PDE5 has been validated as a relevant approach and strategies directed to promote inhibition of PDE5 activity have been applied and suggested as therapeutic tools, in particular, in neuronal and cardiovascular conditions and cancer. Moreover, the introduction of PDE5 inhibitors has revolutionized the treatment of male erectile dysfunction (MED) (Dobhal T, Kaur S, Prakash Sharma O, Hari Kumar S L, Critical Review in Pharmaceutical Sciences (2012) 1(3):13-27). Several PDE5 inhibitors are on the market and are characterized particularly for MED or pulmonary hypertension (PH), in particular pulmonary artery hypertension (PAH) (Papapetropoulos A, Hobbs A J, Topouzis S, British Journal of Pharmacology (2015) 172: 1397-1414; Monica F Z, Murad F, Bian K, OA Biochemistry (2014) Mar. 11; 2(1):3; Beedimani R S, Kalmath B, Int J Pharm Bio Sci (2014) 5(2): 530-539; Wronski S, Cent European J Urol (2014) 67: 314-318; Barone I et al. Oncotarget (2017) 8(58): 99179-99202; Vighi E et al. Oncotarget (2018) 9(4): 5301-5320; Huang W et al. Gastroenterology 2019; 157:672-681; and references cited therein). Most prominent examples of PDE5 inhibitors are Sildenafil, Tadalafil, Vardenafil and Mirodenafil which have been described among others, for example, in WO 99/24433, WO 01/60825, EP 995,751 and WO 2011/075655. Recently, a novel class of very potent PDE5 inhibitors has been described (WO 2017/085056 A1).

Beside the success of the known PDE5 inhibitors, there is still a need for further and more effective drugs and their pharmaceutical compositions for use in the therapeutic treatment or prophylaxis of diseases associated with a disturbed cGMP balance. Moreover, and in general, there is still a need for compounds and their pharmaceutical compositions being beneficial for use in the therapeutic treatment or prophylaxis of diseases associated with cGMP disbalance.

Endothelial dysfunction leads to an imbalance of vasodilator and vasoconstrictor mediators shifted towards the latter. One key mechanism remains impaired endothelial NO generation and associated, reduced activation of soluble guanylyl cyclase (sGC) in adjacent smooth muscle cells. Strategies to increase disturbed cGMP levels by enhancing cGMP in vascular smooth muscle by improving cGMP synthesis and inhibiting its degradation have been described. Examples are combinations of sGC stimulators or activators in combination with PDE5 inhibitors, for example WO 2010/081647 or US2002/0182162.

SUMMARY OF THE INVENTION

We have surprisingly found that dual-pharmacology compounds of the present invention designed as NO-releasing PDE5 inhibitors believed to release NO in addition to its PDE5 inhibition modulate cGMP levels in a more than additive, thus, synergistic fashion. We have further surprisingly found that the compounds of the present invention are highly bound to plasma proteins when they reach blood circulation. High protein binding results in very low free systemic exposure, therefore making the compounds described in the present invention especially prone to local application and local action. The synergistic increase of cGMP results in highly potent vasodilatation, angiogenesis, enhanced microcirculation and inhibition of endothelial dysfunction (see FIG. 1). Thus, the dual-pharmacology NO-releasing PDE5 inhibitors of the present invention are expected to be especially beneficial in treating disorders where NO production is diminished such as in conditions of endothelial dysfunction. Furthermore, the inventive dual-pharmacology NO-releasing PDE5 inhibitors are further believed to be highly beneficial for the treatment of diabetic patients.

Moreover, we have surprisingly found that the compounds of the present invention show even a significantly higher efficacy to elevate intracellular cGMP as compared to known PDE5 inhibitors such as sildenafil or vardenafil. In addition, we discovered a very high plasma protein binding with several compounds of the invention, making them especially prone to local applications and local actions. As a consequence, the novel pyrazolo pyrimidone and imidazo triazinone compounds of the present invention are useful in the therapy and prophylaxis of diseases which are associated with a disturbed cGMP balance.

Due to the potent and selective PDE5 inhibition in combination with stimulation of soluble guanylate cyclase exhibited by compounds of the present invention, cGMP levels are elevated, which in turn can give rise to beneficial vasodilatory, anti-vasospastic, anti-platelet, natriuretic and diuretic activities. Furthermore, the dual-pharmacology NO-releasing PDE5 inhibitors allows the release of nitric oxide for activating the soluble guanylate cyclase as well as the PDE5 inhibition in a more than additive fashion. Surprisingly the compounds of the present innovation increase intracellular cGMP levels even much more compared to equimolar effects of organic nitrate ester and PDE5 inhibitor combinations as depicted in FIG. 3A and FIG. 3B.

Thus, the compounds of the present invention have utility in variety of therapeutic areas where a disturbed cGMP balance occurred and/or PDE5 inhibition is thought to be beneficial. The compounds of the invention are especially suited for local drug application as depicted in FIG. 2. Some of the preferred therapeutic areas are glaucoma, diabetic retinopathy, age dependent macular degeneration, pulmonary artery hypertension (PAH), chronic thromboembolic pulmonary hypertension, male erectile dysfunction, priapism, female sexual dysfunction, wound healing, in particular chronic wound healing, diabetic foot, diabetic foot ulcer, leg ulcer, Raynaud's, male erectile dysfunction, Alzheimer's disease, livedoid vasculopathy, thromboangitis obliterans, chronic anal fissure, skin fibrosis, diabetes, hair loss, skin aging, vascular aging, pulmonary artery hypertension, chronic heart failure, cancer such as breast and gastrointestinal cancers, non-small cell lung cancer, skin cancers such as melanoma, head and neck cancer, myeloma and head and neck squamous cell carcinoma, colon and rectal cancers such as colorectal cancer, and prostate and pancreatic cancers, and in particular colorectal cancer.

Thus, in a first aspect, the present invention provides for a compound of formula I or formula II

I

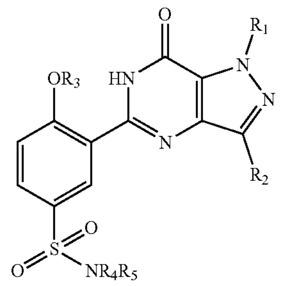

II

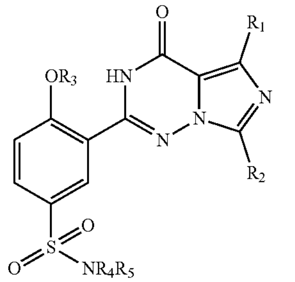

or pharmaceutically acceptable salt, solvate or hydrate thereof, wherein said compound of formula I and said compound of formula II each comprises at least one covalently bound $ONO_2$ or ONO moiety, and wherein preferably said compound of formula I and said compound of formula II each comprises at least one covalently bound $ONO_2$ or ONO moiety and at most four covalently bound $ONO_2$ or ONO moieties;

$R_1$ is $C_1$-$C_3$alkyl;

$R_2$ is H, $C_1$-$C_6$alkyl, $C_3$-$C_6$cycloalkyl, $C_1$-$C_2$alkoxy, $C_2$-$C_4$alkenyl;

$R_3$ is $C_1$-$C_4$alkyl optionally substituted with $C_1$-$C_2$alkoxy, $C_3$-$C_4$cycloalkyl, $C_2$-$C_4$alkenyl;

$R_4$ and $R_5$ are each independently H or $C_1$-$C_6$alkyl optionally substituted with F, OH, ONO, $ONO_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homo-piperazine, 2,5-diazabicyclo[2,2,1]heptane and 3,7-diazabicyclo[3,3,0]octane, wherein said heterocyclic ring is optionally substituted with independently one or more $R_6$, and wherein preferably said heterocyclic ring is optionally substituted with independently one, two, three or four $R_6$, wherein further preferably said heterocyclic ring is optionally substituted with independently one or two $R_6$;

$R_6$ is $C_1$-$C_6$alkyl optionally substituted with independently one or more halogen, OH, ONO, $ONO_2$, $C_1$-$C_3$alkoxy, $C_1$-$C_3$haloalkoxy, $COOR_7$, $NR_8R_9$, $C{=}NR_{10}$;

$R_7$ is H, or $C_1$-$C_4$alkyl optionally substituted with F, OH, ONO, $ONO_2$, $NR_8R_9$;

$R_8$ and $R_9$ are independently H, or $C_1$-$C_4$alkyl optionally substituted with ONO, $ONO_2$;

$R_{10}$ is $C_1$-$C_4$alkyl optionally substituted with F, ONO, $ONO_2$; $C_3$-$C_6$cycloalkyl;

wherein preferably said compound of formula I is not

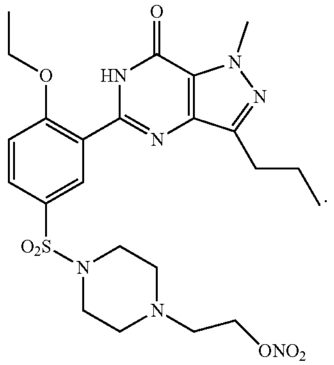

In a further aspect, the present invention provides for a pharmaceutical composition comprising at least one of the inventive compounds of formula I or formula II, or a pharmaceutically acceptable salt, solvate or hydrate thereof, and a pharmaceutically acceptable excipient, adjuvant, or carrier.

In another aspect, the present invention provides for a compound of formula I or formula II, or a pharmaceutical composition, or a pharmaceutically acceptable salt, solvate or hydrate thereof, for use as a medical treatment.

In another aspect, the present invention provides for a compound of formula I or formula II, or a pharmaceutical composition, or a pharmaceutically acceptable salt, solvate or hydrate thereof, for use in a method of treating or preventing a disease alleviated by inhibition of PDE5 in a human or in a non-human mammal, preferably in a human, wherein preferably said disease is selected from glaucoma, diabetic retinopathy, age dependent macular degeneration, wound healing, chronic wound healing, diabetic foot, diabetic foot ulcer, leg ulcer, Raynaud's disease, male erectile dysfunction, priapism, female sexual dysfunction, hair loss, skin aging, vascular aging, pulmonary artery hypertension; livedoid vasculopathy, thromboangitis obliterans, chronic anal fissure, skin fibrosis, stable, unstable and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, achalasia, sickle cell disease (SCD), diabetic nephropathy, inflammatory diseases, stroke, bronchitis, chronic asthma, allergic asthma, allergic rhinitis, diabetic neuropathy, Idiopathic pulmonary fibrosis (IPF), peyronic's disease, by disorders of gut motility like irritable bowel syndrome, liver fibrosis, Alzheimer's disease, chronic heart failure and cancer such as breast and gastrointestinal cancers, non-small cell lung cancer, skin cancers such as melanoma, head and neck cancer, myeloma and head and neck squamous cell carcinoma, colon and rectal cancers such as colorectal cancer, and prostate and pancreatic cancers, and in particular colorectal cancer.

In another aspect, the present invention provides for a compound of formula I or formula II, or a pharmaceutical composition, or a pharmaceutically acceptable salt, solvate or hydrate thereof, for use in a method of treating or preventing a disease in a human or in a non-human mammal, preferably in a human, wherein said disease is selected from glaucoma, diabetic retinopathy, age dependent macular degeneration, wound healing, chronic wound healing, diabetic foot, diabetic foot ulcer, leg ulcer, Raynaud's disease, male erectile dysfunction, priapism, female sexual dysfunction, hair loss, skin aging, vascular aging, pulmonary artery hypertension; livedoid vasculopathy, thromboangitis obliterans, chronic anal fissure, skin fibrosis, stable, unstable and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, achalasia, sickle cell disease (SCD), inflammatory diseases, stroke, bronchitis, chronic asthma, allergic asthma, allergic rhinitis, diabetic neuropathy, Idiopathic pulmonary fibrosis (IPF), peyronic's disease, by disorders of gut motility like irritable bowel syndrome, liver fibrosis, Alzheimer's disease and chronic heart failure, wherein preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer, and cancer such as breast and gastrointestinal cancers, non-small cell lung cancer, skin cancers such as melanoma, head and neck cancer, myeloma and head and neck squamous cell carcinoma, colon and rectal cancers such as colorectal cancer, and prostate and pancreatic cancers, and in particular colorectal cancer.

Further aspects and embodiments of the present invention will be become apparent as this description continues.

DETAILED DESCRIPTION OF THE INVENTION

Figure 1:
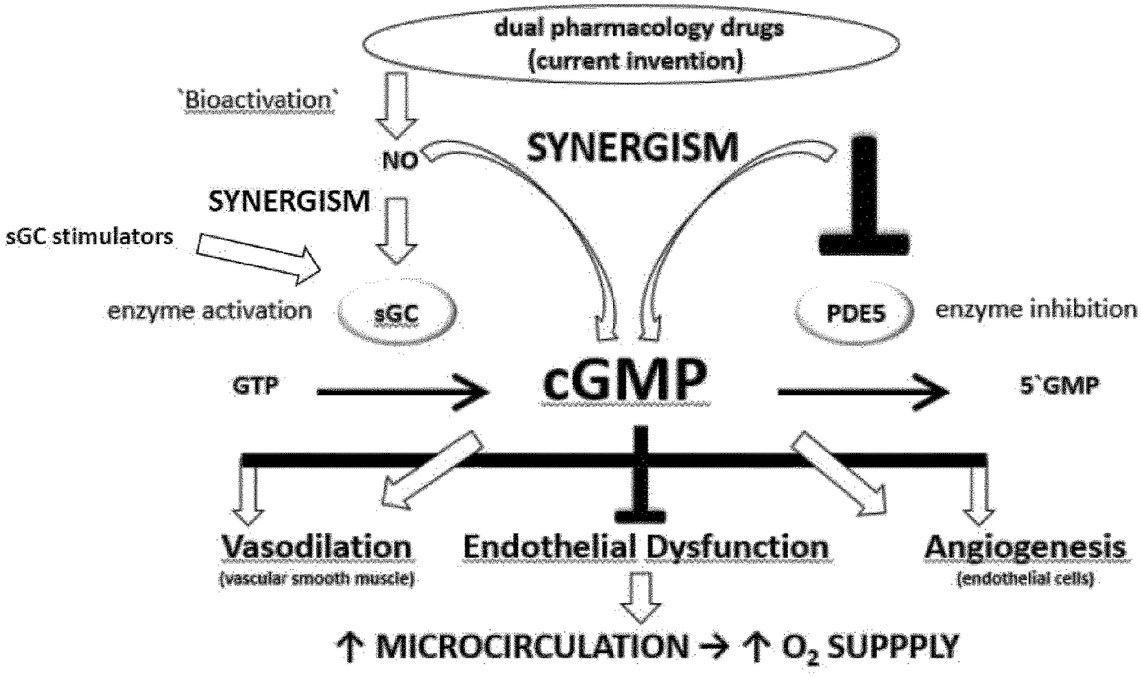
FIG. 1: PDE5 inhibition and activation of soluble guanylate cyclase from one molecule.

Unless defined otherwise, all technical and scientific terms used herein have the same meanings as commonly understood by one of ordinary skill in the art to which this invention belongs. The herein described and disclosed embodiments, preferred embodiments and very preferred embodiments should apply to all aspects and other embodiments, preferred embodiments and very preferred embodiments irrespective of whether is specifically again referred to or its repetition is avoided for the sake of conciseness.

The articles "a" and "an", as used herein, refer to one or to more than one (i.e., to at least one) of the grammatical object of the article. The term "or", as used herein, should be understood to mean "and/or", unless the context clearly indicates otherwise.

We have surprisingly found that the compounds of the present invention are dual-pharmacology NO-releasing PDE5 inhibitors believed to release NO in addition to its PDE5 inhibition resulting in a more than additive stimulation of intracellular cGMP elevation. Moreover, the compounds of the present invention show even a significantly higher efficacy to stimulate cGMP as compared to known single pharmacology PDE5 inhibitors such as sildenafil or vardenafil. Furthermore, the compounds of the present invention are highly bound to plasma proteins when they reach blood circulation making them especially prone to local application and local action.

Thus, in a first aspect, the present invention provides for a compound of formula I or formula II

I

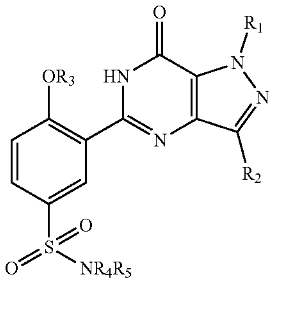

-continued

II

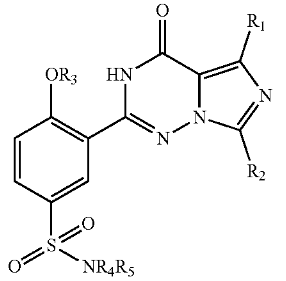

or pharmaceutically acceptable salt, solvate or hydrate thereof, wherein said compound of formula I and said compound of formula II each comprises at least one covalently bound $ONO_2$ or ONO moiety, and wherein preferably said compound of formula I and said compound of formula II each comprises at least one $ONO_2$ or ONO moiety and at most four $ONO_2$ or ONO moieties;

$R_1$ is $C_1$-$C_3$alkyl;

$R_2$ is H, $C_1$-$C_6$alkyl, $C_3$-$C_6$cycloalkyl, $C_1$-$C_2$alkoxy, $C_2$-$C_4$alkenyl;

$R_3$ is $C_1$-$C_4$alkyl optionally substituted with $C_1$-$C_2$alkoxy, $C_3$-$C_4$cycloalkyl, $C_2$-$C_4$alkenyl;

$R_4$ and $R_5$ are each independently H or $C_1$-$C_6$alkyl optionally substituted with F, OH, ONO, $ONO_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homo-piperazine, 2,5-diazabicyclo[2,2,1]heptane and 3,7-diazabicyclo[3,3,0]octane, wherein said heterocyclic ring is optionally substituted with independently one or more $R_6$, and wherein preferably said heterocyclic ring is optionally substituted with independently one, two, three or four $R_6$, wherein further preferably said heterocyclic ring is optionally substituted with independently one or two $R_6$;

$R_6$ is $C_1$-$C_6$alkyl optionally substituted with independently one or more halogen, OH, ONO, $ONO_2$, $C_1$-$C_3$alkoxy, $C_1$-$C_3$haloalkoxy, $COOR_7$, $NR_8R_9$, $C{=}NR_{10}$;

$R_7$ is H, or $C_1$-$C_4$alkyl optionally substituted with F, OH, ONO, $ONO_2$, $NR_8R_9$;

$R_8$ and $R_9$ are independently H, or $C_1$-$C_4$alkyl optionally substituted with ONO, $ONO_2$;

$R_{10}$ is $C_1$-$C_4$alkyl optionally substituted with F, ONO, $ONO_2$; $C_3$-$C_6$cycloalkyl;

wherein said compound of formula I is not

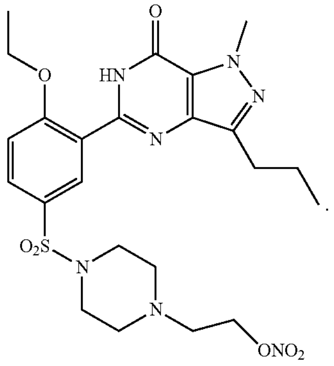

In another aspect, the present invention provides for a compound of formula I or formula II

I

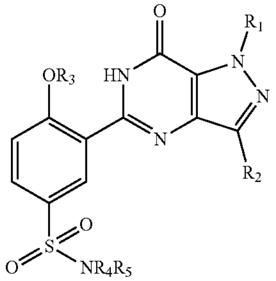

II

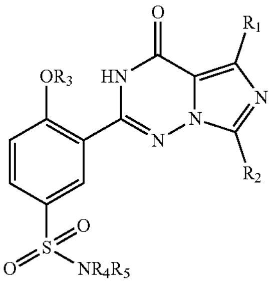

or pharmaceutically acceptable salt, solvate or hydrate thereof, wherein said compound of formula I and said compound of formula II each comprises at least one $ONO_2$ or ONO moiety, and wherein preferably said compound of formula I and said compound of formula II each comprises at least one $ONO_2$ or ONO moiety and at most four $ONO_2$ or ONO moieties;

$R_1$ is $C_1$-$C_3$alkyl;

$R_2$ is H, $C_1$-$C_6$alkyl, $C_3$-$C_6$cycloalkyl, $C_1$-$C_2$alkoxy, $C_2$-$C_4$alkenyl;

$R_3$ is $C_1$-$C_4$alkyl optionally substituted with $C_1$-$C_2$alkoxy, $C_3$-$C_4$cycloalkyl, $C_2$-$C_4$alkenyl;

$R_4$ and $R_5$ are each independently H or $C_1$-$C_6$alkyl optionally substituted with F, OH, ONO, $ONO_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homo-piperazine, 2,5-diazabicyclo[2,2,1]heptane and 3,7-diazabicyclo[3,3,0]octane, wherein said heterocyclic ring is optionally substituted with independently one or more $R_6$, and wherein preferably said heterocyclic ring is optionally substituted with independently one, two, three or four $R_6$, wherein further preferably said heterocyclic ring is optionally substituted with independently one or two $R_6$;

$R_6$ is $C_1$-$C_6$alkyl optionally substituted with independently one or more halogen, OH, ONO, $ONO_2$, $C_1$-$C_3$alkoxy, $C_1$-$C_3$haloalkoxy, $COOR_7$, $NR_8R_9$, $C{=}NR_{10}$;

$R_7$ is H, or $C_1$-$C_4$alkyl optionally substituted with F, OH, ONO, $ONO_2$, $NR_8R_9$;

$R_8$ and $R_9$ are independently H, or $C_1$-$C_4$alkyl optionally substituted with ONO, $ONO_2$;

$R_{10}$ is $C_1$-$C_4$alkyl optionally substituted with F, ONO, $ONO_2$; $C_3$-$C_6$cycloalkyl.

Typically and preferably said compound of formula I is not

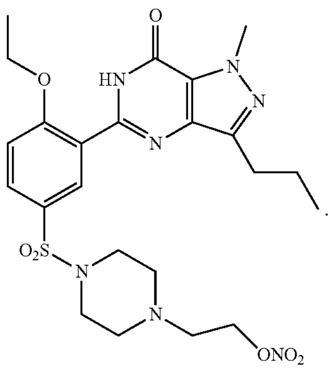

Thus, in a further aspect, the present invention provides for a compound of formula I or II,

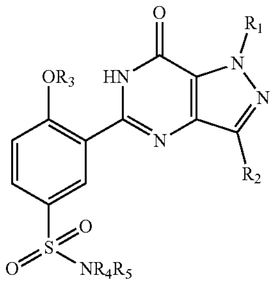

I

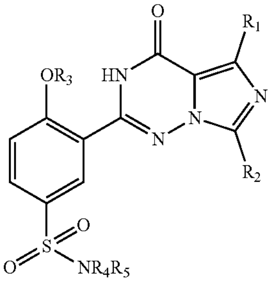

II or pharmaceutically acceptable salt, solvate or hydrate thereof, wherein at least one of $R_4$ and $R_5$ independently of each other comprises at least one, typically and preferably covalently bound, $ONO_2$ or ONO moiety, and wherein preferably at least one of $R_4$ and $R_5$ independently of each other comprises at least one, typically and preferably covalently bound, $ONO_2$ or ONO moiety and at most four, typically and preferably covalently bound, $ONO_2$ or ONO moieties;

$R_1$ is $C_1$-$C_3$alkyl;

$R_2$ is H, $C_1$-$C_6$alkyl, $C_3$-$C_6$cycloalkyl, $C_1$-$C_2$alkoxy, $C_2$-$C_4$alkenyl;

$R_3$ is $C_1$-$C_4$alkyl optionally substituted with $C_1$-$C_2$alkoxy, $C_3$-$C_4$cycloalkyl, $C_2$-$C_4$alkenyl;

$R_4$ and $R_5$ are each independently H or $C_1$-$C_6$alkyl optionally substituted with F, OH, ONO, $ONO_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homo-piperazine, 2,5-diazabicyclo[2,2,1]heptane and 3,7-diazabicyclo[3,3,0]octane, wherein said heterocyclic ring is optionally substituted with independently one or more $R_6$, and wherein preferably said heterocyclic ring is optionally substituted with independently one, two, three or four $R_6$, wherein further preferably said heterocyclic ring is optionally substituted with independently one or two $R_6$;

$R_6$ is $C_1$-$C_6$alkyl optionally substituted with independently one or more halogen, OH, ONO, $ONO_2$, $C_1$-$C_3$alkoxy, $C_1$-$C_3$haloalkoxy, $COOR_7$, $NR_8R_9$, $C{=}NR_{10}$, wherein preferably $R_6$ comprises at least one, typically and preferably covalently bound, $ONO_2$ or ONO moiety and, further preferably, at most four, typically and preferably covalently bound, $ONO_2$ or ONO moieties;

$R_7$ is H, or $C_1$-$C_4$alkyl optionally substituted with F, OH, ONO, $ONO_2$, $NR_8R_9$;

$R_8$ and $R_9$ are independently H, or $C_1$-$C_4$alkyl optionally substituted with ONO, $ONO_2$;

$R_{10}$ is $C_1$-$C_4$alkyl optionally substituted with F, ONO, $ONO_2$; $C_3$-$C_6$cycloalkyl;

wherein said compound of formula I is not

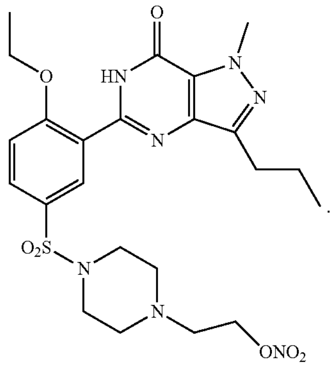

In a further aspect, the present invention provides for a compound of formula I or II

I

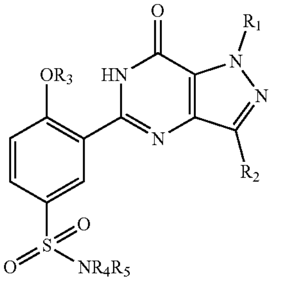

II

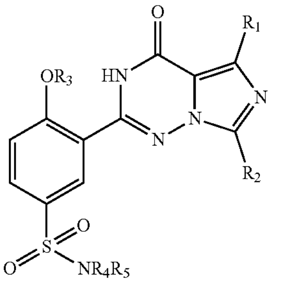

wherein said compound of formula I and said compound of formula II each comprises at least one, typically and preferably covalently bound, $ONO_2$ or ONO moiety, and wherein preferably said compound of formula I and said compound of formula II each comprises at least one, typically and preferably covalently bound, $ONO_2$ or ONO moiety and at most four, typically and preferably covalently bound, $ONO_2$ or ONO moieties;

$R_1$ is $C_1$-$C_3$alkyl;

$R_2$ is H, $C_1$-$C_6$alkyl, $C_3$-$C_6$cycloalkyl, $C_1$-$C_2$alkoxy, $C_2$-$C_4$alkenyl;

$R_3$ is $C_1$-$C_4$alkyl optionally substituted with $C_1$-$C_2$alkoxy, $C_3$-$C_4$cycloalkyl, $C_2$-$C_4$alkenyl;

$R_4$ and $R_5$ are each independently H or $C_1$-$C_6$alkyl optionally substituted with F, OH, ONO, $ONO_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homo-piperazine, 2,5-diazabicyclo[2,2,1]heptane and 3,7-diazabicyclo[3,3,0]octane, wherein said heterocyclic ring is optionally substituted with independently one or more $R_6$, and wherein preferably said heterocyclic ring is optionally substituted with independently one, two, three or four $R_6$, wherein further preferably said heterocyclic ring is optionally substituted with independently one or two $R_6$;

$R_6$ is $C_1$-$C_6$alkyl optionally substituted with independently one or more halogen, OH, ONO, $ONO_2$, $C_1$-$C_3$alkoxy, $C_1$-$C_3$haloalkoxy, $COOR_7$, $NR_8R_9$, $C{=}NR_{10}$, wherein preferably $R_6$ comprises at least one $ONO_2$ or ONO moiety and, further preferably, at most four $ONO_2$ or ONO moieties.

$R_7$ is H, or $C_1$-$C_4$alkyl optionally substituted with F, OH, ONO, $ONO_2$, $NR_8R_9$;

$R_8$ and $R_9$ are independently H, or $C_1$-$C_4$alkyl optionally substituted with ONO, $ONO_2$;

$R_{10}$ is $C_1$-$C_4$alkyl optionally substituted with F, ONO, $ONO_2$; $C_3$-$C_6$cycloalkyl;

wherein said compound of formula I is not

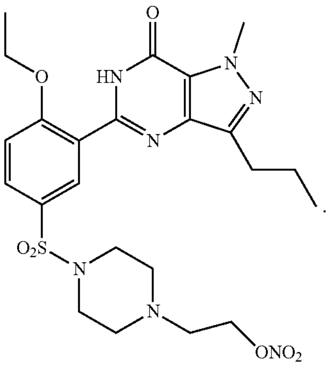

In a further aspect, the present invention provides for a compound of formula I or pharmaceutically acceptable salt, solvate or hydrate thereof, wherein

I

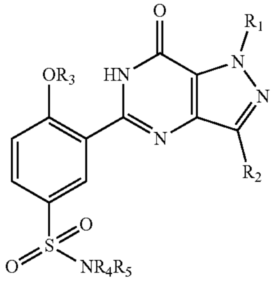

said compound of formula I comprises at least one covalently bound $ONO_2$ or ONO moiety, and wherein preferably said compound of formula I comprises at least one covalently bound $ONO_2$ or ONO moiety and at most four covalently bound $ONO_2$ or ONO moieties;

$R_1$ is $C_1$-$C_3$alkyl;

$R_2$ is H, $C_1$-$C_6$alkyl, $C_3$-$C_6$cycloalkyl, $C_1$-$C_2$alkoxy, $C_2$-$C_4$alkenyl;

$R_3$ is $C_1$-$C_4$alkyl optionally substituted with $C_1$-$C_2$alkoxy, $C_3$-$C_4$cycloalkyl, $C_2$-$C_4$alkenyl;

$R_4$ and $R_5$ are each independently H or $C_1$-$C_6$alkyl optionally substituted with F, OH, ONO, $ONO_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homo-piperazine, 2,5-diazabicyclo[2,2,1]heptane and 3,7-diazabicyclo[3,3,0]octane, wherein said heterocyclic ring is optionally substituted with independently one or more $R_6$, and wherein preferably said heterocyclic ring is optionally substituted with independently one, two, three or four $R_6$, wherein further preferably said heterocyclic ring is optionally substituted with independently one or two $R_6$;

$R_6$ is $C_1$-$C_6$alkyl optionally substituted with independently one or more halogen, OH, ONO, $ONO_2$, $C_1$-$C_3$alkoxy, $C_1$-$C_3$haloalkoxy, $COOR_7$, $NR_8R_9$, $C{=}NR_{10}$, wherein preferably $R_6$ comprises at least one $ONO_2$ or ONO moiety and, further preferably, at most four $ONO_2$ or ONO moieties.

$R_7$ is H, or $C_1$-$C_4$alkyl optionally substituted with F, OH, ONO, $ONO_2$, $NR_8R_9$;

$R_8$ and $R_9$ are independently H, or $C_1$-$C_4$alkyl optionally substituted with ONO, $ONO_2$;

$R_{10}$ is $C_1$-$C_4$alkyl optionally substituted with F, ONO, $ONO_2$; $C_3$-$C_6$cycloalkyl;

wherein said compound of formula I is not

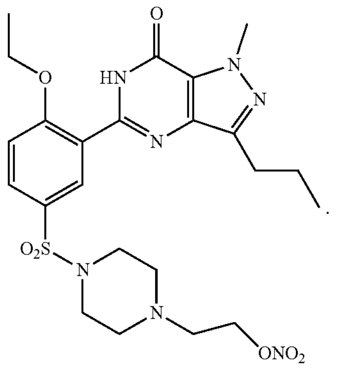

In a further aspect, the present invention provides for a compound of formula I or pharmaceutically acceptable salt, solvate or hydrate thereof, wherein

I

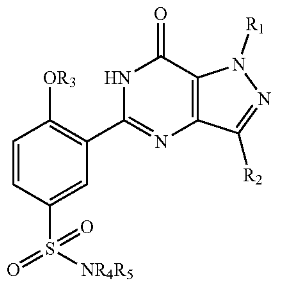

said compound of formula I comprises at least one $ONO_2$ or ONO moiety, and wherein preferably said compound of formula I comprises at least one $ONO_2$ or ONO moiety and at most four $ONO_2$ or ONO moieties;

$R_1$ is $C_1$-$C_3$alkyl;

$R_2$ is H, $C_1$-$C_6$alkyl, $C_3$-$C_6$cycloalkyl, $C_1$-$C_2$alkoxy, $C_2$-$C_4$alkenyl;

$R_3$ is $C_1$-$C_4$alkyl optionally substituted with $C_1$-$C_2$alkoxy, $C_3$-$C_4$cycloalkyl, $C_2$-$C_4$alkenyl;

$R_4$ and $R_5$ are each independently H or $C_1$-$C_6$alkyl optionally substituted with F, OH, ONO, $ONO_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homo-piperazine, 2,5-diazabicyclo[2,2,1]heptane and 3,7-diazabicyclo[3,3,0]octane, wherein said heterocyclic ring is optionally substituted with independently one or more $R_6$, and wherein preferably said heterocyclic ring is optionally substituted with independently one, two, three or four $R_6$, wherein further preferably said heterocyclic ring is optionally substituted with independently one or two $R_6$;

$R_6$ is $C_1$-$C_6$alkyl optionally substituted with independently one or more halogen, OH, ONO, $ONO_2$, $C_1$-$C_3$alkoxy, $C_1$-$C_3$haloalkoxy, $COOR_7$, $NR_8R_9$, $C{=}NR_{10}$, wherein preferably $R_6$ comprises at least one $ONO_2$ or ONO moiety and, further preferably, at most four $ONO_2$ or ONO moieties.

$R_7$ is H, or $C_1$-$C_4$alkyl optionally substituted with F, OH, ONO, $ONO_2$, $NR_8R_9$;

$R_8$ and $R_9$ are independently H, or $C_1$-$C_4$alkyl optionally substituted with ONO, $ONO_2$;

$R_{10}$ is $C_1$-$C_4$alkyl optionally substituted with F, ONO, $ONO_2$; $C_3$-$C_6$cycloalkyl.

Typically and preferably said compound of formula I is not

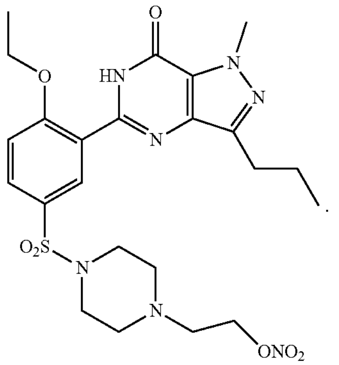

In a preferred embodiment of the present invention, said compound of formula II comprises at least at least one $ONO_2$ or ONO moiety and at most four $ONO_2$ or ONO moieties. In a preferred embodiment of the present invention, said compound of formula II comprises at least at least two $ONO_2$ or ONO moiety and at most four $ONO_2$ or ONO moieties. In a preferred embodiment of the present invention, said compound of formula II comprises at least at least one $ONO_2$ or ONO moiety and at most four $ONO_2$ and ONO moieties. In a preferred embodiment of the present invention, said compound of formula II comprises at least at least two $ONO_2$ or ONO moiety and at most four $ONO_2$ and ONO moieties. In another preferred embodiment of the present invention, said compound of formula II comprises at most four $ONO_2$ or ONO moieties. In another preferred embodiment of the present invention, said compound of formula II comprises at most four $ONO_2$ and ONO moieties.

In a preferred embodiment of the present invention, said compound of formula I comprises at least at least one covalently bound $ONO_2$ or ONO moiety and at most four covalently bound $ONO_2$ or ONO moieties. In a preferred embodiment of the present invention, said compound of formula I comprises at least at least two covalently bound $ONO_2$ or ONO moiety and at most four covalently bound $ONO_2$ or ONO moieties. In a preferred embodiment of the present invention, said compound of formula I comprises at least at least one covalently bound $ONO_2$ or ONO moiety and at most four covalently bound $ONO_2$ and ONO moieties. In a preferred embodiment of the present invention, said compound of formula I comprises at least at least two covalently bound $ONO_2$ or ONO moiety and at most four covalently bound $ONO_2$ and ONO moieties. In another preferred embodiment of the present invention, said compound of formula I comprises at most four covalently bound $ONO_2$ or ONO moieties. In another preferred embodiment of the present invention, said compound of formula I comprises at most four covalently bound $ONO_2$ and ONO moieties.

In a further aspect, the present invention provides for a compound of formula II or pharmaceutically acceptable salt, solvate or hydrate thereof, wherein

II

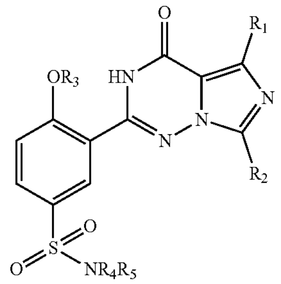

said compound of formula II comprises at least one covalently bound $ONO_2$ or ONO moiety, and wherein preferably said compound of formula II comprises at least one covalently bound $ONO_2$ or ONO moiety and at most four covalently bound $ONO_2$ or ONO moieties;

$R_1$ is $C_1$-$C_3$alkyl;

$R_2$ is H, $C_1$-$C_6$alkyl, $C_3$-$C_6$cycloalkyl, $C_1$-$C_2$alkoxy, $C_2$-$C_4$alkenyl;

$R_3$ is $C_1$-$C_4$alkyl optionally substituted with $C_1$-$C_2$alkoxy, $C_3$-$C_4$cycloalkyl, $C_2$-$C_4$alkenyl;

$R_4$ and $R_5$ are each independently H or $C_1$-$C_6$alkyl optionally substituted with F, OH, ONO, $ONO_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homo-piperazine, 2,5-diazabicyclo[2,2,1]heptane and 3,7-diazabicyclo[3,3,0]octane, wherein said heterocyclic ring is optionally substituted with independently one or more $R_6$, and wherein preferably said heterocyclic ring is optionally substituted with independently one, two, three or four $R_6$, wherein further preferably said heterocyclic ring is optionally substituted with independently one or two $R_6$;

$R_6$ is $C_1$-$C_6$alkyl optionally substituted with independently one or more halogen, OH, ONO, $ONO_2$, $C_1$-$C_3$alkoxy, $C_1$-$C_3$haloalkoxy, $COOR_7$, $NR_8R_9$, $C{=}NR_{10}$, wherein preferably $R_6$ comprises at least one $ONO_2$ or ONO moiety and, further preferably, at most four $ONO_2$ or ONO moieties.

$R_7$ is H, or $C_1$-$C_4$alkyl optionally substituted with F, OH, ONO, $ONO_2$, $NR_8R_9$;

$R_8$ and $R_9$ are independently H, or $C_1$-$C_4$alkyl optionally substituted with ONO, $ONO_2$;

$R_{10}$ is $C_1$-$C_4$alkyl optionally substituted with F, ONO, $ONO_2$; $C_3$-$C_6$cycloalkyl;

wherein said compound of formula I is not

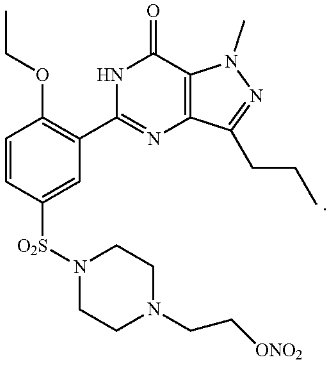

In a further aspect, the present invention provides for a compound of formula II or pharmaceutically acceptable salt, solvate or hydrate thereof, wherein

II

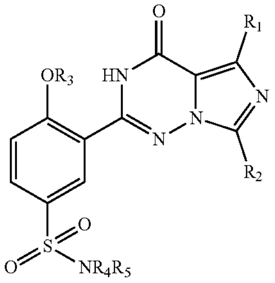

said compound of formula II comprises at least one $ONO_2$ or ONO moiety, and wherein preferably said compound of formula II comprises at least one $ONO_2$ or ONO moiety and at most four $ONO_2$ or ONO moieties;

$R_1$ is $C_1$-$C_3$alkyl;

$R_2$ is H, $C_1$-$C_6$alkyl, $C_3$-$C_6$cycloalkyl, $C_1$-$C_2$alkoxy, $C_2$-$C_4$alkenyl;

$R_3$ is $C_1$-$C_4$alkyl optionally substituted with $C_1$-$C_2$alkoxy, $C_3$-$C_4$cycloalkyl, $C_2$-$C_4$alkenyl;

$R_4$ and $R_5$ are each independently H or $C_1$-$C_6$alkyl optionally substituted with F, OH, ONO, $ONO_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homo-piperazine, 2,5-diazabicyclo[2,2,1]heptane and 3,7-diazabicyclo[3,3,0]octane, wherein said heterocyclic ring is optionally substituted with independently one or more $R_6$, and wherein preferably said heterocyclic ring is optionally substituted with independently one, two, three or four $R_6$, wherein further preferably said heterocyclic ring is optionally substituted with independently one or two $R_6$;

$R_6$ is $C_1$-$C_6$alkyl optionally substituted with independently one or more halogen, OH, ONO, $ONO_2$, $C_1$-$C_3$alkoxy, $C_1$-$C_3$haloalkoxy, $COOR_7$, $NR_8R_9$, $C{=}NR_{10}$, wherein preferably $R_6$ comprises at least one $ONO_2$ or ONO moiety and, further preferably, at most four $ONO_2$ or ONO moieties.

$R_7$ is H, or $C_1$-$C_4$alkyl optionally substituted with F, OH, ONO, $ONO_2$, $NR_8R_9$;

$R_8$ and $R_9$ are independently H, or $C_1$-$C_4$alkyl optionally substituted with ONO, $ONO_2$;

$R_{10}$ is $C_1$-$C_4$alkyl optionally substituted with F, ONO, $ONO_2$; $C_3$-$C_6$cycloalkyl.

Typically and preferably said compound of formula I is not

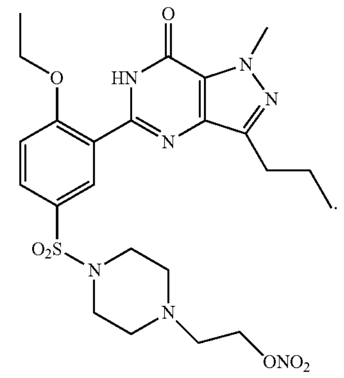

In a preferred embodiment of the present invention, said compound of formula II comprises at least at least one $ONO_2$ or ONO moiety and at most four $ONO_2$ or ONO moieties. In a preferred embodiment of the present invention, said compound of formula II comprises at least at least two $ONO_2$ or ONO moiety and at most four $ONO_2$ or ONO moieties. In a preferred embodiment of the present invention, said compound of formula II comprises at least at least one $ONO_2$ or ONO moiety and at most four $ONO_2$ and ONO moieties. In a preferred embodiment of the present invention, said compound of formula II comprises at least at least two $ONO_2$ or ONO moiety and at most four $ONO_2$ and ONO moieties. In another preferred embodiment of the present invention, said compound of formula II comprises at most four $ONO_2$ or ONO moieties. In another preferred embodiment of the present invention, said compound of formula II comprises at most four $ONO_2$ and ONO moieties.

In a preferred embodiment of the present invention, said compound of formula II comprises at least at least one covalently bound $ONO_2$ or ONO moiety and at most four covalently bound $ONO_2$ or ONO moieties. In a preferred embodiment of the present invention, said compound of formula II comprises at least at least two covalently bound $ONO_2$ or ONO moiety and at most four covalently bound $ONO_2$ or ONO moieties. In a preferred embodiment of the present invention, said compound of formula II comprises at least at least one covalently bound $ONO_2$ or ONO moiety and at most four covalently bound $ONO_2$ and ONO moieties. In a preferred embodiment of the present invention, said compound of formula II comprises at least at least two covalently bound $ONO_2$ or ONO moiety and at most four covalently bound $ONO_2$ and ONO moieties. In another preferred embodiment of the present invention, said compound of formula II comprises at most four covalently bound $ONO_2$ or ONO moieties. In another preferred embodiment of the present invention, said compound of formula II comprises at most four covalently bound $ONO_2$ and ONO moieties.

The term "alkyl", as used herein, refers to a straight or branched hydrocarbon chain radical consisting solely of carbon and hydrogen atoms, containing no unsaturation, having typically and preferably from one to six carbon atoms (e.g., ($C_{1-6}$alkyl), and which typically is attached to the rest of the molecule by a single bond. Whenever it appears herein, a numerical range such as "1 to 6" refers to each integer in the given range. For example, "1 to 6 carbon atoms" means that the alkyl group may consist of 1 carbon atom, 2 carbon atoms, 3 carbon atoms, etc., up to and including 6 carbon atoms, although the definition is also intended to cover the occurrence of the term "alkyl" where no numerical range is specifically designated. Typical alkyl groups include, but are not limited to methyl, ethyl, n-propyl, prop-2-yl, n-butyl, but-2-yl, 2-methyl-prop-1-yl or 2-methyl-prop-2-yl.

The term "alkoxy", as used herein, refers to a "substituted hydroxyl" of the formula (—OR'), wherein R' is an "alkyl", as defined herein, and the oxygen moiety is directly attached to the parent molecule, and thus the term "$C_1$-$C_6$-alkoxy", as used herein, refers to straight chain or branched $C_1$-$C_6$-alkoxy which may be, for example, methoxy, ethoxy, propoxy, iso-propoxy, n-butoxy, sec-butoxy, tert-butoxy, n-pentoxy, neo-pentoxy, n-hexoxy. As described herein, alkoxy may include further substitutents such as halogen atoms leading to haloalkoxy moieties.

The term "alkylene", as used herein, refers to a straight or branched hydrocarbon chain bi-radical derived from alkyl, as defined herein, wherein one hydrogen of said alkyl is cleaved off generating the second radical of said alkylene. Examples of alkylene are, by way of illustration, $—CH_2—$, $—CH_2—CH_2—$, $—CH(CH_3)—$, $—CH_2—CH_2—CH_2—$, $—CH(CH_3)—CH_2—$, or $—CH(CH_2CH_3)—$.

Each cycloalkyl moiety can be in mono- or bi-cyclic form, typically and preferably in mono-cyclic form, and preferably contains 3 to 8 carbon atoms, more preferably 3 to 7 carbon atoms. Examples of monocyclic cycloalkyl moieties include cyclopropyl, cyclobutyl and cyclohexyl.

Each alkenyl moiety either alone or as part of a larger moiety such as alkenyloxy or alkenylene is a straight or branched chain and is preferably $C_2$-$C_6$alkenyl, more preferably $C_2$-$C_4$alkenyl. Each moiety can be of either the (E)- or (Z)-configuration. Examples include vinyl and allyl. A compound of the present invention comprising an alkenyl moiety thus may include, if applicable, either said compound with said alkenyl moiety in its (E)-configuration, said compound with said alkenyl moiety in its (7)-configuration and mixtures thereof in any ratio.

The term "ONO2" refers to the nitrate moiety *—O—$NO_2$ as described herein, wherein the * indicates the attachment to the parent structure and rest of the molecule. Preferably, said ONO2 is a terminal ONO substituent.

The term "ONO" refers to the nitrite moiety *—O—NO as described herein, wherein the * indicates the attachment to the parent structure and rest of the molecule. Preferably, said ONO2 is a terminal ONO2 substituent.

The term "cycloalkoxy" refers, to the group —O-cycloalkyl, wherein a "cycloalkyl", as defined herein, is linked to the oxygen which is directly attached to the parent molecule. Examples include, but are not limited to cyclopropyloxy and cyclohexyloxy. As described herein, cycloalkoxy may include further substitutents such as halogen atoms.

Halogen is fluorine, chlorine, bromine, or iodine.

Each haloalkyl moiety either alone or as part of a larger moiety such as haloalkoxy is an alkyl moiety substituted by one or more of the same or different halogen atoms. Examples include difluoromethyl, trifluoromethyl, chlorodifluoromethyl and 2,2,2-trifluoro-ethyl.

The term "heterocyclic ring" refers to a saturated or partially unsaturated carbocyclic ring containing one to four heteroatoms selected from nitrogen, oxygen and sulfur as ring members. Such rings do not contain adjacent oxygen atoms, adjacent sulfur atoms, or adjacent oxygen and sulfur atoms within the ring. Preferred examples are aziridine, azetidine, pyrollidine, piperidine, morpholine, piperazine, homopiperazine, tetrahydrofurane, dioxane, 2,5-diazabicyclo[2,2,1]heptane and 3,7-diazabicyclo[3,3,0]octane, and further preferred are aziridine, azetidine, pyrollidine, piperidine, morpholine, piperazine, homopiperazine, 2,5-diazabicyclo[2,2,1]heptane and 3,7-diazabicyclo[3,3,0]octane.

Where a moiety is said to be substituted or optionally substituted, preferably there are 1-5 substituents or optionally 1-5 substituents, more preferably 1-4 substituents or optionally 1-4 substituents, more preferably 1-3 substituents or optionally 1-3 substituents, again more preferably 1 or 2 substituents or optionally 1 or 2 substituents, unless it is specifically indicated a different preferred number of substitutions or optional substitutions. Where a moiety is said to be substituted or optionally substituted, and where there are more than one substituent for said substitution or said optional substitution of said moiety, said more than one substituents can either be the same or different.

Certain compounds of formula I or II of the present invention may contain one or two or more centers of chirality and such compounds may be provided as pure enantiomers or pure diastereoisomers as well as mixtures thereof in any ratio. The compounds of the invention also include all tautomeric forms of the compounds of formula I or II. The compounds of formula I or II may also be solvated, especially hydrated, which are also included in the compounds of formula I or II. Solvation and hydration may take place during the preparation process.

As a consequence, the compounds of the present invention and, thus, the compounds of formula I or II include stereoisomers, geometric isomers and tautomers. Furthermore, the compounds of the present invention and, thus, the compounds of formula I or II include solvates or hydrates, pharmaceutically acceptable salts, and solvates or hydrates of the salts thereof.

Compounds of formula I or II of the present invention include pharmaceutically acceptable salts of said compounds. In particular, the term "pharmaceutically acceptable salt" as used herein, refers to pharmaceutically acceptable organic or inorganic salts of a compound of the present invention, in particular acid addition salts. Exemplary salts include, but are not limited to, salts of physiologically acceptable mineral acids, such as hydrochloric acid, sulfuric acid, nitric acid and phosphoric acid, or salts of organic acids, such as methane-sulfonic acid, p-toluenesulfonic acid, lactic acid, malic acid, tartaric acid, acetic acid, trifluoroacetic acid, citric acid, succinic acid, fumaric acid, maleic acid and salicylic acid. Further examples of pharmacologically acceptable salts of the compounds of formula I or II are alkali metal and alkaline earth metal salts such as, for example, sodium, potassium, lithium, calcium or magnesium salts, ammonium salts or salts of organic bases such as, for example, methylamine, dimethylamine, triethylamine, piperidine, ethylenediamine, lysine, choline hydroxide, meglumine, morpholine or arginine salts. Further examples of pharmaceutically acceptable salts of the compounds of formula I or II include the hydrochloride, hydrobromide, sulfate, bisulfate, phosphate, hydrogen phosphate, nitrate, acetate, benzoate, succinate, fumarate, maleate, lactate, citrate, benzenesulphonate, p-toluenesulphonate or the like.

A "solvate" refers to an association or complex of one or more solvent molecules and a compound of the present invention. Examples of solvents that form solvates include, but are not limited to, water, isopropanol, ethanol, methanol, dimethyl sulfoxide (DMSO), ethyl acetate, acetic acid, and ethanolamine. The term "hydrate" refers to the complex where the solvent molecule is water.

Typically and preferably, if referred herein to compounds of formula I, I* or formula II, II* as comprising at least one $ONO_2$ or ONO moiety it is meant that said compounds of formula I, I* or formula II, II* comprise said at least one $ONO_2$ or ONO moiety as at least one covalent bound $ONO_2$ or ONO moiety. Thus, in a preferred embodiment, said compound of formula I or formula II each comprises at least one $ONO_2$ or ONO moiety and at most four $ONO_2$ or ONO moieties. In a preferred embodiment, said compound of formula I or formula II each comprises at least two $ONO_2$ or ONO moieties and at most four $ONO_2$ or ONO moieties. In a preferred embodiment, said compound of formula I or formula II each comprises at least one $ONO_2$ or ONO moiety and at most four $ONO_2$ and ONO moieties. In a preferred embodiment, said compound of formula I or formula II each comprises at least two $ONO_2$ or ONO moieties and at most four $ONO_2$ and ONO moieties. In another preferred embodiment, said compound of formula I or formula II each comprises at most four $ONO_2$ or ONO moieties. In another preferred embodiment, said compound of formula I or formula II each comprises at most four $ONO_2$ and ONO moieties. In another preferred embodiment, said compound of formula I or formula II each comprises at least one $ONO_2$ moiety and at most four $ONO_2$ moieties. In a preferred embodiment, said compound of formula I or formula II each comprises at least two $ONO_2$ moieties and at most four $ONO_2$ moieties. In a preferred embodiment, said compound of formula I or formula II each comprises at least one $ONO_2$ moiety and at most four $ONO_2$ moieties. In a preferred embodiment, said compound of formula I or formula II each comprises at least two $ONO_2$ moieties and at most four $ONO_2$ moieties. In another preferred embodiment, said compound of formula I or formula II each comprises at most four $ONO_2$ moieties. In another preferred embodiment, said compound of formula I or formula II each comprises at most four $ONO_2$ moieties.

In a preferred embodiment of the present invention, said compound of formula I or formula II each comprises exactly one $ONO_2$ moiety. In another preferred embodiment, said compound of formula I or formula II each comprises exactly one ONO moiety. In a preferred embodiment, said compound of formula I or formula II each comprises at least two moieties selected from $ONO_2$ or ONO moieties. In another preferred embodiment, said compound of formula I or formula II each comprises exactly two $ONO_2$ or two ONO moieties. In another preferred embodiment, said compound of formula I or formula II each comprises exactly two $ONO_2$ moieties. In another preferred embodiment, said compound of formula I or formula II each comprises exactly two ONO moieties. In another preferred embodiment, said compound of formula I or formula II each comprises exactly one $ONO_2$ moiety and one ONO moiety. In another preferred embodiment, said compound of formula I or formula II each comprises at least three moieties selected from $ONO_2$ and ONO moieties and at most four $ONO_2$ or ONO moieties. In another preferred embodiment, said compound of formula I or formula II each comprises exactly three $ONO_2$ or three ONO moieties. In another preferred embodiment, said compound of formula I or formula II each comprises exactly three moieties selected from $ONO_2$ and ONO moieties. In another preferred embodiment, said compound of formula I or formula II each comprises exactly four $ONO_2$ or four ONO moieties. In another preferred embodiment, said compound of formula I or formula II each comprises exactly four moieties selected from $ONO_2$ and ONO moieties.

In a preferred embodiment of the present invention, said of compound is a compound of formula I, wherein said compound of formula I comprises exactly one $ONO_2$ moiety. In another preferred embodiment, said compound of formula I comprises exactly one ONO moiety. In a preferred embodiment, said compound of formula I comprises at least two moieties selected from $ONO_2$ or ONO moieties. In another preferred embodiment, said compound of formula I comprises exactly two $ONO_2$ or two ONO moieties. In another preferred embodiment, said compound of formula I comprises exactly two $ONO_2$ moieties. In another preferred embodiment, said compound of formula I comprises exactly two ONO moieties. In another preferred embodiment, said compound of formula I comprises exactly one $ONO_2$ moiety and one ONO moiety. In another preferred embodiment, said compound of formula I comprises at least three moieties selected from $ONO_2$ and ONO moieties and at most four $ONO_2$ or ONO moieties. In another preferred embodiment, said compound of formula I comprises exactly three $ONO_2$ or three ONO moieties. In another preferred embodiment, said compound of formula I comprises exactly three moieties selected from $ONO_2$ and ONO moieties. In another preferred embodiment, said compound of formula I comprises exactly four $ONO_2$ or four ONO moieties. In another preferred embodiment, said compound of formula I comprises exactly four moieties selected from $ONO_2$ and ONO moieties. In another preferred embodiment of the present invention, said of compound is a compound of formula I, and wherein said compound of formula I comprises at least two $ONO_2$ moieties and at most four $ONO_2$ moieties. In another preferred embodiment, said compound of formula I comprises at least three $ONO_2$ moieties and at most four $ONO_2$ moieties. In another preferred embodiment, said compound of formula I comprises exactly three $ONO_2$ moieties. In another preferred embodiment, said compound of formula I comprises exactly three moieties $ONO_2$ moieties. In another preferred embodiment, said compound of formula I comprises exactly four $ONO_2$ ONO moieties.

In a preferred embodiment, said of compound is a compound of formula II, wherein said compound of formula II comprises exactly one $ONO_2$ moiety. In another preferred embodiment, said compound of formula II comprises exactly one ONO moiety. In a preferred embodiment, said compound of formula II comprises at least two moieties selected from $ONO_2$ or ONO moieties. In another preferred embodiment, said compound of formula II comprises exactly two $ONO_2$ or two ONO moieties. In another preferred embodiment, said compound of formula II comprises exactly two $ONO_2$ moieties. In another preferred embodiment, said compound of formula II comprises exactly two ONO moieties. In another preferred embodiment, said compound of formula II comprises exactly one $ONO_2$ moiety and one ONO moiety. In another preferred embodiment, said compound of formula II comprises at least three moieties selected from $ONO_2$ and ONO moieties and at most four $ONO_2$ or ONO moieties. In another preferred embodiment, said compound of formula II comprises exactly three $ONO_2$ or three ONO moieties. In another preferred embodiment, said compound of formula II comprises exactly three moieties selected from $ONO_2$ and ONO moieties. In another preferred embodiment, said compound of formula II comprises exactly four $ONO_2$ or four ONO moieties. In another preferred embodiment, said compound of formula II comprises exactly four moieties selected from $ONO_2$ and ONO moieties. In another preferred embodiment of the present invention, said of compound is a compound of formula II, and wherein said compound of formula II comprises at least two $ONO_2$ moieties and at most four $ONO_2$ moieties. In another preferred embodiment, said compound of formula II comprises at least three $ONO_2$ moieties and at most four $ONO_2$ moieties. In another preferred embodiment, said compound of formula II comprises exactly three $ONO_2$ moieties. In another preferred embodiment, said compound of formula II comprises exactly three moieties $ONO_2$ moieties. In another preferred embodiment, said compound of formula II comprises exactly four $ONO_2$ ONO moieties.

In a preferred embodiment of the present invention, $R_1$ is $C_1$-$C_3$alkyl. In a further preferred embodiment, $R_1$ is $CH_3$ or $C_2H_5$. In a further very preferred embodiment, $R_1$ is $CH_3$.

In a preferred embodiment of the present invention, $R_2$ is H, $C_1$-$C_6$alkyl, $C_3$-$C_6$cycloalkyl, $C_1$-$C_2$alkoxy, $C_2$-$C_4$alkenyl. In a preferred embodiment of the present invention, $R_2$ is H, $C_1$-$C_6$alkyl, $C_3$-$C_4$cycloalkyl, $C_1$-$C_2$alkoxy, $C_2$-$C_4$alkenyl. In a further preferred embodiment, said $R_2$ is H, $C_1$-$C_6$alkyl or $C_3$-$C_4$cycloalkyl. In a further preferred embodiment, $R_2$ is $C_1$-$C_6$alkyl or $C_3$-$C_4$cycloalkyl. In a further preferred embodiment, $R_2$ is $C_1$-$C_3$alkyl or $C_3$-$C_6$cycloalkyl. In a further preferred embodiment, $R_2$ is $C_1$-$C_6$alkyl. In a further preferred embodiment, $R_2$ is $C_1$-$C_3$alkyl. In a further preferred embodiment, $R_2$ is $C_3$-$C_6$cycloalkyl, preferably $C_3$-$C_4$cycloalkyl. In a very preferred embodiment of the present invention, $R_2$ is $C_2$-$C_3$alkyl. In a very preferred embodiment, $R_2$ is n-propyl.

In another preferred embodiment, $R_3$ is $C_1$-$C_4$alkyl optionally substituted with $C_1$-$C_2$alkoxy, $C_3$-$C_4$cycloalkyl, $C_2$-$C_4$alkenyl. In a further preferred embodiment, $R_3$ is $C_1$-$C_4$alkyl optionally substituted with $C_1$-$C_2$alkoxy, $C_3$-$C_4$cycloalkyl. In a further preferred embodiment, $R_3$ is $C_1$-$C_4$alkyl. In a further very preferred embodiment, $R_3$ is ethyl or n-propyl. In a further very preferred embodiment, $R_3$ is ethyl. In a further very preferred embodiment, $R_3$ is n-propyl.

In another preferred embodiment, $R_4$ and $R_5$ are each independently H or $C_1$-$C_6$alkyl optionally substituted with F, OH, ONO, $ONO_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homopiperazine, 2,5-diazabicyclo[2,2,1]heptane and 3,7-diazabicyclo[3,3,0]octane, wherein said heterocyclic ring is optionally substituted with independently one or more independently $R_6$. In another preferred embodiment, $R_6$ is $C_1$-$C_6$alkyl optionally substituted with independently one or more halogen, OH, ONO, $ONO_2$, $C_1$-$C_3$alkoxy, $C_1$-$C_3$haloalkoxy, $COOR_7$, $NR_8R_9$, $C{=}NR_{10}$. In another preferred embodiment, $R_7$ is H, or $C_1$-$C_4$alkyl optionally substituted with F, OH, ONO, $ONO_2$, $NR_8R_9$. In another preferred embodiment, $R_8$ and $R_9$ are each independently H or $C_1$-$C_4$alkyl optionally substituted with ONO, $ONO_2$. In another preferred embodiment, $R_{10}$ is $C_1$-$C_4$alkyl optionally substituted with F, ONO, $ONO_2$; $C_3$-$C_6$cycloalkyl.

In another preferred embodiment, $R_4$ and $R_5$ are each independently H or $C_1$-$C_6$alkyl optionally substituted with F, OH, ONO, $ONO_2$, COOH, $C_1$-$C_3$alkoxy, $C_3$-$C_6$cycloalkyl.

In a further preferred embodiment $R_4$ and $R_5$ are each independently H or $C_1$-$C_6$alkyl optionally substituted with $C_1$-$C_3$alkoxy, $C_3$-$C_6$cycloalkyl; or together with the nitrogen atom to which they are attached form a heterocyclic ring, wherein said heterocyclic ring is selected from aziridine, azetidine, pyrollidine, piperidine, morpholine, piperazine, homopiperazine, 2,5-diazabicyclo[2,2,1]heptane and 3,7-diazabicyclo[3,3,0]octane, wherein said heterocyclic ring is optionally substituted with one or more independently $R_6$.

In another preferred embodiment, $R_4$ and $R_5$ together with the nitrogen atom to which they are attached form a heterocyclic ring, wherein said heterocyclic ring is optionally substituted with independently one or more $R_6$. In another preferred embodiment, $R_4$ and $R_5$ together with the nitrogen atom to which they are attached form a heterocyclic ring, wherein said heterocyclic ring is optionally substituted with independently one, two or three $R_6$. In another preferred embodiment, $R_4$ and $R_5$ together with the nitrogen atom to which they are attached form a heterocyclic ring, wherein said heterocyclic ring is optionally substituted with independently one or two $R_6$. In another preferred embodiment, $R_4$ and $R_5$ together with the nitrogen atom to which they are attached form a heterocyclic ring, wherein said heterocyclic ring is substituted with independently one, two or three $R_6$. In another preferred embodiment, $R_4$ and $R_5$ together with the nitrogen atom to which they are attached form a heterocyclic ring, wherein said heterocyclic ring is substituted with independently one or two $R_6$. In another preferred embodiment, said heterocyclic ring is selected from aziridine, azetidine, pyrollidine, piperidine, morpholine, piperazine, homopiperazine, 2,5-diazabicyclo[2,2,1]heptane and 3,7-diazabicyclo[3,3,0]octane. In another preferred embodiment, said heterocyclic ring, formed by said $R_4$ and $R_5$ together with the nitrogen atom to which they are attached, is selected from aziridine, azetidine, pyrollidine, piperidine, morpholine, piperazine, homopiperazine, 2,5-diazabicyclo[2,2,1]heptane and 3,7-diazabicyclo[3,3,0]octane, wherein said heterocyclic ring is optionally substituted with independently one or more $R_6$, preferably optionally substituted with independently one or two $R_6$.

In another preferred embodiment, said $R_6$ is $C_1$-$C_6$alkyl optionally substituted with independently one or more OH, ONO, $ONO_2$, $C_1$-$C_3$alkoxy, $COOR_7$, $NR_8R_9$, $C{=}NR_{10}$; $R_7$ is H, or $C_1$-$C_4$alkyl optionally substituted with OH, ONO, $ONO_2$; $R_8$ and $R_9$ are each independently H or $C_1$-$C_4$alkyl optionally substituted with ONO, $ONO_2$; $R_{10}$ is $C_1$-$C_4$alkyl optionally substituted with ONO, $ONO_2$; $C_3$-$C_4$cycloalkyl. In another preferred embodiment, said $R_6$ is $C_1$-$C_6$alkyl optionally substituted with independently one or more OH, ONO, $ONO_2$, $C_1$-$C_3$alkoxy, $COOR_7$, preferably said $R_6$ is $C_1$-$C_6$alkyl optionally substituted with independently one or more OH, ONO, $ONO_2$, $C_1$-$C_3$alkoxy; $R_7$ is H, or $C_1$-$C_4$alkyl optionally substituted with OH, ONO, $ONO_2$.

In another preferred embodiment, $R_4$ and $R_5$ together with the nitrogen atom to which they are attached form a heterocyclic ring, wherein said heterocyclic ring is selected from piperidine, piperazine and homopiperazine, wherein said heterocyclic ring is optionally substituted with independently one or more $R_6$. In another preferred embodiment, said heterocyclic ring is optionally substituted with independently one, two or three $R_6$. In another preferred embodiment, said heterocyclic ring is optionally substituted with independently one or two $R_6$. In another preferred embodiment, said heterocyclic ring is substituted with independently one, two or three $R_6$. In another preferred embodiment, said heterocyclic ring is substituted with independently one or two $R_6$. In another very preferred embodiment, said heterocyclic ring is piperidine or piperazine. In another very preferred embodiment, said heterocyclic ring is piperidine. In another very preferred embodiment, said heterocyclic ring is piperazine. In another very preferred embodiment, said heterocyclic ring is piperidine or piperazine. In another very preferred embodiment, said heterocyclic ring is piperidine optionally substituted with independently one or two $R_6$. In another very preferred embodiment, said heterocyclic ring is piperazine optionally substituted with independently one or two $R_6$.

In another preferred embodiment, said $R_6$ is $C_1$-$C_6$alkyl optionally substituted with independently one or more OH, ONO, $ONO_2$, $C_1$-$C_3$alkoxy, $COOR_7$, $NR_8R_9$, $C{=}NR_{10}$; $R_7$ is H, or $C_1$-$C_4$alkyl optionally substituted with OH, ONO, $ONO_2$; $R_8$ and $R_9$ are each independently H or $C_1$-$C_4$alkyl optionally substituted with ONO, $ONO_2$; $R_{10}$ is $C_1$-$C_4$alkyl optionally substituted with ONO, $ONO_2$; $C_3$-$C_4$cycloalkyl. In another preferred embodiment, said $R_6$ is $C_1$-$C_6$alkyl optionally substituted with independently one or more OH, ONO, $ONO_2$, $C_1$-$C_3$alkoxy, $COOR_7$, preferably said $R_6$ is $C_1$-$C_6$alkyl optionally substituted with independently one or more OH, ONO, $ONO_2$, $C_1$-$C_3$alkoxy. In another preferred embodiment, said $R_6$ is $C_1$-$C_6$alkyl substituted with independently one or more OH, ONO, $ONO_2$, $C_1$-$C_3$alkoxy, $COOR_7$, preferably said $R_6$ is $C_1$-$C_6$alkyl optionally substituted with independently one or more OH, ONO, $ONO_2$, $C_1$-$C_3$alkoxy. In another preferred embodiment, said $R_6$ is $C_1$-$C_6$alkyl optionally substituted with independently one or more OH, ONO, $ONO_2$, $C_1$-$C_3$alkoxy, $COOR_7$, preferably said $R_6$ is $C_1$-$C_6$alkyl optionally substituted with independently one or more OH, ONO, $ONO_2$, $C_1$-$C_3$alkoxy; $R_7$ is H, or $C_1$-$C_4$alkyl optionally substituted with OH, ONO, $ONO_2$. In another preferred embodiment, said $R_6$ is $C_1$-$C_6$alkyl optionally substituted with independently one or more OH, ONO, $ONO_2$, $C_1$-$C_3$alkoxy, $C_1$-$C_3$haloalkoxy. In another preferred embodiment, said $R_6$ is $C_1$-$C_6$alkyl substituted with independently one or more OH, ONO, $ONO_2$, $C_1$-$C_3$alkoxy, $C_1$-$C_3$haloalkoxy. In another preferred embodiment, said $R_6$ is $C_1$-$C_6$alkyl optionally substituted with independently one or more OH, ONO, $ONO_2$. In another preferred embodiment, said $R_6$ is $C_1$-$C_6$alkyl substituted with independently one or more OH, ONO, $ONO_2$.

In a further very preferred embodiment, said compound of formula I is a compound of formula I*, and wherein said compound of formula II is a compound of formula II*, or independently for each of said I* and II* a pharmaceutically acceptable salt, solvate or hydrate thereof,

I*

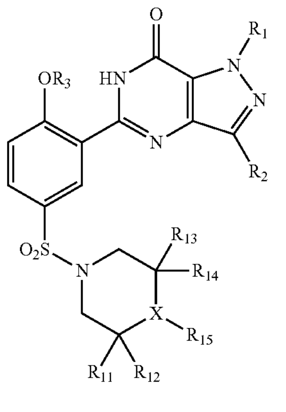

-continued

II*

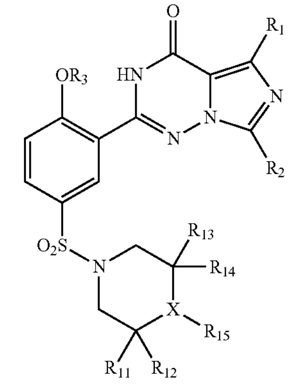

wherein $R_1$, $R_2$, and $R_3$ are as defined herein, preferably wherein $R_1$ is $C_1$-$C_3$alkyl;

$R_2$ is H, $C_1$-$C_6$alkyl, $C_3$-$C_6$cycloalkyl, $C_1$-$C_2$alkoxy, $C_2$-$C_4$alkenyl;

$R_3$ is $C_1$-$C_4$alkyl optionally substituted with $C_1$-$C_2$alkoxy, $C_3$-$C_4$cycloalkyl, $C_2$-$C_4$alkenyl; and wherein X is $CR_{16}$ or N;

$R_{11}$, $R_{12}$, $R_{13}$, $R_{14}$ and $R_{15}$ are independently H, $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$;

$R_{16}$ is H or $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$;

$R_{17}$ is H, or $C_1$-$C_4$alkyl optionally substituted with F, OH, ONO, $ONO_2$;

$R_{18}$ and $R_{19}$ are independently H or $C_1$-$C_4$alkyl optionally substituted with ONO, $ONO_2$;

$R_{20}$ is $C_1$-$C_4$alkyl optionally substituted with F, ONO, $ONO_2$;

wherein at least one of said $R_{11}$, $R_{12}$, $R_{13}$, $R_{14}$, $R_{15}$ and $R_{16}$ comprises independently at least one $ONO_2$ or ONO moiety, wherein preferably at least one of said $R_{11}$, $R_{12}$, $R_{13}$, $R_{14}$, $R_{15}$ and $R_{16}$ comprises independently at least one $ONO_2$ or ONO moiety and wherein said $R_{11}$, $R_{12}$, $R_{13}$, $R_{14}$, $R_{15}$ and $R_{16}$ comprise together at most four moieties selected from $ONO_2$ and ONO moieties. Typically and preferably said compound of formula I* is not

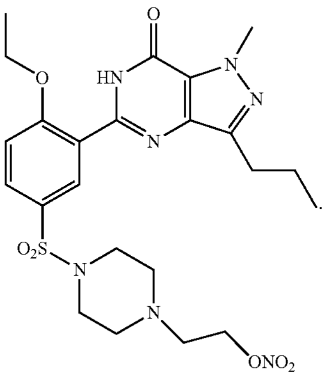

In a further very preferred embodiment, said compound of formula I is a compound of formula I*, and wherein said compound of formula II is a compound of formula II*, or independently for each of said I* and II* a pharmaceutically acceptable salt, solvate or hydrate thereof,

I*

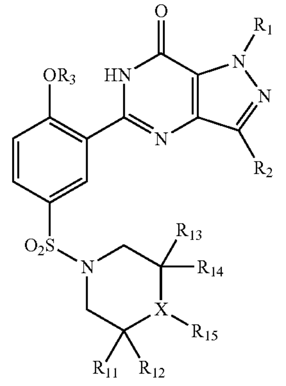

II*

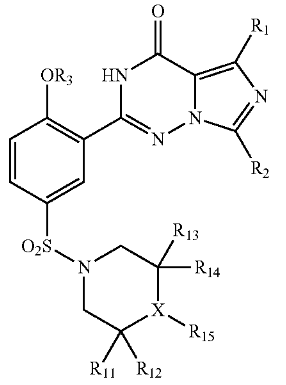

wherein $R_1$, $R_2$, and $R_3$ are as defined herein, preferably wherein $R_1$ is $C_1$-$C_3$alkyl;

$R_2$ is H, $C_1$-$C_6$alkyl, $C_3$-$C_6$cycloalkyl, $C_1$-$C_2$alkoxy, $C_2$-$C_4$alkenyl;

$R_3$ is $C_1$-$C_4$alkyl optionally substituted with $C_1$-$C_2$alkoxy, $C_3$-$C_4$cycloalkyl, $C_2$-$C_4$alkenyl; and wherein X is $CR_{16}$ or N;

$R_{11}$, $R_{12}$, $R_{13}$, $R_{14}$ and $R_{15}$ are independently H, $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$;

$R_{16}$ is H or $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$;

$R_{17}$ is H, or $C_1$-$C_4$alkyl optionally substituted with F, OH, ONO, $ONO_2$;

$R_{18}$ and $R_{19}$ are independently H or $C_1$-$C_4$alkyl optionally substituted with ONO, $ONO_2$;

$R_{20}$ is $C_1$-$C_4$alkyl optionally substituted with F, ONO, $ONO_2$;

wherein at least one of said $R_{11}$, $R_{12}$, $R_{13}$, $R_{14}$, $R_{15}$ and $R_{16}$ comprises independently at least one $ONO_2$ or ONO moiety, wherein preferably at least one of said $R_{11}$, $R_{12}$, $R_{13}$, $R_{14}$, $R_{15}$ and $R_{16}$ comprises independently at least one $ONO_2$ or ONO moiety and wherein said $R_{11}$, $R_{12}$, $R_{13}$, $R_{14}$, $R_{15}$ and $R_{16}$ comprise together at most four moieties selected from $ONO_2$ and ONO moieties;

wherein said compound of formula I* is not

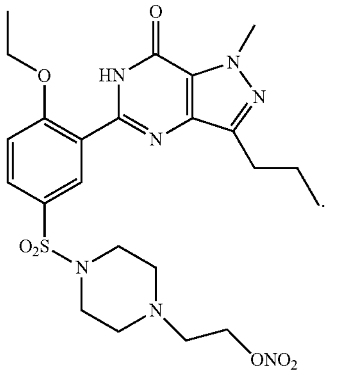

In a preferred embodiment of the present invention, at least one of said $R_{11}$, $R_{12}$, $R_{13}$, $R_{14}$, $R_{15}$ and $R_{16}$ comprises independently at least one $ONO_2$ or ONO moiety and wherein said $R_{11}$, $R_{12}$, $R_{13}$, $R_{14}$, $R_{15}$ and $R_{16}$ comprise together at most four moieties selected from $ONO_2$ and ONO moieties. In a preferred embodiment of the present invention, at least one of said $R_{11}$, $R_{12}$, $R_{13}$, $R_{14}$, $R_{15}$ and $R_{16}$ comprises independently at least two $ONO_2$ or ONO moieties, and said $R_{11}$, $R_{12}$, $R_{13}$, $R_{14}$, $R_{15}$ and $R_{16}$ comprise together at most four moieties selected from $ONO_2$ and ONO moieties.

In a preferred embodiment of the present invention, at least one of said $R_{11}$, $R_{12}$, $R_{13}$, $R_{14}$, $R_{15}$ and $R_{16}$ comprises independently at least one $ONO_2$ moiety and wherein said $R_{11}$, $R_{12}$, $R_{13}$, $R_{14}$, $R_{15}$ and $R_{16}$ comprise together at most four $ONO_2$ moieties. In a preferred embodiment of the present invention, at least one of said $R_{11}$, $R_{12}$, $R_{13}$, $R_{14}$, $R_{15}$ and $R_{16}$ comprises independently at least two $ONO_2$ moieties, and said $R_{11}$, $R_{12}$, $R_{13}$, $R_{14}$, $R_{15}$ and $R_{16}$ comprise together at most four $ONO_2$ moieties.

In a further very preferred embodiment, said compound of formula I is a compound of formula I* or a pharmaceutically acceptable salt, solvate or hydrate thereof,

I*

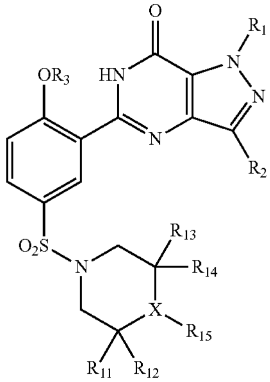

wherein $R_1$, $R_2$, and $R_3$ are as defined herein, preferably wherein $R_1$ is $C_1$-$C_3$alkyl;

$R_2$ is H, $C_1$-$C_6$alkyl, $C_3$-$C_6$cycloalkyl, $C_1$-$C_2$alkoxy, $C_2$-$C_4$alkenyl;

$R_3$ is $C_1$-$C_4$alkyl optionally substituted with $C_1$-$C_2$alkoxy, $C_3$-$C_4$cycloalkyl, $C_2$-$C_4$alkenyl;

and wherein

X is $CR_{16}$ or N;

$R_{11}$, $R_{12}$, $R_{13}$, $R_{14}$ and $R_{15}$ are independently H, $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$;

$R_{16}$ is H or $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$;

$R_{17}$ is H, or $C_1$-$C_4$alkyl optionally substituted with F, OH, ONO, $ONO_2$;

$R_{18}$ and $R_{19}$ are independently H or $C_1$-$C_4$alkyl optionally substituted with ONO, $ONO_2$;

$R_{20}$ is $C_1$-$C_4$alkyl optionally substituted with F, ONO, $ONO_2$;

wherein at least one of said $R_{11}$, $R_{12}$, $R_{13}$, $R_{14}$, $R_{15}$ and $R_{16}$ comprises independently at least one $ONO_2$ or ONO moiety, wherein preferably at least one of said $R_{11}$, $R_{12}$, $R_{13}$, $R_{14}$, $R_{15}$ and $R_{16}$ comprises independently at least one $ONO_2$ or ONO moiety and wherein said $R_{11}$, $R_{12}$, $R_{13}$, $R_{14}$, $R_{15}$ and $R_{16}$ comprise together at most four moieties selected from $ONO_2$ and ONO moieties, wherein said compound of formula I* is not

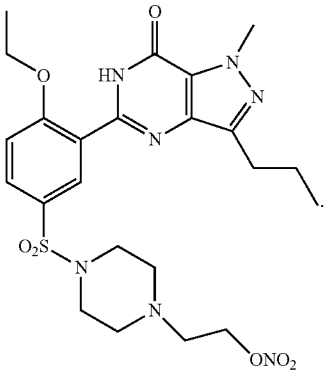

In a further very preferred embodiment, said compound of formula I is a compound of formula I* or a pharmaceutically acceptable salt, solvate or hydrate thereof,

I*

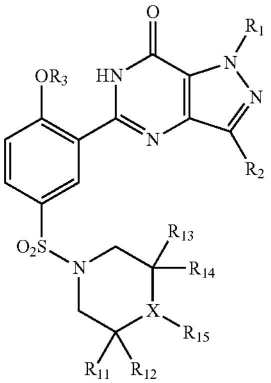

wherein $R_1$, $R_2$, and $R_3$ are as defined herein, preferably wherein $R_1$ is $C_1$-$C_3$alkyl;

$R_2$ is H, $C_1$-$C_6$alkyl, $C_3$-$C_6$cycloalkyl, $C_1$-$C_2$alkoxy, $C_2$-$C_4$alkenyl;

$R_3$ is $C_1$-$C_4$alkyl optionally substituted with $C_1$-$C_2$alkoxy, $C_3$-$C_4$cycloalkyl, $C_2$-$C_4$alkenyl;

X is $CR_{16}$ or N;

$R_{11}$, $R_{12}$, $R_{13}$, $R_{14}$ and $R_{15}$ are independently H, $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$;

$R_{16}$ is H or $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$;

$R_{17}$ is H, or $C_1$-$C_4$alkyl optionally substituted with F, OH, ONO, $ONO_2$;

$R_{18}$ and $R_{19}$ are independently H or $C_1$-$C_4$alkyl optionally substituted with ONO, $ONO_2$;

$R_{20}$ is $C_1$-$C_4$alkyl optionally substituted with F, ONO, $ONO_2$;

wherein at least one of said $R_{11}$, $R_{12}$, $R_{13}$, $R_{14}$, $R_{15}$ and $R_{16}$ comprises independently at least one $ONO_2$ or ONO moiety, wherein preferably at least one of said $R_{11}$, $R_{12}$, $R_{13}$, $R_{14}$, $R_{15}$ and $R_{16}$ comprises independently at least one $ONO_2$ or ONO moiety and wherein said $R_{11}$, $R_{12}$, $R_{13}$, $R_{14}$, $R_{15}$ and $R_{16}$ comprise together at most four moieties selected from $ONO_2$ and ONO moieties. Typically and preferably said compound of formula I is not

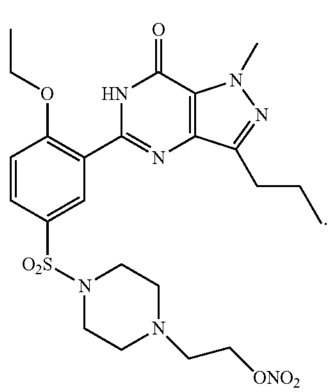

In a further very preferred embodiment, said compound of formula II is a compound of formula II* or a pharmaceutically acceptable salt, solvate or hydrate thereof,

II*

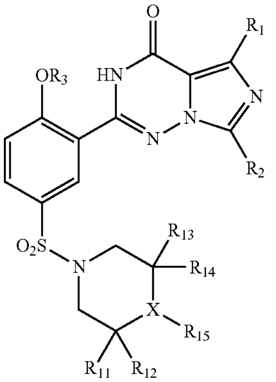

wherein $R_1$, $R_2$, and $R_3$ are as defined herein, preferably wherein $R_1$ is $C_1$-$C_3$alkyl;

$R_2$ is H, $C_1$-$C_6$alkyl, $C_3$-$C_6$cycloalkyl, $C_1$-$C_2$alkoxy, $C_2$-$C_4$alkenyl;

$R_3$ is $C_1$-$C_4$alkyl optionally substituted with $C_1$-$C_2$alkoxy, $C_3$-$C_4$cycloalkyl, $C_2$-$C_4$alkenyl; and wherein X is $CR_{16}$ or N;

$R_{11}$, $R_{12}$, $R_{13}$, $R_{14}$ and $R_{15}$ are independently H, $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$;

$R_{16}$ is H or $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$;

$R_{17}$ is H, or $C_1$-$C_4$alkyl optionally substituted with F, OH, ONO, $ONO_2$;

$R_{18}$ and $R_{19}$ are independently H or $C_1$-$C_4$alkyl optionally substituted with ONO, $ONO_2$;

$R_{20}$ is $C_1$-$C_4$alkyl optionally substituted with F, ONO, $ONO_2$;

wherein at least one of said $R_{11}$, $R_{12}$, $R_{13}$, $R_{14}$, $R_{15}$ and $R_{16}$ comprises independently at least one $ONO_2$ or ONO moiety, wherein preferably at least one of said $R_{11}$, $R_{12}$, $R_{13}$, $R_{14}$, $R_{15}$ and $R_{16}$ comprises independently at least one $ONO_2$ or ONO moiety and wherein said $R_{11}$, $R_{12}$, $R_{13}$, $R_{14}$, $R_{15}$ and $R_{16}$ comprise together at most four moieties selected from $ONO_2$ and ONO moieties.

As indicated, the herein described and disclosed embodiments, preferred embodiments and very preferred embodiments should apply to all aspects and other embodiments, preferred embodiments and very preferred embodiments irrespective of whether is specifically again referred to or its repetition is avoided for the sake of conciseness. Thus, in a further very preferred embodiment, said X is CH or N. In another very preferred embodiment, said X is $CR_{16}$. In another very preferred embodiment, said X is N. In another very preferred embodiment, said X is $CR_{16}$ and said $R_{16}$ is H.

Moreover, in a further very preferred embodiment, one of said $R_{11}$ and $R_{12}$ is H, and the other of said $R_{11}$ and $R_{12}$ is $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$. In a further very preferred embodiment, one of said $R_{11}$ and $R_{12}$ is H, and the other of said $R_{11}$ and $R_{12}$ is $C_1$-$C_6$alkyl substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$.

In a further very preferred embodiment, one of said $R_{11}$ and $R_{12}$ is H, and the other of said $R_{11}$ and $R_{12}$ is H, $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$. In a further very preferred embodiment, one of said $R_{11}$ and $R_{12}$ is H, and the other of said $R_{11}$ and $R_{12}$ is H, $C_1$-$C_6$alkyl substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$.

In a further very preferred embodiment, one of said $R_{11}$ and $R_{12}$ is H, and the other of said $R_{11}$ and $R_{12}$ is H, $C_1$-$C_6$alkyl optionally substituted with independently one or more halogen, OH, ONO, $ONO_2$, $C_1$-$C_3$alkoxy, $C_1$-$C_3$haloalkoxy. In a further very preferred embodiment, one of said $R_{11}$ and $R_{12}$ is H, and the other of said $R_{11}$ and $R_{12}$ is H, $C_1$-$C_6$alkyl substituted with independently one or more halogen, OH, ONO, $ONO_2$, $C_1$-$C_3$alkoxy, $C_1$-$C_3$haloalkoxy.

In a further very preferred embodiment, one of said $R_{13}$ and $R_{14}$ is H, and the other of said $R_{13}$ and $R_{14}$ is $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$. In a further very preferred embodiment, one of said $R_{13}$ and $R_{14}$ is H, and the other of said $R_{13}$ and $R_{14}$ is $C_1$-$C_6$alkyl substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$.

In a further very preferred embodiment, one of said $R_{13}$ and $R_{14}$ is H, and the other of said $R_{13}$ and $R_{14}$ is H, $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$. In a further very preferred embodiment, one of said $R_{13}$ and $R_{14}$ is H, and the other of said $R_{13}$ and $R_{14}$ is H, $C_1$-$C_6$alkyl substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$.

In a further very preferred embodiment, one of said $R_{13}$ and $R_{14}$ is H, and the other of said $R_{13}$ and $R_{14}$ is H, $C_1$-$C_6$alkyl optionally substituted with independently one or more halogen, OH, ONO, $ONO_2$, $C_1$-$C_3$alkoxy, $C_1$-$C_3$haloalkoxy. In a further very preferred embodiment, one of said $R_{13}$ and $R_{14}$ is H, and the other of said $R_{13}$ and $R_{14}$ is H, $C_1$-$C_6$alkyl substituted with independently one or more halogen, OH, ONO, $ONO_2$, $C_1$-$C_3$alkoxy, $C_1$-$C_3$haloalkoxy.

In a further very preferred embodiment, said $R_{15}$ is $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$. In a further very preferred embodiment, said $R_{15}$ is $C_1$-$C_6$alkyl substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$. In a further very preferred embodiment, said $R_{16}$ is H.

In a further very preferred embodiment, said $R_{15}$ is $C_1$-$C_6$alkyl optionally substituted with independently one or more halogen, OH, ONO, $ONO_2$, $C_1$-$C_3$alkoxy, $C_1$-$C_3$haloalkoxy. In a further very preferred embodiment, said $R_{15}$ is $C_1$-$C_6$alkyl optionally substituted with independently one or more, OH, ONO, $ONO_2$, $C_1$-$C_3$alkoxy. In a further very preferred embodiment, said $R_{15}$ is $C_1$-$C_6$alkyl optionally substituted with independently one or more, OH, ONO, $ONO_2$. In a further very preferred embodiment, said $R_{16}$ is H.

In a further very preferred embodiment, said $R_{15}$ is $C_1$-$C_6$alkyl substituted with independently one or more halogen, OH, ONO, $ONO_2$, $C_1$-$C_3$alkoxy, $C_1$-$C_3$haloalkoxy. In a further very preferred embodiment, said $R_{15}$ is $C_1$-$C_6$alkyl substituted with at least two substituents independently selected from halogen, OH, ONO, $ONO_2$, $C_1$-$C_3$alkoxy, $C_1$-$C_3$haloalkoxy. In a further very preferred embodiment, said $R_{15}$ is $C_1$-$C_6$alkyl substituted with independently one or more, OH, ONO, $ONO_2$, $C_1$-$C_3$alkoxy. In a further very preferred embodiment, said $R_{15}$ is $C_1$-$C_6$alkyl substituted with at least two substituents independently selected from halogen, OH, ONO, $ONO_2$, $C_1$-$C_3$alkoxy. In a further very preferred embodiment, said $R_{15}$ is $C_1$-$C_6$alkyl substituted with independently one or more, OH, ONO, $ONO_2$. In a further very preferred embodiment, said $R_{16}$ is H.

In a further very preferred embodiment, said $R_{15}$ is $C_1$-$C_6$alkyl substituted with at least one and at most four substituents independently selected from OH, ONO and $ONO_2$. In a further very preferred embodiment, said $R_{15}$ is $C_1$-$C_6$alkyl substituted with at least two and at most four substituents independently selected from OH, ONO and $ONO_2$. In a further very preferred embodiment, said $R_{15}$ is $C_1$-$C_6$alkyl substituted with one substituent selected from OH, ONO and $ONO_2$. In a further very preferred embodiment, said $R_{15}$ is $C_1$-$C_6$alkyl substituted with two substituents independently selected from OH, ONO and $ONO_2$. In a further very preferred embodiment, said $R_{15}$ is $C_1$-$C_6$alkyl substituted with three substituents independently selected from OH, ONO and $ONO_2$. In a further very preferred embodiment, said $R_{15}$ is $C_1$-$C_6$alkyl substituted with at least two substituents independently selected from OH, ONO and $ONO_2$. In a further very preferred embodiment, said $R_{15}$ is $C_1$-$C_6$alkyl substituted with at least three substituents independently selected from OH, ONO and $ONO_2$. In a further very preferred embodiment, said $R_{16}$ is H.

In a further very preferred embodiment, said $R_{15}$ is $C_1$-$C_6$alkyl substituted with at least one and at most four substituents independently selected from OH and $ONO_2$. In a further very preferred embodiment, said $R_{15}$ is $C_1$-$C_6$alkyl substituted with at least two and at most four substituents independently selected from OH and $ONO_2$. In a further very preferred embodiment, said $R_{15}$ is $C_1$-$C_6$alkyl substituted with one substituent selected from OH and $ONO_2$. In a further very preferred embodiment, said $R_{15}$ is $C_1$-$C_6$alkyl substituted with two substituents independently selected from OH and $ONO_2$. In a further very preferred embodiment, said $R_{15}$ is $C_1$-$C_6$alkyl substituted with three substituents independently selected from OH and $ONO_2$. In a further very preferred embodiment, said $R_{16}$ is H.

In a further very preferred embodiment, said $R_{16}$ is H or $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$. In a further very preferred embodiment, said $R_{16}$ is H.

In a further very preferred embodiment, said $R_{17}$ is H, or $C_1$-$C_4$alkyl optionally substituted with OH, ONO, $ONO_2$.

In a further very preferred embodiment, said $R_{18}$ and $R_{19}$ are each independently H or $C_1$-$C_4$alkyl optionally substituted with ONO, $ONO_2$.

In a further very preferred embodiment, one of said $R_{13}$ and $R_{14}$ is H, and the other of said $R_{13}$ and $R_{14}$ is $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$. In a further very preferred embodiment, one of said $R_{13}$ and $R_{14}$ is H, and the other of said $R_{13}$ and $R_{14}$ is $C_1$-$C_6$alkyl substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$; said $R_{15}$ is $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$; said $R_{16}$ is H or $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$; said $R_{17}$ is H, or $C_1$-$C_4$alkyl optionally substituted with OH, ONO, $ONO_2$; said $R_{18}$ and $R_{19}$ are each independently H or $C_1$-$C_4$alkyl optionally substituted with ONO, $ONO_2$.

In a further very preferred embodiment, one of said $R_{13}$ and $R_{14}$ is H, and the other of said $R_{13}$ and $R_{14}$ is H, $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$. In a further very preferred embodiment, one of said $R_{13}$ and $R_{14}$ is H, and the other of said $R_{13}$ and $R_{14}$ is H, $C_1$-$C_6$alkyl substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$; said $R_{15}$ is $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$; said $R_{16}$ is H or $C_1$-$C_6$alkyl optionally substituted with independently one or more halogen, OH, ONO, $ONO_2$, $C_1$-$C_3$alkoxy, $C_1$-$C_3$haloalkoxy, $COOR_{17}$, $NR_{18}R_{19}$, $C{=}NR_{20}$; said $R_{17}$ is H, or $C_1$-$C_4$alkyl optionally substituted with OH, ONO, $ONO_2$; said $R_{18}$ and $R_{19}$ are each independently H or $C_1$-$C_4$alkyl optionally substituted with ONO, $ONO_2$.

In a further very preferred embodiment, one of said $R_{13}$ and $R_{14}$ is H, and the other of said $R_{13}$ and $R_{14}$ is H, $C_1$-$C_6$alkyl optionally substituted with independently one or more halogen, OH, ONO, $ONO_2$, $C_1$-$C_3$alkoxy, $C_1$-$C_3$haloalkoxy. In a further very preferred embodiment, one of said $R_{13}$ and $R_{14}$ is H, and the other of said $R_{13}$ and $R_{14}$ is H, $C_1$-$C_6$alkyl substituted with independently one or more halogen, OH, ONO, $ONO_2$, $C_1$-$C_3$alkoxy, $C_1$-$C_3$haloalkoxy; said $R_{15}$ is $C_1$-$C_6$alkyl optionally substituted with independently one or more halogen, OH, ONO, $ONO_2$, $C_1$-$C_3$alkoxy, $C_1$-$C_3$haloalkoxy; said $R_{16}$ is H or $C_1$-$C_6$alkyl optionally substituted with independently one or more halogen, OH, ONO, $ONO_2$, $C_1$-$C_3$alkoxy, $C_1$-$C_3$haloalkoxy.

In a further very preferred embodiment, one of said $R_{13}$ and $R_{14}$ is H, and the other of said $R_{13}$ and $R_{14}$ is H, $C_1$-$C_6$alkyl optionally substituted with independently one or more OH, ONO, $ONO_2$, $C_1$-$C_3$alkoxy. In a further very preferred embodiment, one of said $R_{13}$ and $R_{14}$ is H, and the other of said $R_{13}$ and $R_{14}$ is H, $C_1$-$C_6$alkyl substituted with independently one or more OH, ONO, $ONO_2$, $C_1$-$C_3$alkoxy; said $R_{15}$ is $C_1$-$C_6$alkyl optionally substituted with independently one or more, OH, ONO, $ONO_2$, $C_1$-$C_3$alkoxy; said $R_{16}$ is H or $C_1$-$C_6$alkyl optionally substituted with independently one or more, OH, ONO, $ONO_2$, $C_1$-$C_3$alkoxy.

In a further very preferred embodiment, one of said $R_{11}$ and $R_{12}$ is H, and one of said $R_{13}$ and $R_{14}$ is H, and at least one of said $R_{11}$, $R_{12}$, $R_{13}$, $R_{14}$, $R_{15}$ and $R_{16}$ comprises independently at least one $ONO_2$ or ONO moiety and wherein said $R_{11}$, $R_{12}$, $R_{13}$, $R_{14}$, $R_{15}$ and $R_{16}$ comprise together at most four moieties selected from $ONO_2$ and ONO moieties.

In a further very preferred embodiment, one of said $R_{11}$ and $R_{12}$ is H, and one of said $R_{13}$ and $R_{14}$ is H, and at least one of said $R_{11}$, $R_{12}$, $R_{13}$, $R_{14}$, $R_{15}$ and $R_{16}$ comprises independently at least one $ONO_2$ moiety and wherein said $R_{11}$, $R_{12}$, $R_{13}$, $R_{14}$, $R_{15}$ and $R_{16}$ comprise together at most four $ONO_2$ moieties.

In a further very preferred embodiment of the present invention, one of said $R_{11}$ and $R_{12}$ is H, and one of said $R_{13}$ and $R_{14}$ is H, and at least one of said $R_{11}$, $R_{12}$, $R_{13}$, $R_{14}$, $R_{15}$ and $R_{16}$ comprises independently at least two $ONO_2$ or ONO moieties, and said $R_{11}$, $R_{12}$, $R_{13}$, $R_{14}$, $R_{15}$ and $R_{16}$ comprise together at most four moieties selected from $ONO_2$ and ONO moieties.

In a further very preferred embodiment of the present invention, one of said $R_{11}$ and $R_{12}$ is H, and one of said $R_{13}$ and $R_{14}$ is H, and at least one of said $R_{11}$, $R_{12}$, $R_{13}$, $R_{14}$, $R_{15}$ and $R_{16}$ comprises independently at least two $ONO_2$ moieties, and said $R_{11}$, $R_{12}$, $R_{13}$, $R_{14}$, $R_{15}$ and $R_{16}$ comprise together at most four $ONO_2$ moieties.

In a further very preferred embodiment, said $R_{11}$, $R_{12}$, $R_{13}$, $R_{14}$ are H. In a further very preferred embodiment, said $R_{15}$ is $C_1$-$C_6$alkyl substituted with at least one substituent independently selected from OH, ONO and $ONO_2$. In a further very preferred embodiment of the present invention, said $R_{11}$, $R_{12}$, $R_{13}$, $R_{14}$ are H, and said $R_{15}$ is $C_1$-$C_6$alkyl substituted with at least one substituent independently selected from OH, ONO and $ONO_2$. In a further very preferred embodiment, said $R_{16}$ is H or $C_1$-$C_6$alkyl substituted with at least substituent independently selected from OH, ONO and $ONO_2$. In a further very preferred embodiment, said $R_{16}$ is H. In a further very preferred embodiment, said $R_{11}$, $R_{12}$, $R_{13}$, $R_{14}$ are H, said $R_{15}$ is $C_1$-$C_6$alkyl substituted with at least one substituent independently selected from OH, ONO and $ONO_2$, and said $R_{16}$ is H or $C_1$-$C_6$alkyl substituted with at least substituent independently selected from OH, ONO and $ONO_2$. In a further very preferred embodiment, said $R_{11}$, $R_{12}$, $R_{13}$, $R_{14}$ are H, said $R_{15}$ is $C_1$-$C_6$alkyl substituted with at least one substituent independently selected from OH, ONO and $ONO_2$, and said X is N or $CR_{16}$ and said $R_{16}$ is H, and thus said X is N or CH. In a further very preferred embodiment, said $R_{11}$, $R_{12}$, $R_{13}$, $R_{14}$ are H, said $R_{15}$ is $C_1$-$C_6$alkyl substituted with at least one and at most four substituents independently selected from OH, ONO and $ONO_2$, and X is N or $CR_{16}$ and said $R_{16}$ is H, and thus said X is N or CH. In another very preferred embodiment, said X is $CR_{16}$ and said $R_{16}$ is H, thus said X is CH.

In a further very preferred embodiment, said $R_{11}$, $R_{12}$, $R_{13}$, $R_{14}$ are H, and said $R_{15}$ is $C_1$-$C_6$alkyl substituted with at least two substituents independently selected from halogen, OH, ONO, $ONO_2$, $C_1$-$C_3$alkoxy, $C_1$-$C_3$haloalkoxy. In a further very preferred embodiment, said $R_{11}$, $R_{12}$, $R_{13}$, $R_{14}$ are H, and said $R_{15}$ is $C_1$-$C_6$alkyl substituted with at least two, and preferably at most four, substituents independently selected from halogen, OH, ONO and $ONO_2$, $C_1$-$C_3$alkoxy, $C_1$-$C_3$haloalkoxy. In a further very preferred embodiment, said $R_{11}$, $R_{12}$, $R_{13}$, $R_{14}$ are H, and said $R_{15}$ is $C_1$-$C_6$alkyl substituted with at least two, and preferably at most four, substituents independently selected from, OH, ONO and $ONO_2$, $C_1$-$C_3$alkoxy. In a further very preferred embodiment, said $R_{11}$, $R_{12}$, $R_{13}$, $R_{14}$ are H, and said $R_{15}$ is $C_1$-$C_6$alkyl substituted with at least two, and preferably at most four, substituents independently selected from OH, ONO and $ONO_2$. In a further very preferred embodiment, said $R_{11}$, $R_{12}$, $R_{13}$, $R_{14}$ are H, and said $R_{15}$ is $C_1$-$C_6$alkyl substituted with at least two, and preferably at most four, substituents independently selected from OH and $ONO_2$.

In a further very preferred embodiment, said $R_{11}$, $R_{12}$, $R_{13}$, $R_{14}$ are H, and said $R_{15}$ is $C_1$-$C_6$alkyl substituted with at least two substituents independently selected from halogen, OH, ONO, $ONO_2$, $C_1$-$C_3$alkoxy, $C_1$-$C_3$haloalkoxy, and X is N or $CR_{16}$ and said $R_{16}$ is H, and thus said X is N or CH, preferably said X is CH. In a further very preferred embodiment, said $R_{11}$, $R_{12}$, $R_{13}$, $R_{14}$ are H, and said $R_{15}$ is $C_1$-$C_6$alkyl substituted with at least two, and preferably at most four, substituents independently selected from halogen, OH, ONO and $ONO_2$, $C_1$-$C_3$alkoxy, $C_1$-$C_3$haloalkoxy, and X is N or $CR_{16}$ and said $R_{16}$ is H, and thus said X is N or CH, preferably said X is CH. In a further very preferred embodiment, said $R_{11}$, $R_{12}$, $R_{13}$, $R_{14}$ are H, and said $R_{15}$ is $C_1$-$C_6$alkyl substituted with at least two, and preferably at most four, substituents independently selected from, OH, ONO and $ONO_2$, $C_1$-$C_3$alkoxy, and X is N or $CR_{16}$ and said $R_{16}$ is H, and thus said X is N or CH, preferably said X is CH. In a further very preferred embodiment, said $R_{11}$, $R_{12}$, $R_{13}$, $R_{14}$ are H, and said $R_{15}$ is $C_1$-$C_6$alkyl substituted with at least two, and preferably at most four, substituents independently selected from OH, ONO and $ONO_2$, and X is N or $CR_{16}$ and said $R_{16}$ is H, and thus said X is N or CH, preferably said X is CH. In a further very preferred embodiment, said $R_{11}$, $R_{12}$, $R_{13}$, $R_{14}$ are H, and said $R_{15}$ is $C_1$-$C_6$alkyl substituted with at least two, and preferably at most four, substituents independently selected from OH and $ONO_2$, and X is N or $CR_{16}$ and said $R_{16}$ is H, and thus said X is N or CH, preferably said X is CH.

In a further very preferred embodiment, said $R_{11}$, $R_{12}$, $R_{13}$, $R_{14}$ are H, said $R_{15}$ is $C_1$-$C_6$alkyl substituted with at least one substituent independently selected from OH, ONO and $ONO_2$, and said X is $CR_{16}$ and said $R_{16}$ is H. In a further very preferred embodiment, said $R_{11}$, $R_{12}$, $R_{13}$, $R_{14}$ are H, said $R_{15}$ is $C_1$-$C_6$alkyl substituted with at least one and at most four substituents independently selected from OH, ONO and $ONO_2$, and said X is $CR_{16}$ and said $R_{16}$ is H. In a further very preferred embodiment, said $R_{11}$, $R_{12}$, $R_{13}$, $R_{14}$ are H, said $R_{15}$ is $C_1$-$C_6$alkyl substituted with at least one substituent independently selected from OH, ONO and $ONO_2$, and said $R_{16}$ is H or $C_1$-$C_6$alkyl substituted with at least substituent independently selected from OH, ONO and $ONO_2$, and said $R_{15}$ and said $R_{16}$ together comprises at least two moieties independently selected from $ONO_2$ and ONO moieties and together at most four moieties selected from $ONO_2$ and ONO moieties. In a further very preferred embodiment, said $R_{11}$, $R_{12}$, $R_{13}$, $R_{14}$ are H, said $R_{15}$ is $C_1$-$C_6$alkyl substituted with at least one substituent independently selected from OH and $ONO_2$, and said $R_{16}$ is H or $C_1$-$C_6$alkyl substituted with at least substituent independently selected from OH and $ONO_2$, and said $R_{15}$ and said $R_{16}$ together comprises at least two $ONO_2$ moieties and together at most four $ONO_2$ moieties. In a further very preferred embodiment, said $R_{11}$, $R_{12}$, $R_{13}$, $R_{14}$ are H, said $R_{15}$ is $C_1$-$C_6$alkyl substituted with at least one substituent independently selected from OH and $ONO_2$, and said X is N or $CR_{16}$ and said $R_{16}$ is H, and thus said X is N or CH, preferably said X is CH, and said $R_{15}$ comprises at least two $ONO_2$ moieties and together at most four $ONO_2$ moieties. In a further very preferred embodiment, said $R_{11}$, $R_{12}$, $R_{13}$, $R_{14}$ are H, said $R_{15}$ is $C_1$-$C_6$alkyl substituted with at least one substituent independently selected from OH and $ONO_2$, and said X is N or $CR_{16}$ and said $R_{16}$ is H, and thus said X is N or CH, preferably said X is CH, and said $R_{15}$ comprises at least one $ONO_2$ moieties and together at most four $ONO_2$ moieties.

In a further very preferred embodiment, said $R_{11}$, $R_{12}$, $R_{13}$, $R_{14}$ are H, said $R_{15}$ is $C_1$-$C_6$alkyl substituted with at least one substituent independently selected from OH and $ONO_2$, and said X is $CR_{16}$ and said $R_{16}$ is H, preferably said X is CH, and said $R_{15}$ comprises at least two $ONO_2$ moieties and together at most four $ONO_2$ moieties. In a further very preferred embodiment, said $R_{11}$, $R_{12}$, $R_{13}$, $R_{14}$ are H, said $R_{15}$ is $C_1$-$C_6$alkyl substituted with at least one substituent independently selected from OH and $ONO_2$, and said X is $CR_{16}$ and said $R_{16}$ is H, preferably said X is CH, and said $R_{15}$ comprises at least one $ONO_2$ moieties and together at most four $ONO_2$ moieties.

In a further very preferred embodiment, said $R_{11}$, $R_{12}$, $R_{13}$, $R_{14}$ are H, said $R_{15}$ is $C_1$-$C_6$alkyl substituted with one, two or three substituents independently selected from OH, ONO and $ONO_2$, and said $R_{16}$ is H or $C_1$-$C_6$alkyl substituted with one, two or three substituents independently selected from OH, ONO and $ONO_2$, and said $R_{15}$ and said $R_{16}$ together comprises at least one or two moieties selected from $ONO_2$ and ONO moieties and together at most four moieties selected from $ONO_2$ and ONO moieties.

In a further very preferred embodiment, said $R_{11}$, $R_{12}$, $R_{13}$, $R_{14}$ are H, said $R_{15}$ is $C_1$-$C_6$alkyl substituted with one, two or three substituents selected from OH, ONO and $ONO_2$, and said X is N or $CR_{16}$ and said $R_{16}$ is H, and thus said X is N or CH, preferably said X is CH, and said $R_{15}$ comprises at least one or two moieties selected from $ONO_2$ and ONO moieties and together at most four moieties selected from $ONO_2$ and ONO moieties. In a further very preferred embodiment, said $R_{11}$, $R_{12}$, $R_{13}$, $R_{14}$ are H, said $R_{15}$ is $C_1$-$C_6$alkyl substituted with one, two or three substituents independently selected from OH, ONO and $ONO_2$, and said X is N or $CR_{16}$ and said $R_{16}$ is H, and thus said X is N or CH, preferably said X is CH, and said $R_{15}$ comprises at least one $ONO_2$ moiety and at most four $ONO_2$ moieties.

In a further very preferred embodiment, said $R_{11}$, $R_{12}$, $R_{13}$, $R_{14}$ are H, said $R_{15}$ is $C_1$-$C_6$alkyl substituted with one, two or three substituents independently selected from OH, ONO and $ONO_2$, and said X is $CR_{16}$ and said $R_{16}$ is H, preferably said X is CH, and said $R_{15}$ comprises at least one or two moieties selected from $ONO_2$ and ONO moieties and together at most four moieties selected from $ONO_2$ and ONO moieties. In a further very preferred embodiment, said $R_{11}$, $R_{12}$, $R_{13}$, $R_{14}$ are H, said $R_{15}$ is $C_1$-$C_6$alkyl substituted with one, two or three substituents independently selected from OH, ONO and $ONO_2$, and said X is $CR_{16}$ and said $R_{16}$ is H, preferably said X is CH, and said $R_{15}$ comprises at least one $ONO_2$ moiety and at most four $ONO_2$ moieties.

In a further very preferred embodiment, said $R_{11}$, $R_{12}$, $R_{13}$, $R_{14}$ are H, and said $R_{15}$ is selected from $CH_2ONO_2$, $CH_2ONO$, $CH_2CH_2ONO$, $CH_2CH_2ONO_2$, $CH(OH)CH_2ONO_2$, $CH(OH)CH_2ONO$, $CH_2CH_2CH_2ONO_2$, $CH_2CH_2CH_2ONO$, $CH(ONO_2)CH_2OH$, $CH(ONO)CH_2OH$, $CH(ONO_2)CH_2ONO_2$, $CH(ONO)CH_2ONO_2$, $CH(ONO_2)CH_2ONO$, $C(OH)(CH_2ONO_2)CH_2ONO$, $C(OH)(CH_2ONO)CH_2ONO_2$, $C(OH)(CH_2ONO_2)CH_2ONO_2$, $C(OH)(CH_2CH_2ONO)CH_2CH_2ONO_2$, $C(OH)(CH_2CH_2ONO_2)CH_2CH_2ONO$, $C(OH)(CH_2CH_2ONO_2)CH_2CH_2ONO_2$, and wherein preferably said $R_{15}$ is selected from $CH_2ONO_2$, $CH_2CH_2ONO_2$, $CH(OH)CH_2ONO_2$, $CH_2CH_2CH_2ONO_2$, $CH(ONO_2)CH_2OH$, $CH(ONO_2)CH_2ONO_2$, $C(OH)(CH_2ONO_2)CH_2ONO_2$, $C(OH)(CH_2CH_2ONO_2)CH_2CH_2ONO_2$.

In a further very preferred embodiment, said $R_{11}$, $R_{12}$, $R_{13}$, $R_{14}$ are H, and said $R_{15}$ is selected from $CH_2ONO_2$, $CH_2ONO$, $CH_2CH_2ONO$, $CH_2CH_2ONO_2$, $CH(OH)CH_2ONO_2$, $CH(OH)CH_2ONO$, $CH_2CH_2CH_2ONO_2$, $CH_2CH_2CH_2ONO$, $CH(ONO_2)CH_2OH$, $CH(ONO)CH_2OH$, $CH(ONO_2)CH_2ONO_2$, $CH(ONO)CH_2ONO_2$, $CH(ONO_2)$ $CH_2ONO$, $C(OH)(CH_2ONO_2)CH_2ONO$, $C(OH)(CH_2ONO)CH_2ONO_2$, $C(OH)(CH_2ONO_2)CH_2ONO_2$, $C(OH)(CH_2CH_2ONO)CH_2CH_2ONO_2$, $C(OH)(CH_2CH_2ONO_2)CH_2CH_2ONO$, $C(OH)(CH_2CH_2ONO_2)CH_2CH_2ONO_2$, $CH_2CH(CH_2ONO)_2$, $CH_2CH(CH_2ONO_2)_2$, $CH_2CH(CH_2ONO_2)(CH_2ONO)$, $CH_2CH(CH_2ONO_2)(CH_2OH)$, $CH_2CH(CH_2ONO)(CH_2OH)$, $CH_2C(CH_3)(CH_2ONO)_2$, $CH_2C(CH_3)(CH_2ONO)_2$, $CH_2C(CH_3)(CH_2ONO_2)(CH_2ONO)$, $CH_2C(CH_3)(CH_2ONO_2)(CH_2OH)$, $CH_2C(CH_3)(CH_2ONO)(CH_2OH)$, and wherein preferably said $R_{15}$ is selected from $CH_2ONO_2$, $CH_2CH_2ONO_2$, $CH(OH)CH_2ONO_2$, $CH_2CH_2CH_2ONO_2$, $CH(ONO_2)CH_2OH$, $CH(ONO_2)CH_2ONO_2$, $C(OH)(CH_2ONO_2)CH_2ONO_2$, $C(OH)(CH_2CH_2ONO_2)CH_2CH_2ONO_2$, $CH_2CH(CH_2ONO_2)_2$, $CH_2CH(CH_2ONO_2)(CH_2OH)$, $CH_2C(CH_3)(CH_2ONO_2)_2$, $CH_2C(CH_3)(CH_2ONO_2)(CH_2OH)$.

In a further very preferred embodiment, said $R_{11}$, $R_{12}$, $R_{13}$, $R_{14}$ are H, and said $R_{15}$ is selected from $CH_2ONO_2$, $CH_2ONO$, $CH_2CH_2ONO$, $CH(OH)CH_2ONO_2$, $CH(OH)CH_2ONO$, $CH_2CH_2CH_2ONO_2$, $CH_2CH_2CH_2ONO$, $CH(ONO_2)CH_2OH$, $CH(ONO)CH_2OH$, $CH(ONO_2)CH_2ONO_2$, $CH(ONO)CH_2ONO_2$, $CH(ONO_2)CH_2ONO$, $C(OH)(CH_2ONO_2)CH_2ONO$, $C(OH)(CH_2ONO)CH_2ONO_2$, $C(OH)(CH_2ONO_2)CH_2ONO_2$, $C(OH)(CH_2CH_2ONO)CH_2CH_2ONO_2$, $C(OH)(CH_2CH_2ONO_2)CH_2CH_2ONO$, $C(OH)(CH_2CH_2ONO_2)CH_2CH_2ONO_2$, $CH_2CH(CH_2ONO)_2$, $CH_2CH(CH_2ONO_2)_2$, $CH_2CH(CH_2ONO_2)(CH_2ONO)$, $CH_2CH(CH_2ONO_2)(CH_2OH)$, $CH_2CH(CH_2ONO)(CH_2OH)$, $CH_2C(CH_3)(CH_2ONO)_2$, $CH_2C(CH_3)(CH_2ONO)_2$, $CH_2C(CH_3)(CH_2ONO_2)(CH_2ONO)$, $CH_2C(CH_3)(CH_2ONO_2)(CH_2OH)$, $CH_2C(CH_3)(CH_2ONO)(CH_2OH)$, and wherein preferably said $R_{15}$ is selected from $CH_2ONO_2$, $CH(OH)CH_2ONO_2$, $CH_2CH_2CH_2ONO_2$, $CH(ONO_2)CH_2OH$, $CH(ONO_2)CH_2ONO_2$, $C(OH)(CH_2ONO_2)CH_2ONO_2$, $C(OH)(CH_2CH_2ONO_2)CH_2CH_2ONO_2$, $CH_2CH(CH_2ONO_2)_2$, $CH_2CH(CH_2ONO_2)(CH_2OH)$, $CH_2C(CH_3)(CH_2ONO_2)_2$, $CH_2C(CH_3)(CH_2ONO_2)(CH_2OH)$.

In said compound of formula I is a compound of formula I*, wherein $R_1$ is $C_1$-$C_2$alkyl; $R_2$ is $C_1$-$C_3$alkyl or $C_3$-$C_6$cycloalkyl; $R_3$ is $C_1$-$C_4$alkyl; $R_{11}$, $R_{12}$, $R_{13}$, $R_{14}$ are H, said $R_{15}$ is selected from $CH_2ONO_2$, $CH_2ONO$, $CH_2CH_2ONO$, $CH_2CH_2ONO_2$, $CH(OH)CH_2ONO_2$, $CH(OH)CH_2ONO$, $CH_2CH_2CH_2ONO_2$, $CH_2CH_2CH_2ONO$, $CH(ONO_2)CH_2OH$, $CH(ONO)CH_2OH$, $CH(ONO_2)CH_2ONO_2$, $CH(ONO)CH_2ONO_2$, $CH(ONO_2)CH_2ONO$, $C(OH)(CH_2ONO_2)CH_2ONO$, $C(OH)(CH_2ONO)CH_2ONO_2$, $C(OH)(CH_2ONO_2)CH_2ONO_2$, $C(OH)(CH_2CH_2ONO)CH_2CH_2ONO_2$, $C(OH)(CH_2CH_2ONO_2)CH_2CH_2ONO$, $C(OH)(CH_2CH_2ONO_2)CH_2CH_2ONO_2$, and wherein preferably $R_{15}$ is selected from $CH_2ONO_2$, $CH_2CH_2ONO_2$, $CH(OH)CH_2ONO_2$, $CH_2CH_2CH_2ONO_2$, $CH(ONO_2)CH_2OH$, $CH(ONO_2)CH_2ONO_2$, $C(OH)(CH_2ONO_2)CH_2ONO_2$, $C(OH)(CH_2CH_2ONO_2)CH_2CH_2ONO_2$; and preferably $R_{16}$ is H.

In said compound of formula I is a compound of formula P, wherein $R_1$ is $C_1$-$C_2$alkyl; $R_2$ is $C_1$-$C_3$alkyl or $C_3$-$C_6$cycloalkyl; $R_3$ is $C_1$-$C_4$alkyl; $R_{11}$, $R_{12}$, $R_{13}$, $R_{14}$ are H, said $R_{15}$ is selected from $CH_2ONO_2$, $CH_2ONO$, $CH_2CH_2ONO$, $CH_2CH_2ONO_2$, $CH(OH)CH_2ONO_2$, $CH(OH)CH_2ONO$, $CH_2CH_2CH_2ONO_2$, $CH_2CH_2CH_2ONO$, $CH(ONO_2)CH_2OH$, $CH(ONO)CH_2OH$, $CH(ONO_2)CH_2ONO_2$, $CH(ONO)CH_2ONO_2$, $CH(ONO_2)CH_2ONO$, $C(OH)(CH_2ONO_2)CH_2ONO$, $C(OH)(CH_2ONO)CH_2ONO_2$, $C(OH)(CH_2ONO_2)CH_2ONO_2$, $C(OH)(CH_2CH_2ONO)CH_2CH_2ONO_2$, $C(OH)(CH_2CH_2ONO_2)CH_2CH_2ONO$, $C(OH)(CH_2CH_2ONO_2)CH_2CH_2ONO_2$, $CH_2CH(CH_2ONO)_2$, $CH_2CH(CH_2ONO_2)_2$, $CH_2CH(CH_2ONO_2)(CH_2ONO)$, $CH_2CH(CH_2ONO_2)(CH_2OH)$, $CH_2CH(CH_2ONO)(CH_2OH)$, $CH_2C(CH_3)(CH_2ONO)_2$, $CH_2C(CH_3)(CH_2ONO)_2$, $CH_2C(CH_3)(CH_2ONO_2)(CH_2ONO)$, $CH_2C(CH_3)(CH_2ONO_2)(CH_2OH)$, $CH_2C(CH_3)(CH_2ONO)(CH_2OH)$, and wherein preferably $R_{15}$ is selected from $CH_2ONO_2$, $CH_2CH_2ONO_2$, $CH(OH)CH_2ONO_2$, $CH_2CH_2CH_2ONO_2$, $CH(ONO_2)CH_2OH$, $CH(ONO_2)CH_2ONO_2$, $C(OH)(CH_2ONO_2)CH_2ONO_2$, $C(OH)(CH_2CH_2ONO_2)CH_2CH_2ONO_2$, $CH_2CH(CH_2ONO_2)_2$, $CH_2CH(CH_2ONO_2)(CH_2OH)$, $CH_2C(CH_3)(CH_2ONO_2)_2$, $CH_2C(CH_3)(CH_2ONO_2)(CH_2OH)$; and preferably $R_{16}$ is H.

In said compound of formula I is a compound of formula I*, wherein $R_1$ is $C_1$-$C_2$alkyl; $R_2$ is $C_1$-$C_3$alkyl or $C_3$-$C_6$cycloalkyl; $R_3$ is $C_1$-$C_4$alkyl; $R_{11}$, $R_{12}$, $R_{13}$, $R_{14}$ are H, said $R_{15}$ is selected from $CH_2ONO_2$, $CH_2ONO$, $CH_2CH_2ONO$, $CH(OH)CH_2ONO_2$, $CH(OH)CH_2ONO$, $CH_2CH_2CH_2ONO_2$, $CH_2CH_2CH_2ONO$, $CH(ONO_2)CH_2OH$, $CH(ONO)CH_2OH$, $CH(ONO_2)CH_2ONO_2$, $CH(ONO)CH_2ONO_2$, $CH(ONO_2)CH_2ONO$, $C(OH)(CH_2ONO_2)CH_2ONO$, $C(OH)(CH_2ONO)CH_2ONO_2$, $C(OH)(CH_2ONO_2)CH_2ONO_2$, $C(OH)(CH_2CH_2ONO)CH_2CH_2ONO_2$, $C(OH)(CH_2CH_2ONO_2)CH_2CH_2ONO$, $C(OH)(CH_2CH_2ONO_2)CH_2CH_2ONO_2$, $CH_2CH(CH_2ONO)_2$, $CH_2CH(CH_2ONO_2)_2$, $CH_2CH(CH_2ONO_2)(CH_2ONO)$, $CH_2CH(CH_2ONO_2)(CH_2OH)$, $CH_2CH(CH_2ONO)(CH_2OH)$, $CH_2C(CH_3)(CH_2ONO)_2$, $CH_2C(CH_3)(CH_2ONO)_2$, $CH_2C(CH_3)(CH_2ONO_2)(CH_2ONO)$, $CH_2C(CH_3)(CH_2ONO_2)(CH_2OH)$, $CH_2C(CH_3)(CH_2ONO)(CH_2OH)$, and wherein preferably $R_{15}$ is selected from $CH_2ONO_2$, $CH(OH)CH_2ONO_2$, $CH_2CH_2CH_2ONO_2$, $CH(ONO_2)CH_2OH$, $CH(ONO_2)CH_2ONO_2$, $C(OH)(CH_2ONO_2)CH_2ONO_2$, $C(OH)(CH_2CH_2ONO_2)CH_2CH_2ONO_2$, $CH_2CH(CH_2ONO_2)_2$, $CH_2CH(CH_2ONO_2)(CH_2OH)$, $CH_2C(CH_3)(CH_2ONO_2)_2$, $CH_2C(CH_3)(CH_2ONO_2)(CH_2OH)$; and preferably $R_{16}$ is H.

In a further very preferred embodiment, said $R_{15}$ is selected from $CH_2ONO_2$, $CH_2ONO$, $CH_2CH_2ONO$, $CH_2CH_2ONO_2$, and wherein preferably $R_{15}$ is selected from $CH_2ONO_2$ or $CH_2CH_2ONO_2$. In a further very preferred embodiment, said $R_{11}$, $R_{12}$, $R_{13}$, $R_{14}$ are H, and said $R_{15}$ is selected from $CH_2ONO_2$, $CH_2ONO$, $CH_2CH_2ONO$, $CH_2CH_2ONO_2$, and wherein preferably $R_{15}$ is selected from $CH_2ONO_2$ or $CH_2CH_2ONO_2$. In a further very preferred embodiment, said $R_{16}$ is selected from $CH_2ONO_2$, $CH_2ONO$, $CH_2CH_2ONO$, $CH_2CH_2ONO_2$, and wherein preferably $R_{16}$ is selected from $CH_2ONO_2$ or $CH_2CH_2ONO_2$. In a further preferred embodiment, said $R_{15}$ is $C_2$-$C_3$alkyl substituted with OH or $ONO_2$, preferably $C_2$-$C_3$alkyl substituted with one, two or three OH or $ONO_2$, further preferably $C_2$-$C_3$alkyl substituted with one OH, or one or two $ONO_2$.

In a further very preferred embodiment, said $R_{15}$ is selected from $CH_2C(CH_3)(CH_2ONO)_2$, $CH_2C(CH_3)(CH_2ONO)_2$, $CH_2C(CH_3)(CH_2ONO_2)(CH_2ONO)$, $CH_2C(CH_3)(CH_2ONO_2)(CH_2OH)$, $CH_2C(CH_3)(CH_2ONO)(CH_2OH)$, and wherein preferably $R_{15}$ is selected from $CH_2C(CH_3)(CH_2ONO_2)_2$, $CH_2C(CH_3)(CH_2ONO_2)(CH_2OH)$. In a further very preferred embodiment, said $R_{11}$, $R_{12}$, $R_{13}$, $R_{14}$ are H, and said $R_{15}$ is selected from $CH_2C(CH_3)(CH_2ONO)_2$, $CH_2C(CH_3)(CH_2ONO)_2$, $CH_2C(CH_3)(CH_2ONO_2)(CH_2ONO)$, $CH_2C(CH_3)(CH_2ONO_2)(CH_2OH)$, $CH_2C(CH_3)(CH_2ONO)(CH_2OH)$, and wherein preferably $R_{15}$ is selected from $CH_2C(CH_3)(CH_2ONO_2)_2$, $CH_2C(CH_3)(CH_2ONO_2)(CH_2OH)$. In a further very preferred embodiment, said $R_{16}$ is selected from $CH_2C(CH_3)$ $(CH_2ONO)_2$, $CH_2C(CH_3)(CH_2ONO)_2$, $CH_2C(CH_3)(CH_2ONO_2)(CH_2ONO)$, $CH_2C(CH_3)(CH_2ONO_2)(CH_2OH)$, $CH_2C(CH_3)(CH_2ONO)(CH_2OH)$ and wherein preferably $R_{16}$ is selected from $CH_2C(CH_3)(CH_2ONO_2)_2$, $CH_2C(CH_3)(CH_2ONO_2)(CH_2OH)$. In a further preferred embodiment, said $R_{15}$ is $C_3$-$C_6$alkyl substituted with OH or $ONO_2$, preferably $C_3$-$C_6$alkyl substituted with one, two or three OH or $ONO_2$, further preferably $C_3$-$C_6$alkyl substituted with one OH, or one or two $ONO_2$. In a further preferred embodiment, said $R_{15}$ is $C_4$-$C_5$alkyl substituted with OH or $ONO_2$, preferably $C_4$-$C_5$alkyl substituted with one, two or three OH or $ONO_2$, further preferably $C_3$-$C_6$alkyl substituted with one OH, or one or two $ONO_2$.

Further very preferred embodiments of the present invention are represented by individual compounds of formula I or II or pharmaceutically acceptable salts, solvates or hydrates thereof.

Thus, in another very preferred embodiment, said compound of formula I or II is selected from (R)-1-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)ethane-1,2-diyl dinitrate (1a)

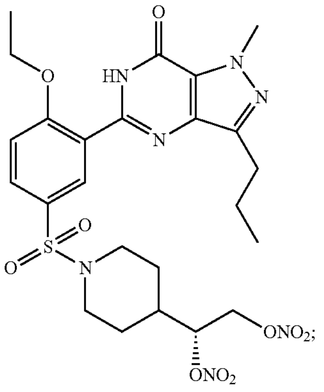

(S)-1-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)ethane-1,2-diyl dinitrate (1b)

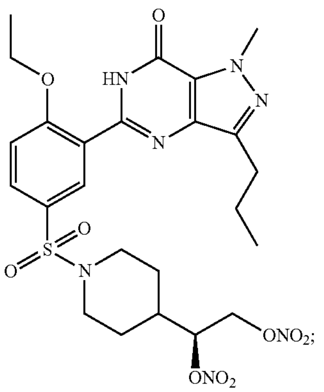

(R)-2-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-2-hydroxyethyl nitrate (1c)

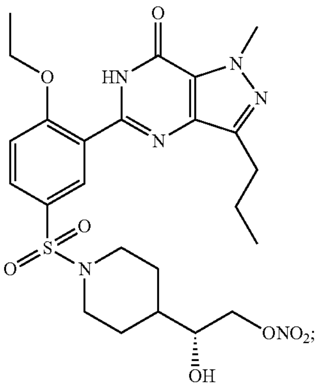

(S)-2-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-2-hydroxyethyl nitrate (1d)

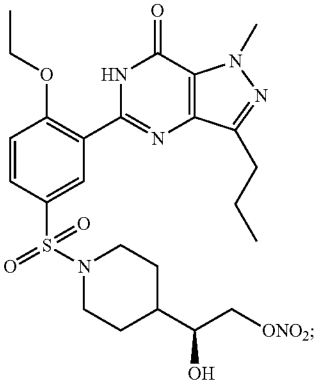

3-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-3-hydroxypropyl nitrate Enantiomer A (1e)

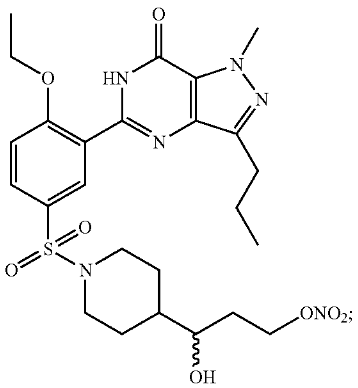

3-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-3-hydroxypropyl nitrate Enantiomer B (1f)

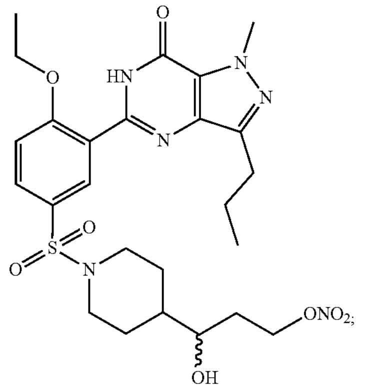

3-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-3,5-dihydroxypentyl nitrate (1g)

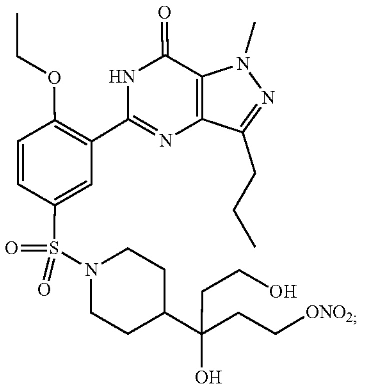

3-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-3-hydroxypentane-1,5-diyl dinitrate (1h)

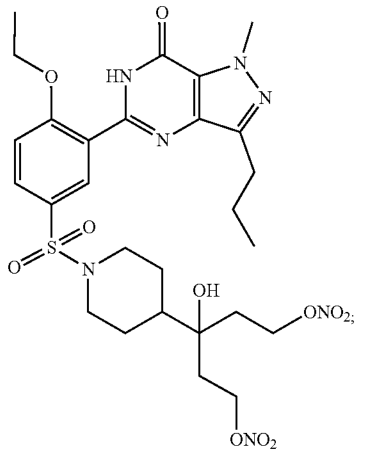

2-((1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)(hydroxy)methyl)propane-1,3-diyl dinitrate (Racemate)

(1i)

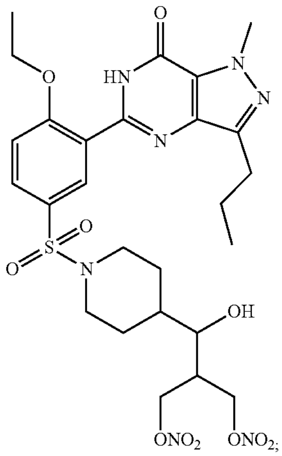

1-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-2-hydroxyethyl nitrate Enantiomer A (1k)

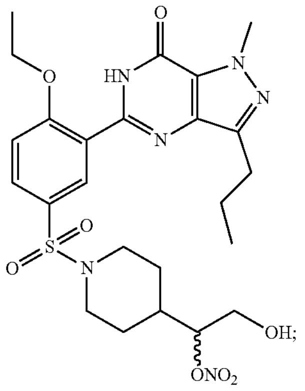

1-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-2-hydroxyethyl nitrate Enantiomer B (1l)

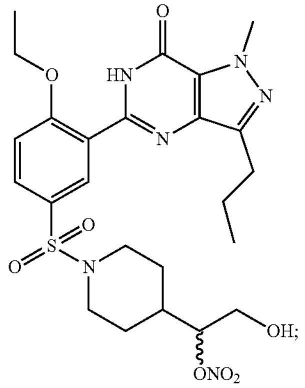

(R)-1-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)ethane-1,2-diyl dinitrate (2a)

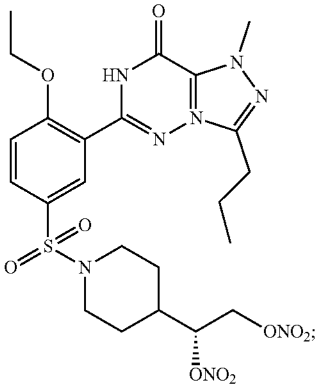

(S)-1-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)ethane-1,2-diyl dinitrate (2b)

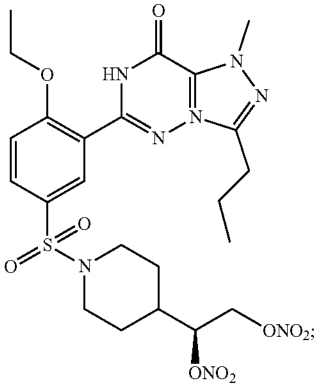

(R)-2-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-hydroxyethyl nitrate (2c)

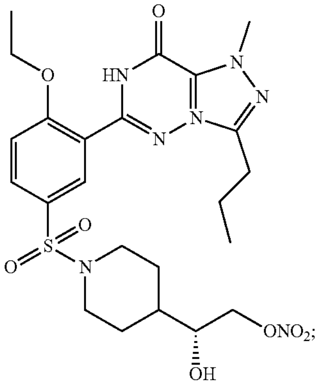

(S)-2-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-hydroxyethyl nitrate (2d)

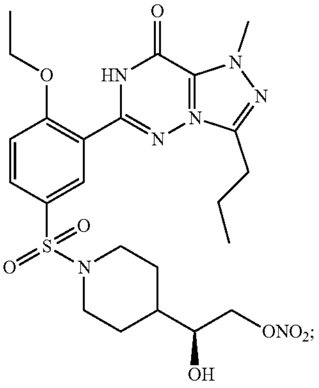

3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-3-hydroxypropyl nitrate Enantiomer A (2e)

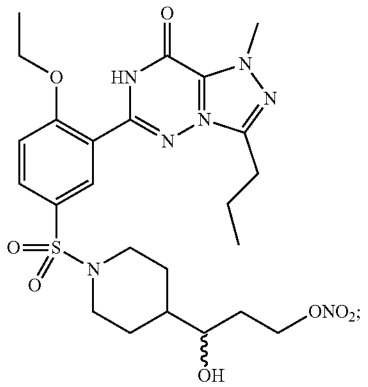

3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-3-hydroxypropyl nitrate Enantiomer B (2f)

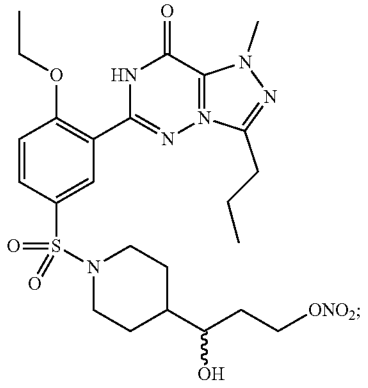

3-(1-((4-ethoxy-3-(5-methyl-4-oxo-7-propyl-3,4-dihydro-imidazo[5,1-f][1,2,4]triazin-2-yl)phenyl)sulfonyl)piperidin-4-yl)-3,5-dihydroxypentyl nitrate (2g)

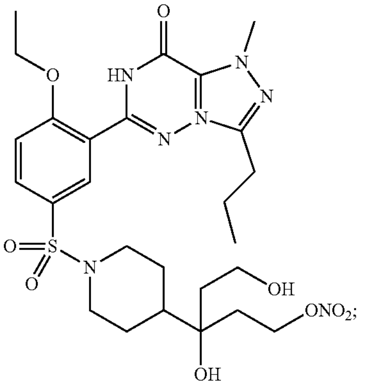

3-(1-((4-ethoxy-3-(5-methyl-4-oxo-7-propyl-3,4-dihydro-imidazo[5,1-f][1,2,4]triazin-2-yl)phenyl)sulfonyl)piperidin-4-yl)-3-hydroxypentane-1,5-diyl dinitrate (2h)

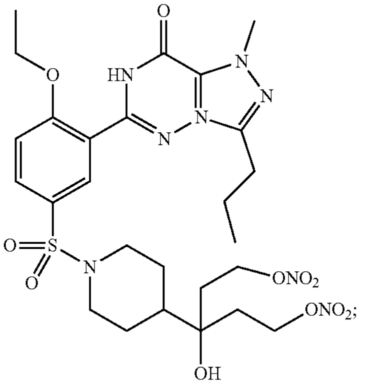

2-((1-((4-ethoxy-3-(5-methyl-4-oxo-7-propyl-3,4-dihydro-imidazo[5,1-f][1,2,4]triazin-2-yl)phenyl)sulfonyl)piperidin-4-yl)(hydroxy)methyl)propane-1,3-diyl dinitrate (2i)

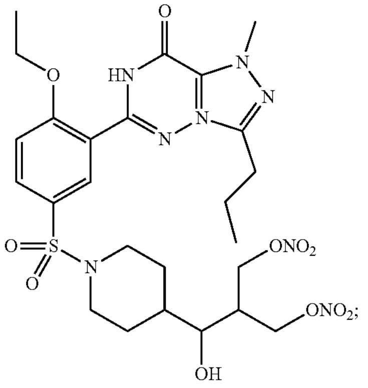

1-(1-((4-ethoxy-3-(5-methyl-4-oxo-7-propyl-3,4-dihydro-imidazo[5,1-f][1,2,4]triazin-2-yl)phenyl)sulfonyl)piperidin-4-yl)-2-hydroxyethyl nitrate Enantiomer A (2k)

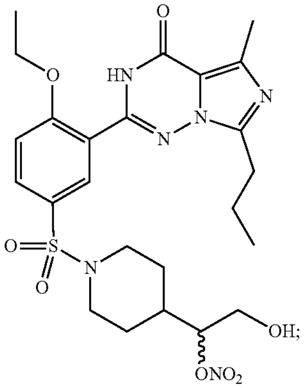

1-(1-((4-ethoxy-3-(5-methyl-4-oxo-7-propyl-3,4-dihydro-imidazo[5,1-f][1,2,4]triazin-2-yl)phenyl)sulfonyl)piperidin-4-yl)-2-hydroxyethyl nitrate Enantiomer B (2l)

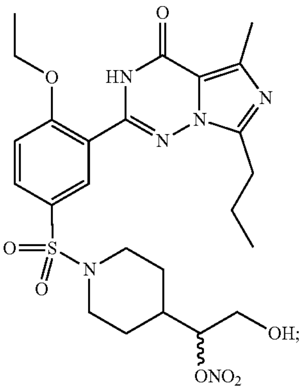

2-((1-((4-ethoxy-3-(5-methyl-4-oxo-7-propyl-3,4-dihydro-imidazo[5,1-f][1,2,4]triazin-2-yl)phenyl)sulfonyl)piperidin-4-yl)methyl)propane-1,3-diyl dinitrate (2m)

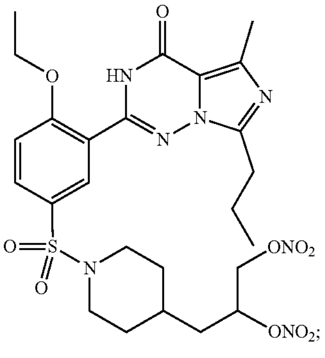

3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-(hydroxymethyl)propyl nitrate (2n)

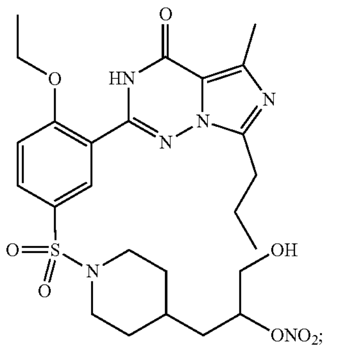

2-((1-((4-ethoxy-3-(5-methyl-4-oxo-7-propyl-3,4-dihydroimidazo[5,1-f][1,2,4]triazin-2-yl)phenyl)sulfonyl)piperidin-4-yl)methyl)-2-methylpropane-1,3-diyl dinitrate (2o)

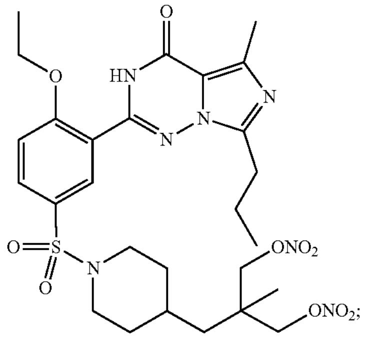

and 3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-(hydroxymethyl)-2-methylpropyl nitrate (2p)

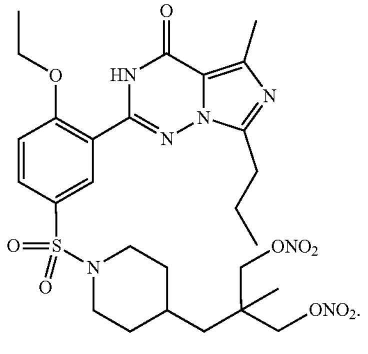

In a further very preferred embodiment, said compound is a compound of formula I, and wherein said compound is selected from (R)-1-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)ethane-1,2-diyl dinitrate (1a);

(S)-1-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)ethane-1,2-diyl dinitrate (1b);

(R)-2-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-2-hydroxyethyl nitrate (1c);

(S)-2-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-2-hydroxyethyl nitrate (1d);

3-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-3-hydroxypropyl nitrate Enantiomer A (1e);

3-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-3-hydroxypropyl nitrate Enantiomer B (1f);

3-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-3,5-dihydroxypentyl nitrate (1g);

3-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-3-hydroxypentane-1,5-diyl dinitrate (1h); and 2-((1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)(hydroxy)methyl)propane-1,3-diyl dinitrate (1i);

1-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-2-hydroxyethyl nitrate Enantiomer A (1k); and 1-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-2-hydroxyethyl nitrate Enantiomer B (1l).

In a further very preferred embodiment, said compound is a compound of formula I, and wherein said compound is selected from (R)-1-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)ethane-1,2-diyl dinitrate (2a);

(S)-1-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)ethane-1,2-diyl dinitrate (2b);

(R)-2-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-hydroxyethyl nitrate (2c);

(S)-2-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-hydroxyethyl nitrate (2d);

3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-3-hydroxypropyl nitrate Enantiomer A (2e);

3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-3-hydroxypropyl nitrate Enantiomer B (2f);

3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-3,5-dihydroxypentyl nitrate (2g);

3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-3-hydroxypentane-1,5-diyl dinitrate (2h);

2-((1-((4-ethoxy-3-(5-methyl-4-oxo-7-propyl-3,4-dihydroimidazo[5,1-f][1,2,4]triazin-2-yl)phenyl)sulfonyl)piperidin-4-yl)(hydroxy)methyl)propane-1,3-diyl dinitrate (2i);

1-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-hydroxyethyl nitrate Enantiomer A (2k);

1-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-hydroxyethyl nitrate Enantiomer B (2l)

2-((1-((4-ethoxy-3-(5-methyl-4-oxo-7-propyl-3,4-dihydroimidazo[5,1-f][1,2,4]triazin-2-yl)phenyl)sulfonyl)piperidin-4-yl)methyl)propane-1,3-diyl dinitrate (2m);

3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-(hydroxymethyl)propyl nitrate (2n);

2-((1-((4-ethoxy-3-(5-methyl-4-oxo-7-propyl-3,4-dihydroimidazo[5,1-f][1,2,4]triazin-2-yl)phenyl)sulfonyl)piperidin-4-yl)methyl)-2-methylpropane-1,3-diyl dinitrate (2o); and 3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-(hydroxymethyl)-2-methylpropyl nitrate (2p).

Figure 2:
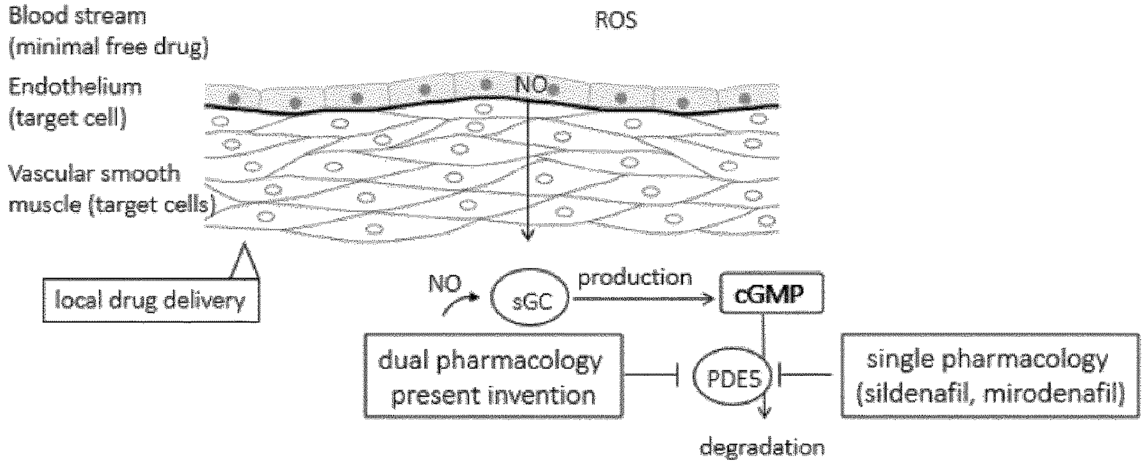
FIG. 2: Dual-pharmacology NO-releasing PDE5 inhibitors addressing disturbed cGMP balance in diseases with disturbed cGMP balance.

It has been shown that compounds of the present invention are potent and selective inhibitors of cGMP specific PDE. Furthermore, it has been found that the compounds of the present invention are dual-pharmacology NO-releasing PDE5 inhibitors believed to release NO in addition to its PDE5 inhibition in a more than additive fashion. Thus, compounds of formula I or II are of interest for use in therapy, specifically for the treatment of a variety of conditions where inhibition of cGMP specific PDE is thought to be beneficial. Given the discovery of strong plasma protein binding the compounds of the present invention are especially suited for local action after local application (see FIG. 2).

Thus, in a further aspect, the present invention provides for a pharmaceutical composition comprising at least one of the inventive compounds of formula I or II, or a pharmaceutically acceptable salt, solvate or hydrate thereof, and a pharmaceutically acceptable excipient, adjuvant, or carrier.

Thus, in a further aspect, the present invention provides for a pharmaceutical composition comprising at least one of the inventive compounds of formula I or a pharmaceutically acceptable salt, solvate or hydrate thereof, and a pharmaceutically acceptable excipient, adjuvant, or carrier.

Thus, in a further aspect, the present invention provides for a pharmaceutical composition comprising at least one of the inventive compounds of formula II, or a pharmaceutically acceptable salt, solvate or hydrate thereof, and a pharmaceutically acceptable excipient, adjuvant, or carrier.

In another aspect, the present invention provides for a pharmaceutical composition comprising exactly one inventive compound of formula I or II, or a pharmaceutically acceptable salt, solvate or hydrate thereof, and a pharmaceutically acceptable excipient, adjuvant, or carrier. Pharmaceutically acceptable excipient, adjuvant, or carrier are known to the skilled person.

In another aspect, the present invention provides for a pharmaceutical composition comprising exactly one inventive compound of formula I or a pharmaceutically acceptable salt, solvate or hydrate thereof, and a pharmaceutically acceptable excipient, adjuvant, or carrier. Pharmaceutically acceptable excipient, adjuvant, or carrier are known to the skilled person.

In another aspect, the present invention provides for a pharmaceutical composition comprising exactly one inventive compound of formula II or a pharmaceutically acceptable salt, solvate or hydrate thereof, and a pharmaceutically acceptable excipient, adjuvant, or carrier. Pharmaceutically acceptable excipient, adjuvant, or carrier are known to the skilled person.

In another aspect, the present invention provides for a compound of formula I or II, or a pharmaceutical composition, or a pharmaceutically acceptable salt, solvate or hydrate thereof, for use as a medicament.

In another aspect, the present invention provides for a compound of formula I or a pharmaceutical composition, or a pharmaceutically acceptable salt, solvate or hydrate thereof, for use as a medicament.

In another aspect, the present invention provides for a compound of formula II or a pharmaceutical composition, or a pharmaceutically acceptable salt, solvate or hydrate thereof, for use as a medicament.

In another aspect, the present invention provides for a compound of formula I or II, or a pharmaceutically acceptable salt, solvate or hydrate thereof, for use as a pharmaceutical. In again another aspect, the present invention provides for a compound of formula I or II, or a pharmaceutically acceptable salt, solvate or hydrate thereof, for use as an animal medicament.

Figure 3A:
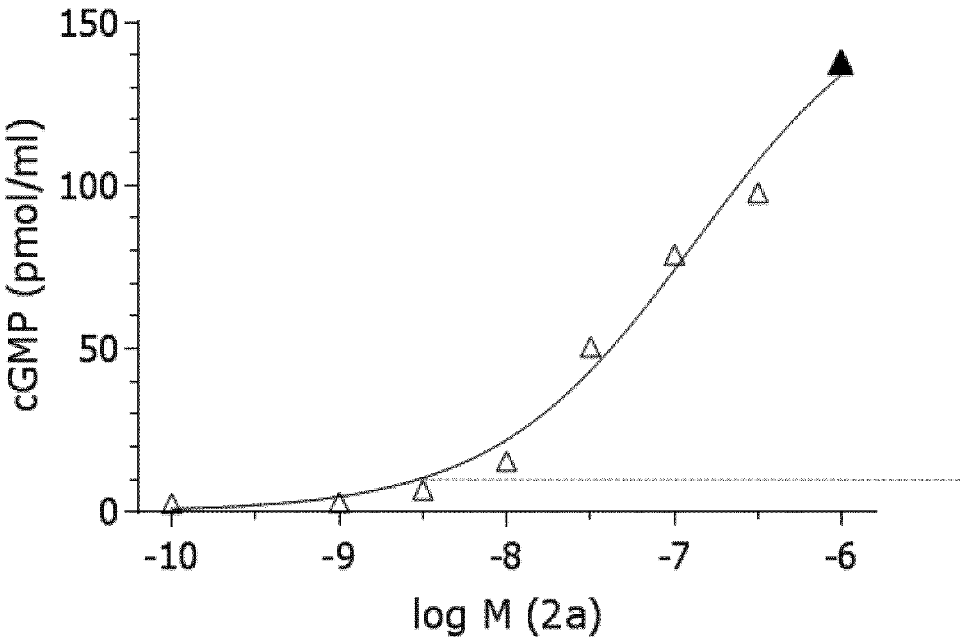
FIG. 3A: Concentration dependent measurements of cyclic guanosine 3'-5'-monophosphate (cGMP) in Human Trabecular Meshwork Cells (HTMC) stimulated with 10 μM Riociguat incubated in presence of 2a, a compound of this invention.
Figure 3B:
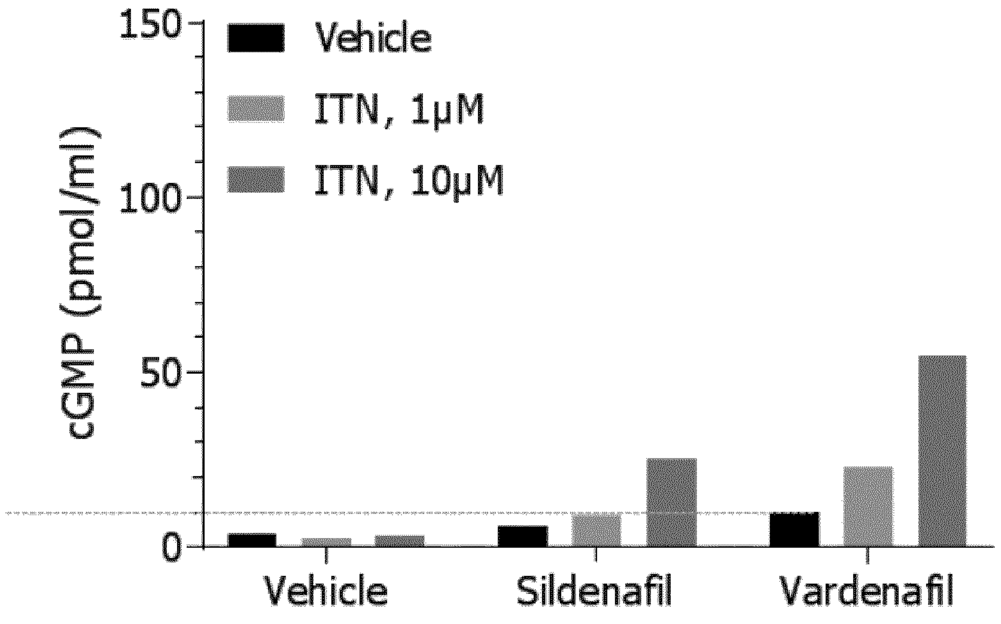
FIG. 3B: Measurements of cyclic guanosine 3'-5'-monophosphate (cGMP) in Human Trabecular Meshwork Cells (HTMC) stimulated with 10 μM Riociguat incubated in presence of 1 μM sildenafil or 1 μM vardenafil and 0, 1, 10 1 μM Isosorbid 2-nitrate.

As shown in FIG. 3A and FIG. 3B over-additive effects as compared to the organic nitrate ester ITN and PDE5 inhibitors sildenafil or vardenafil to elevate cGMP in HTMC in the presence of Riociguat, a soluble guanylate cyclase (sGC) stimulator were obtained with compounds of this invention.

Thus, in another aspect and a preferred embodiment of the present invention, the inventive pharmaceutical compositions further comprise at least one sGC stimulator, wherein preferably said sGC stimulator is selected from the group consisting of riociguat, vericiguat, praliciguat and olinciguat.

Soluble guanylyl cyclase (sGC) stimulators are known in the art and have been described (E S. Buys et al, Nitric Oxide 78 (2018) 72-80; P. Sandner et al, Nitric Oxide 77 (2018) 88-95; P. Sandner et al, Gerontology 63 (2017) 216-227). sGC stimulators are typically small molecule drugs that synergistically increase sGC enzyme activity with NO by binding to sGC and potentiate NO-mediated cGMP signaling. Soluble guanylyl cyclase (sGC) stimulators are typically applied orally. Beside the sGC stimulators already approved by the FDA (Riociguat) or tested in clinical trials (Vericiguat, Praliciguat, Olinciguat) further sGC stimulators are currently in development phase or have been reported such as IW-64630 (E S. Buys et al, Nitric Oxide 78 (2018) 72-80), A-330619, A-344905 and A-778935 (L. N. Miller, et al, Life Sci. 72 (9) (2003) 1015-1025), BAY 41-2272 (A. Straub, et al, Bioorg. Med. Chem. Lett 11 (6) (2001) 781-784; DE19834047; DE19942809), BAY 41-8543 (J. P. Stasch, et al, Br. J. Pharmacol. 135 (2) (2002) 333-343; J. P. Stasch, et al, Br. J. Pharmacol. 135 (2) (2002) 344-35; N. Wilck, et al, JCI Insight 3 (4) (2018); DE19834044), CFM-1571 (D. L. Selwood, et al, J. Med. Chem. 44 (1) (2001) 78-93; WO2000027394), GSK2181236 A (M. H. Costell, et al, Front. Pharmacol. 3 (2012) 128), IWP-051 (T. Nakai, et al, ACS Med. Chem. Lett. 7 (5) (2016) 465-46), IWP-550 (G. Liu, et al, In Experimental Biology (2018) (San Diego)), IWP-854 (J. A. Wales, et al, J. Biol. Chem. 293 (5) (2018) 1850-1864), IWP-953 (P. Ge, et al, Invest. Ophthalmol. Vis. Sci. 57 (3) (2016) 1317-1326), Etriciguat (WO2003086407), Nelociguat (BAY 60-4552, WO 2003095451), and YC-1 (F. N. Ko, et al, Blood 84 (12) (1994) 4226-4233; A. Mulsch, et al, Br. J. Pharmacol. 120 (4) (1997) 681-689, EP667345)

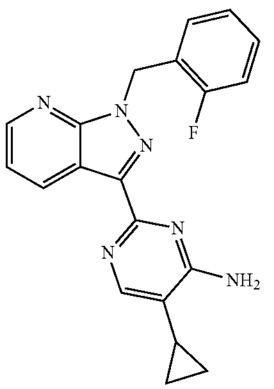

BAY 41-2272

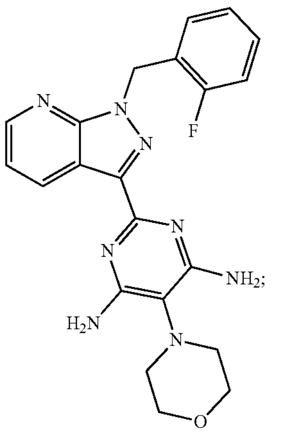

BAY 41-8543

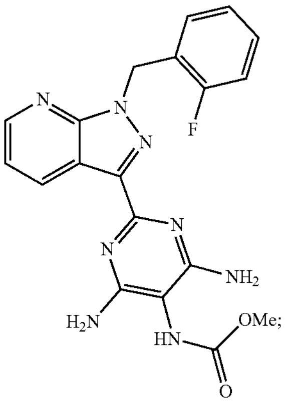

Nelociguat

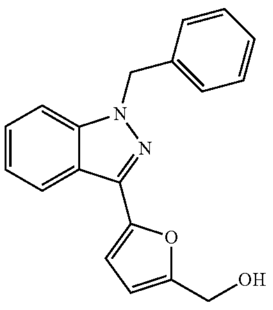

YC-1

-continued

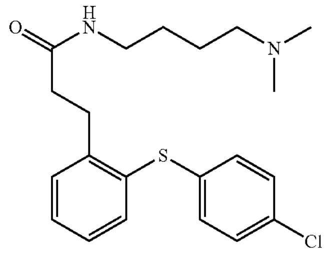

A-344905

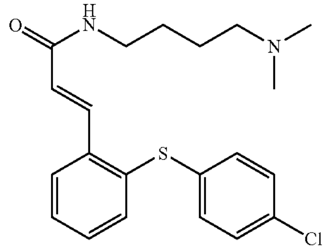

A-344619

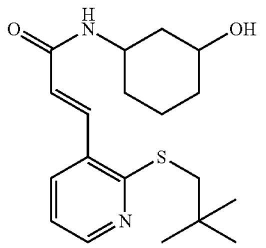

A-778935

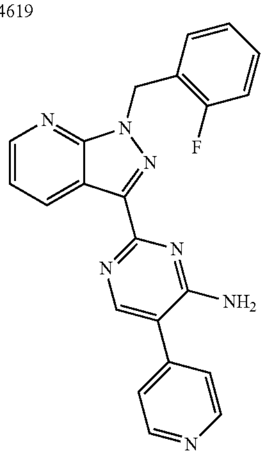

Etriciguat

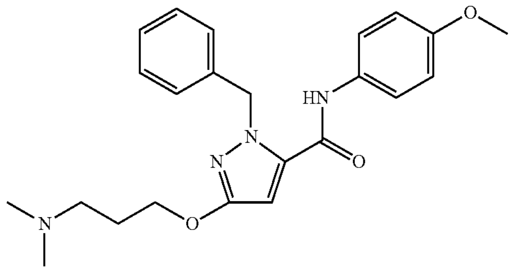

CFM-1571

These and further sGC stimulators have also been described in WO2009032249, WO2009094242, WO2010099054, WO2010065275, WO2011119518, WO2011149921, WO2012058132 and in Tetrahedron Letters (2003), 44(48): 8661-8663.

Thus, in a preferred embodiment, said sGC stimulator is selected from the group consisting Riociguat, Vericiguat, Praliciguat, Olinciguat, IW-64630, A-330619, A-344905, A-778935, BAY 41-2272, BAY 41-8543, CFM-1571, GSK2181236 A, IWP-051, IWP-550, IWP-854, IWP-953, etriciguat, nelociguat and YC-1, and wherein further preferably said sGC stimulator is selected from the group consisting Riociguat, Vericiguat, Praliciguat and Olinciguat.

Riociguat is a well-known stimulator of soluble guanylate cyclase (sGC), is $C_{20}H_{19}FN_8O_2$—Carbamic acid, N-[4,6-diamino-2-[1-[(2-fluorophenyl)methyl]-1H-pyrazolo[3,4-b]pyridin-3-yl]-5-pyrimidinyl]-N-methyl-, methyl ester (J. Mittendorf, et al, ChemMedChem 4 (5) (2009) 853-865; DE19834044):

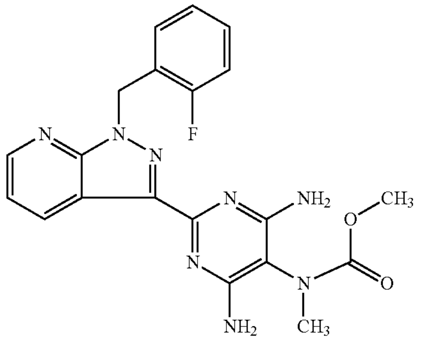 [SMILES: COC(=O)N(C)c1c(N)nc(-c2nn(Cc3ccccc3F)c3ncccc23)nc1N]

Vericiguat is a further known stimulator of soluble guanylate cyclase (sGC), is $C_{19}H_{16}F_2N_8O_2$—Carbamic acid, N-[4,6-diamino-2-[5-fluoro-1-[(2-fluorophenyl)methyl]-1H-pyrazolo[3,4-b]pyridin-3-yl]-5-pyrimidinyl]-, methyl ester (J. P. Stasch, O. V. Evgenov, Handb. Exp. Pharmacol. 218 (2013) 279-313; M. Follmann, et al, J. Med. Chem. 60 (12) (2017) 5146-5161):

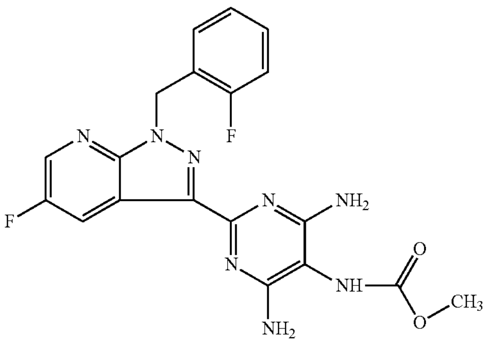 [SMILES: COC(=O)Nc1c(N)nc(-c2nn(Cc3ccccc3F)c3ncc(F)cc23)nc1N]

Praliciguat is a further known stimulator of soluble guanylate cyclase (sGC), is $C_{21}H_{14}F_8N_6O_2$—2-Propanol, 1,1,1,3,3,3,-hexafluoro-2-[[[5-fluoro-2-[1-[(2-fluorophenyl)methyl]-5-(3-isoxazolyl)-1H-pyrazol-3-yl]-4-pyrimidinyl]amino]methyl]-.

(R. Flores-Costa, et al, Br. J. Pharmacol. 175 (6) (2018) 953-967):

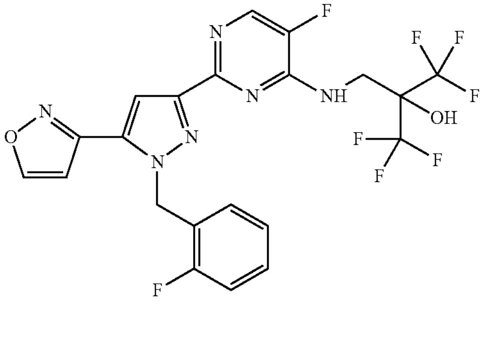 [SMILES: OC(CNc1nc(-c2cc(-c3ccon3)n(Cc3ccccc3F)n2)ncc1F)(C(F)(F)F)C(F)(F)F]

Olinciguat is a further known stimulator of soluble guanylate cyclase (sGC), is $C_{21}H_{16}F_5N_7O_3$—Propanamide, 3,3,3,-trifluoro-2-[[[5-fluoro-2-[1-[(2-fluorophenyl)methyl]-5-(3-isoxazolyl)-1H-pyrazol-3-yl]-4-pyrimidinyl]amino]methyl]-2-hydroxy-, (2R)—

(E S. Buys et al, Nitric Oxide 78 (2018) 72-80):

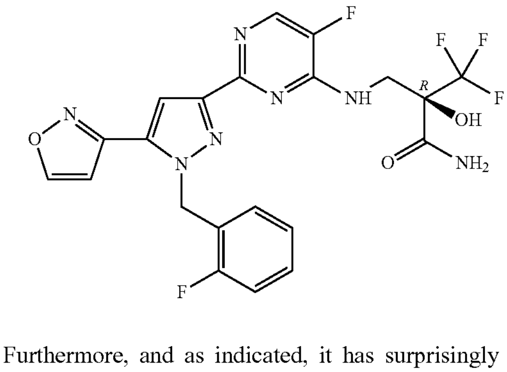

Furthermore, and as indicated, it has surprisingly been found that the compounds as well as the pharmaceutical compositions of the present invention are dual-pharmacology NO-releasing PDE5 inhibitors believed to release NO in addition to its PDE5 inhibition in a more than additive fashion. As a consequence, the novel compounds of the present invention are useful in the therapy and prophylaxis of diseases which are associated with a disturbed cGMP balance. In particular, the compounds of the present invention are activators of soluble guanylyl cyclase (sGC) potent and at the same time selective inhibitors of cyclic guanosine 3'-5'-monophosphate specific phosphodiesterase 5 (cGMP specific PDE5) and thus have utility in variety of therapeutic areas where such inhibition is beneficial.

Some of the preferred therapeutic areas are wound healing, in particular chronic wound healing, diabetic foot, diabetic foot ulcer, leg ulcer, Raynaud's, glaucoma, diabetic retinopathy, age dependent macular degeneration, male erectile dysfunction, female sexual dysfunction, diabetes, hair loss, skin aging, vascular aging, pulmonary artery hypertension and livedoid vasculopathy, thromboangitis obliterans, chronic anal fissure, skin fibrosis.

As a consequence of the selective PDE5 inhibition exhibited by compounds of the present invention, cGMP levels are expected to be elevated, which in turn can give rise to beneficial anti-platelet, anti-vasospastic, vasodilatory, natriuretic and diuretic activities as well as potentiation of the effects of endothelium-derived relaxing factor (EDRF) nitric oxide (NO), nitrovasodilators, atrial natriuretic factor (ANF), brain natriuretic peptide (BNP), C-type natriuretic peptide (CNP) and endothelium-dependent relaxing agents such as bradykinin, acetylcholine and 5-$HT_1$. The compounds of formula I or II therefore have utility in the treatment of a number of disorders, including stable, unstable and variant (Prinzmetal) angina, hypertension, pulmonary hypertension, congestive heart failure, renal failure, atherosclerosis, conditions of reduced blood vessel patency (e.g. post-percutaneous transluminal coronary angioplasty), peripheral vascular disease, vascular disorders such as Raynaud's disease, diabetic retinopathy, age dependent macular degeneration, male erectile dysfunction, female sexual dysfunction, inflammatory diseases, stroke, bronchitis, chronic asthma, allergic asthma, allergic rhinitis, diabetes, glaucoma and diseases characterized by disorders of gut motility like irritable bowel syndrome, wound healing, in particular chronic wound healing, diabetic foot, diabetic foot ulcer, leg ulcer, Alzheimer's disease, hair loss, skin aging, vascular aging, pulmonary artery hypertension and chronic heart failure, cancer such as breast and gastrointestinal cancers, non-small cell lung cancer, skin cancers such as melanoma, head and neck cancer, myeloma and head and neck squamous cell carcinoma, colon and rectal cancers such as colorectal cancer, and prostate and pancreatic cancers, and in particular colorectal cancer.

Thus, in another aspect, the present invention provides for a compound of formula I or II, or a pharmaceutical composition, or a pharmaceutically acceptable salt, solvate or hydrate thereof, for use in a method of treating or preventing a disease alleviated by inhibition of PDE5 in a human or in a non-human mammal, preferably in a human. In another aspect, the present invention provides for a compound of formula I or a pharmaceutical composition, or a pharmaceutically acceptable salt, solvate or hydrate thereof, for use in a method of treating or preventing a disease alleviated by inhibition of PDE5 in a human or in a non-human mammal, preferably in a human. In another aspect, the present invention provides for a compound of formula II or a pharmaceutical composition, or a pharmaceutically acceptable salt, solvate or hydrate thereof, for use in a method of treating or preventing a disease alleviated by inhibition of PDE5 in a human or in a non-human mammal, preferably in a human. Preferably, said disease is selected from wound healing, chronic wound healing, diabetic foot, diabetic foot ulcer, leg ulcer, Raynaud's disease, male erectile dysfunction, priapism, female sexual dysfunction, hair loss, skin aging, vascular aging, pulmonary artery hypertension; livedoid vasculopathy, thromboangitis obliterans, chronic anal fissure, skin fibrosis, stable, unstable and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, achalasia, sickle cell disease (SCD), inflammatory diseases, stroke, bronchitis, chronic asthma, allergic asthma, allergic rhinitis, diabetic neuropathy, Idiopathic pulmonary fibrosis (IPF), peyronic's disease, glaucoma, diabetic retinopathy, age dependent macular degeneration or a disease characterized by disorders of gut motility like irritable bowel syndrome, liver fibrosis, Alzheimer's disease, chronic heart failure, cancer such as breast and gastrointestinal cancers, non-small cell lung cancer, skin cancers such as melanoma, head and neck cancer, myeloma and head and neck squamous cell carcinoma, colon and rectal cancers such as colorectal cancer, and prostate and pancreatic cancers, and in particular colorectal cancer, wherein further preferably said disease is selected from wound healing, chronic wound healing, diabetic foot, diabetic foot ulcer, leg ulcer, diabetic neuropathy, peripheral vascular disease, vascular disorders such as Raynaud's disease, livedoid vasculopathy, thromboangitis obliterans, chronic anal fissure, skin fibrosis, systemic sclerosis (SSc), scleroderma, pulmonary artery hypertension (PAH), chronic thromboembolic pulmonary hypertension, male erectile dysfunction, priapism, female sexual dysfunction and colorectal cancer, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

In again another aspect, the present invention provides for the inventive compound of formula I or II, or the inventive pharmaceutical composition, or a pharmaceutically acceptable salt, solvate or hydrate thereof, for use in a method of treating or preventing a disease in a human or in a non-human mammal, preferably in a human, wherein said disease is selected from wound healing, chronic wound healing, diabetic foot, diabetic foot ulcer, leg ulcer, Raynaud's disease, male erectile dysfunction, priapism, female sexual dysfunction, hair loss, skin aging, vascular aging, pulmonary artery hypertension; livedoid vasculopathy, thromboangitis obliterans, chronic anal fissure, skin fibrosis, stable, unstable and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, achalasia, sickle cell disease (SCD), inflammatory diseases, stroke, bronchitis, chronic asthma, allergic asthma, allergic rhinitis, diabetic neuropathy, Idiopathic pulmonary fibrosis (IPF), peyronic's disease, glaucoma, diabetic retinopathy, age dependent macular degeneration or a disease characterized by disorders of gut motility like irritable bowel syndrome, liver fibrosis, Alzheimer's disease, chronic heart failure, cancer such as breast and gastrointestinal cancers, non-small cell lung cancer, skin cancers such as melanoma, head and neck cancer, myeloma and head and neck squamous cell carcinoma, colon and rectal cancers such as colorectal cancer, and prostate and pancreatic cancers, and in particular colorectal cancer, wherein preferably said disease is selected from wound healing, chronic wound healing, diabetic foot, diabetic foot ulcer, leg ulcer, diabetic neuropathy, peripheral vascular disease, vascular disorders such as Raynaud's disease, livedoid vasculopathy, thromboangitis obliterans, chronic anal fissure, skin fibrosis, systemic sclerosis (SSc), scleroderma, pulmonary artery hypertension (PAH), chronic thromboembolic pulmonary hypertension, male erectile dysfunction, priapism, female sexual dysfunction and colorectal cancer, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

In again another aspect, the present invention provides for the inventive compound of formula I or the inventive pharmaceutical composition, or a pharmaceutically acceptable salt, solvate or hydrate thereof, for use in a method of treating or preventing a disease in a human or in a non-human mammal, preferably in a human, wherein said disease is selected from wound healing, chronic wound healing, diabetic foot, diabetic foot ulcer, leg ulcer, Raynaud's disease, male erectile dysfunction, priapism, female sexual dysfunction, hair loss, skin aging, vascular aging, pulmonary artery hypertension; livedoid vasculopathy, thromboangitis obliterans, chronic anal fissure, skin fibrosis, stable, unstable and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, achalasia, sickle cell disease (SCD), inflammatory diseases, stroke, bronchitis, chronic asthma, allergic asthma, allergic rhinitis, diabetic neuropathy, Idiopathic pulmonary fibrosis (IPF), peyronic's disease, glaucoma, diabetic retinopathy, age dependent macular degeneration or a disease characterized by disorders of gut motility like irritable bowel syndrome, liver fibrosis, Alzheimer's disease, chronic heart failure, cancer such as breast and gastrointestinal cancers, non-small cell lung cancer, skin cancers such as melanoma, head and neck cancer, myeloma and head and neck squamous cell carcinoma, colon and rectal cancers such as colorectal cancer, and prostate and pancreatic cancers, and in particular colorectal cancer, wherein preferably said disease is selected from wound healing, chronic wound healing, diabetic foot, diabetic foot ulcer, leg ulcer, diabetic neuropathy, peripheral vascular disease, vascular disorders such as Raynaud's disease, livedoid vasculopathy, thromboangitis obliterans, chronic anal fissure, skin fibrosis, systemic sclerosis (SSc), scleroderma, pulmonary artery hypertension (PAH), chronic thromboembolic pulmonary hypertension, male erectile dysfunction, priapism, female sexual dysfunction and colorectal cancer, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

In again another aspect, the present invention provides for the inventive compound of formula II or the inventive pharmaceutical composition, or a pharmaceutically acceptable salt, solvate or hydrate thereof, for use in a method of treating or preventing a disease in a human or in a non-human mammal, preferably in a human, wherein said disease is selected from wound healing, chronic wound healing, diabetic foot, diabetic foot ulcer, leg ulcer, Raynaud's disease, male erectile dysfunction, priapism, female sexual dysfunction, hair loss, skin aging, vascular aging, pulmonary artery hypertension; livedoid vasculopathy, thromboangitis obliterans, chronic anal fissure, skin fibrosis, stable, unstable and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, achalasia, sickle cell disease (SCD), inflammatory diseases, stroke, bronchitis, chronic asthma, allergic asthma, allergic rhinitis, diabetic neuropathy, Idiopathic pulmonary fibrosis (IPF), peyronic's disease, glaucoma, diabetic retinopathy, age dependent macular degeneration or a disease characterized by disorders of gut motility like irritable bowel syndrome, liver fibrosis, Alzheimer's disease, chronic heart failure, cancer such as breast and gastrointestinal cancers, non-small cell lung cancer, skin cancers such as melanoma, head and neck cancer, myeloma and head and neck squamous cell carcinoma, colon and rectal cancers such as colorectal cancer, and prostate and pancreatic cancers, and in particular colorectal cancer, wherein preferably said disease is selected from wound healing, chronic wound healing, diabetic foot, diabetic foot ulcer, leg ulcer, diabetic neuropathy, peripheral vascular disease, vascular disorders such as Raynaud's disease, livedoid vasculopathy, thromboangitis obliterans, chronic anal fissure, skin fibrosis, systemic sclerosis (SSc), scleroderma, pulmonary artery hypertension (PAH), chronic thromboembolic pulmonary hypertension, male erectile dysfunction, priapism, female sexual dysfunction and colorectal cancer, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

In again another aspect, the present invention provides for a compound of formula I or II, or a pharmaceutical composition, or a pharmaceutically acceptable salt, solvate or hydrate thereof, for use in a method of treating or preventing a disease by activation of soluble guanylyl cyclase (sGC) and inhibition of PDE5 in a human or in a non-human mammal, preferably in a human. In again another aspect, the present invention provides for a compound of formula I or II, or a pharmaceutical composition, or a pharmaceutically acceptable salt, solvate or hydrate thereof, for use in a method of treating or preventing a disease by activation of soluble guanylyl cyclase (sGC) or inhibition of PDE5 in a human or in a non-human mammal, preferably in a human. In again another aspect, the present invention provides for a compound of formula I or II, or a pharmaceutical composition, or a pharmaceutically acceptable salt, solvate or hydrate thereof, for use in a method of treating a medical condition in a human or in a non-human mammal, preferably in a human, wherein for said medical condition inhibition of PDE5 and/or activation of soluble guanylyl cyclase (sGC) is desired. Very preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

In again another aspect, the present invention provides use of a compound of formula I or II, or a pharmaceutical composition, or a pharmaceutically acceptable salt, solvate or hydrate thereof, for the manufacture of a medicament for the treatment or prevention of a disease by activation of soluble guanylyl cyclase (sGC) and/or inhibition of PDE5 in a human or in a non-human mammal, preferably in a human. In again another aspect, the present invention provides use of a compound of formula I or II, or a pharmaceutical composition, or a pharmaceutically acceptable salt, solvate or hydrate thereof, for the manufacture of a medicament for the treatment or prevention of a disease alleviated by activation of soluble guanylyl cyclase (sGC) and/or inhibition of PDE5 in a human or in a non-human mammal, preferably in a human. In again another aspect, the present invention provides use of a compound of formula I or II, or a pharmaceutical composition, or a pharmaceutically acceptable salt, solvate or hydrate thereof, for the manufacture of a medicament for the treatment a medical condition in a human or in a non-human mammal, preferably in a human, wherein for said medical condition activation of soluble guanylyl cyclase (sGC) and/or inhibition of PDE5 is desired. In again another aspect, the present invention provides use of a compound of formula I or II, or a pharmaceutical composition, or a pharmaceutically acceptable salt, solvate or hydrate thereof, for the manufacture of a medicament for the treatment or prevention of a disease, wherein said disease is selected from wound healing, chronic wound healing, diabetic foot, diabetic foot ulcer, leg ulcer, Raynaud's disease, male erectile dysfunction, priapism, female sexual dysfunction, hair loss, skin aging, vascular aging, pulmonary artery hypertension; livedoid vasculopathy, thromboangitis obliterans, chronic anal fissure, skin fibrosis, stable, unstable and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma, diabetic retinopathy, age dependent macular degeneration or a disease characterized by disorders of gut motility like irritable bowel syndrome, liver fibrosis, Alzheimer's disease, chronic heart failure, cancer such as breast and gastrointestinal cancers, non-small cell lung cancer, skin cancers such as melanoma, head and neck cancer, myeloma and head and neck squamous cell carcinoma, colon and rectal cancers such as colorectal cancer, and prostate and pancreatic cancers, and in particular colorectal cancer, wherein further preferably said disease is selected from wound healing, chronic wound healing, diabetic foot, diabetic foot ulcer, leg ulcer, diabetic neuropathy, peripheral vascular disease, vascular disorders such as Raynaud's disease, livedoid vasculopathy, thromboangitis obliterans, chronic anal fissure, skin fibrosis, systemic sclerosis (SSc), scleroderma, pulmonary artery hypertension (PAH), chronic thromboembolic pulmonary hypertension, male erectile dysfunction, priapism, female sexual dysfunction and colorectal cancer, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

In again another aspect, the present invention provides for a method of treating or preventing a disease by activation of soluble guanylyl cyclase (sGC) and/or inhibition of PDE5 in a human or in a non-human mammal, preferably in a human, comprising administering to said human or said non-human mammal, preferably to said human an effective amount of a compound of formula I or II, or a pharmaceutical composition, or a pharmaceutically acceptable salt, solvate or hydrate thereof. In again another aspect, the present invention provides for a method of treating or preventing a disease alleviated by activation of soluble guanylyl cyclase (sGC) and/or inhibition of PDE5 in a human or in a non-human mammal, preferably in a human, comprising administering to said human or said non-human mammal, preferably to said human an effective amount of a compound of formula I or II, or a pharmaceutical composition, or a pharmaceutically acceptable salt, solvate or hydrate thereof. In again another aspect, the present invention provides for a method of treating a medical condition in a human or in a non-human mammal, preferably in a human, wherein for said medical condition activation of soluble guanylyl cyclase (sGC) and/or inhibition of PDE5 is desired, comprising administering to said human or said non-human mammal, preferably to said human an effective amount of a compound of formula I or II, or a pharmaceutical composition, or a pharmaceutically acceptable salt, solvate or hydrate thereof. In again another aspect, the present invention provides for a method of treating or preventing a disease in a human or in a non-human mammal, preferably in a human, comprising administering to said human or said non-human mammal, preferably to said human, an effective amount of a compound of formula I or II, or a pharmaceutical composition, or a pharmaceutically acceptable salt, solvate or hydrate thereof, and wherein said disease is selected from wound healing, chronic wound healing, diabetic foot, diabetic foot ulcer, leg ulcer, Raynaud's disease, male erectile dysfunction, priapism, female sexual dysfunction, hair loss, skin aging, vascular aging, pulmonary artery hypertension; livedoid vasculopathy, thromboangitis obliterans, chronic anal fissure, skin fibrosis, stable, unstable and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma, diabetic retinopathy, age dependent macular degeneration or a disease characterized by disorders of gut motility like irritable bowel syndrome, liver fibrosis, Alzheimer's disease, chronic heart failure, cancer such as breast and gastrointestinal cancers, non-small cell lung cancer, skin cancers such as melanoma, head and neck cancer, myeloma and head and neck squamous cell carcinoma, colon and rectal cancers such as colorectal cancer, and prostate and pancreatic cancers, and in particular colorectal cancer, wherein further preferably said disease is selected from wound healing, chronic wound healing, diabetic foot, diabetic foot ulcer, leg ulcer, diabetic neuropathy, peripheral vascular disease, vascular disorders such as Raynaud's disease, livedoid vasculopathy, thromboangitis obliterans, chronic anal fissure, skin fibrosis, systemic sclerosis (SSc), scleroderma, pulmonary artery hypertension (PAH), chronic thromboembolic pulmonary hypertension, male erectile dysfunction, priapism, female sexual dysfunction and colorectal cancer, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

In a preferred embodiment of the present invention, said disease or said a medical condition is selected from livedoid vasculopathy, thromboangitis obliterans, chronic anal fissure, skin fibrosis, wound healing, preferably chronic wound healing, diabetic foot, diabetic foot ulcer, leg ulcer, Raynaud's disease, male erectile dysfunction, female sexual dysfunction, diabetes, hair loss, skin aging, vascular aging, pulmonary artery hypertension; stable, unstable, and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma, diabetic retinopathy, age dependent macular degeneration or a disease characterized by disorders of gut motility like irritable bowel syndrome, liver fibrosis, Alzheimer's disease, chronic heart failure, cancer such as breast and gastrointestinal cancers, non-small cell lung cancer, skin cancers such as melanoma, head and neck cancer, myeloma and head and neck squamous cell carcinoma, colon and rectal cancers such as colorectal cancer, and prostate and pancreatic cancers, and in particular colorectal cancer, wherein preferably said disease is selected from livedoid vasculopathy, thromboangitis obliterans, chronic anal fissure, skin fibrosis, wound healing, preferably chronic wound healing, diabetic foot, diabetic foot ulcer, leg ulcer, diabetic neuropathy, peripheral vascular disease, vascular disorders such as Raynaud's disease, systemic sclerosis (SSc), scleroderma, pulmonary artery hypertension (PAH), chronic thromboembolic pulmonary hypertension, diabetes, male erectile dysfunction, priapism, female sexual dysfunction and colorectal cancer, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

There is thus provided as a further aspect of the present invention a compound of formula I or II for use in the treatment of wound healing, preferably chronic wound healing, diabetic foot, diabetic foot ulcer, leg ulcer, Raynaud's disease, male erectile dysfunction, female sexual dysfunction, diabetes, hair loss, skin aging, vascular aging, pulmonary artery hypertension; stable, unstable, and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma, diabetic retinopathy, age dependent macular degeneration or a disease characterized by disorders of gut motility like irritable bowel syndrome, liver fibrosis, Alzheimer's disease, chronic heart failure, cancer such as breast and gastrointestinal cancers, non-small cell lung cancer, skin cancers such as melanoma, head and neck cancer, myeloma and head and neck squamous cell carcinoma, colon and rectal cancers such as colorectal cancer, and prostate and pancreatic cancers, and in particular colorectal cancer, wherein preferably said disease is selected from wound healing, preferably chronic wound healing, diabetic foot, diabetic foot ulcer, leg ulcer, diabetic neuropathy, peripheral vascular disease, vascular disorders such as Raynaud's disease, systemic sclerosis (SSc), scleroderma, pulmonary artery hypertension (PAH), chronic thromboembolic pulmonary hypertension, diabetes, male erectile dysfunction, priapism, female sexual dysfunction and colorectal cancer, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

According to another aspect of the invention, there is provided the use of a compound of formula I or II for the manufacture of a medicament for the treatment of wound healing, preferably chronic wound healing, diabetic foot, diabetic foot ulcer, leg ulcer, Raynaud's disease, male erectile dysfunction, female sexual dysfunction, diabetes, hair loss, skin aging, vascular aging, pulmonary artery hypertension; stable, unstable, and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma, diabetic retinopathy, age dependent macular degeneration or a disease characterized by disorders of gut motility like irritable bowel syndrome, liver fibrosis, Alzheimer's disease, chronic heart failure, cancer such as breast and gastrointestinal cancers, non-small cell lung cancer, skin cancers such as melanoma, head and neck cancer, myeloma and head and neck squamous cell carcinoma, colon and rectal cancers such as colorectal cancer, and prostate and pancreatic cancers, and in particular colorectal cancer, wherein preferably said disease is selected from wound healing, preferably chronic wound healing, diabetic foot, diabetic foot ulcer, leg ulcer, diabetic neuropathy, peripheral vascular disease, vascular disorders such as Raynaud's disease, systemic sclerosis (SSc), scleroderma, pulmonary artery hypertension (PAH), chronic thromboembolic pulmonary hypertension, diabetes, male erectile dysfunction, priapism, female sexual dysfunction and colorectal cancer, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

In a further aspect, the invention provides a method of treating wound healing, preferably chronic wound healing, diabetic foot, diabetic foot ulcer, leg ulcer, Raynaud's disease, male erectile dysfunction, female sexual dysfunction, diabetes, hair loss, skin aging, vascular aging, pulmonary artery hypertension; stable, unstable, and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma, diabetic retinopathy, age dependent macular degeneration or a disease characterized by disorders of gut motility like irritable bowel syndrome, liver fibrosis, Alzheimer's disease, chronic heart failure, cancer such as breast and gastrointestinal cancers, non-small cell lung cancer, skin cancers such as melanoma, head and neck cancer, myeloma and head and neck squamous cell carcinoma, colon and rectal cancers such as colorectal cancer, and prostate and pancreatic cancers, and in particular colorectal cancer, wherein preferably said disease is selected from wound healing, preferably chronic wound healing, diabetic foot, diabetic foot ulcer, leg ulcer, diabetic neuropathy, peripheral vascular disease, vascular disorders such as Raynaud's disease, systemic sclerosis (SSc), scleroderma, pulmonary artery hypertension (PAH), chronic thromboembolic pulmonary hypertension, diabetes, male erectile dysfunction, priapism, female sexual dysfunction and colorectal cancer, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer, in a human or in non-human mammal, preferably in a human, said method comprises administering to said human or said non-human mammal, preferably to said human, an effective amount of a compound of formula I or II.

In a very preferred embodiment of the present invention, said disease or said a medical condition is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, skin aging, glaucoma, diabetic retinopathy, age dependent macular degeneration, Retinopathia pigmentosa wound healing, chronic wound healing, diabetic foot, diabetic foot ulcer, leg ulcer, diabetic neuropathy and pressure ulcer.

In a very preferred embodiment of the present invention, said disease or said a medical condition is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

In a very preferred embodiment of the present invention, said disease or said a medical condition is selected from wound healing, preferably chronic wound healing, diabetic foot, diabetic foot ulcer and leg ulcer, pulmonary artery hypertension and male erectile dysfunction and livedoid vasculopathy, thromboangitis obliterans, chronic anal fissure, skin fibrosis.

Chronic, non-healing skin wounds such as in diabetes mellitus are governed by complex disease mechanisms including impaired angiogenesis, defective microcirculation, and endothelial dysfunction. Diabetic foot ulcer and chronic wounds are a major source of morbidity and is a leading cause of hospitalizations in diabetic patients. It afflicts 15% of diabetes patients (275 Mio) and is a huge burden to patients and payers (12 billion $/year). 3-4% of all diabetic patients will get lower limb amputations every year. Ultra-potent PDE5 inhibitors or compounds integrating highly potent activation of soluble guanylyl cyclase (sGC) and/or inhibition of PDE5 and activation of nitric oxide dependent soluble guanylate cyclase as the ones of the present invention can be expected to accelerate wound healing.

As used herein, the terms "treatment", "treat", "treated" or "treating" refer to prophylaxis and/or therapy. In one embodiment, the terms "treatment", "treat", "treated" or "treating" refer to a therapeutic treatment. In another embodiment, the terms "treatment", "treat", "treated" or "treating" refer to a prophylactic treatment. Preferably, beneficial or desired clinical results of said treatment include, but are not limited to, alleviation of symptoms, diminishment of extent of disease or medical condition, stabilized (i.e., not worsening) state of disease or medical condition, delay or slowing of disease or medical condition progression, amelioration or palliation of the disease or medical condition state.

As used herein, the term "effective amount" refers to an amount necessary or sufficient to realize a desired biologic effect. Preferably, the term "effective amount" refers to an amount of a compound of formula I or II of the present invention that (i) treats or prevents the particular disease, medical condition, or disorder, (ii) attenuates, ameliorates, or eliminates one or more symptoms of the particular disease, medical condition, or disorder, or (iii) prevents or delays the onset of one or more symptoms of the particular disease, medical condition, or disorder described herein. An effective amount of the inventive compound of formula I or II, or said pharmaceutical composition, would be the amount that achieves this selected result, and such an amount could be determined as a matter of routine by a person skilled in the art. Further preferably, the term "effective amount", as used herein, refers to an amount necessary or sufficient to be effective to activation of soluble guanylyl cyclase (sGC) and/or increase the inhibition of PDE5, typically and preferably as determined in Example 53, or to increase the formation of cGMP, typically and preferably as determined in Example 55. The effective amount can vary depending on the particular composition being administered and the size of the subject. One of ordinary skill in the art can empirically determine the effective amount of a particular composition of the present invention without necessitating undue experimentation.

The term "mammal", as used herein, includes, but is not limited to, humans, mice, rats, guinea pigs, monkeys, dogs, cats, horses, cows, pigs, and sheep. The term "mammal", as used herein, preferably refers to humans.

The compounds of formula I and the pharmaceutical compositions of the present invention may be administered by any suitable route, for example by oral, buccal, sublingual, rectal, vaginal, intranasal, nasal, topical, intradermal, transdermal, subcutaneous, intraocular injection, transcutaneous, enteral, local, intravenous, intraperitoneal or parenteral administration, which forms another aspect of the present invention. Other routes are known in the art that could also be employed such as by way of chirurgical inlets. Thus, a device may be used for administration, such as conventional needles and syringes, micro needles, patches (e.g. as in WO 98/20734), needle free injection systems (e.g. as in WO 1999027961 A1), spray devices and the like, depending on the dose form and administration route. The device may be pre-filled or coated with the inventive compound or pharmaceutical composition.

The term "topical administration" is used in its broadest sense to include administration to a surface on the body that is generally open to the surroundings. This includes not only the skin but also the nasal and oral passages and the genitalia. Thus, topical administration can include application to the skin, application to the nasal passages, application to the oral cavity (including the upper throat), and application to the genitalia. Topical formulations have been available in a variety of forms, including creams, ointments, solutions, lotions, suspensions, pastes, emulsions, foams and the like. Water miscible creams have generally been employed for moist or weeping lesions, whereas ointments have been generally chosen for dry, lichenified or scaly lesions or where a more occlusive effect has been required. Lotions have generally been useful when minimal application to a large or hair-bearing area has been required or for the treatment of exudative lesions. The term "local administration" is used herein to refer to topical administration as well as administration to the eyes.

Combination therapies, as described herein, i.e. the use of at least two inventive compounds or pharmaceutical compositions of the present invention, but in particular the use of an inventive compound and a sGC stimulator in accordance with the present invention, may involve co-administration or sequential administration, and in particular of the inventive compound of formula I or formula II or the pharmaceutical composition and the at least one sGC stimulator.

The inventive compounds of formula I or formula II, pharmaceutical compositions or combination products, preferably and including the inventive compound of formula I or formula II or the pharmaceutical composition and the at least one sGC stimulator, can be administered to any subject, preferably human, that can experience the beneficial effects of the inventive compounds, compositions or products, as described herein. Thus, the inventive compounds of formula I or formula II, pharmaceutical compositions or combination products as described herein can be administered by any means that achieve their intended purpose. For example, administration can be by oral, buccal, sublingual, rectal, vaginal, intranasal, nasal, topical, intradermal, transdermal, subcutaneous, intraocular injection, transcutaneous, enteral, local, intravenous, intraperitoneal or parenteral administration. Typically the co-administration or sequential administration is effected by the same type of administration, even though different type of administrations such as a local application for the compounds of formula I or formula II, or the pharmaceutical compositions and an oral administration of the at least one sGC stimulator is also envisaged and encompassed within the present invention.

The inventive compounds of formula I or II can be prepared according to the reaction scheme 1 and scheme 2.

These schemes represent the synthesis of generic compounds of formula I or II and forms part of the present invention.

Compounds of formula I, can easily be obtained starting from commercially available sildenafil or pyrazolo[4,3-d]pyrimidin-7-ones by acidic sulfonamide hydrolysis leading to hydrolysis leads to the intermediate sulfonic acid as outlined in Scheme 1. Acidic hydrolysis leads to the intermediate sulfonic acid IV. Alternatively, the sulfonic acids can also be obtained described in literature (EP 463756 A1/19920102, see also review Dunn P. J. Organic Process Research & Development (2005), 9(1), 88-97). Formation of the chlorosulfonic acid derivative V and treatment with amines VI leads to the sulfonamides VII. Nitration using acetyl nitrate leads to compounds I.

In analogy compounds of formula II, can easily be obtained starting from commercially available vardenafil or 2-phenylimidazotriazinones by acidic sulfonamide hydrolysis leading to hydrolysis leads to the intermediate sulfonic acid VIII as outlined in Scheme 2. Acidic hydrolysis leads to the intermediate sulfonic acid VIII. Alternatively the sulfonic acids can also be obtained described in literature (WO 2002089808/20021114). Formation of the chlorosulfonic acid derivative IX and treatment with amines VI leads to the sulfonamides X. Nitration using acetyl nitrate leads to compounds II.

Scheme 1

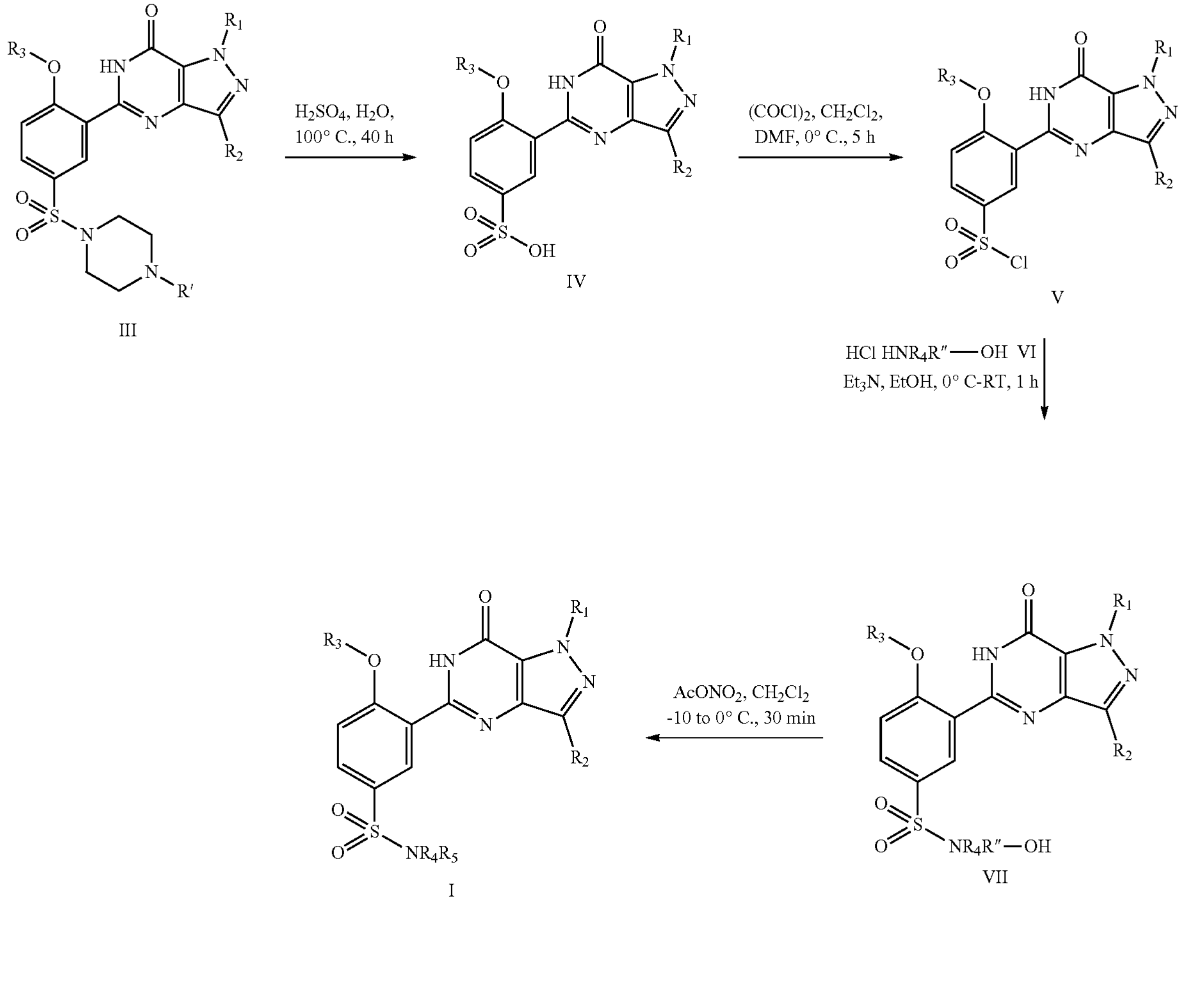

III

IV

V

VII

I

Scheme 2
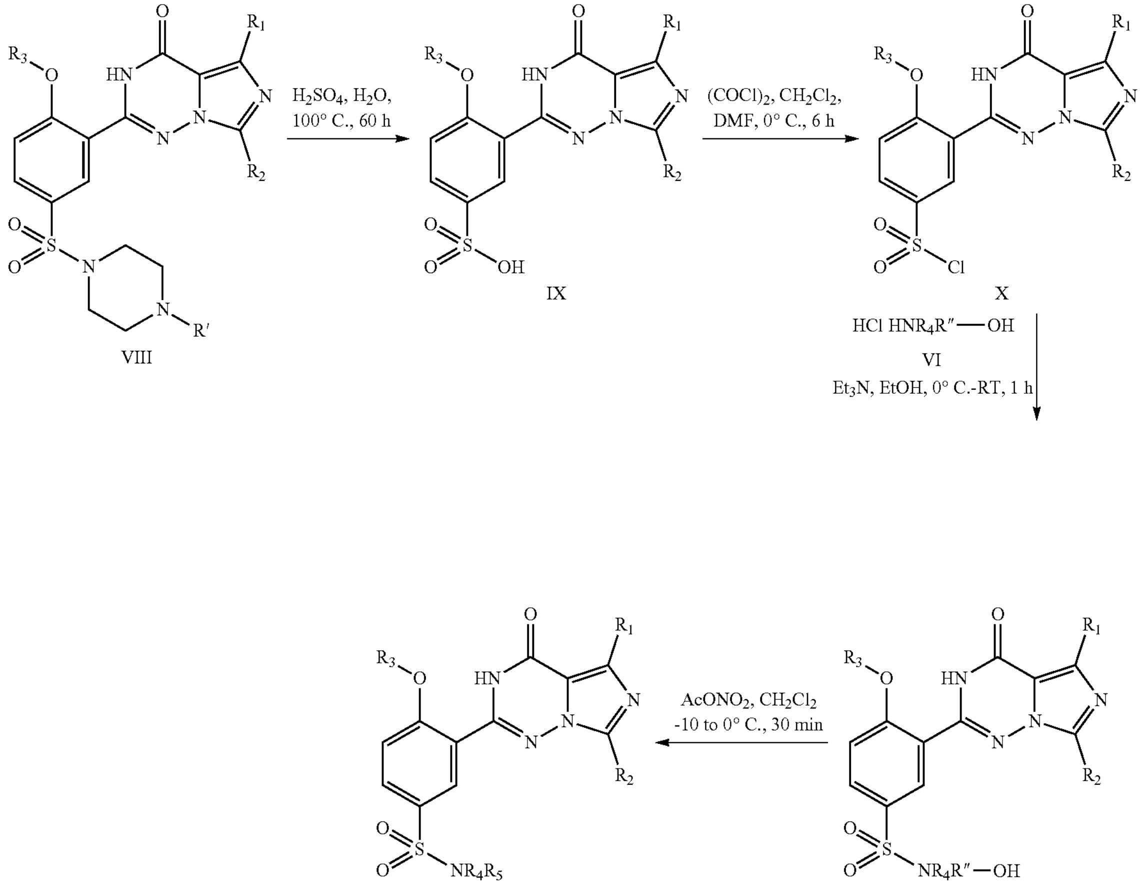
VIII IX X XI II
EXAMPLES
The synthesis of preferred compounds of formula I and II are exemplified below, typically preceded by a reaction scheme. The following examples further illustrate the present invention, but should not be construed in any way as to limit its scope.
Scheme 3
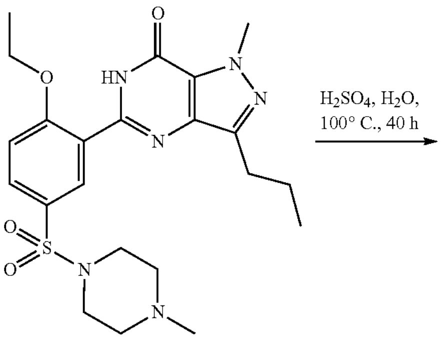
Sildenafil
-continued
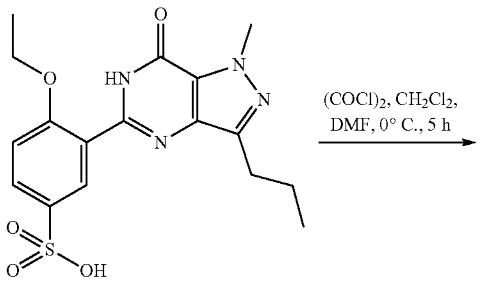
1
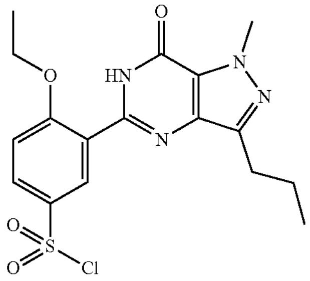
2

-continued

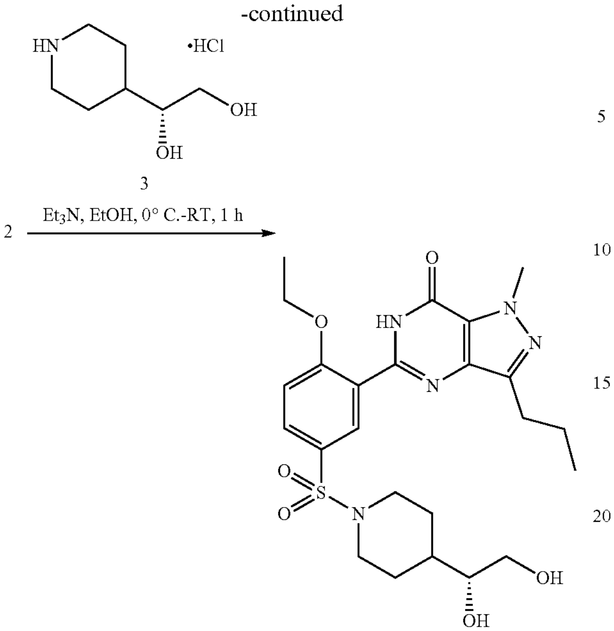

3

2

4

Example 1

4-ethoxy-3-(1-methyl-7-oxo-3-propyl-6,7-dihydro-1H-pyrazolo[4,3-d]pyrimidin-5-yl)benzene Sulfonic Acid (1)

To a stirred solution of 5-(2-ethoxy-5-((4-methylpiperazin-1-yl)sulfonyl)phenyl)-1-methyl-3-propyl-1,6-dihydro-7H-pyrazolo[4,3-d]pyrimidin-7-one (Sildenafil) (1.0 g, 2.10 mmol) in water (21 mL), was added concentrated sulphuric acid (16 mL) drop wise at room temperature for 1 h. After addition, the reaction was heated to 100° C. for 40 h. Reaction was monitored by TLC and LCMS analysis. After completion, the reaction mixture was cooled to 0° C. and neutralized (pH~7-8) with 25% aqueous NaOH solution (90 mL). The resultant heterogeneous mixture was concentrated under reduced pressure until water was removed completely. The resultant residue was treated with 10% methanol in dichloromethane (3×300 mL) and filtered. The combined organic filtrates were dried over anhydrous $Na_2SO_4$ and concentrated under reduced pressure. The crude product was purified by reverse phase column chromatography (C-18 column; Grace System) by eluting with 5-10% gradient acetonitrile with water to afford the title compound 1 (410 mg, 50% yield) as a white solid. $^1H$ NMR (300 MHz, DMSO-$d_6$) δ ppm 11.90 (br s, 1H; $D_2O$ exchangeable) 7.76-7.52 (m, 2H) 7.02-6.99 (m, 1H), 4.11 (s, 3H), 4.10-4.06 (m, 2H), 2.76-2.72 (m, 2H), 1.75-1.67 (m, 2H), 1.29-1.26 (m, 3H), 0.91 (t, J=7.5 Hz, 3H); LCMS(ESI): m/z 393.3 $[M+H]^+$; purity~99.8%.

Example 2

(R)-5-(5-((4-(1,2-dihydroxyethyl)piperidin-1-yl)sulfonyl)-2-ethoxyphenyl)-1-methyl-3-propyl-1,6-dihydro-7H-pyrazolo[4,3-d]pyrimidin-7-one (4)

To a stirred solution of 4-ethoxy-3-(1-methyl-7-oxo-3-propyl-6,7-dihydro-1H-pyrazolo[4,3-d]pyrimidin-5-yl)benzenesulfonic acid 1 (230 mg, 0.6 mmol) in $CH_2Cl_2$ (14 mL) and DMF (0.23 mL) was added oxalyl chloride (0.3 mL, 3.6 mmol) drop wise at 0° C. under argon atmosphere. The reaction mixture was stirred at 0° C. for 5 h. After completion of reaction (monitored by TLC), the reaction solution was concentrated under reduced pressure at below 20° C. and back filled with argon atmosphere. The crude liquid was co-distilled with $CH_2Cl_2$ (2×6 mL) to afford the crude product 2 as a pale yellow liquid.

Meanwhile (R)-1-(piperidin-4-yl)ethane-1,2-diol hydrochloride 3 (prepared according to the procedures given in WO2005026145 A1) (220 mg, 1.2 mmol) in ethanol (14 mL) was treated with Amberlyst A-21 ion exchange resin (1.1 g; 5 wt/wt) at room temperature for 2 h and filtered. To the filtrate, triethylamine (1.3 mL, 9.0 mmol) was added drop wise at 0° C. followed by a solution of crude product 2 in $CH_2Cl_2$ (5 mL) at 0° C. under inert atmosphere. The reaction mixture was warmed to room temperature and stirred for 1 h. After completion of reaction (monitored by LCMS), the reaction mixture was purified directly by reverse phase column chromatography (C-18 column; Grace System) by eluting with 25% acetonitrile with water to afford the title compound 4 (23.8 mg) as an off-white solid. $^1H$ NMR (400 MHz, DMSO-$d_6$) δ ppm 12.24 (br s, 1H; $D_2O$ exchangeable), 7.85 (d, J=2.4 Hz, 1H), 7.82 (dd, J=8.8, 2.4 Hz, 1H), 7.36 (d, J=8.8 Hz, 1H), 4.45-4.38 (m, 2H; $D_2O$ exchangeable), 4.20 (q, J=6.9 Hz, 2H), 4.16 (s, 3H), 3.67-3.64 (m, 2H), 3.33-3.25 (m, 2H), 3.22-3.16 (m, 1H), 2.79-2.75 (m, 2H), 2.21-2.14 (m, 2H), 1.79-1.69 (m, 3H), 1.61-1.57 (m, 1H), 1.41-1.25 (m, 6H), 0.94 (t, J=7.3 Hz, 3H); LCMS (ESI): m/z 520.5 $[M+H]^+$; purity~99.7%.

Scheme 4

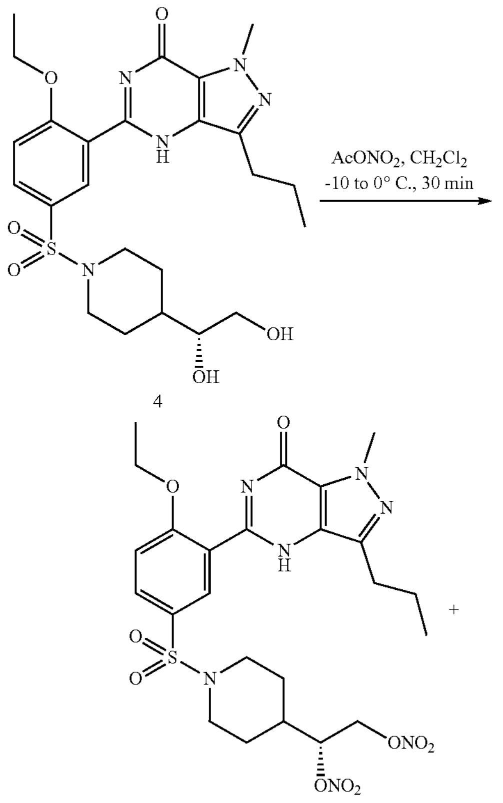

4

1a

-continued

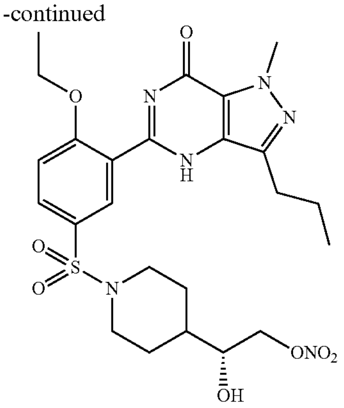

1c

Example 3

(R)-1-(1-((4-ethoxy-3-(1-methyl-7-oxo-3-propyl-4,7-dihydro-1H-pyrazolo[4,3-d]pyrimidin-5-yl)phenyl)sulfonyl)piperidin-4-yl)ethane-1,2-diyl dinitrate (1a) and (R)-2-(1-((4-ethoxy-3-(1-methyl-7-oxo-3-propyl-4,7-dihydro-1H-pyrazolo[4,3-d]pyrimidin-5-yl)phenyl)sulfonyl) piperidin-4-yl)-2-hydroxyethyl Nitrate (1c)

To a stirred solution of (R)-5-(5-((4-(1,2-dihydroxyethyl) piperidin-1-yl)sulfonyl)-2-ethoxyphenyl)-1-methyl-3-propyl-1,4-dihydro-7H-pyrazolo[4,3-d]pyrimidin-7-one (4) (140 mg, 0.27 mmol) in $CH_2Cl_2$ (2.8 mL) was added a solution of freshly prepared acetyl nitrate (0.24 mL) [(acetyl nitrate was prepared separately by addition of fuming $HNO_3$ (0.04 mL; 6.0 eq) drop wise in to acetic anhydride (0.20 mL, 1:5 of $HNO_3$)) slowly at −10° C. under argon atmosphere (Note: temperature should not be raised above 0° C.))] drop wise at −10° C. under argon atmosphere. The reaction mixture was stirred at 0° C. for 30 min. After completion of reaction (monitored by TLC), the reaction mixture was quenched with saturated $NaHCO_3$ solution (~15 mL; pH-7-8) at 0° C. The resultant solution was extracted with $CH_2Cl_2$ (3×10 mL). The combined organic layer was washed with brine (15 mL) and dried over anhydrous $Na_2SO_4$ and concentrated under reduced pressure. The crude product was purified by preparative HPLC (XBridge C18 column) using 40-100% gradient acetonitrile. The appropriate fractions were lyophilized to afford 1a (33.6 mg) as a white solid and 1c (46.3 mg) as a white solid.

1a analytical data: $^1H$ NMR (400 MHz, DMSO-$d_6$) δ ppm 12.17 (br s, 1H; $D_2O$ exchangeable), 7.86 (d, J=2.4 Hz, 1H), 7.82 (dd, J=8.8, 2.4 Hz, 1H), 7.36 (d, J=8.8 Hz, 1H), 5.33-5.30 (m, 1H), 4.94 (dd, J=12.7, 2.4 Hz, 1H), 4.71 (dd, J=12.7, 5.8 Hz, 1H), 4.20 (q, J=7.1 Hz, 2H), 4.16 (s, 3H), 3.71-3.68 (m, 2H), 2.79-2.75 (m, 2H), 2.27-2.20 (m, 2H), 1.82-1.70 (m, 5H), 1.49-1.36 (m, 2H), 1.33 (t, J=7.1 Hz, 3H), 0.94 (t, J=7.6 Hz, 3H); LCMS (ESI): m/z 610.0 $[M+H^+]$; purity~98.7%.

1c analytical data: $^1H$ NMR (400 MHz, DMSO-$d_6$) δ ppm 12.18 (br s, 1H; $D_2O$ exchangeable), 7.86 (d, J=2.4 Hz, 1H), 7.82 (dd, J=8.8, 2.4 Hz, 1H), 7.36 (d, J=8.8 Hz, 1H), 5.22 (d, J=5.4 Hz, 1H; $D_2O$ exchangeable), 4.52 (dd, J=11.2, 2.9 Hz, 1H), 4.37 (dd, J=11.2, 7.3 Hz, 1H), 4.21 (d, J=6.9 Hz, 2H), 4.16 (s, 3H), 3.70-3.66 (m, 2H), 3.54-3.51 (m, 1H), 2.79-2.75 (m, 2H), 2.24-2.17 (m, 2H), 1.82-1.70 (m, 3H), 1.65-1.62 (m, 1H), 1.40-1.30 (m, 6H), 0.94 (t, J=7.3 Hz, 3H); LCMS (ESI): m/z 564.9 $[M+H^+]$; purity~99.5%.

Scheme 5

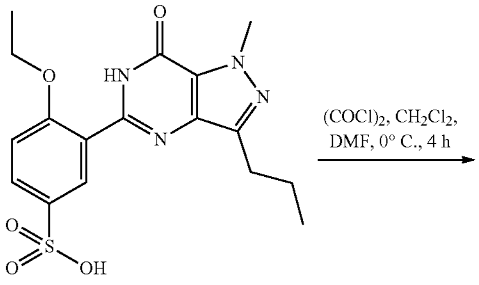

1

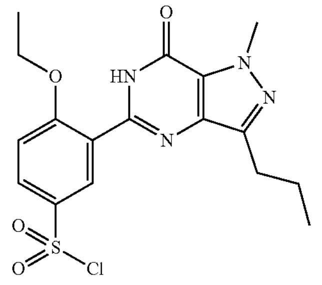

2

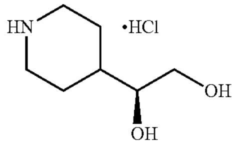

5

Et3N, EtOH, 0° C.-RT, 12 h

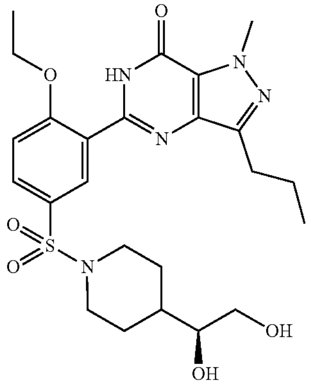

6

Example 4

(S)-5-(5-((4-(1,2-dihydroxyethyl)piperidin-1-yl) sulfonyl)-2-ethoxyphenyl)-1-methyl-3-propyl-1,6-dihydro-7H-pyrazolo[4,3-d]pyrimidin-7-one (6)

To a stirred solution of 4-ethoxy-3-(1-methyl-7-oxo-3-propyl-6,7-dihydro-1H-pyrazolo[4,3-d]pyrimidin-5-yl)benzenesulfonic acid 1 (150 mg, 0.38 mmol) in $CH_2Cl_2$ (9 mL) and DMF (0.15 mL) was added oxalyl chloride (0.2 mL, 2.29 mmol) drop wise at 0° C. under argon atmosphere. The reaction mixture was stirred at 0° C. for 4 h. After completion of reaction (monitored by TLC), the reaction solution was concentrated under reduced pressure at below 20° C. and back filled with argon atmosphere. The crude liquid was co-distilled with $CH_2Cl_2$ (5 mL) to afford 150 mg of the crude product 2 as a pale yellow liquid.

Meanwhile (S)-1-(piperidin-4-yl)ethane-1,2-diol hydrochloride (5, prepared according to the procedures given in WO2005026145 A1) (133 mg, 0.73 mmol) in ethanol (9 mL) was treated with Amberlyst A-21 ion exchange resin (665 mg; 5 w/w) at room temperature for 2 h and filtered. To the filtrate, triethylamine (0.76 mL, 5.48 mmol) was added drop wise at 0° C. followed by a solution of crude product 2 in $CH_2Cl_2$ (3 mL) at 0° C. under inert atmosphere. The reaction mixture was warmed to room temperature and stirred for 12 h. After completion of reaction (monitored by LCMS), the reaction mixture was purified directly by reverse phase column chromatography (C-18 column; Grace System) by eluting with 25-35% gradient acetonitrile with water to afford the title compound 6 (48 mg) as a white solid. $^1$H NMR (400 MHz, DMSO-$d_6$) δ ppm 12.24 (br s, 1H; $D_2O$ exchangeable), 7.85 (d, J=2.4 Hz, 1H), 7.82 (dd, J=8.8, 2.4 Hz, 1H), 7.36 (d, J=8.8 Hz, 1H), 4.45-4.38 (m, 2H; $D_2O$ exchangeable), 4.20 (q, J=6.9 Hz, 2H), 4.16 (s, 3H), 3.67-3.64 (m, 2H), 3.33-3.25 (m, 2H), 3.22-3.16 (m, 1H), 2.79-2.75 (m, 2H), 2.21-2.14 (m, 2H), 1.79-1.69 (m, 3H), 1.61-1.57 (m, 1H), 1.41-1.25 (m, 6H), 0.94 (t, J=7.3 Hz, 3H); LCMS (ESI): m/z 520.2 $[M+H]^+$; purity~99.6%.

Scheme 6

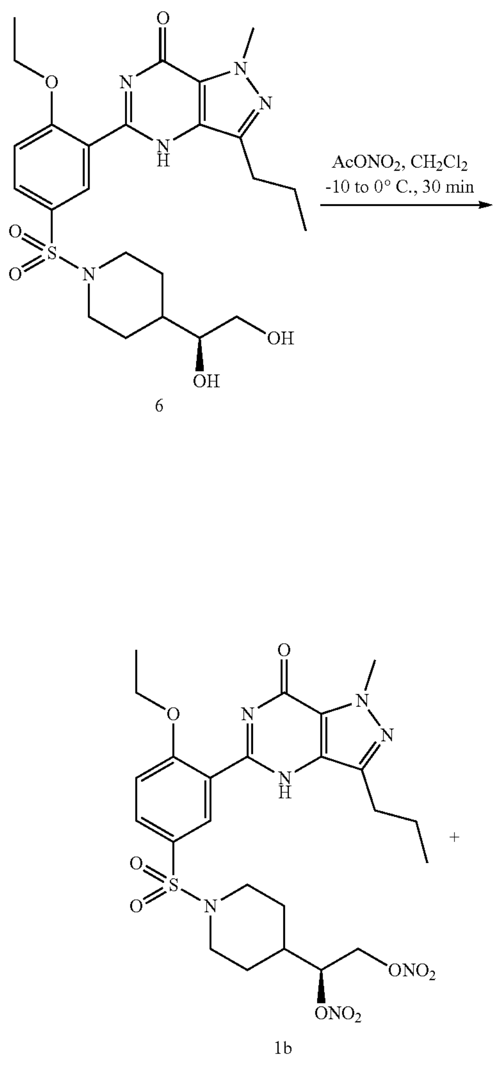

6

1b

-continued

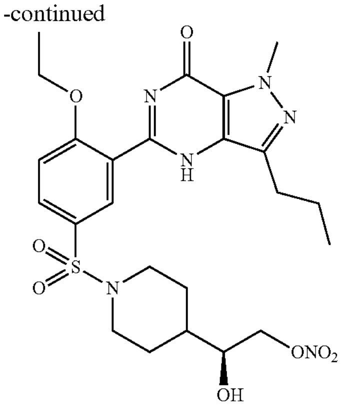

1d

Example 5

(S)-1-(1-((4-ethoxy-3-(1-methyl-7-oxo-3-propyl-4,7-dihydro-1H-pyrazolo[4,3-d]pyrimidin-5-yl)phenyl) sulfonyl)piperidin-4-yl)ethane-1,2-diyl dinitrate (1b) and (S)-2-(1-((4-ethoxy-3-(1-methyl-7-oxo-3-propyl-4,7-dihydro-1H-pyrazolo[4,3-d]pyrimidin-5-yl) phenyl)sulfonyl) piperidin-4-yl)-2-hydroxyethyl Nitrate (1d)

To a stirred solution of (S)-5-(5-((4-(1,2-dihydroxyethyl) piperidin-1-yl)sulfonyl)-2-ethoxyphenyl)-1-methyl-3-propyl-1,4-dihydro-7H-pyrazolo[4,3-d]pyrimidin-7-one (6) (120 mg, 0.23 mmol) in $CH_2Cl_2$ (1.8 mL) was added a solution of freshly prepared acetyl nitrate (0.18 mL) [(acetyl nitrate was prepared separately by addition of fuming $HNO_3$ (0.03 mL; 6.0 eq) drop wise in to acetic anhydride (0.15 mL, 1:5 of $HNO_3$)) slowly at −10° C. under argon atmosphere (Note: temperature should not be raised above 0° C.))] drop wise at −10° C. under argon atmosphere. The reaction mixture was stirred at 0° C. for 30 min. After completion of reaction (monitored by TLC), the reaction mixture was quenched with saturated $NaHCO_3$ solution (~10 mL; pH-7-8) at 0° C. The resultant solution was extracted with $CH_2Cl_2$ (3×10 mL). The combined organic layer was washed with brine (15 mL) and dried over anhydrous $Na_2SO_4$ and concentrated under reduced pressure. The crude product was purified by preparative HPLC (XBridge C18 column) using 40-100% gradient acetonitrile. The appropriate fractions were lyophilized to afford 1b (31 mg) as a white solid and 1d (10.2 mg) as a white solid.

1b analytical data: $^1$H NMR (400 MHz, DMSO-$d_6$) δ ppm 12.17 (br s, 1H; $D_2O$ exchangeable), 7.86 (d, J=2.4 Hz, 1H), 7.82 (dd, J=8.8, 2.4 Hz, 1H), 7.36 (d, J=8.8 Hz, 1H), 5.33-5.30 (m, 1H), 4.94 (dd, J=12.7, 2.4 Hz, 1H), 4.71 (dd, J=12.7, 5.8 Hz, 1H), 4.20 (q, J=7.1 Hz, 2H), 4.16 (s, 3H), 3.71-3.68 (m, 2H), 2.79-2.75 (m, 2H), 2.27-2.20 (m, 2H), 1.82-1.70 (m, 5H), 1.49-1.36 (m, 2H), 1.33 (t, J=7.1 Hz, 3H), 0.94 (t, J=7.6 Hz, 3H); LCMS (ESI): m/z 610.0 $[M+H^+]$; purity~99.5%.

1d analytical data: $^1$H NMR (400 MHz, DMSO-$d_6$) δ ppm 12.18 (br s, 1H; $D_2O$ exchangeable), 7.86 (d, J=2.4 Hz, 1H), 7.82 (dd, J=8.8, 2.4 Hz, 1H), 7.36 (d, J=8.8 Hz, 1H), 5.22 (d, J=5.4 Hz, 1H; $D_2O$ exchangeable), 4.52 (dd, J=11.2, 2.9 Hz, 1H), 4.37 (dd, J=11.2, 7.3 Hz, 1H), 4.21 (d, J=6.9 Hz, 2H), 4.16 (s, 3H), 3.70-3.66 (m, 2H), 3.54-3.51 (m, 1H), 2.79-2.75 (m, 2H), 2.24-2.17 (m, 2H), 1.82-1.70 (m, 3H), 1.65-

1.62 (m, 1H), 1.40-1.30 (m, 6H), 0.94 (t, J=7.3 Hz, 3H); LCMS (ESI): m/z 565.3 [M+$H^+$]; purity~97.1%.

Scheme 7

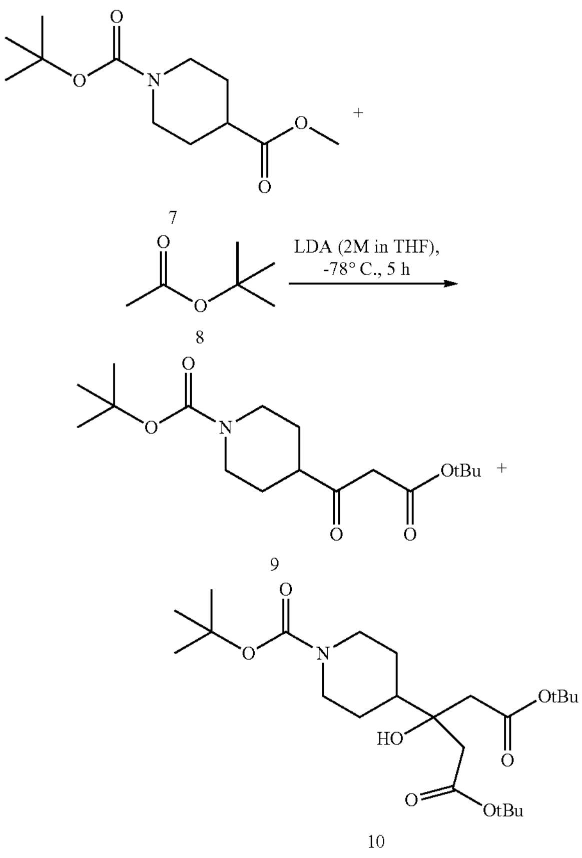

Example 6 tert-butyl 4-(3-(tert-butoxy)-3-oxopropanoyl)piperidine-1-carboxylate (9) and di-tert-butyl 3-(1-(tert-butoxycarbonyl)piperidin-4-yl)-3-hydroxypentanedioate (10)

To a stirred solution of tert-butyl acetate 8 (214.8 g, 1.85 mol) in THF (300 mL), was added lithium diisopropylamide solution 2.0 M in THF (462 mL, 0.924 mol) at −78° C. and stirred for 1 h. To the reaction mixture, added tert-butyl 4-formylpiperidine-1-carboxylate 7 (7.5 g, 0.0308 mol) at −78° C. and stirred for 4 h at same temperature. After completion of reaction (monitored by TLC), the reaction mixture was quenched with 10% aqueous ammonium chloride solution (150 mL) at −78° C. The solution was warmed to room temperature and extracted with ethyl acetate (2×400 mL). The combined organic layer was washed with brine (400 mL), dried over anhydrous $Na_2SO_4$ and concentrated under reduced pressure. Note: Reaction was performed in two lots (2×7.5 g scale). The obtained crude mixture from both the batches was combined and purified by silica gel column chromatography (eluted with 30% ethyl acetate with petroleum ether) to afford 37.5 g of title compounds 9 & 10 as a mixture (57% of 9 & 42% of 10 by LCMS analysis) as a brown liquid. The enriched mixture was purified by reverse phase preparative HPLC (Column: Kromosil (25*150 mm), 10 um; Mobile phase: (A): 100% water (B): 100% Acetonitrile, Flow rate: 19 mL/min, Gradient-(T/% B): 0/65, 1/65, 12/85, 14/85, 16/99, 18/99, 18.05/65, 20/65, Solubility: ACN+$H_2O$). Pure fractions were lyophilized to afford tert-butyl 4-(3-(tert-butoxy)-3-oxopropanoyl)piperidine-1-carboxylate 9 (6.2 g; 30% yield; fast eluted compound) as a pale yellow liquid and di-tert-butyl 3-(1-(tert-butoxycarbonyl)piperidin-4-yl)-3-hydroxypentanedioate 10 (7.0 g; 25% yield, late eluted compound) as a colorless liquid.

tert-butyl 4-(3-(tert-butoxy)-3-oxopropanoyl)piperidine-1-carboxylate (9) data: $^1$H NMR (400 MHz, $CDCl_3$) δ ppm 4.14-4.09 (m, 2H), 3.40 (s, 2H), 2.82-2.74 (m, 2H), 2.64-2.58 (m, 1H), 1.87-1.81 (m, 2H), 1.57-1.47 (m, 2H), 1.49 (s, 9H), 1.46 (s, 9H); LCMS (ELSD): m/z 328.26 [M+$H^+$]; purity~99%.

di-tert-butyl 3-(1-(tert-butoxycarbonyl)piperidin-4-yl)-3-hydroxypentanedioate (10) data: $^1$H NMR (400 MHz, $CDCl_3$) δ ppm 4.31 (s, 1H), 4.26-4.10 (br m, 2H), 2.64-2.50 (m, 6H), 1.76-1.61 (m, 3H), 1.46-1.39 (m, 27H), 1.32-1.25 (m, 2H); LCMS (ELSD): m/z 444.36 [M+$H^+$]; purity~99%.

Scheme 8

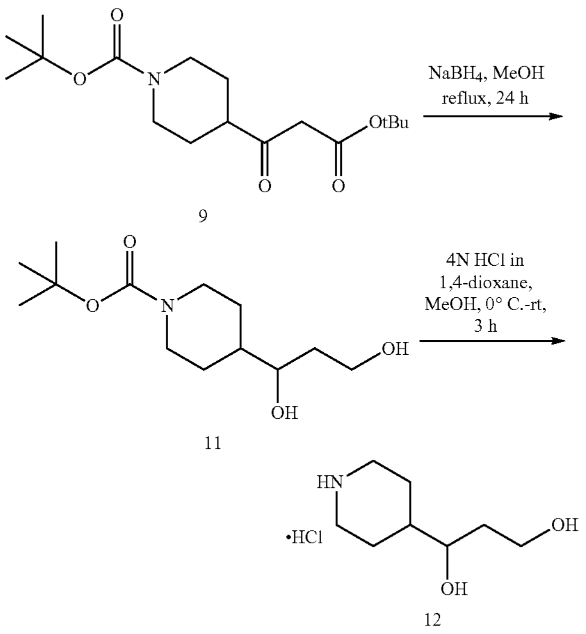

Example 7 tert-butyl 4-(1,3-dihydroxypropyl)piperidine-1-carboxylate (11)

To a stirred solution of tert-butyl 4-(3-(tert-butoxy)-3-oxopropanoyl)piperidine-1-carboxylate 9 (4.5 g, 13.75 mmol) in methanol (45 mL), was added sodium borohydride (4.04 g, 106.8 mmol) portions wise at 0° C. for 20 min and allowed the reaction to room temperature. The reaction mixture was slowly heated to reflux temperature and stirred for 24 h. After completion of reaction (monitored by TLC), the reaction mixture was cooled to 0° C. and quenched with ice water (50 mL) and extracted into dichloromethane (3×100 mL). The combined organic layers were washed with brine (100 mL), dried over anhydrous sodium sulfate and concentrated under reduced pressure to afford title compound 11 (3.2 g, 90%) as a colorless liquid. $^1$H NMR (300 MHz, DMSO-$d_6$) δ ppm 4.39 (br s, 1H), 3.99-3.92 (m, 2H), 3.53-3.38 (m, 4H), 2.66-2.53 (m, 2H), 1.67-1.61 (m, 1H), 1.56-1.23 (m, 12H), 1.23-0.98 (m, 3H); LCMS (ELSD; ESI): m/z found 260.32 [M+H$^+$]; purity~93.68%.

Example 8

1-(piperidin-4-yl)propane-1,3-diol Hydrochloride (12)

To a stirred solution of tert-butyl 4-(1,3-dihydroxypropyl) piperidine-1-carboxylate 11 (3.0 g, 11.57 mmol) in methanol (30 mL) was added 4N HCl solution in 1,4-dioxane (30 mL) at 0° C. and stirred at room temperature for 3 h. After completion of reaction (monitored by TLC), the reaction mixture was concentrated under reduced pressure. The resultant residue was lyophilized to afford title compound 12 (2.1 g, 92%) as a semi solid, which was taken as such for next step. $^1$H NMR (300 MHz, DMSO-$d_6$) δ ppm 9.04 (br s 1H), 8.64 (br s, 1H), 4.52 (br s, 2H), 3.53-3.50 (m, 2H), 3.46-3.41 (m, 1H), 3.27-3.17 (m, 2H), 2.83-2.71 (m, 2H), 1.81-1.72 (m, 1H), 1.61-1.43 (m, 6H).

Scheme 9

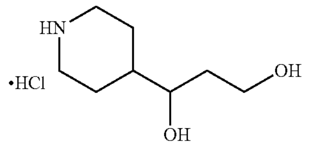

12

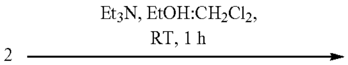

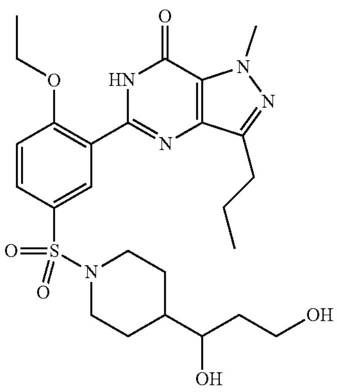

13

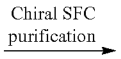

-continued

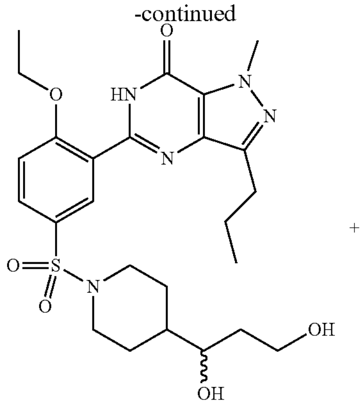

14-1

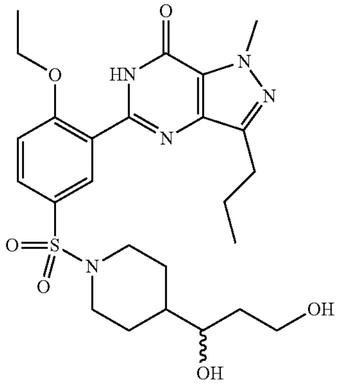

14-2

Example 9

5-(5-((4-(1,3-dihydroxypropyl)piperidin-1-yl)sulfonyl)-2-ethoxyphenyl)-1-methyl-3-propyl-1,6-dihydro-7H-pyrazolo[4,3-d]pyrimidin-7-one (13)

To a stirred solution of 1-(piperidin-4-yl)propane-1,3-diol hydrochloride (12) (314 mg, 1.60 mmol) in ethanol (18 mL) was added Amberlyst A-21 basic resin (1.5 g) and stirred at room temperature. After 3 h stirring, the ethanolic solution was filtered (resin beads were removed). To the filtrate was added triethylamine (1.01 mL, 7.31 mmol) drop wise at 0° C. and stirred for min. To this, a solution of 4-ethoxy-3-(1-methyl-7-oxo-3-propyl-6,7-dihydro-1H-pyrazolo[4,3-d]pyrimidin-5-yl)benzenesulfonyl chloride 2 (300 mg, 0.73 mmol) in dichloromethane (18 mL) was added at 0° C. under inert atmosphere. The reaction mixture was allowed to stir at room temperature for 1 h. After completion of reaction (monitored by LCMS), the reaction mixture was concentrated under reduced pressure. Note: Reaction was repeated on 300 mg scale of sulfonyl chloride 2. The resultant residue from both the batches were combined and purified (without workup) by reverse phase column chromatography (C18-40 g column; Grace System; eluted with 45-50% gradient acetonitrile with water) to afford 120 mg of title compound with 84% purity, which was re-purified by reverse phase preparative HPLC (Column used: YMC TRIAT (25*150) mm, 10 nm); Mobile phase: (A): 100% water, (B): Acetonitrile; Flow rate: 19 mL/min; Gradient—(T/% B): 0/30, 1/30, 11/70, 11.1/99, 13/99, 13.1/30, 15/30; Solubility: ACN+$H_2O$+THF). Pure fractions were lyophilized to afford the title compound 13 (80 mg, 10% yield) as a white solid.

LCMS (ESI): m/z found 534.12 [M+H$^+$]; purity~98.8%. 80 mg of 13 was subjected to chiral preparative SFC purification to afford 34 mg of enantiomer 14-1 and 35 mg of enantiomer 14-2 as a white solid.

Analytical SFC Conditions

Column/dimensions: Chiralpak AD-H (4.6×250 mm), 5μ

% CO2: 70.0%

% Co solvent: 30.0% (0.5% IP amine in Isopropanol)

Total Flow: 3.0 g/min

Back Pressure: 100.0 bar

Temperature: 30.0° C.

UV: 214.0 nm

Preparative SFC Conditions

Column/dimensions: Chiralpak AD-H (30×250 mm), 5μ

% CO2: 85.0%

% Co solvent: 15.0% (0.5% IP amine in Isopropanol)

Total Flow: 60.0 g/min

Back Pressure: 90.0 bar

UV: 214.0 nm

Stack time: 10.0 min

Load/Inj: 6.5 mg

Solubility: 14 ml Methanol

No of injections: 16

Instrument details: Make/Model: SFC-080

14 Peak-1 analytical data: White solid.

$^1$H NMR (400 MHz, DMSO-d$_6$) δ ppm 12.19 (br s, 1H), 7.84 (d, J=2.3 Hz, 1H), 7.80 (dd, J=8.8, 2.3 Hz, 1H), 7.34 (d, J=8.8 Hz, 1H), 4.35 (d, J=5.9 Hz, 1H), 4.31 (br s, 1H), 4.19 (q, J=7.1 Hz, 2H), 4.15 (s, 3H), 3.71-3.66 (m, 2H), 3.51-3.43 (m, 2H), 3.33-3.29 (m, 1H), 2.78-2.74 (m, 2H), 2.21-2.11 (m, 2H), 1.78-1.69 (m, 3H), 1.62-1.58 (m, 1H), 1.52-1.43 (m, 1H), 1.40-1.14 (m, 7H), 0.94 (t, J=7.4 Hz, 3H); LCMS (ESI): m/z found 534.65 [M+H$^+$]; purity~98.85%; UPLC: purity~96.48%; Chiral SFC: 98.56% ee; 99.283% with RT: 8.92 min; (Column: Chiralpak AD-H (4.6*250) mm, 5 μm, Co-Solvent name: 0.5% IPAmine in iso-propanol, % Co-Solvent: 30%, Flow rate: 3.0 ml/min, outlet pressure: 100 bar; Temp: 30° C., UV: 214 nm).

14 Peak-2 analytical data: White solid.

$^1$H NMR (400 MHz, DMSO-d$_6$) δ ppm 12.19 (br s, 1H), 7.84 (d, J=2.3 Hz, 1H), 7.80 (dd, J=8.8, 2.3 Hz, 1H), 7.34 (d, J=8.8 Hz, 1H), 4.35 (d, J=5.9 Hz, 1H), 4.31 (br s, 1H), 4.19 (q, J=7.1 Hz, 2H), 4.15 (s, 3H), 3.71-3.66 (m, 2H), 3.51-3.43 (m, 2H), 3.33-3.29 (m, 1H), 2.78-2.74 (m, 2H), 2.21-2.11 (m, 2H), 1.78-1.69 (m, 3H), 1.62-1.58 (m, 1H), 1.52-1.43 (m, 1H), 1.40-1.14 (m, 7H), 0.94 (t, J=7.4 Hz, 3H); LCMS (ESI): found m/z 534.65 [M+H$^+$]; purity~99.94%; UPLC: purity~98.90%; Chiral SFC: 90.98% ee; 95.494% with RT: 10.24 min; (Column: Chiralpak AD-H (4.6*250) mm, 5 μm, Co-Solvent name: 0.5% IPAmine in iso-propanol, % Co-Solvent: 30%, Flow rate: 3.0 ml/min, outlet pressure: 100 bar; Temp: 30° C., UV: 214 nm).

Scheme 10

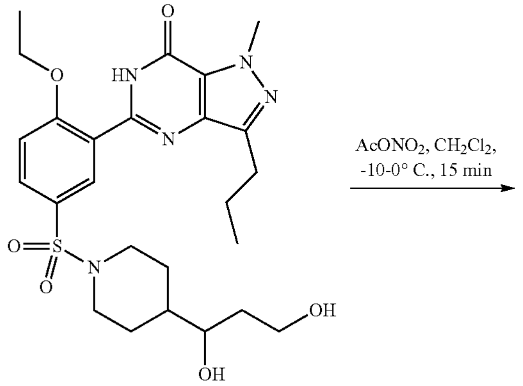

13

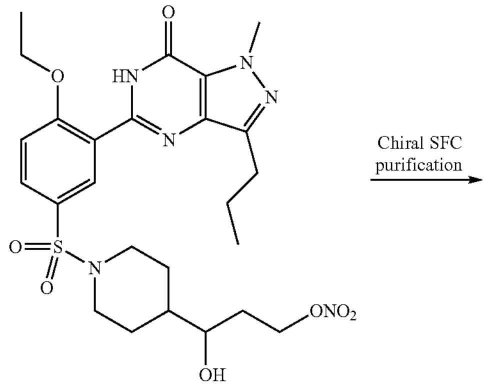

1ef

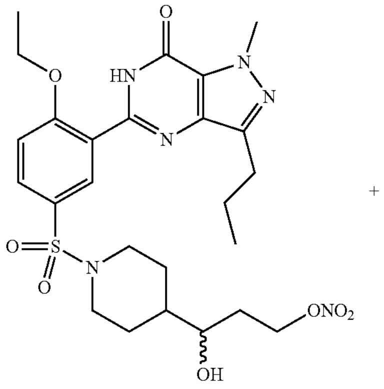

1e

-continued

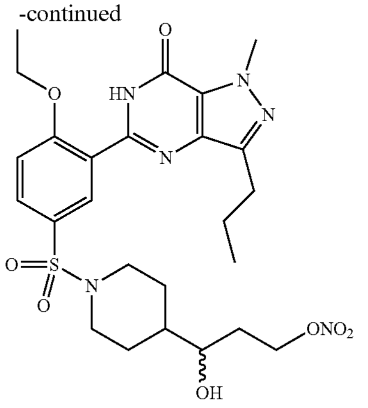

1f

Example 10

3-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-3-hydroxypropyl Nitrate (1ef)

To a stirred solution of 5-(5-((4-(1,3-dihydroxypropyl)piperidin-1-yl)sulfonyl)-2-ethoxyphenyl)-1-methyl-3-propyl-1,6-dihydro-7H-pyrazolo[4,3-d]pyrimidin-7-one (13) (170 mg, 0.318 mmol) in dichloromethane (8.5 mL) was added freshly prepared solution of acetyl nitrate (0.2 mL) [(acetyl nitrate was prepared separately by addition of fuming $HNO_3$ (0.03 mL, 2.23 mmol) drop wise in to acetic anhydride (0.17 mL, 1:5 of fuming $HNO_3$) drop wise at −10° C. under argon atmosphere (Note: temperature should not be raised to 0° C.))] drop wise at −5° C. under argon atmosphere. The reaction was stirred at −5-0° C. for 30 min. After completion of reaction (monitored by TLC), the reaction mixture was quenched with chilled saturated $NaHCO_3$ solution (15 mL) at 0° C. The resultant solution was warmed to room temperature and extracted with dichloromethane (2×10 mL). The combined organic layer was washed with brine (10 mL), dried over anhydrous $Na_2SO_4$ and concentrated under reduced pressure. The crude product was purified by reverse phase column chromatography (Grace System; C18-12 g column; eluted with 50-55% gradient acetonitrile with water). Pure fractions were lyophilized to afford the title compound 1ef (47 mg, 25%) as a white solid. LCMS (ESI): m/z 579.45 [M+H$^+$]; purity~88.71%.

47 mg of 1ef was subjected to chiral preparative SFC purification to afford 10.1 mg of 1e as a white solid and 11.5 mg of 1f as a white solid.

Analytical SFC Conditions

Column/dimensions: Chiralpak AD-H (4.6×250 mm), 5μ

% $CO_2$: 70.0%

% Co solvent: 30.0% (30 mm Methanolic ammonia in iso-propanol)

Total Flow: 3.0 g/min

Back Pressure: 100.0 bar

Temperature: 30.0° C.

UV: 214.0 nm

Preparative SFC Conditions

Column/dimensions: Chiralpak AD-H (30×250 mm), 5μ

% $CO_2$: 85.0%

% Co solvent: 15.0% (30 mm Methanolic ammonia in iso-propanol)

Total Flow: 70.0 g/min

Back Pressure: 90.0 bar

UV: 214.0 nm

Stack time: 9.0 min

Load/Inj: 2.2 mg

Solubility: 20 mL of methanol

No of injections: 18

Instrument details: Make/Model: SFC-80

1e analytical data: White solid.

$^1$H NMR (400 MHz, DMSO-$d_6$) δ ppm 12.17 (br s, 1H), 7.85 (d, J=2.3 Hz, 1H), 7.82 (dd, J=8.8, 2.3 Hz, 1H), 7.36 (d, J=8.8 Hz, 1H), 4.78 (d, J=5.9 Hz, 1H), 4.61-4.54 (m, 2H), 4.20 (q, J=7.3 Hz, 2H), 4.15 (s, 3H), 3.71-3.66 (m, 2H), 3.40-3.37 (m, 1H), 2.79-2.75 (m, 2H), 2.20-2.13 (m, 2H), 1.80-1.70 (m, 3H), 1.64-1.57 (m, 2H), 1.38-1.15 (m, 7H), 0.94 (t, J=7.3 Hz, 3H); LCMS (ESI): m/z found 579.23 [M+H$^+$]; purity~95.09%; UPLC: purity~95.14%; Chiral SFC: 98.38% ee; 99.19% with RT: 2.64 min; (Column: Chiralpak AD-3 (4.6*150) mm, 3 μm, Co-Solvent name: 0.5% IPAmine in iso-propanol, % Co-Solvent: 30%, Flow rate: 3.0 ml/min, outlet pressure: 1500 psi; Temp: 30° C., UV: 220 nm).

1f analytical data: White solid.

$^1$H NMR (400 MHz, DMSO-$d_6$) δ ppm 12.17 (br s, 1H), 7.85 (d, J=2.3 Hz, 1H), 7.82 (dd, J=8.8, 2.3 Hz, 1H), 7.36 (d, J=8.8 Hz, 1H), 4.78 (d, J=5.9 Hz, 1H), 4.61-4.54 (m, 2H), 4.20 (q, J=7.3 Hz, 2H), 4.15 (s, 3H), 3.71-3.66 (m, 2H), 3.40-3.37 (m, 1H), 2.79-2.75 (m, 2H), 2.20-2.13 (m, 2H), 1.80-1.70 (m, 3H), 1.64-1.57 (m, 2H), 1.38-1.15 (m, 7H), 0.94 (t, J=7.3 Hz, 3H); LCMS (ESI): m/z found 579.19 [M+H$^+$]; purity~99.20%; UPLC: purity~98.46%; Chiral SFC: 95.22% ee; 97.61% with RT: 3.60 min; (Column: Chiralpak AD-3 (4.6*150) mm, 3 μm, Co-Solvent name: 0.5% IPAmine in iso-propanol, % Co-Solvent: 30%, Flow rate: 3.0 ml/min, outlet pressure: 1500 psi; Temp: 30° C., UV: 220 nm).

Scheme 11

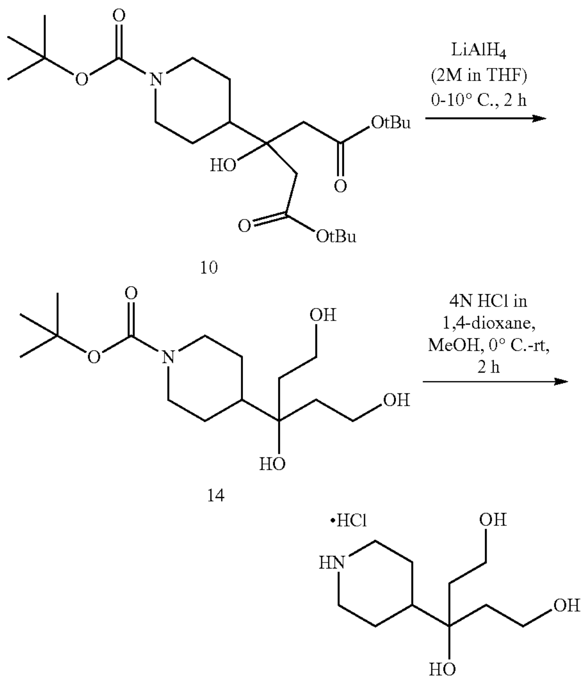

10

14

15

Example 11 tert-butyl 4-(1,3,5-trihydroxypentan-3-yl)piperidine-1-carboxylate (14)

To a stirred solution of di-tert-butyl 3-(1-(tert-butoxycarbonyl) piperidin-4-yl)-3-hydroxypentanedioate 10 (250 mg, 0.563 mmol) in THF (5 mL), was added lithium aluminium hydride solution 2.0 M in THF (1.68 mL, 3.38 mmol) at 0° C. and stirred at cooled temperature (0-10° C.) for 2 h. After completion of reaction (monitored by TLC), the reaction mixture was quenched with wet sodium sulphate (0.6 g) at 0° C. The solution was stirred room temperature for 3 h, filtered. The filtrate was concentrated under reduced pressure. The crude product was purified by reverse phase preparative HPLC (Column used: XBRIDGE C18 (19*250 mm) 5 μm, Mobile phase: (A): water, (B): Acetonitrile; Flow rate: 19 mL/min; Gradient—(T/% B): 0/20, 11/30, 11.1/100, 13/100, 13.1/20, 15/20; Solubility: DMSO). Pure fractions were lyophilized to afford analytically pure title compound 14 (18 mg; 10% yield) as a brown liquid. $^1H$ NMR (400 MHz, DMSO-$d_6$) δ ppm 4.40 (br s, 2H), 4.15 (br s, 1H), 4.04-3.93 (m, 2H), 3.52-3.48 (m, 4H), 2.61-2.53 (m, 2H), 1.62-1.43 (m, 7H), 1.39 (s, 9H), 1.17-1.08 (m, 2H); LCMS (ELSD): m/z 304.30 [M+$H^+$]; purity~99%.

Note: Reaction was repeated on different scales ranging from 0.25 to 3 g scales. The crude product was directly taken for next reaction without purification.

Example 12

3-(piperidin-4-yl)pentane-1,3,5-triol Hydrochloride (15)

To a stirred solution of tert-butyl 4-(1,3,5-trihydroxypentan-3-yl)piperidine-1-carboxylate 14 (1.3 g, 4.29 mmol) in methanol (13 mL) was added 4M hydrogen chloride solution in 1,4-dioxane (13 mL) at 0° C. and stirred at room temperature for 2 h. After completion of reaction (monitored by TLC), the reaction mixture was concentrated under reduced pressure, and lyophilized to afford title 15 (800 mg; 77%) as a pale yellow semi solid, which was directly taken for next reaction. LCMS (ELSD): m/z found 204.27 [M+$H^+$]; purity~99.7%.

Scheme 12

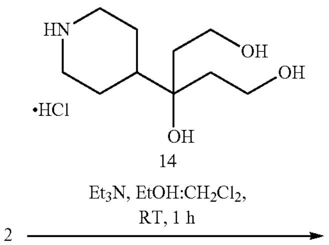

-continued

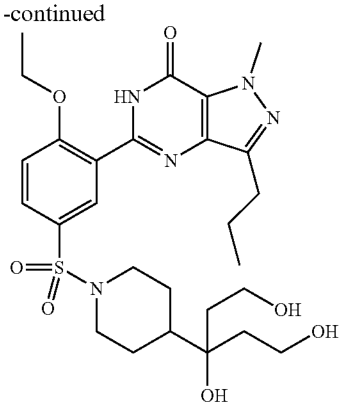

15

Example 13

5-(2-ethoxy-5-((4-(1,3,5-trihydroxypentan-3-yl)piperidin-1-yl)sulfonyl)phenyl)-1-methyl-3-propyl-1,6-dihydro-7H-pyrazolo[4,3-d]pyrimidin-7-one (15)

To a stirred solution of 3-(piperidin-4-yl)pentane-1,3,5-triol hydrochloride (14) (153 mg, 0.69 mmol) in ethanol (14.4 mL) was added triethylamine (0.6 mL, 4.38 mmol) drop wise at 0° C. and stirred at room temperature for 30 min. To this, a solution of 4-ethoxy-3-(1-methyl-7-oxo-3-propyl-6,7-dihydro-1H-pyrazolo[4,3-d]pyrimidin-5-yl)benzenesulfonyl chloride 2 (120 mg, 0.29 mmol) in dichloromethane (7.2 mL) was added at 0° C. under inert atmosphere. The reaction mixture was allowed to stir at room temperature for 1 h. After completion of reaction (monitored by LCMS), the reaction mixture was concentrated under reduced pressure. The resultant residue was diluted with 20 ml of ice-cold water and extracted with dichloromethane (30 mL). Organic layer was dried over anhydrous $Na_2SO_4$ and evaporated under reduced pressure. The crude product was purified by reverse phase column chromatography (C18-12 g column; Grace System; eluted with 30-35% gradient acetonitrile with water). Pure fractions were lyophilized to afford the title compound 15 (70 mg, 37% yield) as a white solid. $^1H$ NMR (400 MHz, DMSO-$d_6$) δ ppm 12.17 (br s, 1H), 7.85 (d, J=2.3 Hz, 1H), 7.81 (dd, J=8.8, 2.3 Hz, 1H), 7.36 (d, J=8.8 Hz, 1H), 4.36 (t, J=4.9 Hz, 2H), 4.23-4.15 (m, 6H), 3.73-3.69 (m, 2H), 3.49-3.41 (m, 4H), 2.80-2.75 (m, 2H), 2.16-2.09 (m, 2H), 1.78-1.69 (m, 4H), 1.58-1.47 (m, 4H), 1.36-1.17 (m, 6H), 0.94 (t, J=7.3 Hz, 3H); LCMS (ESI): m/z found 578.48 [M+H]$^+$; purity~97.6%; UPLC: purity~95.7%.

Scheme 13

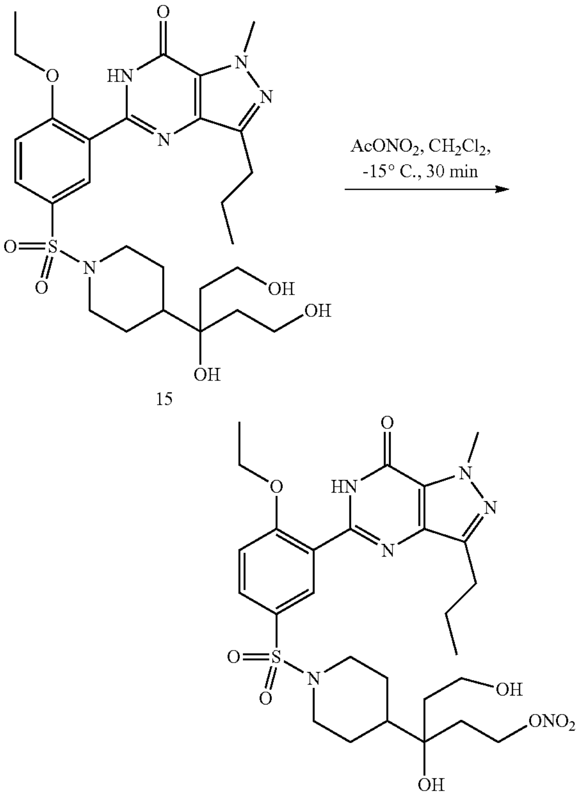

15

1g

Example 14

3-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-3,5-dihydroxypentyl Nitrate (1g)

To a stirred solution of 5-(2-ethoxy-5-((4-(1,3,5-trihydroxypentan-3-yl)piperidin-1-yl)sulfonyl)phenyl)-1-methyl-3-propyl-1,6-dihydro-7H-pyrazolo[4,3-d]pyrimidin-7-one 15 (100 mg, 0.173 mmol) in $CH_2Cl_2$ (3 mL) was added a solution of freshly prepared acetyl nitrate (0.06 mL) [(acetyl nitrate was prepared separately by addition of fuming $HNO_3 \cdot NO_2$ (0.01 mL; 3.0 eq) drop wise in to acetic anhydride (0.05 mL, 1:5 of $HNO_3NO_2$)) slowly at −15° C. under argon atmosphere (Note: temperature should not be raised above 0° C.))] drop wise at −15° C. under argon atmosphere. The reaction mixture was stirred at same temperature for 30 min. After completion of reaction (monitored by TLC), the reaction was quenched with saturated $NaHCO_3$ solution (5 mL) at 0° C. The resultant solution was extracted with $CH_2Cl_2$ (2×5 mL). The combined organic layer was washed with brine (5 mL) and dried over anhydrous $Na_2SO_4$ and concentrated under reduced pressure. The crude (41% of desired mono nitrate and 16% of dinitrate, based on LCMS analysis) was purified by reverse phase column chromatography (Grace System; C18-12 g column; eluted with 50-55% gradient acetonitrile with water). Pure fractions were lyophilized to afford the title compound 1g (21.7 mg; 36%) as a white solid. $^1H$ NMR (400 MHz, DMSO-$d_6$) δ ppm 12.19 (br s, 1H), 7.86 (d, J=2.3 Hz, 1H), 7.82 (dd, J=8.8, 2.3 Hz, 1H), 7.37 (d, J=8.8 Hz, 1H), 4.57-4.53 (m, 2H), 4.49-4.45 (m, 2H), 4.20 (q, J=7.3 Hz, 2H), 4.16 (s, 3H), 3.73-3.69 (m, 2H), 3.50-3.44 (m, 2H), 2.79-2.75 (m, 2H), 2.18-2.11 (m, 2H), 1.79-1.68 (m, 6H), 1.58-1.52 (m, 2H), 1.46-1.24 (m, 6H), 0.94 (t, J=7.3 Hz, 3H); LCMS (ESI): m/z 623.24 [M+H$^+$]; purity~96.4%; UPLC: purity~95.5%.

Scheme 14

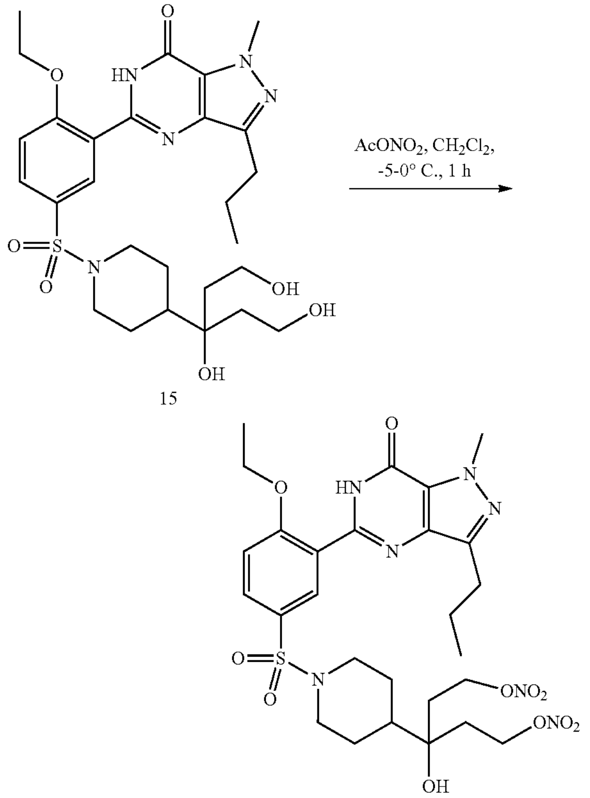

15

1h

Example 15

3-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-3-hydroxypentane-1,5-diyl Dinitrate (1h)

To a stirred solution of 5-(2-ethoxy-5-((4-(1,3,5-trihydroxypentan-3-yl)piperidin-1-yl)sulfonyl)phenyl)-1-methyl-3-propyl-1,6-dihydro-7H-pyrazolo[4,3-d]pyrimidin-7-one 15 (50 mg, 0.086 mmol) in $CH_2Cl_2$ (1.5 mL) was added a solution of freshly prepared acetyl nitrate (0.056 mL) [(acetyl nitrate was prepared separately by addition of fuming $HNO_3 \cdot NO_2$ (0.009 mL; 5.0 eq) drop wise in to acetic anhydride (0.047 mL, 1:5 of $HNO_3NO_2$)) slowly at −10° C. under argon atmosphere (Note: temperature should not be raised above 0° C.))] drop wise at −5-0° C. under argon atmosphere. The reaction mixture was stirred at −5-0° C. for 1 h. After completion of reaction (monitored by TLC), the reaction was quenched with saturated $NaHCO_3$ solution (5 mL) at 0° C. The resultant solution was extracted with $CH_2Cl_2$ (2×5 mL). The combined organic layer was washed with brine (5 mL) and dried over anhydrous $Na_2SO_4$ and concentrated under reduced pressure. The crude product was purified by reverse phase column chromatography (Grace System; C18-12 g column; eluted with 70-75% gradient acetonitrile with water). Pure fractions were lyophilized to afford the title compound 1h (21 mg; 36%) as a white solid. $^1H$ NMR (400 MHz, DMSO-$d_6$) δ ppm 12.17 (br s, 1H), 7.87 (d, J=2.3 Hz, 1H), 7.83 (dd, J=8.8, 2.3 Hz, 1H), 7.37 (d, J=8.8 Hz, 1H), 4.77 (s, 1H), 4.58-4.54 (m, 4H), 4.20 (q, J=7.3 Hz, 2H), 4.15 (s, 3H), 3.75-3.70 (m, 2H), 2.79-2.75 (m, 2H), 2.21-2.16 (m, 2H), 1.82-1.60 (m, 8H), 1.36-1.29 (m, 6H), 0.94 (t, J=7.3 Hz, 3H); LCMS (ESI): m/z found 668.48 [M+H$^+$]; purity~95.1%; UPLC: purity~95.1%

Scheme 14

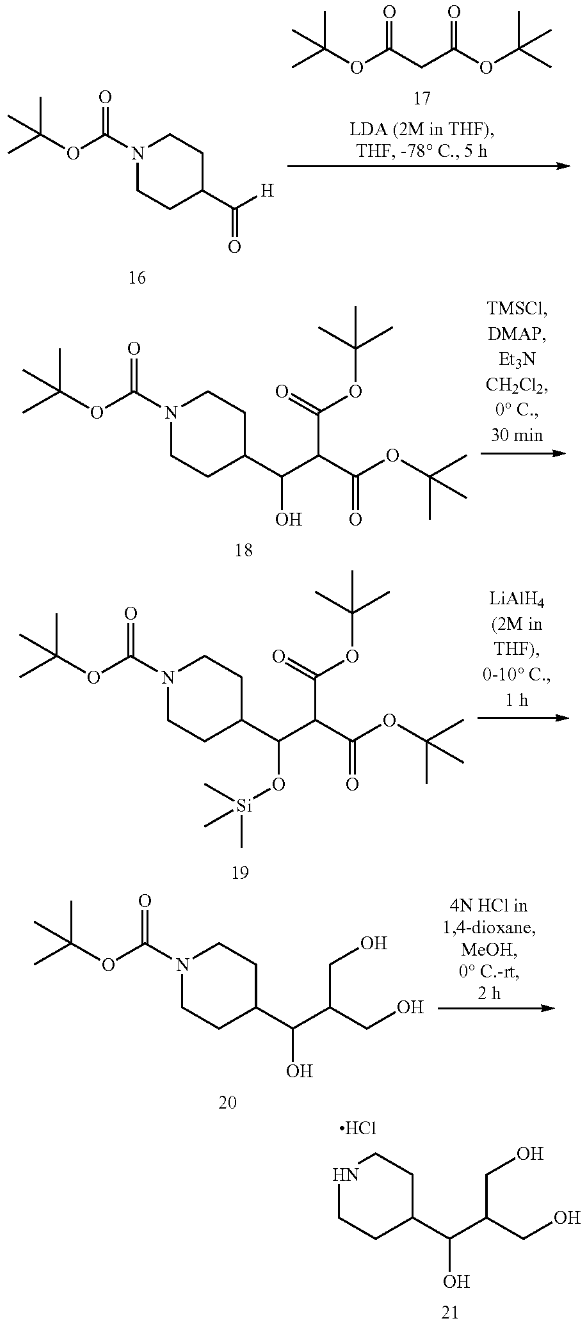

17

16

18

19

20

21

Example 16 di-tert-butyl 2-((1-(tert-butoxycarbonyl)piperidin-4-yl)(hydroxy)methyl)malonate (18)

To a stirred solution of di-tert-butyl malonate 17 (52.5 mL, 234.43 mmol) in THF (200 mL) was added lithium diisopropylamide solution (2.0 M in THF; 94 mL; 188 mmol) drop wise at −78° C. under inert atmosphere for 20 min and stirred for 1 h at same temperature. To this, a solution of tert-butyl 4-formylpiperidine-1-carboxylate 16 (10.0 g, 46.89 mmol) in THF (40 mL) was added drop wise at −78° C. for 15 min and stirred for 4 h at same temperature. After completion of reaction (monitored by TLC), the reaction mixture was quenched with saturated aqueous $NH_4Cl$ solution (70 mL) and warmed to room temperature and stirred for 10 min. Resultant solution was extracted with ethyl acetate (2×200 mL). The combined organic layer was washed with brine (2×50 mL), dried over anhydrous $Na_2SO_4$ and concentrated under reduced pressure. The crude product was purified by silica gel column chromatography (eluted with 10-15% gradient ethyl acetate in petroleum ether) to afford 18 (6.0 g, 29% yield) as pale yellow liquid. $^1H$ NMR (400 MHz, $CDCl_3$) δ ppm 4.22-4.14 (m, 2H), 3.87-3.83 (m, 1H), 3.45 (br d, J=6.1 Hz, 1H), 3.38 (d, J=5.3 Hz, 1H), 2.70-2.58 (m, 2H), 1.92-1.87 (m, 1H), 1.54-1.50 (m, 2H), 1.49-1.47 (m, 27H), 1.39-1.31 (m, 2H); LCMS (ELSD, ESI): m/z found 430.39 [M+H]$^+$; purity~99.5%.

Example 17 di-tert-butyl 2-((1-(tert-butoxycarbonyl)piperidin-4-yl)((trimethylsilyl)oxy)methyl)malonate (19)

To a stirred solution of di-tert-butyl 2-((1-(tert-butoxycarbonyl)piperidin-4-yl)(hydroxy)methyl)malonate 18 (5.0 g, 11.64 mmol) in $CH_2Cl_2$ (50 mL) were added triethylamine (5.0 mL, 34.92 mmol) followed by 4-dimethylaminopyridine (1.42 g; 11.64 mmol) at room temperature under inert atmosphere and stirred for 10 min. Reaction mixture was cooled to 0° C. and added trimethylsilyl chloride (2.22 mL, 17.5 mmol) drop wise and stirred at same temperature for 30 min. After completion of reaction (monitored by TLC), the reaction mixture was diluted in $CH_2Cl_2$ (100 mL), washed with saturated $NaHCO_3$ solution (100 mL), brine (100 mL), dried over $Na_2SO_4$ and concentrated under reduced pressure. Note: Reaction was performed in two lots (1×5.0 g; 1×3.5 g). The crude product from both the batches were combined and purified by column chromatography (neutral alumina; eluted with 0-5% gradient ethyl acetate in petroleum ether) to afford 19 (7.0 g, 70%) as a pale yellow liquid. $^1H$ NMR (400 MHz, $CDCl_3$) δ ppm 4.17-4.09 (m, 3H), 3.38 (d, J=7.2 Hz, 1H), 2.65-2.59 (m, 2H), 1.71-1.67 (m, 1H), 1.56-1.52 (m, 2H), 1.47-1.45 (m, 27H), 1.36-1.27 (m, 2H), 0.11 (s, 9H). LCMS (ELSD, ESI): m/z found 502.43 [M+H]$^+$; purity~99.3%.

Example 18 tert-butyl 4-(1,3-dihydroxy-2-(hydroxymethyl)propyl)piperidine-1-carboxylate (20)

To a stirred solution of di-tert-butyl 2-((1-(tert-butoxycarbonyl)piperidin-4-yl)((trimethylsilyl)oxy)methyl)malonate 19 (7.0 g, 13.95 mmol) in THF (210 mL) was added lithium aluminium hydride (2.0 M solution in THF; 28.0 mL, 56.0 mmol) drop wise at 0° C. under inert atmosphere and allowed to stir at 0-10° C. for 1 h under inert atmosphere. After completion of reaction (monitored by TLC), the reaction mixture was quenched with by addition of saturated $Na_2SO_4$ solution (~6.0 mL) drop wise at 0° C. for 30 min. The reaction mixture was allowed to room temperature and stirred for 2 h. The resultant heterogeneous mixture was diluted with ethyl acetate (200 mL), filtered and washed with methanol (2×100 mL) thoroughly. The filtrate was concentrated under reduced pressure. The crude product was purified by column chromatography (neutral alumina; eluted with 0-10% methanolic ammonia in dichloromethane) to afford title compound 20 (1.75 g, 43%) as gummy liquid. $^1$H NMR (300 MHz, DMSO-$d_6$) δ ppm 4.38-4.24 (m, 3H), 4.01-3.92 (m, 2H), 3.67-3.32 (m, 5H), 2.62-2.53 (m, 2H), 1.78-1.51 (m, 4H), 1.49 (s, 9H), 1.18-1.04 (m, 2H).

Example 19

2-(hydroxymethyl)-1-(piperidin-4-yl)propane-1,3-diol Hydrochloride (21)

To a stirred solution of tert-butyl 4-(1,3-dihydroxy-2-(hydroxymethyl)propyl)piperidine-1-carboxylate 20 (1.75 g, 6.05 mmol) in methanol (17.5 mL) was added hydrogen chloride solution 4.0 M in 1,4-dioxane (17.5 mL) drop wise at 0° C. under inert atmosphere. The reaction mixture was allowed to room temperature and stirred for 2 h. After completion of reaction (monitored by TLC), the reaction solution was concentrated under reduced pressure and lyophilized to afford crude title compound (1.4 g) as a gummy liquid, which was used as such for next step. $^1$H NMR (400 MHz, DMSO-$d_6$) δ ppm 8.80 (br s, 2H), 3.63-3.58 (m, 1H), 3.50-3.39 (m, 3H), 3.33-3.31 (m, 1H), 3.27-3.24 (m, 2H), 2.86-2.74 (m, 2H), 1.91-1.87 (m, 1H), 1.74-1.36 (m, 5H) (—OH protons not observed; exchanged with moisture); LCMS (ELSD, ESI): m/z 190.21 [M+H]$^+$; purity~99%.

Scheme 15

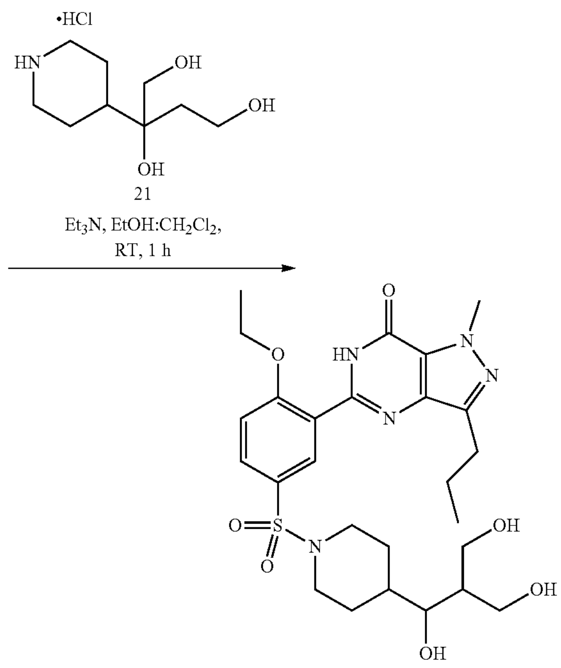

21

2

22

Example 20

5-(5-((4-(1,3-dihydroxy-2-(hydroxymethyl)propyl)piperidin-1-yl)sulfonyl)-2-ethoxyphenyl)-1-methyl-3-propyl-1,6-dihydro-7H-pyrazolo[4,3-d]pyrimidin-7-one (22)

To a stirred solution of 2-(hydroxymethyl)-1-(piperidin-4-yl)propane-1,3-diol hydrochloride (21) (200 mg, 0.88 mmol) in ethanol (18 mL) was added triethylamine (0.8 mL, 5.48 mmol) drop wise at 0° C. and stirred at room temperature for 30 min. To this, a solution of 4-ethoxy-3-(1-methyl-7-oxo-3-propyl-6,7-dihydro-1H-pyrazolo[4,3-d]pyrimidin-5-yl)benzenesulfonyl chloride 2 (150 mg, crude) in dichloromethane (9 mL) was added at 0° C. under inert atmosphere. The reaction mixture was allowed to stir at room temperature for 1 h. After completion of reaction (monitored by LCMS), the reaction solution was concentrated under reduced pressure to afford the residue. Note: Reaction was performed in two lots (1×150 mg; 1×100 mg). The reaction residues from both the batches were combined and purified (without workup) purified by reverse phase column chromatography (Grace System; C18-12 g column; eluted with 25-35% gradient acetonitrile in water). Pure fractions were lyophilized to afford title compound 22 (23 mg, 6% overall yield in two steps) as an off-white solid. $^1$H NMR (400 MHz, DMSO-$d_6$) δ ppm 12.18 (br s, 1H), 7.85 (d, J=2.3 Hz, 1H), 7.82 (dd, J=8.8, 2.3 Hz, 1H), 7.36 (d, J=8.8 Hz, 1H), 4.37 (d, J=5.9 Hz, 1H), 4.32 (t, J=4.9 Hz, 1H), 4.28 (t, J=4.9 Hz, 1H), 4.24-4.18 (m, 2H), 4.16 (s, 3H), 3.68-3.64 (m, 2H), 3.59-3.52 (m, 1H), 3.44-3.33 (m, 3H), 3.31-3.27 (m, 1H), 2.79-2.75 (m, 2H), 2.20-2.11 (m, 2H), 1.86-1.83 (m, 1H), 1.78-1.70 (m, 2H), 1.62-1.53 (m, 2H), 1.40-1.11 (m, 6H), 0.94 (t, J=7.3 Hz, 3H); LCMS (ESI): m/z found 564.51 [M+H$^+$]; purity~99.6%; UPLC: purity~99.1%.

Scheme 16

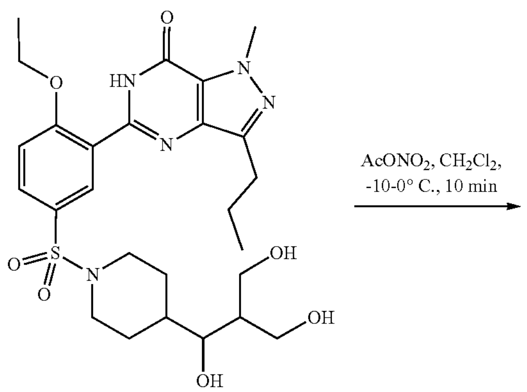

22

-continued

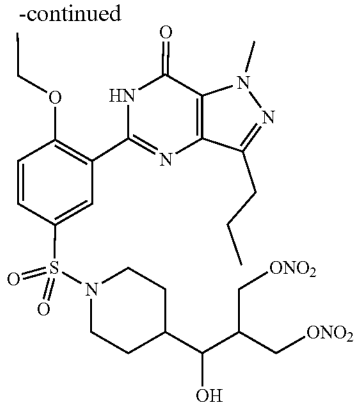

1i

Example 21

2-((1-((4-ethoxy-3-(1-methyl-7-oxo-3-propyl-6,7-dihydro-1H-pyrazolo[4,3-d]pyrimidin-5-yl)phenyl) sulfonyl)piperidin-4-yl)(hydroxy)methyl)propane-1,3-diyl Dinitrate (1i)

To a stirred solution of 5-(5-((4-(1,3-dihydroxy-2-(hydroxymethyl)propyl)piperidin-1-yl)sulfonyl)-2-ethoxyphenyl)-1-methyl-3-propyl-1,6-dihydro-7H-pyrazolo[4,3-d]pyrimidin-7-one 22 (55 mg, 0.098 mmol) in dichloromethane (4 mL) was added a freshly prepared acetyl nitrate (0.42 mL; acetyl nitrate was prepared separately by addition of fuming $HNO_3$ (0.07 mL, 3.21 mmol) drop wise in to acetic anhydride (0.35 mL, 1:5 Vol of fuming $HNO_3$) at −10° C. under inert atmosphere (Note: temperature should not be raised to 0° C.) drop wise at −10° C. allowed to 0° C. and stirred for 10 min. After completion of reaction (monitored by TLC), the reaction was quenched with saturated $NaHCO_3$ solution (10 mL) at 0° C. and extracted with dichloromethane (2×10 mL). The combined organic layer was washed with brine (10 mL), dried over anhydrous $Na_2SO_4$ and concentrate under reduced pressure. The crude product was purified by reverse phase column chromatography (Grace System; C18-12 g column; eluted with 45-55% gradient acetonitrile in water). Pure fractions were lyophilized to afford title compound 1i (12.3 mg, 19%) as a white solid. $^1H$ NMR (400 MHz, DMSO-$d_6$) δ ppm 12.17 (br s, 1H), 7.87 (d, J=2.3 Hz, 1H), 7.83 (dd, J=8.8, 2.3 Hz, 1H), 7.37 (d, J=8.8 Hz, 1H), 5.19 (d, J=6.4 Hz, 1H), 4.70-4.66 (m, 1H), 4.59-4.44 (m, 3H), 4.21 (q, J=7.3 Hz, 2H), 4.16 (s, 3H), 3.72-3.67 (m, 2H), 3.40-3.38 (m, 1H), 2.79-2.75 (m, 2H), 2.32-2.28 (m, 1H), 2.21-2.15 (m, 2H), 1.91-1.87 (m, 1H), 1.78-1.71 (m, 2H), 1.63-1.59 (m, 1H), 1.39-1.20 (m, 6H), 0.94 (t, J=7.34 Hz, 3H); LCMS (ESI): m/z found 654.20 [M+H$^+$]; purity~98.0%; UPLC: purity~97.3%.

Scheme 17

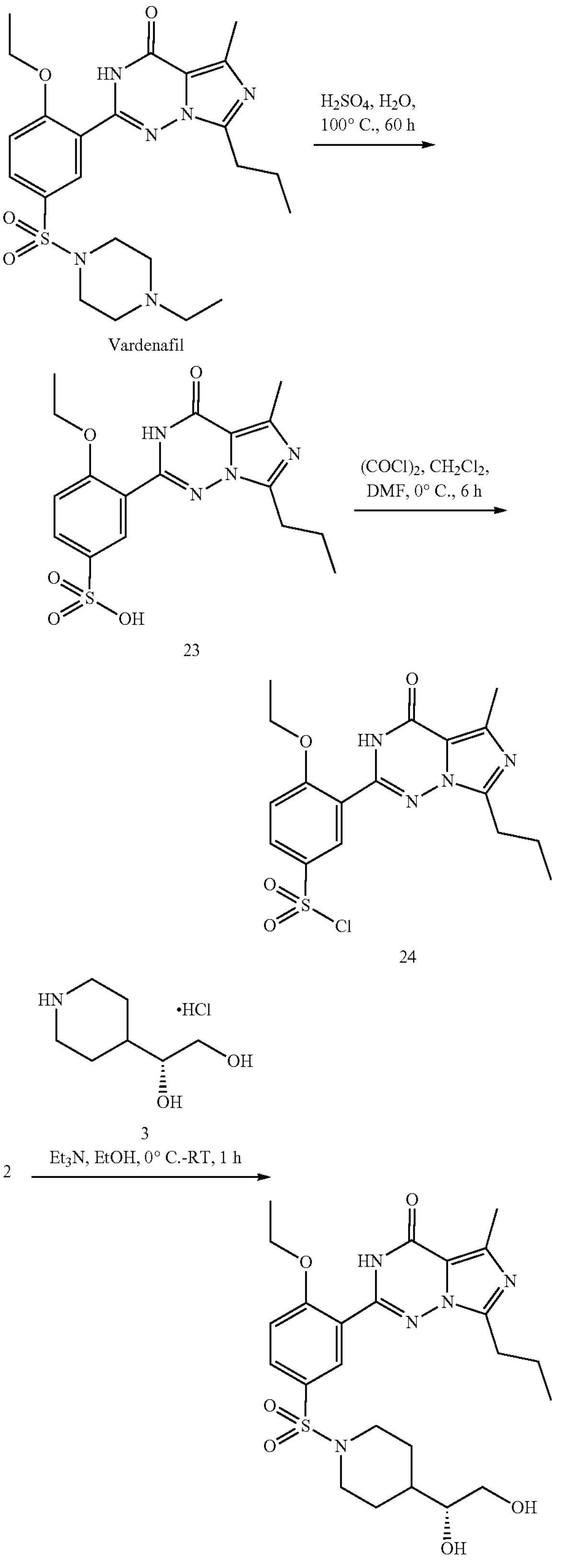

Vardenafil

23

24

3

25

Example 22

4-ethoxy-3-(5-methyl-4-oxo-7-propyl-3,4-dihydro-imidazo[5,1-f][1,2,4]triazin-2-yl)benzene Sulfonic Acid (23)

To a stirred solution of 2-(2-ethoxy-5-((4-ethylpiperazin-1-yl)sulfonyl)phenyl)-5-methyl-7-propylimidazo[5,1-f][1,2,4]triazin-4(3H)-one (Vardenafil) (500 mg, 1.02 mmol) in water (10.5 mL), was added concentrated sulphuric acid (8.0 mL) drop wise at room temperature. After addition, the reaction was heated to 100° C. for 60 h. After completion of reaction (monitored by TLC and LCMS), the reaction mixture was cooled to −10° C. and neutralized with 25% aqueous NaOH solution (~40 mL). The resultant heterogeneous mixture was concentrated under reduced pressure until the water removed completely. The resultant residue was treated with 20% methanol in dichloromethane (5×100 ml) and filtered. The combined organic filtrates were dried over anhydrous $Na_2SO_4$ and concentrated under reduced pressure. The crude product was co-distilled with toluene (2×50 mL), triturated with diethyl ether (20 mL), filtered and dried under vacuum to afford the title compound 23 (500 mg) as an off-white solid; which was used in next step without further purification. $^1H$ NMR (400 MHz, DMSO-$d_6$) δ ppm 11.63 (br s, 1H), 7.62 (d, J=2.4 Hz, 1H), 7.49 (dd, J=8.8, 2.4 Hz, 1H), 6.91 (d, J=8.8 Hz, 1H), 4.01 (q, J=6.8 Hz, 2H), 2.74-2.70 (m, 2H), 2.42 (s, 3H), 1.72-1.65 (m, 2H), 1.23 (t, J=6.8 Hz, 3H), 0.89 (t, J=7.3 Hz, 3H); LCMS (ESI): m/z 393.3 $[M+H^+]$; purity~85.1%.

Example 23

(R)-2-(5-((4-(1,2-dihydroxyethyl)piperidin-1-yl)sulfonyl)-2-ethoxyphenyl)-5-methyl-7-propyl imidazo[5,1-f][1,2,4]triazin-4(3H)-one (25)

To a stirred solution of 4-ethoxy-3-(5-methyl-4-oxo-7-propyl-3,4-dihydroimidazo[5,1-f][1,2,4]triazin-2-yl)benzene sulfonic acid 23 (100 mg, 0.26 mmol) in $CH_2Cl_2$ (6 mL) and DMF (0.1 mL) was added oxalyl chloride (0.1 mL, 1.3 mmol) at 0° C. drop wise under argon atmosphere. The reaction mixture was stirred at 0° C. for 5 h. After completion of reaction (monitored by TLC), the reaction was concentrated at below 20° C. under reduced pressure and the vacuum was backfilled with argon atmosphere. The residue obtained was co-distilled with $CH_2Cl_2$ (2×6 mL) to afford the crude product 24 as a pale yellow liquid.

Meanwhile (R)-1-(piperidin-4-yl)ethane-1,2-diol hydrochloride (3, prepared according to the procedures given in WO 2005026145 A1) (95 mg, 0.52 mmol) in ethanol (6 mL) solution was treated with Amberlyst A-21 ion exchange resin (5 wt/wt) at room temperature for 2 h and filtered. To the filtrate, triethylamine (0.5 mL, 3.9 mmol) was added drop wise at 0° C. followed by above crude product 24 in $CH_2Cl_2$ (3 mL) was added solution at 0° C. under inert atmosphere. The reaction mixture was warmed to room temperature and stirred for 1 h. After completion of reaction (monitored by LCMS), the reaction mixture was directly purified by reverse phase column chromatography (C-18 column; Grace System) by eluting with 30% acetonitrile with water. NOTE: Reaction was performed in two lots (2×100 mg) and purified as described above to afford the title compound 25 (23.2 mg) as a white solid. $^1H$ NMR (400 MHz, DMSO-$d_6$) δ ppm 11.65 (br s, 1H; $D_2O$ exchangeable), 7.87-7.83 (m, 2H), 7.37 (d, J=8.3 Hz, 1H), 4.44-4.38 (m, 2H; $D_2O$ exchangeable), 4.21 (q, J=7.2 Hz, 2H), 3.68-3.64 (m, 2H), 3.31-3.25 (m, 2H), 3.22-3.16 (m, 1H), 2.84-2.81 (m, 2H), 2.48 (s, 3H), 2.21-2.13 (m, 2H), 1.77-1.68 (m, 3H), 1.58-1.53 (m, 1H), 1.38-1.27 (m, 6H), 0.92 (t, J=7.6 Hz, 3H); LCMS(ESI): m/z 520.5 $[M+H]^+$; purity~99.5%.

Scheme 18

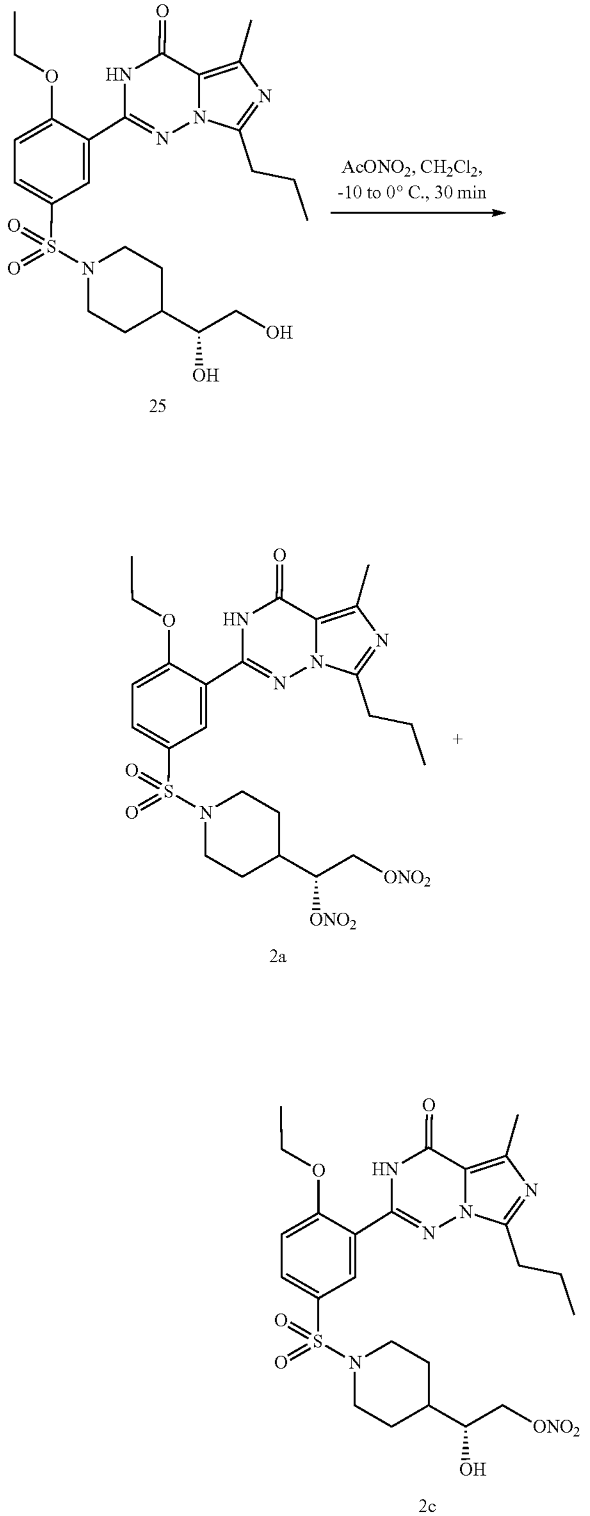

25

2a

+

2c

Example 24

(R)-1-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)ethane-1,2-diyl Dinitrate (2a) and (R)-2-(1-((4-ethoxy-3-(5-methyl-4-oxo-7-propyl-3,4-dihydroimidazo[5,1-f][1,2,4]triazin-2-yl)phenyl)sulfonyl) piperidin-4-yl)-2-hydroxyethyl Nitrate (2c)

To a stirred solution of (R)-2-(5-((4-(1,2-dihydroxyethyl)piperidin-1-yl)sulfonyl)-2-ethoxyphenyl)-5-methyl-7-propyl imidazo[5,1-f][1,2,4]triazin-4(3H)-one (25) (110 mg, 0.21 mmol) in $CH_2Cl_2$ (2.0 mL) was added a solution of freshly prepared acetyl nitrate (0.18 mL) [(acetyl nitrate was prepared separately by addition of fuming $HNO_3$ (0.03 mL; 6.0 eq) drop wise in to acetic anhydride (0.15 mL, 1:5 of $HNO_3$)) slowly at −10° C. under argon atmosphere (Note: temperature should not be raised above 0° C.))] drop wise at −10° C. under argon atmosphere. The reaction mixture was stirred at 0° C. for 30 min. After completion of reaction (monitored by TLC), the reaction mixture was quenched with saturated $NaHCO_3$ solution (~10 mL) at 0° C. The resultant solution was extracted with $CH_2Cl_2$ (2×10 mL). The combined organic layer was washed with brine (15 mL) and dried over anhydrous $Na_2SO_4$ and concentrated under reduced pressure. The crude was purified by preparative HPLC (XBridge C18 column) using 40-100% gradient acetonitrile. The appropriate fractions were lyophilized to afford 2a (38.4 mg) as a white solid and 2c (18.8 mg) as a white solid.

2a analytical data: $^1H$ NMR (400 MHz, DMSO-$d_6$) δ ppm 11.66 (br s, 1H; $D_2O$ exchangeable), 7.89-7.84 (m, 2H), 7.38 (d, J=9.2 Hz, 1H), 5.35-5.31 (m, 1H), 4.95 (dd, J=12.7, 2.4 Hz, 1H), 4.71 (dd, J=12.7, 6.1 Hz, 1H), 4.21 (q, J=7.1 Hz, 2H), 3.72-3.68 (m, 2H), 2.84-2.80 (m, 2H), 2.48 (s, 3H), 2.26-2.21 (m, 2H), 1.82-1.69 (m, 5H), 1.51-1.37 (m, 2H), 1.33 (t, J=7.1 Hz, 3H), 0.92 (t, J=7.3 Hz, 3H); LCMS (ESI): m/z 610 [$M+H^+$]; purity~99%.

2c analytical data: $^1H$ NMR (400 MHz, DMSO-$d_6$) δ ppm 11.66 (br s, 1H; $D_2O$ exchangeable), 7.87-7.83 (m, 2H), 7.37 (d, J=9.2 Hz, 1H), 5.23 (d, J=5.8 Hz, 1H; $D_2O$ exchangeable), 4.53 (dd, J=11.2, 3.4 Hz, 1H), 4.38 (dd, J=11.2, 7.3 Hz, 1H), 4.20 (q, J=7.1 Hz, 2H), 3.70-3.65 (m, 2H), 3.55-3.51 (m, 1H), 2.84-2.80 (m, 2H), 2.48 (s, 3H), 2.24-2.17 (m, 2H), 1.81-1.69 (m, 3H), 1.68-1.61 (m, 1H), 1.38-1.26 (m, 6H), 0.92 (t, J=7.3 Hz, 3H); LCMS (ESI): m/z 565.05 [$M+H^+$]; purity~99.7%.

Scheme 19

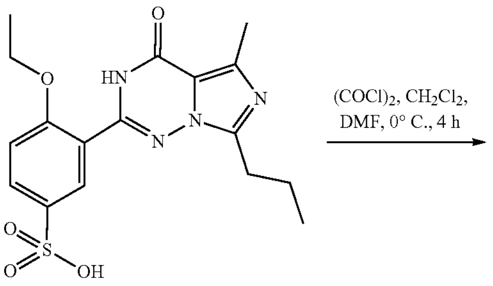

23

-continued

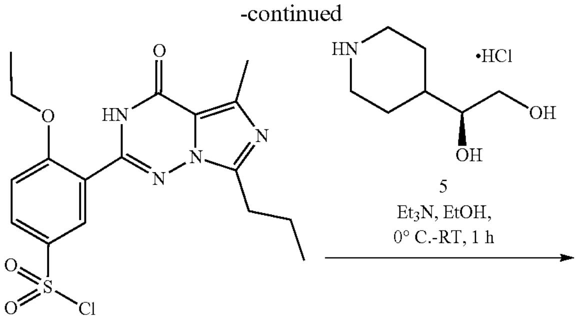

24

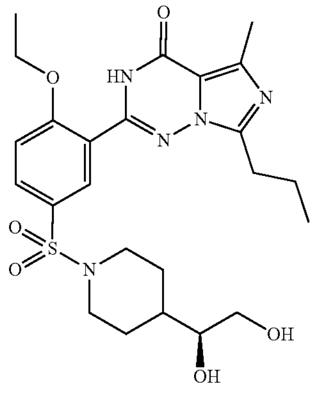

26

Example 25

(S)-2-(5-((4-(1,2-dihydroxyethyl)piperidin-1-yl)sulfonyl)-2-ethoxyphenyl)-5-methyl-7-propyl imidazo[5,1-f][1,2,4]triazin-4(3H)-one (26)

To a stirred solution of 4-ethoxy-3-(5-methyl-4-oxo-7-propyl-3,4-dihydroimidazo[5,1-f][1,2,4]triazin-2-yl)benzene sulfonic acid 23 (300 mg, 0.76 mmol) in $CH_2Cl_2$ (18 mL) and DMF (0.3 mL) was added oxalyl chloride (0.41 mL, 4.59 mmol) at 0° C. drop wise under argon atmosphere. The reaction mixture was stirred at 0° C. for 4 h. After completion of reaction (monitored by TLC), the reaction was concentrated at below 20° C. under reduced pressure and the vacuum was backfilled with argon atmosphere. The residue obtained was co-distilled with $CH_2Cl_2$ (9 mL) to afford the crude product 24 as a pale yellow liquid.

Meanwhile (S)-1-(piperidin-4-yl)ethane-1,2-diol hydrochloride (5) (270 mg, 1.53 mmol) in ethanol (18 mL) solution was treated with Amberlyst A-21 ion exchange resin (5 wt/wt) at room temperature for 2 h and filtered. To the filtrate, triethylamine (1.06 mL, 7.6 mmol) was added drop wise at 0° C. followed by above crude product 24 in $CH_2Cl_2$ (3 mL) was added solution at 0° C. under inert atmosphere. The reaction mixture was warmed to room temperature and stirred for 1 h. After completion of reaction (monitored by LCMS), the reaction mixture was directly purified by reverse phase column chromatography (C-18 column; Grace System) by eluting with 30% acetonitrile with water to afford the title compound 26 (50 mg) as a white solid. $^1H$ NMR (400 MHz, DMSO-$d_6$) δ ppm 11.63 (br s, 1H; $D_2O$ exchangeable), 7.87-7.83 (m, 2H), 7.37 (d, J=8.3 Hz, 1H), 4.44-4.38 (m, 2H; $D_2O$ exchangeable), 4.21 (q, J=7.2 Hz, 2H), 3.68-3.64 (m, 2H), 3.31-3.25 (m, 2H), 3.22-3.16 (m, 1H), 2.84-2.81 (m, 2H), 2.48 (s, 3H), 2.21-

2.13 (m, 2H), 1.77-1.68 (m, 3H), 1.58-1.53 (m, 1H), 1.38-1.27 (m, 6H), 0.92 (t, J=7.6 Hz, 3H); LCMS(ESI): m/z 520.5 $[M+H]^+$; purity~96.9%.

Scheme 20

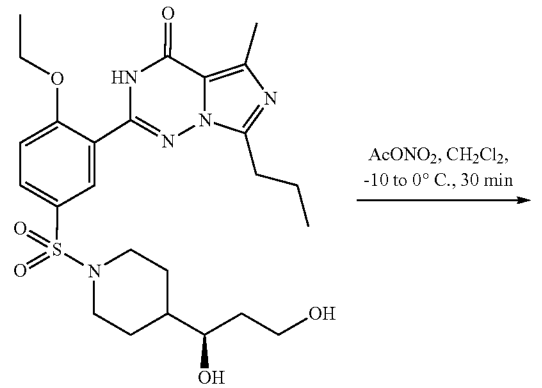

26

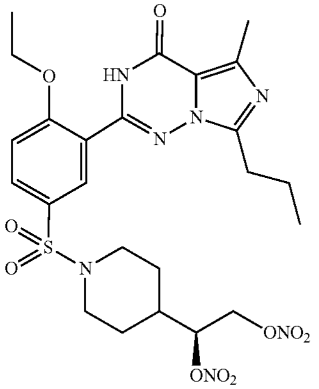

\+

2b

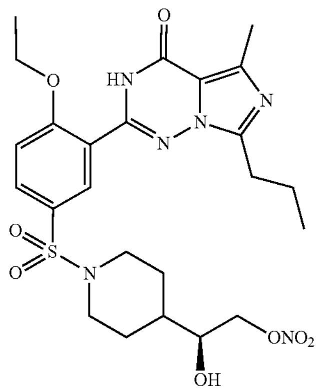

2d

Example 26

(S)-1-(1-((4-ethoxy-3-(5-methyl-4-oxo-7-propyl-3,4-dihydroimidazo[5,1-f][1,2,4]triazin-2-yl)phenyl) sulfonyl)piperidin-4-yl)ethane-1,2-diyl Dinitrate (2b) and (S)-2-(1-((4-ethoxy-3-(5-methyl-4-oxo-7-propyl-3,4-dihydroimidazo[5,1-f][1,2,4]triazin-2-yl) phenyl)sulfonyl) piperidin-4-yl)-2-hydroxyethyl Nitrate (2d)

To a stirred solution of (S)-2-(5-((4-(1,2-dihydroxyethyl) piperidin-1-yl)sulfonyl)-2-ethoxyphenyl)-5-methyl-7-propyl imidazo[5,1-f][1,2,4]triazin-4(3H)-one (26) (150 mg, 0.29 mmol) in $CH_2Cl_2$ (2.5 mL) was added a solution of freshly prepared acetyl nitrate (0.22 mL) [(acetyl nitrate was prepared separately by addition of fuming $HNO_3$ (0.037 mL; 6.0 eq) drop wise in to acetic anhydride (0.18 mL, 1:5 of $HNO_3$)) slowly at −10° C. under argon atmosphere (Note: temperature should not be raised above 0° C.))] drop wise at −10° C. under argon atmosphere. The reaction mixture was stirred at 0° C. for 30 min. After completion of reaction (monitored by TLC), the reaction mixture was quenched with saturated $NaHCO_3$ solution (20 mL) at 0° C. The resultant solution was extracted with $CH_2Cl_2$ (3x30 mL). The combined organic layer was washed with brine (15 mL) and dried over anhydrous $Na_2SO_4$ and concentrated under reduced pressure. The crude product was purified by preparative HPLC (XBridge C18 column) using 40-100% gradient acetonitrile. The appropriate fractions were lyophilized to afford 2b (26 mg) as a white solid and 2d (19 mg) as a white solid.

2b analytical data: $^1H$ NMR (400 MHz, DMSO-$d_6$) δ ppm 11.66 (br s, 1H; $D_2O$ exchangeable), 7.87-7.84 (m, 2H), 7.37 (d, J=9.2 Hz, 1H), 5.35-5.31 (m, 1H), 4.95 (dd, J=12.7, 2.4 Hz, 1H), 4.71 (dd, J=12.7, 6.1 Hz, 1H), 4.21 (q, J=7.1 Hz, 2H), 3.72-3.68 (m, 2H), 2.84-2.80 (m, 2H), 2.48 (s, 3H), 2.26-2.21 (m, 2H), 1.82-1.69 (m, 5H), 1.51-1.37 (m, 2H), 1.33 (t, J=7.1 Hz, 3H), 0.92 (t, J=7.3 Hz, 3H); LCMS (ESI): m/z 610 $[M+H^+]$; purity~99.2%.

2d analytical data: $^1H$ NMR (400 MHz, DMSO-$d_6$) δ ppm 11.66 (br s, 1H; $D_2O$ exchangeable), 7.87-7.83 (m, 2H), 7.37 (d, J=9.2 Hz, 1H), 5.23 (d, J=5.8 Hz, 1H; $D_2O$ exchangeable), 4.53 (dd, J=11.2, 3.4 Hz, 1H), 4.38 (dd, J=11.2, 7.3 Hz, 1H), 4.20 (q, J=7.1 Hz, 2H), 3.70-3.65 (m, 2H), 3.55-3.51 (m, 1H), 2.84-2.80 (m, 2H), 2.48 (s, 3H), 2.24-2.17 (m, 2H), 1.81-1.69 (m, 3H), 1.68-1.61 (m, 1H), 1.38-1.26 (m, 6H), 0.92 (t, J=7.3 Hz, 3H); LCMS (ESI): m/z 565.3 $[M+H^+]$; purity~97%.

Scheme 21

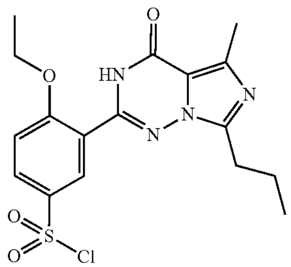

24

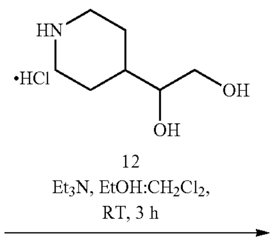

12

Et3N, EtOH:CH2Cl2,
RT, 3 h

-continued

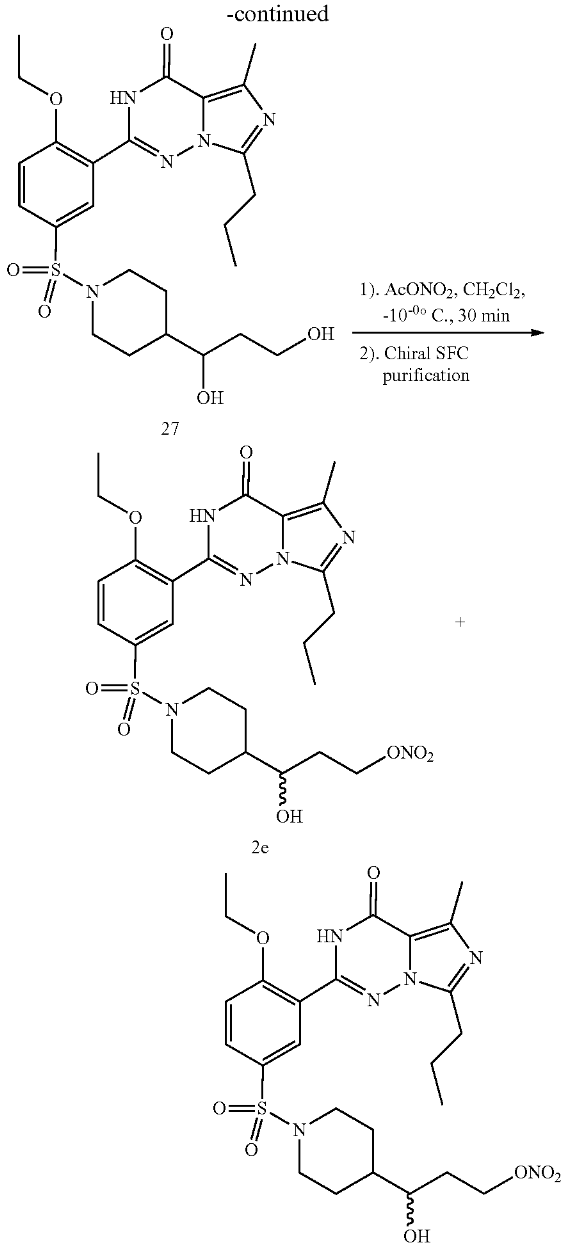

27 2e + 2f

Example 27

2-(5-((4-(1,3-dihydroxypropyl)piperidin-1-yl)sulfonyl)-2-ethoxyphenyl)-5-methyl-7-propylimidazo[5,1-f][1,2,4]triazin-4(3H)-one (27)

To a stirred solution of 1-(piperidin-4-yl)propane-1,3-diol hydrochloride (12) (373 mg, 1.91 mmol) in ethanol (18 mL) was added Amberlyst A-21 basic resin (1.5 g) and stirred at room temperature. After 3 h stirring, the ethanolic solution was filtered (resin beads were removed). To the filtrate was added triethylamine (1.06 mL, 7.65 mmol) drop wise at 0° C. and stirred for 15 min. To this, a solution of 4-ethoxy-3-(5-methyl-4-oxo-7-propyl-3,4-dihydroimidazo[5,1-f][1,2,4]triazin-2-yl)benzenesulfonyl chloride 24 (300 mg, 0.76 mmol) in dichloromethane (18 mL) was added at 0° C. under inert atmosphere. The reaction mixture was allowed to stir at room temperature for 3 h. After completion of reaction (monitored by LCMS), the reaction mixture was concentrated under reduced pressure to afford the crude product. Note: Reaction was repeated in three batches as described above (2×300 mg & 100 mg=700 mg of sulfonyl chloride 4). The resultant residue from the three batches were combined and purified (without workup) by reverse phase column chromatography (C18-40 g column; Grace System; eluted with 45-50% gradient acetonitrile with water). Pure fractions were lyophilized to afford the title compound 27 (Racemate) (170 mg, 17% yield) as a white solid. LCMS (ESI): m/z found 534.58 [M+H$^+$]; purity~94%.

Example 28

3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-3-hydroxypropyl Nitrate (2e, 2f)

To a stirred solution of 2-(5-((4-(1,3-dihydroxypropyl)piperidin-1-yl)sulfonyl)-2-ethoxyphenyl)-5-methyl-7-propylimidazo[5,1-f][1,2,4]triazin-4(3H)-one (27) (200 mg, 0.375 mmol) in dichloromethane (10 mL) was added freshly prepared solution of acetyl nitrate (0.235 mL) [(acetyl nitrate was prepared separately by addition of fuming $HNO_3$ (0.039 mL, 1.87 mmol) drop wise in to acetic anhydride (0.196 mL, 1:5 of fuming $HNO_3$) drop wise at −10° C. under argon atmosphere (Note: temperature should not be raised to 0° C.))] drop wise at −5° C. under argon atmosphere. The reaction was stirred at −5-0° C. for 30 min. After completion of reaction (monitored by TLC), the reaction mixture was quenched with chilled saturated $NaHCO_3$ solution (10 mL) at 0° C. The resultant solution was warmed to room temperature and extracted with dichloromethane (2×10 mL). The combined organic layer was washed with brine (20 mL), dried over anhydrous $Na_2SO_4$ and concentrated under reduced pressure. The crude product was purified by reverse phase column chromatography (Grace System; C18-12 g column; eluted with 50-55% gradient acetonitrile with water). Pure fractions were lyophilized to afford the title compound 2e and 2f as a racemate (70 mg, 31%) as a white solid. LCMS (ESI): m/z 579.45 [M+H$^+$]; purity~96.72%.

70 mg of the racemate was subjected to chiral preparative SFC purification to afford 21.2 mg of 2e as a white solid and 25.6 mg of 2f as a white solid.

Analytical SFC Conditions

- Column/dimensions: Chiralpak AD-H (4.6×250 mm), 5μ
- % $CO_2$: 70.0%
- % Co solvent: 30.0% (100% Ethanol)
- Total Flow: 3.0 g/min
- Back Pressure: 100.0 bar
- Temperature: 30.0° C.
- UV: 214.0 nm Preparative SFC Conditions

- Column/dimensions: Chiralpak AD-H (30×250 mm), 5μ
- % $CO_2$: 80.0%
- % Co solvent: 20.0% (100% Ethanol)
- Total Flow: 70.0 g/min
- Back Pressure: 90.0 bar
- UV: 214.0 nm
- Stack time: 6.7 min
- Load/Inj: 4.2 mg
- Solubility: 20 mL of methanol
- No of injections: 18
- Instrument details: Make/Model: SFC-80

2e analytical data: White solid.

$^1$H NMR (400 MHz, DMSO-$d_6$) δ ppm 11.66 (br s, 1H), 7.88-7.83 (m, 2H), 7.37 (d, J=8.2 Hz, 1H), 4.79 (d, J=5.8 Hz, 1H), 4.61-4.52 (m, 2H), 4.20 (q, J=6.8 Hz, 2H), 3.71-3.64 (m, 2H), 3.33-3.28 (m, 1H), 2.84-2.80 (m, 2H), 2.48 (s, 3H), 2.21-2.13 (m, 2H), 1.81-1.59 (m, 4H), 1.66-1.56 (m, 2H), 1.39-1.12 (m, 6H), 0.92 (t, J=7.3 Hz, 3H); LCMS (ESI): m/z found 579.23 [M+H$^+$]; purity~96.07%; UPLC: purity~95.08%; Chiral SFC: 99.34% ee; 99.67% with RT: 2.17 min; (Column: Chiralpak AD-3 (4.6*150) mm, 3 μm, Co-Solvent name: 0.5% DEA in Ethanol, % Co-Solvent: 30%, Flow rate: 3.0 g/min, outlet pressure: 1500 psi; Temp: 30° C., UV: 250 nm).

2f: White solid.

$^1$H NMR (400 MHz, DMSO-$d_6$) δ ppm 11.66 (br s, 1H), 7.88-7.83 (m, 2H), 7.37 (d, J=8.2 Hz, 1H), 4.79 (d, J=5.8 Hz, 1H), 4.61-4.52 (m, 2H), 4.20 (q, J=6.8 Hz, 2H), 3.71-3.64 (m, 2H), 3.33-3.28 (m, 1H), 2.84-2.80 (m, 2H), 2.48 (s, 3H), 2.21-2.13 (m, 2H), 1.81-1.59 (m, 4H), 1.66-1.56 (m, 2H), 1.39-1.12 (m, 6H), 0.92 (t, J=7.3 Hz, 3H); LCMS (ESI): m/z found 579.19 [M+H$^+$]; purity~99.96%; UPLC: purity~99.65%; Chiral SFC: 97.80% ee; 98.90% with RT: 3.08 min; (Column: Chiralpak AD-3 (4.6*150) mm, 3 μm, Co-Solvent name: 0.5% DEA in Ethanol, % Co-Solvent: 30%, Flow rate: 3.0 g/min, outlet pressure: 1500 psi; Temp: 30° C., UV: 250 nm).

Scheme 22

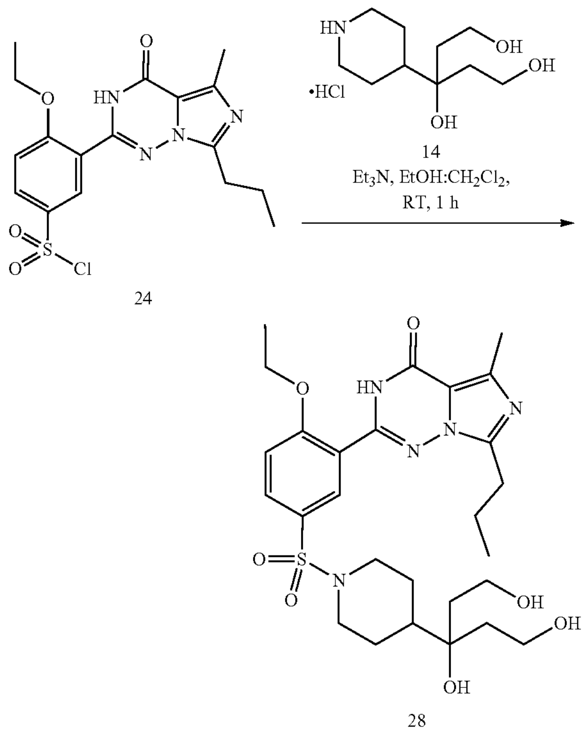

24

14

28

Example 29

2-(2-ethoxy-5-((4-(1,3,5-trihydroxypentan-3-yl)piperidin-1-yl)sulfonyl)phenyl)-5-methyl-7-propylimidazo[5,1-f][1,2,4]triazin-4(3H)-one (28)

To a stirred solution of 3-(piperidin-4-yl)pentane-1,3,5-triol hydrochloride (14) (243 mg, 1.02 mmol) in ethanol (12 mL) was added triethylamine (0.7 mL, 5.10 mmol) drop wise at 0° C. and stirred at room temperature for 30 min. To this, a solution of 4-ethoxy-3-(5-methyl-4-oxo-7-propyl-3,4-dihydroimidazo[5,1-f][1,2,4]triazin-2-yl)benzenesulfonyl chloride 24 (200 mg, 0.510 mmol) in dichloromethane (12 mL) was added at 0° C. under inert atmosphere. The reaction mixture was allowed to stir at room temperature for 1 h. After completion of reaction (monitored by LCMS), the reaction mixture was concentrated under reduced pressure. Note: Reaction was repeated on 200 mg, 100 mg scales of sulfonyl chloride 4. The resultant residue from the three batches were combined and purified (without workup) by reverse phase column chromatography (C18-40 g column; Grace System; eluted with 45-50% gradient acetonitrile with water). Pure fractions were lyophilized to afford the title compound 28 (120 mg; 16%) as a white solid. $^1$H NMR (400 MHz, DMSO-$d_6$) δ ppm 11.62 (br s, 1H), 7.87-7.83 (m, 2H), 7.37 (d, J=8.8 Hz, 1H), 4.37 (t, J=4.8 Hz, 2H), 4.24-4.17 (m, 2H), 4.16 (s, 1H), 3.73-3.67 (m, 2H), 3.49-3.34 (m, 4H), 2.84-2.80 (m, 2H), 2.48 (s, 3H), 2.16-2.09 (m, 2H), 1.78-1.68 (m, 4H), 1.59-1.47 (m, 4H), 1.36-1.15 (m, 6H), 0.92 (t, J=7.3 Hz, 3H); LCMS(ESI): m/z 578.49 [M+H]$^+$; purity~98.41%.

Scheme 23

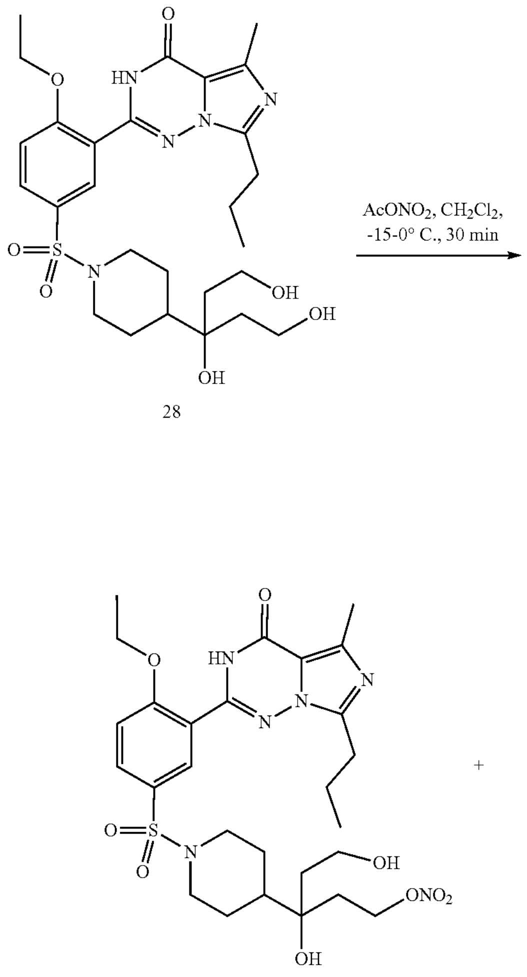

28

+

2g

-continued

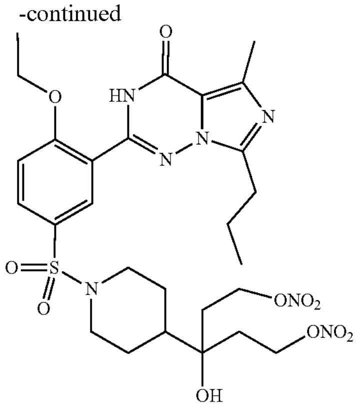

2h

Example 30

3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-3,5-dihydroxypentyl Nitrate (2g) and 3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-3-hydroxypentane-1,5-diyl Dinitrate (2h)

To a stirred solution of 2-(2-ethoxy-5-((4-(1,3,5-trihydroxypentan-3-yl)piperidin-1-yl)sulfonyl)phenyl)-5-methyl-7-propylimidazo[5,1-f][1,2,4]triazin-4(3H)-one (28) (100 mg, 0.173 mmol) in dichloromethane (5 mL) was added freshly prepared solution of acetyl nitrate (0.06 mL) [(acetyl nitrate was prepared separately by addition of fuming $HNO_3$ (0.01 mL, 0.519 mmol) drop wise in to acetic anhydride (0.05 mL, 1:5 of fuming $HNO_3$) drop wise at −10° C. under argon atmosphere (Note: temperature should not be raised to 0° C.))] drop wise at −10° C. under argon atmosphere. The reaction was stirred at −5-0° C. for 30 min. After completion of reaction (monitored by TLC), the reaction mixture was quenched with chilled saturated $NaHCO_3$ solution (10 mL) at 0° C. The resultant solution was warmed to room temperature and extracted with dichloromethane (2×10 mL). The combined organic layer was washed with brine (10 mL), dried over anhydrous $Na_2SO_4$ and concentrated under reduced pressure. The obtained crude mixture was purified by reverse phase column chromatography (Grace System; Reveleris® C18 column-40 g; eluted with 48-53% linear gradient of acetonitrile with water). Pure fractions were lyophilized to afford the title compound 2g (8.4 mg; 8% yield; fast eluted compound) as a white solid & 2h (35.6 mg; 31% yield; late eluted compound) as a white solid.

2g analytical data: White solid. $^1H$ NMR (400 MHz, DMSO-$d_6$) δ ppm 11.66 (br s, 1H), 7.88-7.82 (m, 2H), 7.37 (d, J=8.8 Hz, 1H), 4.60-4.54 (m, 2H), 4.49-4.44 (m, 2H), 4.21 (q, J=6.8 Hz, 2H), 3.74-3.69 (m, 2H), 3.50-3.44 (m, 2H), 2.84-2.80 (m, 2H), 2.48 (s, 3H), 2.20-2.13 (m, 2H), 1.78-1.67 (m, 6H), 1.59-1.52 (m, 2H), 1.38-1.22 (m, 6H), 0.92 (t, J=7.3 Hz, 3H); LCMS (ESI): m/z 623.24 [M+H$^+$]; purity~97.23%.

2h analytical data: White solid. $^1H$ NMR (400 MHz, DMSO-$d_6$) δ ppm 11.62 (br s, 1H), 7.88-7.83 (m, 2H), 7.37 (d, J=8.8 Hz, 1H), 4.78 (s, 1H), 4.56 (t, J=7.3 Hz, 4H), 4.21 (q, J=6.8 Hz, 2H), 3.75-3.70 (m, 2H), 2.84-2.80 (m, 2H), 2.48 (s, 3H), 2.32-2.26 (m, 2H), 1.83-1.68 (m, 8H), 1.35-1.25 (m, 6H), 0.92 (t, J=7.3 Hz, 3H); LCMS (ES): m/z 668.24 [M+H$^+$]; purity~98.31%.

Scheme 24

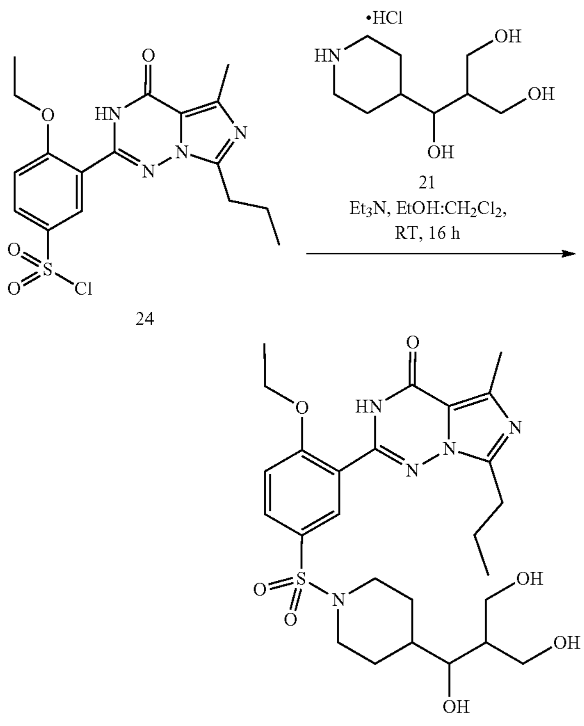

29

Example 31

2-(5-((4-(1,3-dihydroxy-2-(hydroxymethyl)propyl)piperidin-1-yl)sulfonyl)-2-ethoxyphenyl)-5-methyl-7-propylimidazo[5,1-f][1,2,4]triazin-4(3H)-one (29)

To a stirred solution of 2-(hydroxymethyl)-1-(piperidin-4-yl)propane-1,3-diol hydrochloride (21) (200 mg, 0.88 mmol) in ethanol (18 mL) was added amberlyst A-21 base resin (1.0 g) at room temperature and stirred for 2 h. The reaction solution was filtered through a Buchner funnel and washed with ethanol (6.0 mL). To this filtrate, added triethylamine (0.51 mL, 3.65 mmol) drop wise at 0° C. and stirred for 30 min. To this, a solution of 4-ethoxy-3-(5-methyl-4-oxo-7-propyl-3,4-dihydroimidazo[5,1-f][1,2,4]triazin-2-yl)benzenesulfonyl chloride 24 (150 mg, 0.365 mmol) in dichloromethane (9 mL) was added at 0° C. under inert atmosphere. The reaction mixture was allowed to stir at room temperature for 16 h. After completion of reaction (monitored by LCMS), the reaction solution was concentrated under reduced pressure to afford the residue. Note: Reaction was performed in three lots (1×100 mg; 2×150 mg). The reaction residues from the three batches were combined and purified (without workup) by reverse phase column chromatography (Grace System; Reveleris® C18-40 g column; eluted with 30-35% gradient acetonitrile in water). Pure fractions were lyophilized to afford title compound 29 (100 mg, 18% overall yield in two steps) as a white solid. $^1H$ NMR (400 MHz, DMSO-$d_6$) δ ppm 11.81 (br s, 1H), 7.88-7.83 (m, 2H), 7.37 (d, J=8.8 Hz, 1H), 4.38-4.25

(m, 3H), 4.21 (q, J=6.8 Hz, 2H), 3.72-3.62 (m, 2H), 3.58-3.52 (m, 1H), 3.46-3.38 m, 4H), 2.84-2.80 (m, 2H), 2.48 (s, 3H), 2.21-2.12 (m, 2H), 1.87-1.82 (m, 1H), 1.78-1.69 (m, 2H), 1.63-1.52 (m, 2H), 1.41-1.20 (m, 6H), 0.92 (t, J=7.3 Hz, 3H); LCMS (ESI): m/z found 564.22 [M+H$^+$]; purity~95.18%; UPLC: purity~95.12%.

Scheme 25

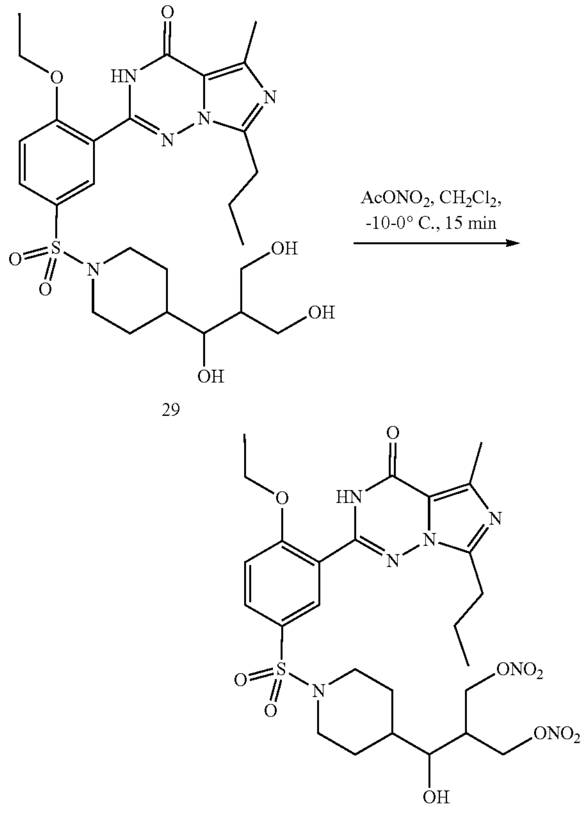

29

2i

Example 32

2-((1-((4-ethoxy-3-(5-methyl-4-oxo-7-propyl-3,4-dihydroimidazo[5,1-f][1,2,4]triazin-2-yl)phenyl) sulfonyl)piperidin-4-yl)(hydroxy)methyl)propane-1,3-diyl Dinitrate (2i)

To a stirred solution of 2-(5-((4-(1,3-dihydroxy-2-(hydroxymethyl)propyl)piperidin-1-yl)sulfonyl)-2-ethoxyphenyl)-5-methyl-7-propylimidazo[5,1-f][1,2,4]triazin-4(3H)-one 29 (80 mg, 0.142 mmol) in dichloromethane (8 mL) was added a freshly prepared acetyl nitrate (0.6 mL; acetyl nitrate was prepared separately by addition of fuming $HNO_3$ (0.1 mL, 4.59 mmol) drop wise in to acetic anhydride (0.5 mL, 1:5 Vol of fuming $HNO_3$) at −10° C. under inert atmosphere (Note: temperature should not be raised to 0° C.) drop wise at 0° C. and stirred for 15 min. After completion of reaction (monitored by TLC), the reaction was quenched with saturated $NaHCO_3$ solution (15 mL) at 0° C. and extracted with dichloromethane (2×10 mL). The combined organic layer was washed with brine (10 mL), dried over anhydrous $Na_2SO_4$ and concentrate under reduced pressure. The crude product was purified by reverse phase column chromatography (Grace System; Reveleris® C18-12 g column; eluted with 45% gradient acetonitrile in water). Pure fractions were lyophilized to afford title compound 2i (33.9 mg, 36%) as a white solid. $^1$H NMR (400 MHz, DMSO-d$_6$) δ ppm 11.67 (s, 1H), 7.91-7.79 (m, 2H), 7.38 (d, J=8.8 Hz, 1H), 5.19 (d, J=5.8 Hz, 1H), 4.71-4.68 (m, 1H), 4.61-4.42 (m, 3H), 4.21 (q, J=6.8 Hz, 2H), 3.71-3.65 (m, 2H), 3.39-3.32 (m, 1H), 2.84-2.80 (m, 2H), 2.48 (s, 3 H), 2.33-2.28 (m, 1H), 2.24-2.13 (m, 2H), 1.91-1.85 (m, 1H), 1.78-1.69 (m, 2H), 1.63-1.59 (m, 1H), 1.42-1.19 (m, 6H), 0.92 (t, J=7.3 Hz, 3H); LCMS (ESI): m/z found 654.54 [M+H$^+$]; purity~98.64%; UPLC: purity~97.98%.

Scheme 26

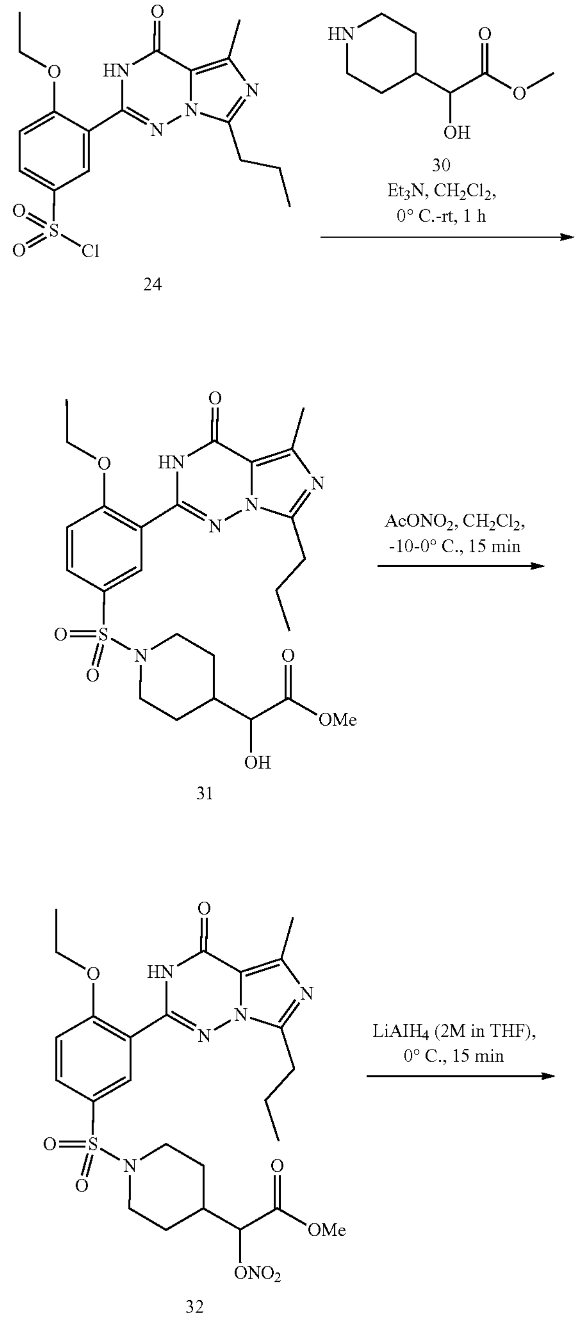

24

30

31

32

-continued

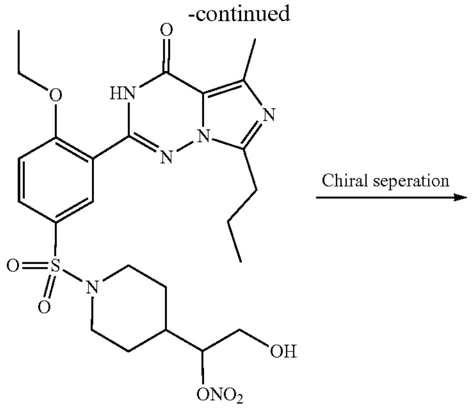

33

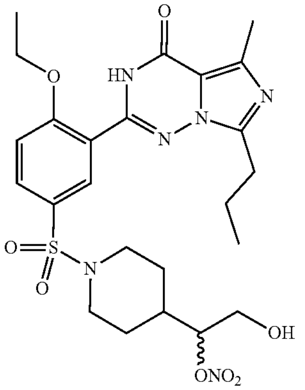

+

2k

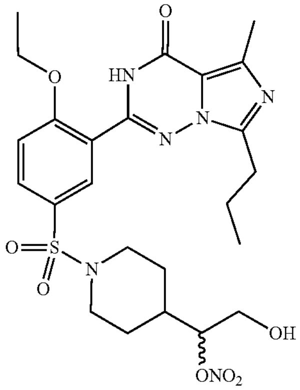

21

Example 33 methyl 2-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-hydroxyacetate (31)

To a stirred solution of methyl 2-hydroxy-2-(piperidin-4-yl)acetate 30 (200 mg, 0.70 mmol) in $CH_2Cl_2$ (12 mL) was added triethylamine (1.0 mL, 7.35 mmol) at 0° C. in drop wise under argon atmosphere and stirred for 30 min. To the reaction mixture, a solution of 4-ethoxy-3-(5-methyl-4-oxo-7-propyl-3,4-dihydroimidazo[1,5-f][1,2,4]triazin-2-yl)benzene-1-sulfonyl chloride 24 (200 mg, 0.49 mmol) in $CH_2Cl_2$ (8 mL) was added drop wise at 0° C. The reaction mixture was warmed to room temperature and stirred for 1 h. After completion of reaction (monitored by TLC & LCMS), the reaction mixture was diluted in $CH_2Cl_2$ (20 mL) and washed with water (20 mL). The organic layer was separated, dried over anhydrous $Na_2SO_4$ and concentrated under reduced pressure. Note: Reaction was performed in three batches (1×100 mg; 2×200 mg). The obtained crude product of three batches were combined and purified by reverse phase column chromatography (Grace System; Reveleris® C-18 column; eluted with 35% gradient acetonitrile with water). The pure fractions were concentrated until acetonitrile solvent was completely removed. The resultant aqueous solution was extracted with ethyl acetate (2×75 mL). The combined the organic layer was dried over anhydrous $Na_2SO_4$ and concentrated under reduced pressure to afford the title compound 31 (300 mg, ~42% yield) as a white solid. $^1H$ NMR (300 MHz, DMSO-$d_6$) δ ppm 11.64 (s, 1H), 7.86-7.81 (m, 2H), 7.37 (d, J=8.8 Hz, 1H), 5.44 (d, J=5.8 Hz, 1H), 4.21 (q, J=6.9 Hz, 2H), 3.89-3.83 (m, 1H), 3.71-3.59 (m, 5H), 2.85-2.81 (m, 2H), 2.28-2.17 (m, 2H), 1.80-1.66 (m, 2H), 1.62-1.43 (m, 3H), 1.42-1.09 (m, 8H), 0.92 (t, J=7.3 Hz, 3H); LCMS (ESI): m/z 548.20 [M+H$^+$]; purity~93.19%.

Example 34 methyl 2-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-(nitrooxy)acetate (32)

To a stirred solution of methyl 2-(1-((4-ethoxy-3-(5-methyl-4-oxo-7-propyl-3,4-dihydroimidazo[5,1-f][1,2,4]triazin-2-yl)phenyl) sulfonyl)piperidin-4-yl)-2-hydroxyacetate 31 (150 mg, 0.27 mmol) in dichloromethane (7.5 mL) was added a freshly prepared solution of acetyl nitrate (1.0 mL) [(acetyl nitrate was prepared separately by addition of fuming $HNO_3$ (0.17 mL, 7.8 mmol) drop wise in to acetic anhydride (0.83 mL, 1:5 of fuming $HNO_3$) drop wise at −10° C. under argon atmosphere (Note: temperature should not be raised to 0° C.))] drop wise at 0° C. under argon atmosphere. The reaction was stirred at 0° C. for 15 min. After completion of reaction (monitored by TLC), the reaction mixture was quenched with chilled saturated $NaHCO_3$ solution (30 mL) at 0° C. The resultant solution was warmed to room temperature and extracted with dichloromethane (2×20 mL). The combined organic layer was washed with brine (25 mL), dried over anhydrous $Na_2SO_4$ and concentrated under reduced pressure to afford the crude title compound 32 (170 mg) as a semi solid, which was used immediately for next reaction without purification. LCMS (ESI): m/z 593.22 [M+H$^+$]; purity~90.49%.

Example 35

1-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-hydroxyethyl Nitrate (33-Racemate)

To a stirred solution of methyl 2-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-(nitrooxy)acetate 32 (170 mg, crude) in THF (8.5 mL) was added 2M $LiAlH_4$ solution in THF (0.43 mL, 0.86 mmol) in drop wise at 0° C. under argon atmosphere and stirred for 15 min at 0° C. After completion of reaction (monitored by TLC), the reaction mixture was quenched with saturated $Na_2SO_4$ solution (1.0 mL) in drop wise at 0° C. and allowed to room temperature and stirred for 2 h. The resulted solution was filtered through Celite bed and washed with ethyl acetate (25 mL). The filtrate was washed with brine (25 mL), dried over anhydrous $Na_2SO_4$ and concentrated under reduced pressure. Note: Reaction was performed in three batches (1×60 mg; 1×110 mg; 1×170 mg). The obtained crude of three batches were combined and purified by reverse phase column chromatography (Grace System; Reveleris® C18-40 g column; eluted with 40% gradient acetonitrile with water). The pure fractions were combined and concentrated until acetonitrile solvent was completely removed. The resultant aqueous solution was extracted with ethyl acetate (2×75 mL). The combined the organic layer and dried over anhydrous $Na_2SO_4$ and concentrated under reduced pressure to afford the title compound 33-racemate (128 mg) as an off-white solid. LCMS (ESI): m/z 565.23 [M+H$^+$]; purity~94.90%; Chiral SFC: Peak-1: 49.77% at RT=9.97 min; Peak-2: 50.23% at RT 12.26 min (Column: Chiralpak AD-H (250*4.6) mm; 5 um; Co-solvent: 25%, Co-solvent name: isopropyl alcohol, Outlet pressure: 100 bar, Temperature: 30° C.; UV: 214 nm).

128 mg of 33-racemate was separated by chiral preparative SFC purification to afford 26.0 mg of 2k-Peak-1 as an off-white solid and 8.9 mg of 2i-Peak-2 as an off-white solid.

Analytical SFC Conditions:

- Column/dimensions: Chiralpak AD-H (250×4.6) mm, 5um
- % of $CO_2$: 75%
- % of Co-solvent: 25% (100% isopropyl alcohol)
- Flow: 3.0 g/min
- Back pressure: 100.0 bar
- Temperature: 30° C.
- Wave length: 214 nm Preparative SFC Conditions:

- Column/dimensions: Chiralpak AD-H (250×30) mm, 5um
- % of $CO_2$: 85%
- % of Co-solvent: 15% (0.5% isopropyl amine in isopropyl alcohol)
- Flow: 60.0 g/min
- Back pressure: 90.0 bar
- Wave length: 214 nm
- Solubility: 20 mL of methanol
- Load ability/Inj: 2.8 mg
- Total no of injections: 34
- Instrument details: Make/Model: SFC-080

2k-16-Peak-1 Analytical Data:

$^1$H NMR (300 MHz, DMSO-d$_6$) δ ppm 11.61 (br s, 1H), 7.89-7.81 (m, 2H), 7.37 (d, J=8.8 Hz, 1H), 5.08-4.91 (m, 2H), 4.21 (q, J=6.9 Hz, 2H), 3.72-3.49 (m, 4H), 2.85-2.80 (m, 2H), 2.48 (s, 3H), 2.28-2.19 (m, 2H), 1.82-1.62 (m, 5H), 1.41-1.24 (m, 5H), 0.92 (t, J=7.3 Hz, 3H); LCMS (ESI): m/z 565.23 [M+H$^+$]; purity~99.84%; UPLC: purity~98.44%; Chiral SFC: 96.99% ee; 98.49% at RT 8.65 min (Column: Chiralpak AD-H (250*4.6) mm; 5 um; Co-solvent: 25%, Co-solvent name: isopropyl alcohol, Outlet pressure: 100 bar, Temperature: 30° C.; UV: 214 nm).

2i-Peak-2 Analytical Data:

$^1$H NMR (300 MHz, DMSO-d$_6$) δ ppm 11.61 (br s, 1H), 7.89-7.81 (m, 2H), 7.37 (d, J=8.8 Hz, 1H), 5.08-4.91 (m, 2H), 4.21 (q, J=6.9 Hz, 2H), 3.72-3.49 (m, 4H), 2.85-2.80 (m, 2H), 2.48 (s, 3H), 2.28-2.19 (m, 2H), 1.82-1.62 (m, 5H), 1.41-1.24 (m, 5H), 0.92 (t, J=7.3 Hz, 3H); LCMS (ESI): m/z 565.23 [M+H$^+$]; purity~99.60%; UPLC: purity~99.0%; Chiral SFC: 97.17% ee; 98.58% at RT 10.72 min (Column: Chiralpak AD-H (250*4.6) mm; 5 um; Co-solvent: 25%, Co-solvent name: isopropyl alcohol, Outlet pressure: 100 bar, Temperature: 30° C.; UV: 214 nm).

Scheme 27

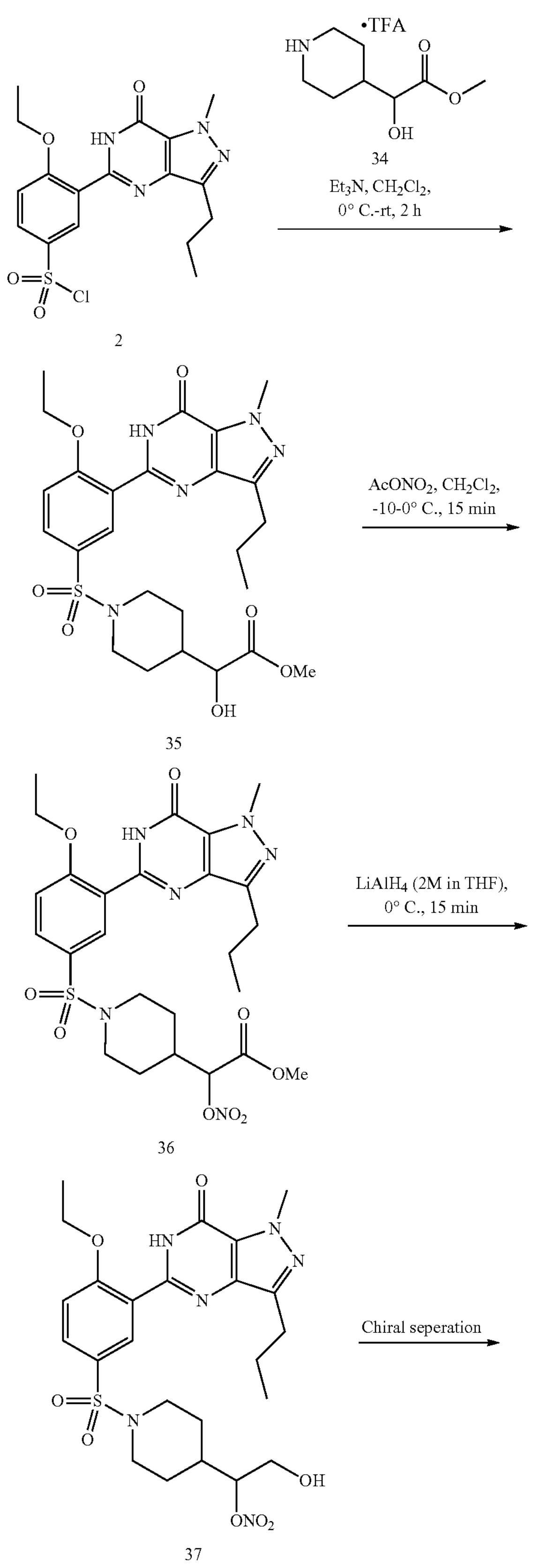

-continued

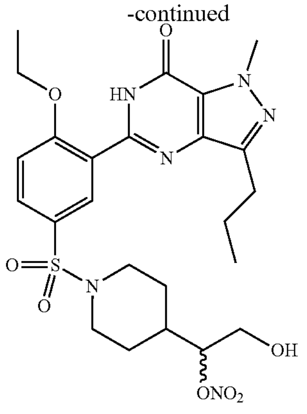

+

1k

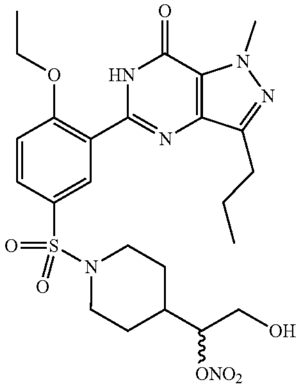

11

Example 36 methyl 2-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-2-hydroxyacetate (35)

To a stirred solution of methyl 2-hydroxy-2-(piperidin-4-yl)acetate, 2,2,2-trifluoroacetate salt (34) (870 mg, 3.04 mmol) in $CH_2Cl_2$ (50 mL) was added triethylamine (2.5 mL, 18.26 mmol) at 0° C. drop wise under argon atmosphere and stirred for 30 min. To the reaction mixture, a solution of 4-ethoxy-3-(5-methyl-4-oxo-7-propyl-3,4-dihydroimidazo [1,5-f][1,2,4]triazin-2-yl)benzene-1-sulfonyl chloride (2) (500 mg, 1.217 mmol) in $CH_2Cl_2$ (25 mL) was added drop wise at 0° C. and stirred for 15 min. The reaction mixture was warmed to room temperature and stirred for 2 h. Note: Reaction was performed in two batches (2×500 mg). After completion of reaction (monitored by TLC), both the reaction mixtures were concentrated and the resultant residue was diluted with water (50 mL) and extracted with ethyl acetate (2×100 mL). The combined organic layer was dried over anhydrous $Na_2SO_4$ and concentrated under reduced pressure. The obtained crude product was purified by reverse phase column chromatography (Reveleris® C-18 column; Grace System) by eluting with 35% gradient acetonitrile with water. The pure fractions were concentrated until acetonitrile solvent was completely removed. The resultant aqueous solution was extracted with ethyl acetate (2×150 mL). The combined the organic layer was dried over anhydrous $Na_2SO_4$ and concentrated under reduced pressure to afford the title compound 35 (400 mg, ~26% yield) as a white solid. $^1$H NMR (400 MHz, DMSO-$d_6$) δ ppm 11.20 (br s, 1H; $D_2O$ exchangeable), 7.85-7.79 (m, 2H), 7.36 (d, J=8.8 Hz, 1H), 5.43 (d, J=6.4 Hz, 1H; $D_2O$ exchangeable), 4.21 (q, J=6.8 Hz, 2H), 4.16 (s, 3H), 3.88-3.85 (m, 1H), 3.68-3.64 (m, 2H), 3.60 (s, 3H), 2.79-2.75 (m, 2H), 2.22-2.17 (m, 2H), 1.77-1.70 (m, 2H), 1.60-1.51 (m, 3H), 1.41-1.30 (m, 5H), 0.94 (t, J=7.2 Hz, 3H); LCMS (ESI): m/z 548.34 [M+H$^+$]; purity~92.24%.

Example 37 methyl 2-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-2-(nitrooxy)acetate (36)

To a stirred solution of methyl 2-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-2-hydroxyacetate (35) (200 mg, 0.365 mmol) in dichloromethane (10 mL) was added freshly prepared solution of acetyl nitrate (1.44 mL) [(acetyl nitrate was prepared separately by addition of fuming $HNO_3$ (0.24 mL, 10.70 mmol) drop wise in to acetic anhydride (1.2 mL, 1:5 of fuming $HNO_3$) drop wise at −10° C. under argon atmosphere (Note: temperature should not be raised to 0° C.))] drop wise at 0° C. under argon atmosphere. The reaction was stirred at 0° C. for 15 min. After completion of reaction (monitored by TLC), the reaction mixture was quenched with chilled saturated $NaHCO_3$ solution (25 mL) at 0° C. The resultant solution was warmed to room temperature and extracted with dichloromethane (2×20 mL). The combined organic layer was washed with brine (25 mL), dried over anhydrous $Na_2SO_4$ and concentrated under reduced pressure to afford the crude title compound 36 (250 mg) as a semi solid, which was used immediately for next reaction without purification. LCMS (ESI): m/z 593.08 [M+H$^+$]; purity~81%.

Example 38

1-(1-((4-ethoxy-3-(1-methyl-7-oxo-3-propyl-6,7-dihydro-1H-pyrazolo[4,3-d]pyrimidin-5-yl)phenyl) sulfonyl)piperidin-4-yl)-2-hydroxyethyl Nitrate (37)

To a stirred solution of methyl 2-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-2-(nitrooxy) acetate 36 (250 mg, 81% pure) in THF (12.5 mL) was added 2M $LiAlH_4$ solution in THF (0.4 mL, 0.844 mmol) in drop wise at 0° C. under argon atmosphere and stirred for 15 min at 0° C. After completion of reaction (monitored by TLC), the reaction mixture was quenched with saturated $Na_2SO_4$ solution (0.4 mL) in drop wise at 0° C. and allowed to room temperature and stirred for 2 h. The resulted solution was filtered through Celite bed and washed with ethyl acetate (25 mL), dried over anhydrous $Na_2SO_4$ and concentrated under reduced pressure. NOTE: Reaction was performed in two batches (2×250 mg) as described above. The obtained crude product from both the batches were combined and purified by reverse phase column chromatography (Reveleris® C18-40 g column; Grace System) by eluting with 40-45% gradient acetonitrile with water. The pure fractions were combined and concentrated until acetonitrile solvent was completely removed. The resultant aqueous solution was extracted with ethyl acetate (2×100 mL). The combined the organic layer and dried over anhydrous $Na_2SO_4$ and concentrated under reduced pressure to afford the title compound 37 (240 mg; 58% overall yield in two steps) as a white solid. LCMS (ESI): m/z 565.34 [M+H$^+$]; purity~95.65%; Chiral SFC: Peak-1: 49.67% at RT=7.56 min; Peak-2: ~49.81% at RT 8.63 min (Column: Chiralpak AD-H (250*4.6) mm; 5 um; Co-solvent: 25%, Co-solvent name: Isopropanol, Outlet pressure: 100 bar, Temperature: 30° C., UV: 214 nm).

215 mg of 37 was subjected to chiral preparative SFC purification to afford 52.9 mg of 1k as a white solid and 45.5 mg of 1l as a white solid.

Analytical SFC Conditions:

Column/dimensions—Chiralpak AD-H (250×4.6) mm, Sum

% of $CO_2$ 75%

% of Co-solvent 25% (100% isopropanol)

Flow 3.0 g/min

Back pressure 100.0 bar

Temperature 30° C.

Wave length 214 nm

Preparative NP-HPLC Conditions:

Column/dimensions: Chiralpak AD-H (250×30) mm, Sum

% of $CO_2$ 75%

% of Co-solvent 25% (100% isopropanol)

Flow 90.0 g/min

Back pressure 100.0 bar

Wave length 214 nm

Solubility 30 mL methanol

Load ability/Inj 5.5 mg/Inj

Total no of injections: 40

1k: $^1$H NMR (400 MHz, DMSO-d$_6$) δ ppm 12.20 (br s, 1H; $D_2O$ exchangeable), 7.86-7.80 (m, 2H), 7.36 (d, J=8.8 Hz, 1H), 5.05 (d, J=5.2 Hz, 1H; $D_2O$ exchangeable), 4.98-4.93 (m, 1H), 4.20 (q, J=6.8 Hz, 2H), 4.16 (s, 3H), 3.70-3.61 (m, 3H), 3.56-3.50 (m, 1H), 2.79-2.75 (m, 2H), 2.26-2.17 (m, 2H), 1.78-1.68 (m, 5H), 1.41-1.30 (m, 5H), 0.94 (t, J=7.2 Hz, 3H); LCMS (ESI): m/z 565.26 [M+H]$^+$; purity~96.73%; UPLC: 98.84%; Chiral SFC: 98.12% ee; 99.06% at RT 7.68 min (Column: Chiralpak AD-3 (150*4.6) mm; 3 um; Co-solvent: 35%, Co-solvent name: methanol, Outlet pressure: 1500 psi, Temperature: 30° C., UV: 215 nm).

1l: 12.20 (br s, 1H; $D_2O$ exchangeable), 7.86-7.80 (m, 2H), 7.36 (d, J=8.8 Hz, 1H), 5.05 (d, J=5.2 Hz, 1H; $D_2O$ exchangeable), 4.98-4.93 (m, 1H), 4.20 (q, J=6.8 Hz, 2H), 4.16 (s, 3H), 3.70-3.61 (m, 3H), 3.56-3.50 (m, 1H), 2.79-2.75 (m, 2H), 2.26-2.17 (m, 2H), 1.78-1.68 (m, 5H), 1.41-1.30 (m, 5H), 0.94 (t, J=7.2 Hz, 3H); LCMS (ESI): m/z 565.26 [M+H]$^+$; purity~98.15%; UPLC: 99.17%; Chiral SFC: 91.84% ee; 95.92% at RT 8.92 min (Column: Chiralpak AD-3 (150*4.6) mm; 3 um; Co-solvent: 35%, Co-solvent name: methanol, Outlet pressure: 1500 psi, Temperature: 30° C., UV: 215 nm).

Scheme 28

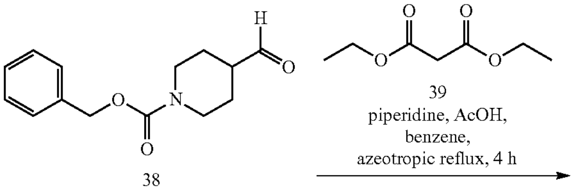

38

-continued

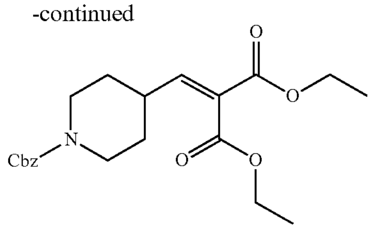

40

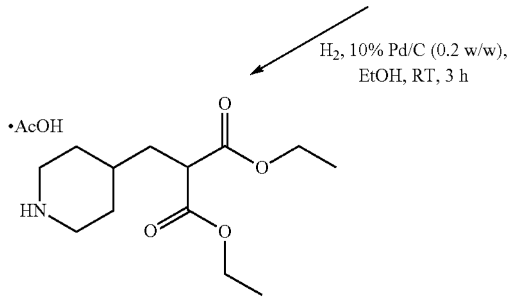

41

Example 39

Diethyl 2-((1-(benzyloxycarbonyl)piperidin-4-yl) methylene)malonate (40)

To a stirred solution of benzyl 4-formylpiperidine-1-carboxylate 38 (2.5 g, 10.10 mmol) and diethyl malonate 39 (2.16 mL, 14.14 mmol) in benzene (30 mL), were added piperidine (0.1 mL, 1.01 mmol) and acetic acid (0.12 mL, 2.02 mmol) at room temperature with azeotropic set up. The reaction mixture was heated to reflux temperature and stirred for 4 h. After completion of reaction (monitored by TLC), the reaction mixture was cooled to room temperature and diluted with ethyl acetate (50 mL). The reaction solution was washed with saturated aqueous $NaHCO_3$ solution (50 mL), saturated aqueous $NH_4Cl$ solution (50 mL) and brine (50 mL). The organic layer was separated, dried over anhydrous $Na_2SO_4$ and concentrated under reduced pressure and purified by normal phase column chromatography (silica gel—40 g; Grace System) by eluting with 10-15% ethyl acetate with petroleum ether to afford the title compound 40 (2.5 g, ~59% yield) as a pale yellow liquid. $^1$H NMR (400 MHz, $CDCl_3$) δ ppm 7.37-7.30 (m, 5H), 6.74 (d, J=10.4 Hz, 1H), 5.13 (s, 2H), 4.34-4.14 (m, 6H), 2.89-2.74 (m, 2H), 2.65-2.56 (m, 1H), 1.75-1.68 (m, 2H), 1.46-1.35 (m, 2H), 1.34-1.24 (m, 6H); LCMS (ESI): m/z 390.36 [M+H$^+$]; purity~93.99%.

Example 40

Diethyl 2-(piperidin-4-ylmethyl)malonate as Acetic Acid Salt (41)

To a stirred solution of diethyl 2-((1-(benzyloxycarbonyl) piperidin-4-yl)methylene)malonate 40 (900 mg, 2.31 mmol) in ethanol (18 mL), was added 10% palladium on carbon 50% wet (0.18 g, 0.2 w/w) at room temperature. The reaction mixture was strip off with argon for twice and applied $H_2$ pressure through balloon (25 psi) at room temperature and stirred for 3 h. After completion of reaction (monitored by 1HNMR), the reaction mixture was filtered through a Celite bed and washed with ethanol (10 mL). The filtrate was concentrated completely under reduced pressure to afford the title 41 (630 mg, 81% yield) as a colourless liquid, which was used as such for next step. $^1$H NMR (400 MHz, $CDCl_3$) δ ppm 4.22-4.16 (m, 4H), 3.46-3.42 (m, 1H), 3.08-3.03 (m, 2H), 2.59-2.52 (m, 2H), 1.96 (s, 3H), 1.85-1.82 (m, 2H), 1.71-1.65 (m, 2H), 1.43-1.32 (m, 1H), 1.28-1.23 (m, 6H), 1.18-1.07 (m, 2H); LCMS (ESI): m/z 258.36 [M+H$^+$]; purity~99.82%.

Scheme 29

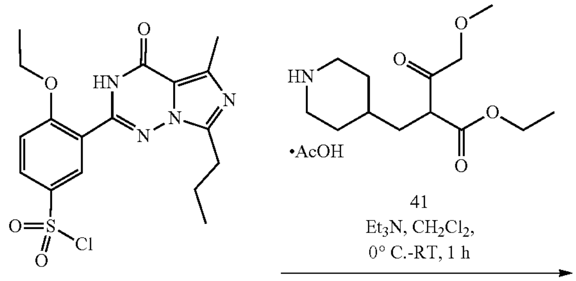

24

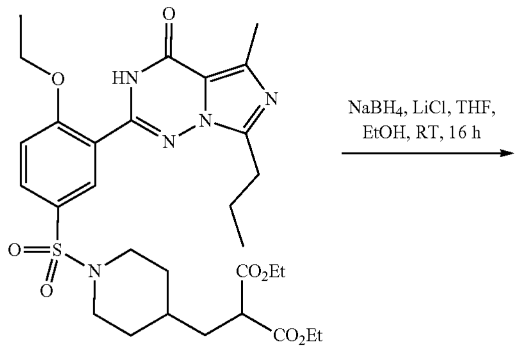

42

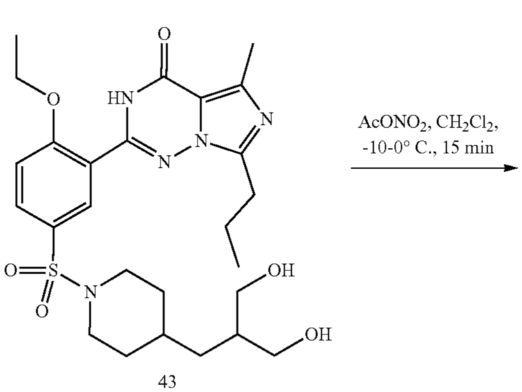

43

-continued

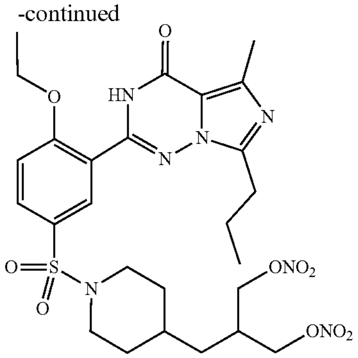

2m

Example 41

Diethyl 2-((1-((4-ethoxy-3-(5-methyl-4-oxo-7-propyl-3,4-dihydroimidazo[5,1-f][1,2,4]triazin-2-yl) phenyl)sulfonyl)piperidin-4-yl)methyl)malonate (42)

To a stirred solution of diethyl 2-(piperidin-4-ylmethyl) malonate acetic acid salt 41 (627 mg, 1.97 mmol) in $CH_2Cl_2$ (50 mL) was added triethylamine (2.6 mL, 18.3 mmol) at 0° C. in drop wise under argon atmosphere and stirred for 30 min. To the reaction mixture, a solution of 4-ethoxy-3-(5-methyl-4-oxo-7-propyl-3,4-dihydroimidazo[1,5-f][1,2,4]triazin-2-yl)benzene-1-sulfonyl chloride 24 (500 mg, 1.22 mmol) in $CH_2Cl_2$ (25 mL) was added drop wise at 0° C. and stirred for 15 min. The reaction mixture was warmed to room temperature and stirred for 1 h. After completion of reaction (monitored by TLC), the reaction mixture was diluted in $CH_2Cl_2$ (50 mL), washed with water (50 mL) and brine (50 mL). The organic layer was separated, dried over anhydrous $Na_2SO_4$ and concentrated under reduced pressure and purified by reverse phase column chromatography (Reveleris® C-18 column; Grace System) by eluting with 60% gradient acetonitrile with water. The pure fractions were concentrated until acetonitrile solvent was completely removed. The resultant aqueous solution was extracted with ethyl acetate (2×50 mL). The combined the organic layer was dried over anhydrous $Na_2SO_4$ and concentrated under reduced pressure to afford the title compound 42 (150 mg, 19% yield) as an off-white solid. $^1$H NMR (400 MHz, DMSO-$d_6$) δ ppm 11.62 (br s, 1H), 7.87-7.83 (m, 2H), 7.36 (d, J=8.4 Hz, 1H), 4.20 (q, J=7.2 Hz, 2H), 4.12-4.04 (m, 4H), 3.63-3.58 (m, 2H), 3.52-3.47 (m, 1H), 2.84-2.80 (m, 2H), 2.48 (s, 3H), 2.23-2.16 (m, 2H), 1.76-1.67 (m, 6H), 1.32 (t, J=7.2 Hz, 3H), 1.20-1.09 (m, 9H), 0.92 (d, J=7.2 Hz, 3H); LCMS (ESI): m/z 632.47 [M+H]$^+$; purity~82.06%.

Example 42

2-(2-ethoxy-5-(4-(3-hydroxy-2-(hydroxymethyl) propyl)piperidin-1-ylsulfonyl)phenyl)-5-methyl-7-propylimidazo[1,5-f][1,2,4]triazin-4(3H)-one (43)

In a RB flask, sodium borohydride (110 mg, 2.91 mmol) and lithium chloride (3 mg, 0.073 mmol) were suspended in THF (2.0 mL) and ethanol (2.0 mL) under argon atmosphere at room temperature. To this, added a solution of diethyl 2-((1-(4-ethoxy-3-(5-methyl-4-oxo-7-propyl-3,4-dihydroimidazo[1,5-f][1,2,4]triazin-2-yl)phenylsulfonyl)piperidin-4-yl)methyl)malonate 42 (115 mg, 0.182 mmol) in THF (1.0 mL) and ethanol (1.0 mL) drop wise at room temperature and stirred for 16 h. NOTE: Reaction was performed in three batches (1×10 mg, 1×25 mg, 1×115 mg). After completion of reaction (monitored by TLC), the reaction mixture was quenched with ice water (4 mL) and extracted with ethyl acetate (5×25 mL). The organic layers were combined and concentrated. The obtained crude product from all the batches were combined and purified by reverse phase preparative HPLC (Column: X-BRIDGE C18 (250*19) mm 5 um, Mobile phase A: 10 mM aqueous ammonium bicarbonate solution, B: 100% acetonitrile, Flow rate: 19 ml/min; Method T/% B=0/40, 11/40, 11.1/100, 13/100, 13.1/40, 15/4). Pure fractions were lyophilized to afford the title compound 43 (45 mg, 34% yield) as a white solid. $^1$H NMR (400 MHz, DMSO-$d_6$) δ ppm 11.65 (br s, 1H; $D_2O$ exchangeable), 7.87-7.83 (m, 2H), 7.37 (br d, J=8.8 Hz, 1H), 4.26 (br t, J=5.52 Hz, 2H; $D_2O$ exchangeable), 4.20 (q, J=7.2 Hz, 2H), 3.63-3.59 (m, 2H), 3.31-3.25 (m, 4H), 2.84-2.80 (m, 2H), 2.49 (s, 3H), 2.25-2.19 (m, 2H), 1.76-1.68 (m, 4H), 1.52-1.48 (m, 1H), 1.35-1.26 (m, 4H), 1.15-1.04 (m, 4H), 0.92 (t, J=7.2 Hz, 3H); LCMS (ESI): m/z 548.14 $[M+H]^+$; purity~97.52%, UPLC: purity~96.72%.

Example 43

2-((1-(4-ethoxy-3-(5-methyl-4-oxo-7-propyl-3,4-dihydroimidazo[1,5-f][1,2,4]triazin-2-yl)phenylsulfonyl)piperidin-4-yl)methyl)propane-1,3-diyl Dinitrate (2m)

To a stirred solution of 2-(2-ethoxy-5-(4-(3-hydroxy-2-(hydroxymethyl)propyl)piperidin-1-ylsulfonyl)phenyl)-5-methyl-7-propylimidazo[1,5-f][1,2,4]triazin-4(3H)-one 43 (105 mg, 0.192 mmol) in dichloromethane (4 mL) was added freshly prepared solution of acetyl nitrate (1.32 mL) [(acetyl nitrate was prepared separately by addition of fuming $HNO_3$ (0.22 mL, 10.09 mmol) drop wise in to acetic anhydride (1.1 mL, 1:5 of fuming $HNO_3$) drop wise at −10° C. under argon atmosphere (Note: temperature should not be raised to 0° C.))] drop wise at 0° C. under argon atmosphere and stirred for 15 min. After completion of reaction (monitored by TLC), the reaction mixture was quenched with chilled saturated $NaHCO_3$ solution (20 mL) at 0° C. The resultant solution was warmed to room temperature and extracted with dichloromethane (15 mL). The combined organic layer was washed with brine (20 mL), dried over anhydrous $Na_2SO_4$ and concentrated under reduced pressure. NOTE: Reaction was performed in two batches (1×25 mg, 1×105 mg). The obtained crude product was combined and purified by reverse phase column chromatography (Reveleris® C-18 column; Grace System) by eluting with 60-65% gradient acetonitrile with water. The pure fractions were lyophilized to afford the title compound 2m (34.1 mg, 23% yield) as a white solid. $^1$H NMR (400 MHz, DMSO-$d_6$) δ ppm 11.65 (br s, 1H; $D_2O$ exchangeable), 7.88-7.83 (m, 2H), 7.37 (br d, J=8.4 Hz, 1H), 4.52-4.42 (m, 4H), 4.20 (q, J=7.2 Hz, 2H), 3.66-3.60 (m, 2H), 2.84-2.80 (m, 2H), 2.47 (s, 3H), 2.34-2.19 (m, 3H), 1.76-1.69 (m, 4H), 1.40-1.23 (m, 6H), 1.20-1.10 (m, 2H), 0.92 (t, J=7.2 Hz, 3H); LCMS (ESI): m/z 638.19 $[M+H]^+$; purity~98.06%, HPLC: 98.25%.

Scheme 30

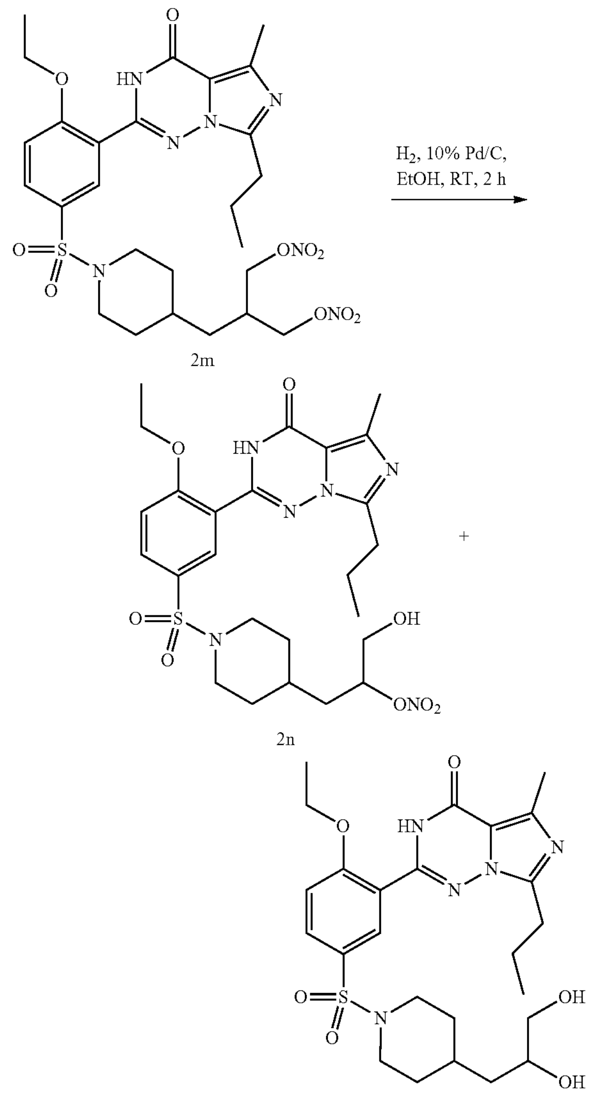

2m

+

2n

43

Example 44

3-(1-(4-ethoxy-3-(5-methyl-4-oxo-7-propyl-3,4-dihydroimidazo[1,5-f][1,2,4]triazin-2-yl)phenylsulfonyl) piperidin-4-yl)-2-(hydroxymethyl)propyl Nitrate (2n)

To a stirred solution of 2-((1-(4-ethoxy-3-(5-methyl-4-oxo-7-propyl-3,4-dihydroimidazo[1,5-f][1,2,4]triazin-2-yl) phenylsulfonyl)piperidin-4-yl)methyl)propane-1,3-diyl dinitrate 2m (110 mg, 0.172 mmol) in ethanol (11 mL), was added 10% palladium on carbon 50% wet (22 mg, 0.2 w/w) at room temperature. The reaction mixture was strip off with argon for twice and applied $H_2$ pressure through balloon (25 psi) to room temperature and stirred for 2 h. After completion of reaction (monitored by TLC), the reaction mixture was filtered through Celite bed and washed with ethanol (5 mL). The filtrate was concentrated completely under reduced pressure. The obtained crude mixture was purified by reverse phase preparative HPLC (column: Luna C18 (150*25) mm 10 um; Mobile phase A: 100% water, B: 100% ACN; Method T/% B=0/50, 1/50, 10/80, 10.1/100, 13/100, 13.1/50, 15/50; Flow rate: 19 ml/min) to afford the title compound 2n (31.2 mg, 28% yield) as an off-white solid and 43 (28.6 mg, 26% yield) as a white solid.

TOP-V1-27 analytical data: $^1H$ NMR (400 MHz, DMSO-$d_6$) δ ppm 11.63 (br s, 1H; $D_2O$ exchangeable), 7.88-7.83 (m, 2H), 7.37 (br d, J=8.8 Hz, 1H), 4.66 (t, J=5.2 Hz, 1H; $D_2O$ exchangeable), 4.47-4.39 (m, 2H), 4.20 (q, J=7.2 Hz, 2H), 3.65-3.60 (m, 2H), 3.43-3.26 (m, 2H), 2.84-2.80 (m, 2H), 2.48 (s, 3H), 2.25-2.19 (m, 2H), 1.89-1.77 (m, 1H), 1.76-1.69 (m, 4H), 1.35-1.08 (m, 8H), 0.92 (t, J=7.2 Hz, 3H); LCMS (ESI): m/z 593.16 $[M+H]^+$; purity~96.69%, HPLC: 98.45%.

Scheme 31

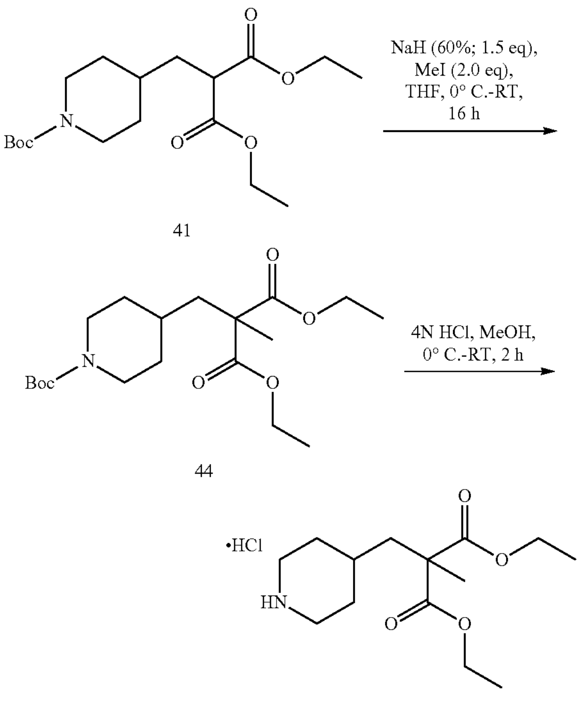

41

44

45

Example 45

Diethyl 2-((1-(tert-butoxycarbonyl)piperidin-4-yl) methyl)-2-methylmalonate (44)

To the suspension of NaH (60% in dispersion oil, 503 mg, 12.57 mmol) in dry THF (20 mL) under argon atmosphere, was added a solution of diethyl 2-((1-(tert-butoxycarbonyl) piperidin-4-yl)methyl)malonate 41 (3.0 g, 8.4 mmol) in THF (20 mL) drop wise at room temperature and stirred for 30 min. To this, added a solution of methyl iodide (1.05 mL, 16.8 mmol) in THF (10 mL) drop wise at 0° C. The reaction mixture was allowed to stir at room temperature for 16 h. After completion of reaction (monitored by TLC), the reaction mixture was quenched with crushed ice (5.0 g) and extracted with ethyl acetate (2×50 mL). The combined organic layer was washed with brine (50 mL), dried over anhydrous $Na_2SO_4$ and concentrated under reduced pressure and purified by Silica gel column chromatography by eluting with 10-15% ethyl acetate with petroleum ether to afford the title compound 44 (1.3 g, 45% overall yield in two steps) as a thick liquid. $^1H$ NMR (400 MHz, $CDCl_3$) δ ppm 4.20-4.13 (m, 4H), 4.06-3.95 (m, 2H), 2.70-2.61 (m, 2H), 1.87 (d, J=6.0 Hz, 2H), 1.60-1.54 (m, 2H), 1.49-1.41 (m, 13H), 1.27-1.21 (m, 6H), 1.19-1.10 (m, 2H); LCMS (ESI): m/z 372.23 $[M+H^+]$; purity~99.64%.

Example 46

Diethyl 2-methyl-2-(piperidin-4-ylmethyl)malonate Hydrochloride (45)

To a stirred solution of diethyl 2-((1-(tert-butoxycarbonyl)piperidin-4-yl)methyl)-2-methylmalonate 44 (1.2 g, 3.23 mmol) in methanol (12 mL) was added 4M hydrochloric acid in 1,4-dioxane (12 mL) drop wise at 0° C. under argon atmosphere. The reaction mixture was allowed to stir at room temperature for 2 h. After completion of reaction (monitored by TLC), the reaction solution was concentrated under reduced pressure, co-distilled with methanol (2×10 mL) dried under vacuum to afford the crude title 45 (750 mg) as a thick liquid, which was directly taken to next reaction without purification. $^1H$ NMR (400 MHz, $CDCl_3$) δ ppm 9.52 (br s, 1H), 9.22 (br s, 1H), 4.19-4.12 (m, 4H), 3.48-3.36 (m, 2H), 2.90-2.76 (m, 2H), 1.94-1.81 (m, 3H), 1.75-1.62 (m, 2H), 1.42 (s, 3H), 1.34-1.20 (m, 6H), 0.92-0.82 (m, 2H).

Scheme 32

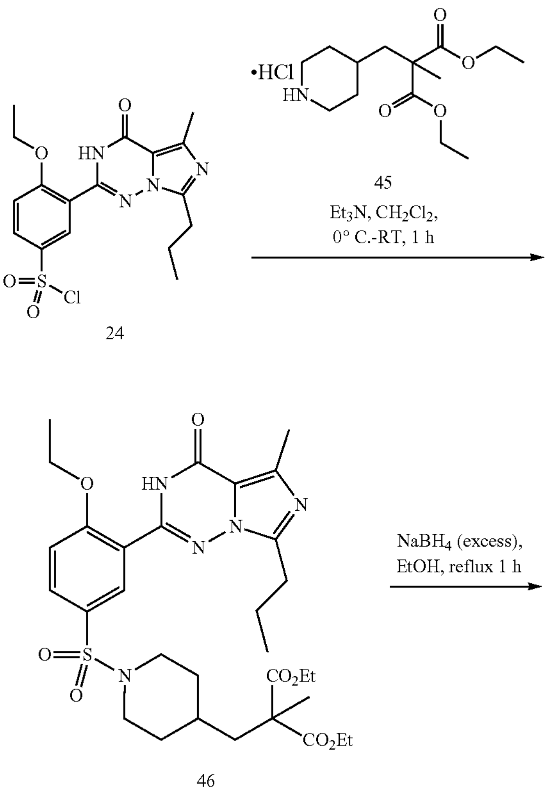

45

24

46

-continued

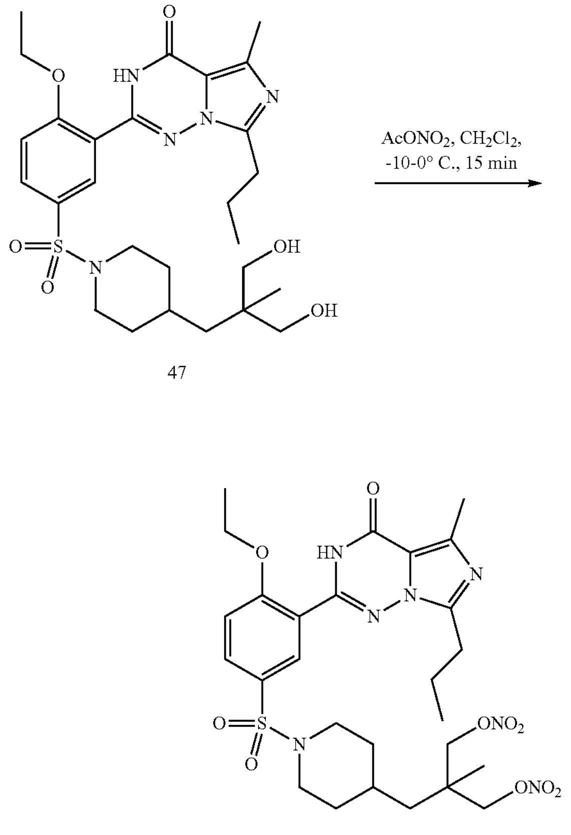

47

2o

Example 47

Diethyl 2-((1-((4-ethoxy-3-(5-methyl-4-oxo-7-propyl-3,4-dihydroimidazo[5,1-f][1,2,4]triazin-2-yl) phenyl)sulfonyl)piperidin-4-yl)methyl)-2-methylmalonate (46)

To a stirred solution of diethyl 2-(piperidin-4-ylmethyl) malonate hydrochloride salt 45 (750 mg, 2.436 mmol) in $CH_2Cl_2$ (50 mL) was added Amberlyst A-21 base resin (3.75 g) at room temperature and stirred for 2 h and then filtered. To the filtrate, added triethylamine (2.5 mL, 18.26 mmol) at 0° C. in drop wise under argon atmosphere and stirred for 30 min. To the reaction mixture, a solution of 4-ethoxy-3-(5-methyl-4-oxo-7-propyl-3,4-dihydroimidazo[1,5-f][1,2,4]triazin-2-yl)benzene-1-sulfonyl chloride 24 (500 mg, 1.22 mmol) in $CH_2Cl_2$ (25 mL) was added drop wise at 0° C. and stirred for 15 min. The reaction mixture was warmed to room temperature and stirred for 1 h. After completion of reaction (monitored by TLC), the reaction mixture was diluted in $CH_2Cl_2$ (75 mL) and washed with water (2×50 mL). The organic layer was separated, dried over anhydrous $Na_2SO_4$ and concentrated under reduced pressure. The obtained crude product was purified by trituration with n-pentane (3×10 mL) and decanted the solvent, dried under vacuum to afford the title compound 46 (300 mg, ~30% yield) as semi solid, which was directly taken to next reaction. LCMS (ESI): m/z 646.29 $[M+H^+]$; purity~84.28%.

Example 48

2-(2-ethoxy-5-((4-(3-hydroxy-2-(hydroxymethyl)-2-methylpropyl)piperidin-1-yl)sulfonyl)phenyl)-5-methyl-7-propylimidazo[5,1-f][1,2,4]triazin-4(3H)-one (47)

To a stirred solution of diethyl 2-((1-((4-ethoxy-3-(5-methyl-4-oxo-7-propyl-3,4-dihydroimidazo[5,1-f][1,2,4]triazin-2-yl)phenyl)sulfonyl)piperidin-4-yl)methyl)-2-methylmalonate 46 (215 mg, 0.33 mmol) in ethanol (10.75 mL) was added sodium borohydride (500 mg, 13.22 mmol) at room temperature under argon atmosphere. The reaction mixture was warmed to reflux temperature (80° C.) and stirred for 1 h. After completion of reaction (monitored by TLC), the reaction mixture was quenched with ice water (5 mL) and extracted with ethyl acetate (2×15 mL). The combined organic layer was dried over anhydrous Na2SO4 and concentrated under reduced pressure. NOTE: Reaction was performed in three batches (1×10 mg, 1×60 mg, 1×215 mg). The obtained crude product from three batches were combined and purified by reverse phase column chromatography (Reveleris® C-18 column; Grace System) by eluting with 30-35% gradient acetonitrile with water. The pure fractions were lyophilized to afford the title compound 47 (80 mg, ~37% yield) as a white solid. $^1H$ NMR (400 MHz, DMSO-$d_6$) δ ppm 11.65 (br s, 1H; $D_2O$ exchangeable), 7.86-7.83 (m, 2H), 7.36 (br d, J=8.8 Hz, 1H), 4.26 (br t, J=5.2 Hz, 2H; $D_2O$ exchangeable), 4.20 (q, J=7.2 Hz, 2H), 3.55-3.51 (m, 2H), 3.12 (d, J=5.2 Hz, 4H), 2.84-2.80 (m, 2H), 2.48 (s, 3H), 2.27-2.22 (m, 2H), 1.76-1.70 (m, 4H), 1.35-1.26 (m, 4H), 1.23-1.15 (m, 2H), 1.10-1.07 (m, 2H), 0.92 (t, J=7.2 Hz, 3H), 0.68 (s, 3H); LCMS (ESI): m/z 562.21 $[M+H]^+$; purity~99.36%, UPLC: 98.70%.

Example 49

2-((1-((4-ethoxy-3-(5-methyl-4-oxo-7-propyl-3,4-dihydroimidazo[5,1-f][1,2,4]triazin-2-yl)phenyl) sulfonyl)piperidin-4-yl)methyl)-2-methylpropane-1,3-diyl Dinitrate (2o)

To a stirred solution of 2-(2-ethoxy-5-((4-(3-hydroxy-2-(hydroxymethyl)-2-methylpropyl)piperidin-1-yl)sulfonyl) phenyl)-5-methyl-7-propylimidazo[5,1-f][1,2,4]triazin-4 (3H)-one 47 (50 mg, 0.09 mmol) in dichloromethane (2 mL) was added freshly prepared solution of acetyl nitrate (0.12 mL) [(acetyl nitrate was prepared separately by addition of fuming $HNO_3$ (0.02 mL, 0.917 mmol) drop wise in to acetic anhydride (0.1 mL, 1:5 of fuming $HNO_3$) drop wise at −10° C. under argon atmosphere (Note: temperature should not be raised to 0° C.))] drop wise at 0° C. under argon atmosphere and stirred for 15 min. After completion of reaction (monitored by TLC), the reaction mixture was quenched with chilled saturated $NaHCO_3$ solution (15 mL) at 0° C. The resultant solution was warmed to room temperature and extracted with dichloromethane (10 mL). The combined organic layer was washed with brine (10 mL), dried over anhydrous $Na_2SO_4$ and concentrated under reduced pressure. NOTE: Reaction was performed in two batches (1×25 mg, 1×50 mg). The crude product from both the batches were combined and purified by reverse phase column chromatography (Reveleris® C-18 column; Grace System) by eluting with 60-65% gradient acetonitrile with water. The pure fractions were combined and concentrated until acetonitrile solvent was completely removed. The resultant aqueous solution was extracted with ethyl acetate (2×20 mL). The combined the organic layer was dried over anhydrous $Na_2SO_4$, concentrated under reduced pressure and lyophilized to afford the title compound 2o (32 mg, ~36% yield) as a white solid. $^1$H NMR (400 MHz, DMSO-$d_6$) δ ppm 11.63 (br s, 1H; $D_2O$ exchangeable), 7.87-7.81 (m, 2H), 7.37 (br d, J=8.8 Hz, 1H), 4.38 (s, 4H), 4.20 (q, J=7.2 Hz, 2H), 3.59-3.54 (m, 2H), 2.84-2.79 (m, 2H), 2.47 (s, 3H), 2.28-2.22 (m, 2H), 1.76-1.66 (m, 4H), 1.45-1.21 (m, 8H), 0.98 (s, 3H), 0.92 (t, J=7.2 Hz, 3H); LCMS (ESI): m/z 652.20 [M+H]$^+$; purity~97.87%, UPLC: 97.04%.

Scheme 33

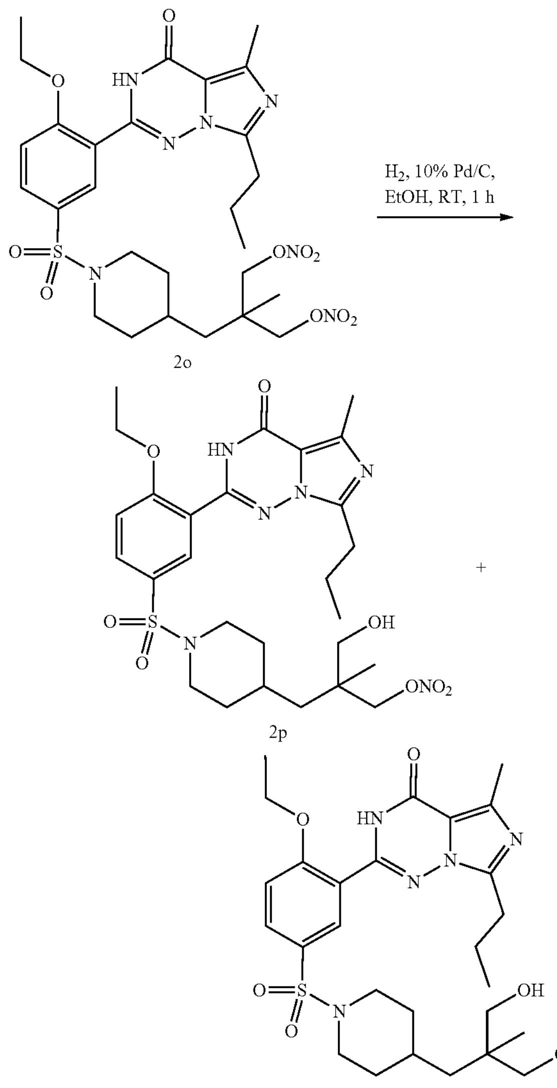

2o

+

2p

47

Example 50

3-(1-((4-ethoxy-3-(5-methyl-4-oxo-7-propyl-3,4-dihydroimidazo[5,1-f][1,2,4]triazin-2-yl)phenyl) sulfonyl)piperidin-4-yl)-2-(hydroxymethyl)-2-methylpropyl Nitrate (2p)

To a stirred solution of 2-((1-((4-ethoxy-3-(5-methyl-4-oxo-7-propyl-3,4-dihydroimidazo[5,1-f][1,2,4]triazin-2-yl)phenyl)sulfonyl)piperidin-4-yl)methyl)-2-methylpropane-1,3-diyl dinitrate 2o (150 mg, 0.23 mmol) in ethanol (15 mL), was added 10% palladium on carbon 50% wet (30 mg, 0.2 w/w) at room temperature. The reaction mixture was strip off with argon gas twice and applied $H_2$ pressure through balloon (25 psi) at room temperature and stirred for 1 h. After completion of reaction (monitored by TLC), the reaction mixture was filtered through a Celite bed and washed with ethanol (10 mL). The filtrate was concentrated under reduced pressure. The obtained crude mixture was purified by reverse phase preparative HPLC (column: Luna C18 (150*25) mm, 10 um, mobile phase A: 10 mM aqueous ammonium bicarbonate solution, B: 100% acetonitrile; method T/% B=0/45, 1/45, 10/80, 13/90, 13.1/100, 15/100, 15.1/45, 17/45; Flow rate: 19 mL/min). Pure fractions were lyophilized to afford the title compound 2p (34.9 mg, 29% yield) as a white solid and 47 (13 mg) as a white solid.

2p analytical data: $^1$H NMR (400 MHz, DMSO-$d_6$) δ ppm 11.63 (br s, 1H; $D_2O$ exchangeable), 7.87-7.82 (m, 2H), 7.37 (d, J=8.4 Hz, 1H), 4.77 (t, J=5.6 Hz, 1H; $D_2O$ exchangeable), 4.29 (s, 2H), 4.20 (q, J=7.2 Hz, 2H), 3.58-3.53 (m, 2H), 3.20-3.13 (m, 2H), 2.84-2.80 (m, 2H), 2.48 (s, 3H), 2.30-2.23 (m, 2H), 1.76-1.64 (m, 4H), 1.38-1.30 (m, 4H), 1.26-1.17 (m, 4H), 0.92 (t, J=7.2 Hz, 3H), 0.83 (s, 3H); LCMS (ESI): m/z 607.20 [M+H$^+$]; purity~98.47%, UPLC (Area %): 98.43%.

Example 51

Phosphodiesterase-5 Activity Assay

As shown in FIG. 1 the compounds of this invention act synergistically by stimulating the producing enzyme (sGC) of cGMP and inhibition of the main degrading enzyme (PDE5). The compounds 1a-2p are precursors of NO. In biological systems the organic nitrate group is believed to be reduced to NO, which activates sGC. Both the nitrate-ester compounds as well as the resulting metabolites inhibit PDE5 with very high potencies. The synergistic activity resulting from the modulation of both enzymes (activation of cGC and inhibition of PDE5) results in an unprecedented potency and efficacy.

The inhibition of recombinant human (rh) PDE5A by test compounds is measured in a radiometric assay based on Scintillation Proximity Assay (SPA) technology. The substrate [3H] cGMP/cGMP is hydrolysed to [3H] 5'GMP/5'GMP contingent on the activity of rhPDE5A. The ensuing [3H] 5'GMP/5'GMP but not [3H] cGMP/cGMP binds to SPA yttrium silicate beads in the presence of $Zn^{++}$ stimulating the scintillant within the bead to emit light that is detected by a ß-counter. The assay is performed in a 96 well format.

The assay is done in 20 mM Tris HCl pH 7.4, 5 mM $MgCl_2$, 0.5 μM cGMP/[3H] cGMP (about 60000 dpm/well) substrate with rhPDE5A1 (GST tagged, SIGMA E9034) added to an amount not exceeding 20% cGMP hydrolysis within 20 min in Tris 20 mM pH 7.4 supplemented with 0.01% bovine serum albumin (BSA) in the presence of test compounds or vehicle (0.1% DMSO). The final assay volume amounts to 100 μl and the reaction is run for 20 min at 37° C.

The hydrolysis of [3H] cGMP/cGMP by rhPDE5A is terminated by adding SPA beads at 50 μl/well (Perkin Elmer, RPNQ0024), pre-diluted in water as per manufacturer's instructions and supplemented with 3-isobutyl-1-methylxanthine (1 mM). Beads are allowed to sediment for at least 30 min before measurement in a Wallac Microbeta 2 (Perkin Elmer).

In general, test compounds are added at seven different concentrations from 1 pM to 1 μM in log steps. Percent inhibition values compared to vehicle control (0.1% DMSO) are calculated and IC50 values calculated using GraphPad Prism 7.03 software. Results (IC50) are given as the mean from at least two independent experiments each performed in triplicate.

TABLE 1

| Compound | IC50 |
|---|---|
| Sildenafil | $7.7 \times 10^{-9}$ M |
| Vardenafil | $3.3 \times 10^{-10}$ M |
| 1a | $5.0 \times 10^{-9}$ M |
| 1b | $4.9 \times 10^{-9}$ M |
| 1c | $1.0 \times 10^{-9}$ M |
| 1d | $1.2 \times 10^{-9}$ M |
| 1e | $4.6 \times 10^{-9}$ M |
| 1f | $3.8 \times 10^{-9}$ M |
| 1g | $4.8 \times 10^{-9}$ M |
| 1h | $4.7 \times 10^{-9}$ M |
| 1i | $4.2 \times 10^{-9}$ M |
| 1k | $5.5 \times 10^{-10}$ M |
| 1l | $6.9 \times 10^{-10}$ M |
| 2a | $4.2 \times 10^{-10}$ M |
| 2b | $2.8 \times 10^{-10}$ M |
| 2c | $1.4 \times 10^{-10}$ M |
| 2d | $1.6 \times 10^{-10}$ M |
| 2e | $2.0 \times 10^{-10}$ M |
| 2f | $3.0 \times 10^{-10}$ M |
| 2g | $3.7 \times 10^{-10}$ M |
| 2h | $1.0 \times 10^{-9}$ M |
| 2i | $1.5 \times 10^{-9}$ M |
| 2k | $2.6 \times 10^{-10}$ M |
| 2l | $1.7 \times 10^{-10}$ M |
| 2m | $4.4 \times 10^{-10}$ M |
| 2n | $4.7 \times 10^{-10}$ M |
| 2o | $5.2 \times 10^{-10}$ M |
| 2p | $1.1 \times 10^{-10}$ M |
| 4 | $1.5 \times 10^{-9}$ M |
| 6 | $1.6 \times 10^{-9}$ M |
| 14-1 | $4.4 \times 10^{-9}$ M |
| 14-2 | $3.9 \times 10^{-9}$ M |
| 15 | $2.0 \times 10^{-9}$ M |
| 22 | $8.5 \times 10^{-9}$ M |
| 24 | $4.0 \times 10^{-10}$ M |
| 25 | $8.0 \times 10^{-11}$ M |
| 26 | $7.0 \times 10^{-11}$ M |
| 27 | $4.0 \times 10^{-10}$ M |
| 28 | $1.9 \times 10^{-10}$ M |
| 29 | $3.7 \times 10^{-10}$ M |
| 43 | $1.3 \times 10^{-10}$ M |
| 47 | $2.2 \times 10^{-11}$ M |

Example 52

Measurements of Human Plasma Protein Binding

An aliquot of 200 μL of human plasma containing test compound was spiked into donor well (red chamber) of the insert. 350 μL of PBS was spiked into receiver well (white chamber) of the insert.

The samples were matrix equilibrated with opposite matrix (25 μL of plasma/buffer sample was matched with 25 μL of blank buffer/plasma). Matrix matched samples were precipitated with 200 μL of acetonitrile containing internal standard. Samples were vortexed at 1000 rpm for 5 min and centrifuged at 4000 rpm for 10 min. Supernatant was separated, diluted 2 fold with water and analysed in LC-MS/MS. (Table 2).

TABLE 2

| Compound | % Unbound in human plasma | % Bound in human plasma |
|---|---|---|
| 1c | 1.18 | 98.82 |
| 1i | 0.15 | 99.85 |
| 2a | 0.20 | 99.80 |
| 2d | 1.73 | 98.27 |
| 2g | 1.71 | 98.29 |
| 2h | 0.23 | 99.77 |
| 2i | 0.01 | 99.99 |
| 2m | 0.08 | 99.92 |
| 2n | 0.52 | 99.48 |
| 2o | 0.05 | 99.95 |
| 2p | 0.34 | 99.66 |
| 22 | 3.6 | 96.4 |
| 28 | 6.90 | 93.10 |
| 43 | 2.2 | 97.8 |
| Sildenafil | 4.19 | 95.79 |

Example 53

Cellular cGMP Assays

Examples (Test compounds) were characterized for their potency and efficacy to elevate cGMP in cellular systems such as human trabecular meshwork cells (Table 3), human platelets (Table 5) and rat aortic smooth muscle cells (Table 4).

Human trabecular meshwork cells (ABC Biopply AG, Solothurn, Switzerland) or rat aortic smooth muscle cells (Sigma Aldrich AG, Buchs, Switzerland) were plated in a 96 well plate precoated with collagen (Collagen Type I solution from rat tail, Sigma; diluted to 0.1 mg/ml) at 20.000 cells per well and grown in corresponding Trabecular Meshwork (ABC Supply AG) or Smooth Muscle (Sigma AG) Growth medium as provided by the manufacturers. After 18 h medium was exchanged and new medium added supplemented with 5 mM GSH. The next day culture medium was exchanged to DMEM with low glucose supplemented with 5 mM GSH. Cells were pre-incubated with 10 μM Riociguat (soluble guanylate cyclase stimulator; Lucerna-Chem AG, Luzern, Switzerland) for 15 min before test or reference compounds or vehicle was added to a final incubation volume of 100 μl per well. At the end of the incubation time (see below) the reaction was terminated by adding HCl (0.16M), IBMX (Isobutylmethylxanthin) (2 mM) in DMSO (2%) to the culture medium, final concentrations per well are given in brackets. Following a 20 sec on a plate shaker (200 rpm) the plate was immediately frozen at −80° C.

cGMP was determined by a commercially available ELISA kit, as described in the Example 39. As shown in FIG. 3A and FIG. 3B over-additive effects from the organic nitrate ester ITN and PDE5 inhibitors sildenafil or vardenafil to elevate cGMP in HTMC was obtained with a compound of this invention 2a. By extrapolation from nonlinear regression a concentration of 2.6 nM/12.4 nM 2a or 10.6 nM/50.8 nM 2a reveals equipotent to 1 μM/10 μM ITN & 1 μM Vardenafil or 10 μM ITN & 1 μM Sildenafil to elevate cGMP in HTMC in this experiment under the current experimental conditions.

TABLE 3

| | Human Trabecular Meshwork Cells | |
|---|---|---|
| Cpd | Ratio Maximum cGMP increase vs Baseline | Concentration (nM) for 3-fold or 2-fold* cGMP increase vs Baseline |
| 25 | 22.3 | 58.5 |
| 2p | 46.1 | 1.4* |
| 2o | 86.9 | 1.9* |
| 2g | 109.1 | 22.2* |
| 2c | 52.1 | 10.1 |
| 2a | 101.7 | 4.2 |
| 4 | 12.4 | 99.8 |
| 1c | 61.9 | 25.1 |
| 1a | 55.7 | 26.7 |

TABLE 4

| | Rat aortic smooth muscle cells | |
|---|---|---|
| Cpd | Ratio Maximum cGMP increase vs Baseline | Concentration (nM) for 3-fold cGMP increase vs Baseline |
| 25 | 0.89 | >10000 |
| 2c | 5.93 | 729 |
| 2a | 10.58 | 293 |
| 4 | 1.04 | >10000 |
| 1c | 3.47 | 1300 |
| 1a | 4.44 | 222 |

Example 54

Effects of test and reference compounds on total cGMP in human platelets were investigated as described by Dunkern and Hatzelmann (Cell Signal. 17: 331-9, 2005) with modifications. Briefly, buffy coats (acquired form SRK Blutspende Zurich) were 4-fold diluted in 150 mM sodium chloride solution containing 0.9% sodium citrate and centrifuged at 200 g for 10 min. The resulting platelet-rich plasma was supplemented with a 1/10 volume of ACD solution (85 mM sodium citrate, 111 mM D-glucose, 71 mM citric acid, pH 4.4) and apyrase (Sigma AG) to a final concentration of 2 U/ml. After another centrifugation (1400 g, 10 min) the cellular pellet was resuspended in Ca2+/Mg2+-free Hepes-Tyrode buffer (134 mM NaCl, 12 mM $NaHCO_3$, 2.9 mM KCl, 0.36 mM NaH2PO4, 5 mM HEPES, 5 mM glucose, 0.5% (w/v) bovine serum albumin, pH 7.4) and platelets were counted.

Platelets were used at 9×107 cells in 100 µl per well and after adding test and reference compounds the incubation volume was 200 µl per well in Hepes-Tyrode. Experiments in platelets were done in presence of 1 µM riociguat and 100 nM BAY 190954 (PDE2 inhibitor) (Lucerna Chem AG) and test/reference compounds were added after a preincubation time of 15 min. At the end of the incubation time (see below) the reaction was terminated by adding 20 µl of 2N HCl per well. Following a 20 sec on a plate shaker (300 rpm) the plate was left for 15 min and then centrifuged at 1000×g for 5 min. Supernatants were stored at −80° C.

cGMP was determined by a commercially available ELISA kit (Direct cGMP ELISA kit, Enzo Life Sciences AG, Lauren, Switzerland) with a lower detection limit of 0.08 pmol/ml using the acetylation protocol following manufacturer's instructions. Results are given as the means from at least two independent experiments each in triplicate.

To study concentration-dependent effects on total cGMP test and reference compounds were investigated from 0.1 nM to 1 µM in half-logarithmic steps with an incubation time of 2 h. To examine the time course the incubation times were (min) 10, 30, 60, 90, 120 at 1 µM of test or reference compound.

Compounds were diluted from stock solutions in DMSO. The final concentration of DMSO in all wells including the vehicle controls was 0.2% for human trabecular meshwork and rat aortic smooth muscle cells and 0.3% for platelets.

Concentration or time dependent effects on cGMP were analyzed by nonlinear regression using Graph Pad Software that allowed to extrapolate concentrations of test and reference compounds resulting in a 2-fold and 3-fold increase in cGMP (ECx2, ECx3), the fold maximum increase of cGMP over Vehicle control (Emax, fold), the concentration of test and reference compounds to achieve half maximum cGMP increase (EC50). From time course experiments, the time to half of the maximum cGMP increase with 1 µM of test compound has been extrapolated (t0.5max).

TABLE 5

| | Human Platelets | |
|---|---|---|
| Cpd | Ratio Maximum cGMP increase vs Baseline | Concentration (nM) for 3-fold cGMP or 2-fold* increase vs Baseline |
| 47 | 39.0 | — |
| 43 | 28.5 | — |
| 25 | 23.3 | 5.9 |
| 2p | 204.1 | 102* |
| 2o | 202.8 | 120* |
| 2m | 262.3 | — |
| 2n | 161.0 | — |
| 2i | 932.9 | — |
| 2h | 171.3 | — |
| 2g | 183.5 | — |
| 2c | 105.4 | 4.3 |
| 2a | 152.5 | 3.3 |
| 4 | 6.4 | 92.6 |
| 1c | 26.1 | 33.3 |
| 1a | 67.4 | 57 |

Example 55

Measurements of cGMP in Human Pulmonary Artery Smooth Muscle Cells (hPASMC)

Human Pulmonary Artery Smooth Muscle Cells (hPASMC) were purchased from Clonetics™ Lonza (Lonza, reference number CC-2581) and cultured in Clonetics™ smooth muscle growth medium (Clonetics™ SmGM™-2 with BulletKit™ growth factor supplements (Lonza, reference number CC-3182) at 37° C. in 5% $CO_2$. Culture medium was replaced each 48 hours. Cells were grown in 75 $cm^2$ culture plates.

48 h before the experiments, cells were trypsinized (Trypsin kit One ReagentPack™ (CC-5034), Lonza) and plated in 96 well plates precoated with collagen I at 10000 cells per well. 24 h before the experiments culture medium was replaced by serum-reduced (0.5% FBS) medium.

Immediately before the experiments, medium was exchanged and hPASMC incubated in presence of the inventive compounds 1c, 2a and vardenafil (in concentrations of $1\times10^{-11}$ M (0.1 pM)-$1\times10^{-6}$M (1 uM)), or vehicle (0.1% DMSO) over 30 min.

Figure 4:
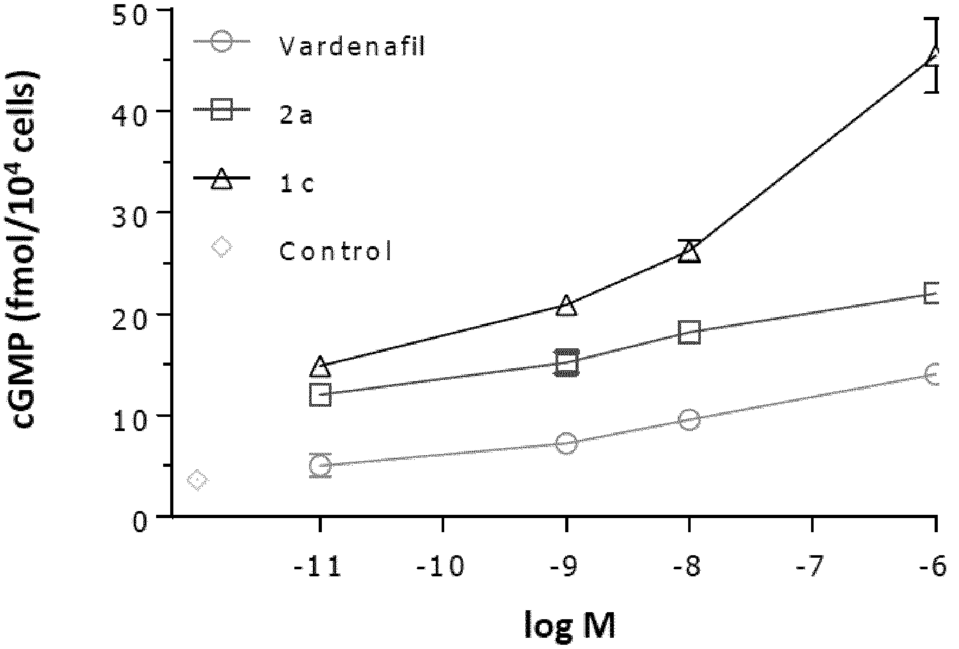
FIG. 4: Human pulmonary artery smooth muscle cells (hPASMC) incubated in presence of the compounds of the inventions 2a and 1c or the reference PDE5 inhibitor vardenafil.

Measurements of intracellular cGMP were performed using the Amersham cGMP EIA System (GE Healthcare, RPN226) following the instructions of the manufacturer. The assay has a sensitivity of 2 fmol cGMP per well. Briefly, incubations were terminated by adding Amersham's lysis buffer 1 and cells left for 10 min under agitation to ensure complete lysis. cGMP in samples was then acetylated using triethylamine and acetic anhydride and determined by a competitive ELISA. The ELISA is based on the competition between acetylated cGMP in cell culture lysates and a peroxidase-labelled cGMP conjugate for limited binding sites on a cGMP specific antiserum immobilized on pre-coated 96 well MTP. cGMP was determined based on a standard curve. Results were expressed as fmol cGMP in $10^4$ cells as means+/−SE from 3 independent experiments in triplicates (FIG. 4). Surprisingly, the inventive compounds 2a and 1c show a significantly higher efficacy in increasing cGMP level as compared to the reference inhibitor vardenafil, which is as potent, or even much more potent PDE5 inhibitor (see Table 1) compared to the inventive compounds 2a and 1c.

The invention claimed is:

1. A compound of formula I or formula II:

I

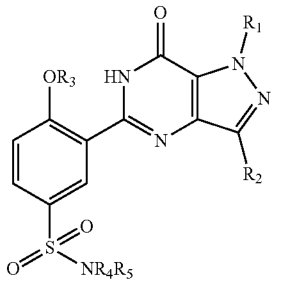

II

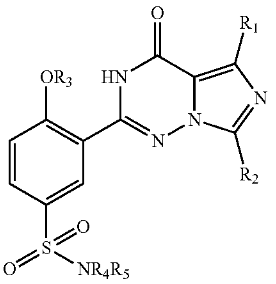

or pharmaceutically acceptable salt, solvate or hydrate thereof, wherein said compound of formula I and said compound of formula II each comprises at least one covalently bound $ONO_2$ or ONO moiety;

$R_1$ is $C_1$-$C_3$alkyl;

$R_2$ is H, $C_1$-$C_6$alkyl, $C_3$-$C_6$cycloalkyl, $C_1$-$C_2$alkoxy, or $C_2$-$C_4$alkenyl;

$R_3$ is $C_1$-$C_4$alkyl optionally substituted with $C_1$-$C_2$alkoxy, $C_3$-$C_4$cycloalkyl, or $C_2$-$C_4$alkenyl;

$R_4$ and $R_5$, together with the nitrogen atom to which they are attached, form a heterocyclic ring, wherein said heterocyclic ring is piperidine, wherein said heterocyclic ring is optionally substituted with one or more $R_6$;

$R_6$ is $C_1$-$C_6$alkyl optionally substituted with one or more substituents independently selected from halogen, OH, ONO, $ONO_2$, $C_1$-$C_3$alkoxy, $C_1$-$C_3$haloalkoxy, $COOR_7$, $NR_8R_9$, and $C{=}NR_{10}$;

$R_7$ is H or $C_1$-$C_4$alkyl optionally substituted with one or more substituents independently selected from F, OH, ONO, $ONO_2$, and $NR_8R_9$;

$R_8$ and $R_9$ are independently H or $C_1$-$C_4$alkyl optionally substituted with one or more substituents independently selected from ONO and $ONO_2$;

$R_{10}$ is $C_1$-$C_4$alkyl optionally substituted with one or more substituents independently selected from F, ONO, $ONO_2$, and $C_3$-$C_6$cycloalkyl.

2. The compound of claim 1, wherein $R_1$ is methyl or ethyl.

3. The compound of claim 1, wherein $R_2$ is $C_1$-$C_3$alkyl or $C_3$-$C_6$cycloalkyl.

4. The compound of claim 1, wherein $R_3$ is $C_1$-$C_4$alkyl.

5. The compound of claim 1, wherein $R_6$ is $C_1$-$C_6$alkyl optionally substituted with one or more substituents independently selected from OH, ONO, $ONO_2$, and $C_1$-$C_3$alkoxy.

6. The compound of claim 1, wherein said compound of formula I is a compound of formula I*, and wherein said compound of formula II is a compound of formula II*, or independently a pharmaceutically acceptable salt, solvate or hydrate thereof,

I*

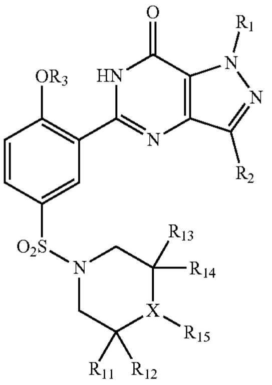

II*

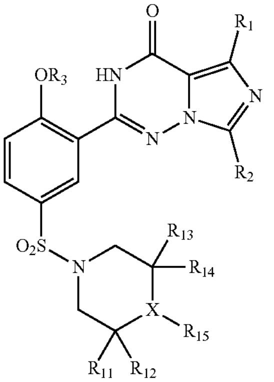

wherein

X is $CR_{16}$;

$R_1$, $R_{12}$, $R_{13}$, $R_{14}$ and $R_{15}$ are independently H or $C_1$-$C_6$alkyl optionally substituted with one or more substituents independently selected from halogen, OH, ONO, $ONO_2$, $C_1$-$C_3$alkoxy, $C_1$-$C_3$haloalkoxy, $COOR_{17}$, $NR_{18}R_{19}$, and $C{=}NR_{20}$;

$R_{16}$ is H or $C_1$-$C_6$alkyl optionally substituted with one or more substituents independently selected from halogen, OH, ONO, $ONO_2$, $C_1$-$C_3$alkoxy, $C_1$-$C_3$haloalkoxy, $COOR_{17}$, $NR_{18}R_{19}$, and $C{=}NR_{20}$;

$R_{17}$ is H or $C_1$-$C_4$alkyl optionally substituted with F, OH, ONO, or $ONO_2$;

$R_{18}$ and $R_{19}$ are independently H or $C_1$-$C_4$alkyl optionally substituted with ONO or $ONO_2$;

$R_{20}$ is $C_1$-$C_4$alkyl optionally substituted with F, ONO, or $ONO_2$;

wherein at least one of said $R_{11}$, $R_{12}$, $R_{13}$, $R_{14}$, $R_{15}$ and $R_{16}$ comprises independently at least one covalently bonded $ONO_2$ or ONO moiety.

7. The compound according to claim 6, wherein one of said $R_{13}$ and $R_{14}$ is H, and the other of said $R_{13}$ and $R_{14}$ is H or $C_1$-$C_6$alkyl optionally substituted with one or more substituents independently selected from halogen, OH, ONO, $ONO_2$, $C_1$-$C_3$alkoxy, $C_1$-$C_3$haloalkoxy, $COOR_{17}$, $NR_{18}R_{19}$, and $C{=}NR_{20}$; said $R_{15}$ is $C_1$-$C_6$alkyl optionally substituted with one or more substituents independently selected from halogen, OH, ONO, $ONO_2$, $C_1$-$C_3$alkoxy, $C_1$-$C_3$haloalkoxy, $COOR_{17}$, $NR_{18}R_{19}$, and $C{=}NR_{20}$; and said $R_{16}$ is H or $C_1$-$C_6$alkyl optionally substituted with one or more substituents independently selected from halogen, OH, ONO, $ONO_2$, $C_1$-$C_3$alkoxy, $C_1$-$C_3$haloalkoxy, $COOR_{17}$, $NR_{18}R_{19}$, and $C{=}NR_{20}$.

8. The compound of claim 6, wherein one of said $R_{13}$ and $R_{14}$ is H, and the other of said $R_{13}$ and $R_{14}$ is H or $C_1$-$C_6$alkyl optionally substituted with one or more substituents independently selected from halogen, OH, ONO, $ONO_2$, $C_1$-$C_3$alkoxy, and $C_1$-$C_3$haloalkoxy; said $R_{15}$ is $C_1$-$C_6$alkyl optionally substituted with one or more substituents independently selected from halogen, OH, ONO, $ONO_2$, $C_1$-$C_3$alkoxy, and $C_1$-$C_3$haloalkoxy; and said $R_{16}$ is H or $C_1$-$C_6$alkyl optionally substituted with one or more substituents independently selected from halogen, OH, ONO, $ONO_2$, $C_1$-$C_3$alkoxy, and $C_1$-$C_3$haloalkoxy.

9. The compound of claim 6, wherein one of said $R_{11}$ and $R_{12}$ is H, and the other of said $R_{11}$ and $R_{12}$ is H or $C_1$-$C_6$alkyl optionally substituted with one or more substituents independently selected from halogen, OH, ONO, $ONO_2$, $C_1$-$C_3$alkoxy, $C_1$-$C_3$haloalkoxy, $COOR_{17}$, $NR_{18}R_{19}$, and $C{=}NR_{20}$;

one of said $R_{13}$ and $R_{14}$ is H, and the other of said $R_{13}$ and $R_{14}$ is H or $C_1$-$C_6$alkyl optionally substituted with one or more substituents independently selected from halogen, OH, ONO, $ONO_2$, $C_1$-$C_3$alkoxy, $C_1$-$C_3$haloalkoxy, $COOR_{17}$, $NR_{18}R_{19}$, and $C{=}NR_{20}$;

$R_{15}$ is $C_1$-$C_6$alkyl optionally substituted with one or more substituents independently selected from halogen, OH, ONO, $ONO_2$, $C_1$-$C_3$alkoxy, $C_1$-$C_3$haloalkoxy, $COOR_{17}$, $NR_{18}R_{19}$, and $C{=}NR_{20}$;

$R_{16}$ is H or $C_1$-$C_6$alkyl optionally substituted with one or more substituents independently selected from halogen, OH, ONO, $ONO_2$, $C_1$-$C_3$alkoxy, $C_1$-$C_3$haloalkoxy, $COOR_{17}$, $NR_{18}R_{19}$, and $C{=}NR_{20}$;

wherein $R_{17}$ is H or $C_1$-$C_4$alkyl optionally substituted with one or more substituents independently selected from OH, ONO, and $ONO_2$;

$R_{18}$ and $R_{19}$ are each independently H or $C_1$-$C_4$alkyl optionally substituted with one or more substituents independently selected from ONO and $ONO_2$.

10. The compound according to claim 1, wherein said compound is selected from:

(R)-1-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)ethane-1,2-diyl dinitrate (1a);

(S)-1-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)ethane-1,2-diyl dinitrate (1b);

(R)-2-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-2-hydroxyethyl nitrate (1c);

(S)-2-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-2-hydroxyethyl nitrate (1d);

3-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-3-hydroxypropyl nitrate Enantiomer A (1e);

3-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-3-hydroxypropyl nitrate Enantiomer B (1f);

3-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-3,5-dihydroxypentyl nitrate (1g);

3-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-3-hydroxypentane-1,5-diyl dinitrate (1h);

2-((1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)(hydroxy)methyl)propane-1,3-diyl dinitrate (1i);

1-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-2-hydroxyethyl nitrate Enantiomer A (1k);

1-(1-((4-ethoxy-3-(1-methyl-7-oxo-3-propyl-6,7-dihydro-1H-pyrazolo[4,3-d]pyrimidin-5-yl)phenyl)sulfonyl)piperidin-4-yl)-2-hydroxyethyl nitrate Enantiomer B (1l);

(R)-1-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)ethane-1,2-diyl dinitrate (2a);

(S)-1-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)ethane-1,2-diyl dinitrate (2b);

(R)-2-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-hydroxyethyl nitrate (2c);

(S)-2-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-hydroxyethyl nitrate (2d);

3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-3-hydroxypropyl nitrate Enantiomer A (2e);

3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-3-hydroxypropyl nitrate Enantiomer B (2f);

3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-3,5-dihydroxypentyl nitrate (2g);

3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-3-hydroxypentane-1,5-diyl dinitrate (2h);

2-((1-((4-ethoxy-3-(5-methyl-4-oxo-7-propyl-3,4-dihydroimidazo[5,1-f][1,2,4]triazin-2-yl)phenyl)sulfonyl)piperidin-4-yl)(hydroxy)methyl)propane-1,3-diyl dinitrate (2i);

1-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-hydroxyethyl nitrate Enantiomer A (2k);

1-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-hydroxyethyl nitrate Enantiomer B (2l);

2-((1-((4-ethoxy-3-(5-methyl-4-oxo-7-propyl-3,4-dihydroimidazo[5,1-f][1,2,4]triazin-2-yl)phenyl)sulfonyl)piperidin-4-yl)methyl)propane-1,3-diyl dinitrate (2m);

3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-(hydroxymethyl)propyl nitrate (2n);

2-((1-((4-ethoxy-3-(5-methyl-4-oxo-7-propyl-3,4-dihydroimidazo[5,1-f][1,2,4]triazin-2-yl)phenyl)sulfonyl)piperidin-4-yl)methyl)-2-methylpropane-1,3-diyl dinitrate (2o); and 3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-(hydroxymethyl)-2-methylpropyl nitrate (2p).

11. A pharmaceutical composition comprising at least one of the compounds of formula I or formula II of claim 1, or a pharmaceutically acceptable salt, solvate or hydrate thereof, and a pharmaceutically acceptable excipient, adjuvant, or carrier.

12. The compound of claim 2, wherein $R_1$ is methyl.

13. The pharmaceutical composition of claim 11, wherein said pharmaceutical composition further comprises at least one sGC stimulator.

14. The pharmaceutical composition of claim 13, wherein said sGC stimulator is selected from the group consisting of riociguat, vericiguat, praliciguat, and olinciguat.

15. The compound of claim 1, wherein said heterocyclic ring is substituted with one or two $R_6$.

16. The compound of claim 15, wherein said $R_6$ is $C_1$-$C_6$ alkyl substituted with one or more OH, ONO, or $ONO_2$.

17. The compound of claim 1, wherein said compound is 2-((1-((4-ethoxy-3-(5-methyl-4-oxo-7-propyl-3,4-dihydroimidazo[5,1-f][1,2,4]triazin-2-yl)phenyl)sulfonyl)piperidin-4-yl)methyl)-2-methylpropane-1,3-diyl dinitrate; or a pharmaceutically acceptable salt thereof.

18. The compound of claim 1, wherein said compound is 3-(1-((4-ethoxy-3-(5-methyl-4-oxo-7-propyl-3,4-dihydroimidazo[5,1-f][1,2,4]triazin-2-yl)phenyl)sulfonyl)piperidin-4-yl)-2-(hydroxymethyl)-2-methylpropyl nitrate; or a pharmaceutically acceptable salt thereof.

* * * * *